(12) United States Patent
May et al.

(10) Patent No.: US 9,884,921 B2
(45) Date of Patent: Feb. 6, 2018

(54) BISPECIFIC HETERODIMERIC DIABODIES AND USES THEREOF

(71) Applicant: Pfizer Inc., New York, NY (US)

(72) Inventors: Chad Michael May, Tarrytown, NY (US); Adam Reid Root, Byfield, MA (US); William A. Brady, San Diego, CA (US); Lioudmila Gennadievna Tchistiakova, Stoneham, MA (US); Lidia Mosyak, Newton, MA (US); Laird Bloom, Needham, MA (US); Paul A. Moore, North Bethesda, MD (US); Leslie S. Johnson, Darnestown, MD (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/751,704

(22) Filed: Jun. 26, 2015

(65) Prior Publication Data

US 2016/0002357 A1    Jan. 7, 2016

Related U.S. Application Data

(60) Provisional application No. 62/148,920, filed on Apr. 17, 2015, provisional application No. 62/019,762, filed on Jul. 1, 2014.

(51) Int. Cl.
  *C07K 16/28*    (2006.01)
  *C07K 16/46*    (2006.01)
  *C07K 16/18*    (2006.01)

(52) U.S. Cl.
  CPC .......... *C07K 16/468* (2013.01); *C07K 16/18* (2013.01); *C07K 16/28* (2013.01); *C07K 16/2809* (2013.01); *C07K 2317/31* (2013.01); *C07K 2317/524* (2013.01); *C07K 2317/526* (2013.01); *C07K 2317/56* (2013.01); *C07K 2317/565* (2013.01); *C07K 2317/626* (2013.01); *C07K 2317/72* (2013.01); *C07K 2317/732* (2013.01); *C07K 2317/76* (2013.01); *C07K 2317/94* (2013.01)

(58) Field of Classification Search
  CPC .. C07K 16/26; C07K 16/468; C07K 16/2809; C07K 2317/626; C07K 2317/565; C07K 2317/31; C07K 2317/56
  USPC .......................... 424/136.1; 530/387.3, 387.9
  See application file for complete search history.

(56) References Cited

U.S. PATENT DOCUMENTS

| | | | |
|---|---|---|---|
| 4,642,334 A | 2/1987 | Moore et al. |
| 4,816,397 A | 3/1989 | Boss et al. |
| 4,816,567 A | 3/1989 | Cabilly et al. |
| 4,946,778 A | 8/1990 | Ladner et al. |
| 5,091,513 A | 2/1992 | Huston et al. |
| 5,731,168 A | 3/1998 | Carter et al. |
| 5,739,281 A | 4/1998 | Thøgersen et al. |
| 5,747,654 A | 5/1998 | Pastan et al. |
| 5,811,267 A | 9/1998 | Ring |
| 5,837,242 A | 11/1998 | Holliger et al. |
| 5,844,094 A | 12/1998 | Hudson et al. |
| 5,856,456 A | 1/1999 | Whitlow et al. |
| 5,869,620 A | 2/1999 | Whitlow et al. |
| 5,877,291 A | 3/1999 | Mezes et al. |
| 5,959,083 A | 9/1999 | Bosslet et al. |
| 5,969,108 A | 10/1999 | McCafferty et al. |
| 5,989,830 A | 11/1999 | Davis et al. |
| 6,031,072 A | 2/2000 | Blaschuk et al. |
| 6,129,914 A | 10/2000 | Weiner et al. |
| 6,331,415 B1 | 12/2001 | Cabilly et al. |
| 6,476,198 B1 | 11/2002 | Kang |
| 6,485,910 B1 | 11/2002 | Walker et al. |
| 6,534,633 B1 | 3/2003 | Weidanz et al. |
| 6,670,453 B2 | 12/2003 | Frenken et al. |
| 6,759,518 B1 | 7/2004 | Kontermann et al. |
| 6,783,961 B1 | 8/2004 | Edwards et al. |
| 6,815,540 B1 | 11/2004 | Plückthun et al. |
| 6,833,441 B2 | 12/2004 | Wang et al. |
| 7,112,324 B1 | 9/2006 | Dorken et al. |
| 7,129,330 B1 | 10/2006 | Little et al. |
| 7,183,076 B2 | 2/2007 | Arathoon et al. |
| 7,189,507 B2 | 3/2007 | Mack et al. |
| 7,235,641 B2 | 6/2007 | Kufer et al. |
| 7,319,139 B2 | 1/2008 | Braslawsky et al. |
| 7,452,537 B2 | 11/2008 | Bauer et al. |
| 7,456,153 B2 | 11/2008 | Blaschuk et al. |
| 7,635,472 B2 | 12/2009 | Kufer et al. |
| 7,700,097 B2 | 4/2010 | Braslawsky et al. |
| 7,727,535 B2 | 6/2010 | Shaw |

(Continued)

FOREIGN PATENT DOCUMENTS

| EP | 1025854 A1 | 8/2000 |
|---|---|---|
| EP | 2361936 A1 | 8/2011 |

(Continued)

OTHER PUBLICATIONS

Chen et al. Clinical Pharmacology & Therapeutics | vol. 100 No. 3 | Sep. 2016: 232-241.*

(Continued)

*Primary Examiner* — Lynn A Bristol
(74) *Attorney, Agent, or Firm* — Maria V. Marucci

(57) ABSTRACT

Bispecific heterodimeric diabody molecules and uses thereof in the treatment of cancer. The bispecific heterodimeric diabody molecules comprise two polypeptide chains that associate to form two epitope binding sites recognizing the P-cadherin tumor cell associated antigen and the CD3 T cell antigen.

34 Claims, 44 Drawing Sheets

(56) References Cited

U.S. PATENT DOCUMENTS

| | | |
|---|---|---|
| 7,728,114 B2 | 6/2010 | Mach et al. |
| 7,754,208 B2 | 7/2010 | Ledbetter et al. |
| 7,754,209 B2 | 7/2010 | Ledbetter et al. |
| 7,812,128 B2 | 10/2010 | Aburatani et al. |
| 7,820,166 B2 | 10/2010 | Lanzavecchia |
| 7,951,917 B1 | 5/2011 | Arathoon et al. |
| 7,951,918 B2 | 5/2011 | Glaser et al. |
| 7,977,095 B2 | 7/2011 | Bonyhadi et al. |
| 7,998,695 B2 | 8/2011 | Nakamura et al. |
| 8,030,461 B2 | 10/2011 | Kojima |
| 8,067,005 B1 | 11/2011 | Chapman et al. |
| 8,106,161 B2 | 1/2012 | Ledbetter et al. |
| 8,227,577 B2 | 7/2012 | Klein et al. |
| 8,236,308 B2 | 8/2012 | Kischel et al. |
| 8,247,194 B2 | 8/2012 | Raum et al. |
| 8,263,064 B2 | 9/2012 | Karin et al. |
| 8,383,590 B2 | 2/2013 | Tsunoda et al. |
| 8,394,926 B2 | 3/2013 | Lutterbüse et al. |
| 8,435,749 B2 | 5/2013 | Togashi et al. |
| 8,455,249 B2 | 6/2013 | Aburatani et al. |
| 8,455,444 B2 | 6/2013 | Nishmura et al. |
| 8,535,677 B2 | 9/2013 | Rohlff et al. |
| 8,569,450 B2 | 10/2013 | Pass et al. |
| 8,586,714 B2 | 11/2013 | Ghayur et al. |
| 8,603,986 B2 | 12/2013 | Blaschuk et al. |
| 8,629,246 B2 | 1/2014 | Humphreys et al. |
| 8,658,774 B2 | 2/2014 | Williams et al. |
| 8,703,132 B2 | 4/2014 | Imhof-Jung et al. |
| 8,722,859 B2 | 5/2014 | Miller et al. |
| 8,784,821 B1 | 7/2014 | Kufer et al. |
| 8,796,424 B2 | 8/2014 | Croasdale et al. |
| 8,815,211 B2 | 8/2014 | Nino et al. |
| 8,846,042 B2 | 9/2014 | Zhou |
| 8,871,912 B2 | 10/2014 | Davis et al. |
| 9,017,669 B2 | 4/2015 | Shiba et al. |
| 9,029,508 B2 | 5/2015 | Ghayur et al. |
| 9,045,528 B2 | 6/2015 | Ruker et al. |
| 9,062,101 B2 | 6/2015 | Barghorn et al. |
| 9,127,061 B2 | 9/2015 | Zhang et al. |
| 9,150,664 B2 | 10/2015 | Kufer et al. |
| 2002/0142000 A1 | 10/2002 | Digan et al. |
| 2002/0155604 A1 | 10/2002 | Ledbetter et al. |
| 2003/0194406 A1 | 10/2003 | Reinhard et al. |
| 2003/0228570 A1 | 12/2003 | Tom et al. |
| 2004/0018493 A1 | 1/2004 | Anastasio et al. |
| 2004/0038886 A1 | 2/2004 | Finney et al. |
| 2004/0047854 A1 | 3/2004 | Black et al. |
| 2004/0053245 A1 | 3/2004 | Tang et al. |
| 2004/0180046 A1 | 9/2004 | Himawan |
| 2004/0219643 A1 | 11/2004 | Winter et al. |
| 2005/0037439 A1 | 2/2005 | Bourner et al. |
| 2005/0069549 A1 | 3/2005 | Herman |
| 2005/0079170 A1 | 4/2005 | Le Gall et al. |
| 2005/0118164 A1 | 6/2005 | Herman |
| 2005/0176934 A1 | 8/2005 | Kipriyanov et al. |
| 2006/0172344 A1 | 8/2006 | Endo et al. |
| 2006/0204493 A1 | 9/2006 | Huang et al. |
| 2006/0240001 A1 | 10/2006 | Bauer et al. |
| 2007/0004909 A1 | 1/2007 | Johnson et al. |
| 2007/0036783 A1 | 2/2007 | Humeau et al. |
| 2007/0048301 A1 | 3/2007 | Bodary-Winter et al. |
| 2007/0053835 A1 | 3/2007 | DeSauvage et al. |
| 2007/0065437 A1 | 3/2007 | Elson et al. |
| 2007/0184444 A1 | 8/2007 | Abbas et al. |
| 2009/0060910 A1 | 3/2009 | Johnson et al. |
| 2009/0148905 A1 | 6/2009 | Ashman et al. |
| 2009/0155275 A1 | 6/2009 | Wu et al. |
| 2009/0162359 A1 | 6/2009 | Klein et al. |
| 2009/0169572 A1 | 7/2009 | Nakatsuru et al. |
| 2009/0214526 A1 | 8/2009 | Lazar et al. |
| 2009/0214535 A1 | 8/2009 | Igawa et al. |
| 2009/0232811 A1 | 9/2009 | Klein et al. |
| 2010/0150918 A1 | 6/2010 | Kufer et al. |
| 2010/0174053 A1 | 7/2010 | Johnson et al. |
| 2010/0310451 A1 | 12/2010 | Maret et al. |
| 2011/0020221 A1 | 1/2011 | Berman et al. |
| 2011/0053787 A1 | 3/2011 | Brulliard et al. |
| 2011/0054151 A1 | 3/2011 | Lazar et al. |
| 2011/0064743 A1 | 3/2011 | Hammond et al. |
| 2011/0165161 A1 | 7/2011 | Lin et al. |
| 2011/0183924 A1 | 7/2011 | Mintz et al. |
| 2011/0229476 A1 | 9/2011 | Liu et al. |
| 2011/0262439 A1 | 10/2011 | Kufer et al. |
| 2011/0274692 A1 | 11/2011 | White et al. |
| 2011/0275787 A1 | 11/2011 | Kufer et al. |
| 2011/0293619 A1 | 12/2011 | Kufer et al. |
| 2012/0034228 A1 | 2/2012 | Kufer et al. |
| 2012/0039916 A1 | 2/2012 | Zurawski et al. |
| 2012/0184716 A1 | 7/2012 | Fischer et al. |
| 2012/0195900 A1 | 8/2012 | Ghayor et al. |
| 2012/0201746 A1 | 8/2012 | Liu et al. |
| 2012/0231023 A1 | 9/2012 | Zurawski et al. |
| 2012/0237442 A1 | 9/2012 | Rossi et al. |
| 2012/0244155 A1 | 9/2012 | Lecine et al. |
| 2012/0251541 A1 | 10/2012 | Baurin et al. |
| 2012/0269826 A1 | 10/2012 | McKee et al. |
| 2012/0283415 A1 | 11/2012 | Humphreys et al. |
| 2012/0283418 A1 | 11/2012 | Wu et al. |
| 2012/0294857 A1 | 11/2012 | Sentman et al. |
| 2012/0301465 A1 | 11/2012 | Dutartre et al. |
| 2012/0316071 A1 | 12/2012 | Smider et al. |
| 2013/0011401 A1 | 1/2013 | Huber et al. |
| 2013/0058936 A1 | 3/2013 | Bruenker et al. |
| 2013/0058937 A1 | 3/2013 | Auer et al. |
| 2013/0058947 A1 | 3/2013 | Stull et al. |
| 2013/0058960 A1 | 3/2013 | Bhakta et al. |
| 2013/0060011 A1 | 3/2013 | Bruenker et al. |
| 2013/0066054 A1 | 3/2013 | Humphreys et al. |
| 2013/0078249 A1 | 3/2013 | Ast et al. |
| 2013/0010586 A1 | 4/2013 | Riegler et al. |
| 2013/0129730 A1 | 5/2013 | Kufer et al. |
| 2013/0156769 A1 | 6/2013 | Kufer et al. |
| 2013/0189261 A1 | 7/2013 | Odegard et al. |
| 2013/0295121 A1 | 11/2013 | Johnson et al. |
| 2013/0317201 A1 | 11/2013 | Ishii et al. |
| 2014/0004081 A1 | 1/2014 | Cobbold et al. |
| 2014/0010814 A1 | 1/2014 | Benhar et al. |
| 2014/0056897 A1 | 2/2014 | Buelow et al. |
| 2014/0065142 A1 | 3/2014 | Roschke et al. |
| 2014/0079689 A1 | 3/2014 | Elliott et al. |
| 2014/0099318 A1 | 4/2014 | Huang et al. |
| 2014/0112914 A1 | 4/2014 | Nezu et al. |
| 2014/0112926 A1 | 4/2014 | Liu et al. |
| 2014/0161800 A1 | 6/2014 | Blankenship et al. |
| 2014/0178368 A1 | 6/2014 | Sharp et al. |
| 2014/0193408 A1 | 7/2014 | Huber et al. |
| 2014/0206846 A1 | 7/2014 | Beckmann |
| 2014/0242081 A1 | 8/2014 | Hammond et al. |
| 2015/0037334 A1 | 2/2015 | Kufer et al. |
| 2015/0119555 A1 | 4/2015 | Jung et al. |
| 2015/0175697 A1 | 6/2015 | Bonvini et al. |
| 2015/0183875 A1 | 7/2015 | Cobbold et al. |
| 2015/0232557 A1 | 8/2015 | Tan et al. |
| 2017/0073395 A1* | 3/2017 | Finlay .................. C07K 16/00 |

FOREIGN PATENT DOCUMENTS

| | | |
|---|---|---|
| EP | 2848686 A2 | 3/2015 |
| WO | 91/01752 A1 | 2/1991 |
| WO | 95/09917 A1 | 4/1995 |
| WO | 95/16037 A1 | 6/1995 |
| WO | 98/41613 A1 | 9/1998 |
| WO | 00/06605 A2 | 2/2000 |
| WO | 01/57188 A2 | 8/2001 |
| WO | 02/072635 A2 | 9/2002 |
| WO | 02/097395 A2 | 12/2002 |
| WO | 2004/081026 A2 | 9/2004 |
| WO | 2004/110345 A2 | 12/2004 |
| WO | 2005/028507 A1 | 3/2005 |
| WO | 2005/035572 A2 | 4/2005 |
| WO | 2006/020258 A2 | 2/2006 |
| WO | 2007/075672 A2 | 7/2007 |
| WO | 2007/106507 A2 | 9/2007 |
| WO | 2008/102557 A1 | 8/2008 |

(56) References Cited

FOREIGN PATENT DOCUMENTS

| WO | 2008/124858 A2 | 10/2008 |
| WO | 2010/001585 A1 | 1/2010 |
| WO | 2010/040545 A1 | 4/2010 |
| WO | 2011/071541 A2 | 6/2011 |
| WO | 2012/018687 A1 | 2/2012 |
| WO | 2012/057315 A1 | 5/2012 |
| WO | 2012/158818 A2 | 11/2012 |
| WO | 2012/162583 A1 | 11/2012 |
| WO | 2013/013700 A1 | 1/2013 |
| WO | 2013/041687 A1 | 3/2013 |
| WO | 2013/041865 A1 | 3/2013 |
| WO | 2013/166448 A1 | 11/2013 |

OTHER PUBLICATIONS

Root et al. (Antibodies, (Mar. 4, 2016) vol. 5, No. 1. arn. 6. (abstract)).*
Fisher et al. (Cancer Research, (Aug. 1, 2015) vol. 75, No. 15, Supp. Suppl. 1. Abstract No. 2476; 106th Annual Meeting of the American Association for Cancer Research, AACR 2015. Philadelphia, PA, United States. Apr. 18-Apr. 22, 2015).*
Giddabasappa, et al. (Cancer Research, (Aug. 1, 2015) vol. 75, No. Suppl. 15, pp. 5111; 106th Annual Meeting of the American-Association-for-Cancer-Research (AACR). Philadelphia, PA, USA. Apr. 18-22, 2015. Amer Assoc Canc Res.*
Chen et al. (Clinical Pharmacology & Therapeutics vol. 100 No. 3 | 232-241 (Sep. 2016)).*
Root et al. (Antibodies 2016, 5, 6;1-30).*
Albergaria et al, "ICI 182,780 induces P-cadherin overexpression in breast cancer cells through chromatin remodelling at the promoter level: a role for C/EBPβ in CDH3 gene activation", Human Molecular Genetics 19 (13):2554-2566 (2010).
Bargou et al, "Tumor Regression in Cancer Patients by Very Low Doses of a T Cell-Engaging Antibody", Science (2008) 321(5891):974-977.
Brinkmann et al, "Phage display of disulfide-stabilized Fv fragments", Journal of Immunological Methods 182:41-50 (1995).
Bussemakers et al, "Complex Cadherin Expression in Human Prostate Cancer Cells", International Journal of Cancer 85(3):446-450 (2000).
Carmichael et al, "The Crystal Structure of an Anti-CEA scFv Diabody Assembled from T84.66 scFvs in VL-to-VH Orientation: Implications for Diabody Flexibility", Journal of Molecular Biology 326(2):341-351 (2003).
Cavallaro et al, "Adhesion molecule signalling: not always a sticky business", Nature Reviews Molecular Cell Biology 12(3):189-197 (2011)
Chichili et al, "A CD3×CD123 bispecific DART for redirecting host T cells to myelogenous leukemia: Preclinical activity and safety in nonhuman primates", Science Translational Medicine 7(289):289ra82 (2015).
Chothia et al, "Conformations of immunoglobulin hypervariable regions", Nature 342:877-883 (1989).
de Boer et al, "Changing Roles of Cadherins and Catenins during Progression of Squamos Intraepithelial Lesions in the Uterine Cervix", American Journal of Pathology 155(2):505-515 (1999).
de Parades et al, "Formalin Application in the Treatment of Chronic Radiation-Induced Hemorrhagic Proctitis—An Effective But Not Risk-Free Procedure: A Prospective Study of 33 Patients", Diseases of the Colon & Rectum 48 (8):1535-1541 (2005).
Ellman et al, "Biosynthetic Method for Introducing Unnatural Amino Acids Site-Specifically into Proteins", Methods in Enzymology 202:301-336 (1991).
Gamallo et al, "The Prognostic Significance of P-Cadherin in Infiltrating Ductal Breast Carcinoma", Mod Pathol 14 (7):650-654 (2001).
Gumbiner, "Regulation of Cadherin Adhesive Activity", The Journal of Cell Biology 148(3):399-403 (2000).

Hardy et al, "Aberrant P-cadherin expression is an early event in hyperplastic and dysplastic transformation in the colon", Gut 50(4):513-519 (2002).
Hardy et al, "Transient P-cadherin expression in radiation proctitis; a model of mucosal injury and repair", Journal of Pathology 197(2):194-200 (2002).
Hirai et al, "Expression and role of E- and P-cadherin adhesion molecules in embryonic histogenesis; I. Lung epithelial morphogenesis", Development 105:263-270 (1989).
Huehls et al, "Bispecific T-cell engagers for cancer immunotherapy", Immunology and Cell Biology 93(3):290-296 (2015).
Imai et al, "Identification of a Novel Tumor-Associated Antigen, Cadherin 3/P-Cadherin, as a Possible Target for Immunotherapy of Pancreatic, Gastric, and Colorectal Cancers", Clinical Cancer Research 14(20):6487-6495 (2008).
Jankowski et al, "Alterations in classical cadherins associated with progression in ulcerative and Crohn's colitis", Laboratory Investigations 78(9):1155-1167 (1998).
Johnson et al, "Effector Cell Recruitment with Novel Fv-based Dual-affinity Re-targeting Protein Leads to Potent Tumor Cytolysis and in Vivo B-cell Depletion", Journal of Molecular Biology 399(3):436-449 (2010).
Klinger et al, "Immunopharmacologic response of patients with B-lineage acute lymphoblastic leukemia to continuous infusion of T cell-engaging CD19/CD3-bispecific BiTE antibody blinatumomab", Blood 119(26):6226-6233 (2012).
Lee et al, "CYP-Mediated Therapeutic Protein-Drug Interactions; Clinical Findings, Proposed Mechanisms and Regulatory Implications", Clin Pharmacokinet 49(5):295-310 (2010).
Mac Callum et al, "Antibody-antigen Interactions: Contact Analysis and Binding Site Topography", J. Mol. Biol. 262:732-745 (1996).
Mahmood et al, "Drug Interaction Studies of Therapeutic Proteins or Monoclonal Antibodies", Journal of Clinical Pharmacology 47(12):1540-1554 (2007).
Makabe et al, "Thermodynamic Consequences of Mutations in Vernier Zone Residues of a Humanized Anti-human Epidermal Growth Factor Receptor Murine Antibody, 528", The Journal of Biological Chemistry 283(2):1156-1166 (2008).
Maude et al, "Managing Cytokine Release Syndrome Associated With Novel T Cell-Engaging Therapies", Cancer J 20(2):119-122 (2014).
Moore et al, "Application of dual affinity retargeting molecules to achieve optimal redirected T-cell killing of B-cell lymphoma", Blood 117(17):4542-4551 (2011).
Nose et al, "A Novel Cadherin Cell Adhesion Molecule: Its Expression Patterns Associated with Implantation and Organogenesis of Mouse Embryos", The Journal of Cell Biology 103(No. 6, Pt 2):2649-2658 (1986).
Palacios et al, "Anomalous Expression of P-Cadherin in Breast Carcinoma", American Journal of Pathology 146 (3):605-612 (1995).
PCT International Search Report and Written Opinion for PCT/IB2015/054829 dated Oct. 19, 2015.
Perisic et al, "Crystal structure of a diabody, a bivalent antibody fragment", 2(12):1217-1226 (1994).
Pospechova et al, "Changes in the expression of P-cadherin in the normal, cryptorchid and busulphan-treated rat testis", International Journal of Andrology 30:430-438 (2007).
Radice et al, "Precocious Mammary Gland Development in P-Cadherin-deficient Mice", The Journal of Cell Biology 139(4):1025-1032 (1997).
Ramesh et al, "Cytokines and Chemokines at the Crossroads of Neuroinflammation, Neurodegeneration, and Neuropathic Pain", Mediators of Inflammation, vol. 2013, Article ID 480739 (2013).
Rasbridge et al, "Epithelial (E-) and placental (P-) cadherin cell adhesion molecule expression in breast carcinoma", Journal of Pathology 169(2):245-250 (1993).
Raziuddin et al, "Soluble Interleukin 2 Receptor Levels in Serum and its Relationship to T Cell Abnormality and Clinical Manifestations of the Disease in Patients with Systemic Lupus Erythematosus", Journal of Rheumatology 18 (6):831-836 (1991).

(56) References Cited

OTHER PUBLICATIONS

Reusch et al, "A tetravalent bispecific TandAb (CD19/CD3), AFM11, efficiently recruits T cells for the potent lysis of CD19+ tumor cells", Mabs 7(3):584-604 (2015).
Sanders et al, "Aberrant P-cadherin expression is a feature of clonal expansion in the gastrointestinal tract associated with repair and neoplasia", Journal of Pathology 190(5):526-530 (2000).
Schrieber et al, "Factors influencing immune complex localisation", Rheumatol Int 4:95-109 (1984).
Schulz et al, "Proteolytic Cleavage of CD25, the α Subunit of the Human T Cell Interleukin 2 Receptor, by Der p 1, a Major Mite Allergen with Cysteine Protease Activity", J. Exp. Med. 187(2):271-275 (1998).
Shimoyama et al, "Cadherin Cell-Adhesion Molecules in Human Epithelial Tissues and Carcinomas", Cancer Research 49(8):2128-2133 (1989).
Shimoyama et al, "Molecular Cloning of a Human Ca2+-dependent Cell-Cell Adhesion Molecule Homologous to Mouse Placental Cadherin: Its Low Expression in Human Placental Tissues", The Journal of Cell Biology 109 (4):1787-1794 (1989).
Smith-Garvin et al, "T Cell Activation", Annu Rev Immunol 27:591-619 (2009).
Stefansson et al, "Prognostic impact of histological grade and vascular invasion compared with tumour cell proliferation in endometrial carcinoma of endometrioid type", Histopathology 44(5):472-479 (2004).
Taniuchi et al, "Overexpressed P-Cadherin/CDH3 Promotes Motility of Pancreatic Cancer Cells by Interacting with p120ctn and Activating Rho-Family GTPases", Cancer Research 65(8):3092-3099 (2005).
Tonikian et al, "Identifying specificity profiles for peptide recognition modules from phage-displayed peptide libraries", Nature Protocols 2(6):1368-1386 (2007).
Williams et al, "Expression of cadherins and catenins in oral epithelial dysplasia and squamos cell carcinoma", Journal of Oral Pathology and Medicine 27(7):308-317 (1998).
Yasui et al, "Expression of P-Cadherin in gastric carcinomas and its reduction in tumor progression", International Journal of Cancer 54(1):49-52 (1993).
Yun et al, "In Vivo Antitumor Activity of Anti-CD3-induced Activated Killer Cells", Cancer Research 49:4770-4774 (1989).
Zhang et al, "PF-03732010: A Fully Human Monoclonal Antibody against P-Cadherin with Antitumor and Antimetastatic Activity", Clinical Cancer Research 16(21):5177-5188 (2010).
Alt et al, "Novel tetravalent and bispecific IgG-like antibody molecules combining single-chain diabodies with the immunoglobulin gamma1 Fc or CH3 region", FEBS Letters 454:90-94 (1999).
Apostolovic et al, "pH-Sensitivity of the E3/K3 Heterodimeric Coiled Coil", Biomacromolecules 9:3173-3180 (2008).
Armour et al, "Recombinant human IgG molecules lacking Fcgamma receptor I binding and monocyte triggering activities", European Journal of Immunology 29(8):2613-2624 (1999).
Arndt et al, "Helix-stabilized Fv (hsFv) Antibody Fragments: Substituting the Constant Domains of a Fab Fragment for a Heterodimeric Coiled-coil Domain", J. Mol. Biol. 312:221-228 (2001).
Arndt et al, "Comparison of In Vivo Selection and Rational Design of Heterodimeric Coiled Coils", Structure 10:1235-1248 (2002).
Asano et al, "A diabody for cancer immunotherapy and its functional enhancement by fusion of human Fc region", Abstract 3P-683, J. Biochem 76(8):992 (2004).
Boucher et al, "Protein detection by Western blot via coiled-coil interactions", Analytical Biochemistry 399:138-140 (2010).
Cuesta et al, "Multivalent antibodies: when design surpasses evolution", Trends in Biotechnology 28:355-362 (2010).
De Crescenzo et al, "Real-Time Monitoring of the Interactions of Two-Stranded de Novo Designed Coiled-Coils: Effect of Chain Length on the Kinetic and Thermodynamic Constants of Binging", Biochemistry 42:1754-1793 (2003).

de Kruif et al, "Leucine Zipper Dimerized Bivalent and Bispecific scFv Antibodies from a Semi-synthetic Antibody Phage Display Library", The Journal of Biological Chemistry 271(13):7630-7634 (1996).
Fernandez-Rodriguez et al, "Induced heterodimerization and purification of two target proteins by a synthetic coiled-coil tag", Protein Science 21:511-519 (2012).
Gao et al, "Efficient inhibition of multidrug-resistant human tumors with a recombinant bispecific anti-P-glycoprotein x anti-CD3 diabody", Leukemia 18:513-520 (2004).
Ghosh et al, "End-to-end and end-to-middle interhelical interactions: new classes of interacting helix pairs in protein structures", Acta Crystallographica D65:1032-1041 (2009).
Grigoryan et al, "Structural specificity in coiled-coil interactions", Current Opinion in Structural Biology 18:477-483 (2008).
Holliger et al, "'Diabodies': Small bivalent and bispecific antibody fragments', Proc. Natl. Acad. Sci. USA 90:6444-6448 (1993).
Holliger et al, "Engineered antibody fragments and the rise of single domains", Nature Biotechnology 23 (9):1126-1136 (2005).
Hudson et al, "High avidity scFv multimers; diabodies and triabodies", Journal of Immunological Methods 231:177-189 (1999).
Kontermann et al, "Complement recruitment using bispecific diabodies", Nature Biotechnology 15:629-631 (1997).
Kontermann et al, "Recombinant bispecific antibodies for cancer therapy", Acta Pharmacologica Sinica 26(1):1-9 (2005).
Kortt et al, "Dimeric and trimeric antibodies: high avidity scFvs for cancer targeting", Biomolecular Engineering 18:95-108 (2001).
Le et al, "*Escherichia coli* expression and refolding of E/K-coil-tagged EGF generates fully bioactive EGF for diverse applications", Protein Expression and Purification 64:108-117 (2009).
Litowski et al, "Designing Heterodimeric Two-stranded α-Helical Coiled-coils", The Journal of Biological Chemistry 277(40):37272-37279 (2002).
Lu et al, "Di-diabody: a novel tetravalent bispecific antibody molecule by design", Journal of Immunological Methods 279:219-232 (2003).
Lu et al, "The effect of variable domain orientation and arrangement on the antigen-binding activity of a recombinant human bispecific diabody", Biochemical and Biophysical Research Communications 318:507-513 (2004).
Lu et al, "A Fully Human Recombinant IgG-like Bispecific Antibody to Both the Epidermal Growth Factor Receptor and the Insulin-like Growth Factor Receptor for Enhanced Antitumor Activity", The Journal of Biological Chemistry 280 (20):19665-19672 (2005).
MacroGenics Press Release, "MacroGenics Enters Global Research Collaboration and License Agreement with Pfizer", Oct. 26, 2010 http://www.macrogenics.com/printer_press_releases-288.html.
Marvin et al, "Recombinant approaches to IgG-like bispecific antibodies", Acta Pharmacologica Sinica 26(6):649-658 (2005).
Mertens et al, "New Recombinant Bi- and Trispecific Antibody Derivatives", In: Novel Frontiers in The Production of Compounds for Biomedical Use, vol. 1; van Broekhoven, A. et al. (Eds.); Kluwer Academic Publishers, Dordrecht, The Netherlands; pp. 195-208 (2001).
Olafsen et al, "Covalent disulfide-linked anti-CEA diabody allows site-specific conjugation and radiolabeling for tumor targeting applications", Protein Engineering, Design & Selection 17(1):21-27 (2004).
Pack et al, "Miniantibodies: Use of Amphipathic Helices to Produce Functional, Flexibly Linked Dimeric Fv Fragments with High Avidity in *Escherichia coli*", Biochemistry 31(6):1579-1584 (1992).
Steplewski et al, "Biological activity of human-mouse IgG1, IgG2, IgG3, and IgG4 chimeric monoclonal antibodies with antitumor specificity", Proc. Natl. Acad. Sci. USA 85:4852-4856 (1988).
Stork et al, "A novel tri-functional antibody fusion protein with improved pharmacokinetic properties generated by fusing a bispecific single-chain diabody with an albumin-binding domain from *Streptococcal* protein G", Protein Engineering, Design & Selection 20(11):569-576 (2007).

(56) References Cited

OTHER PUBLICATIONS

Straussman et al, "Kinking the Coiled Coil—Negatively Charged Residues at the Coiled-coil Interface", J. Mol. Biol. 366:1232-1242 (2007).
Takemura et al, "Construction of a diabody (small recombinant bispecific antibody) using a refolding system", Protein Engineering 13(8):583-588 (2000).
Todorovska et al, "Design and application of diabodies, triabodies and tetrabodies for cancer targeting", Journal of Immunological Methods 248:47-66 (2001).
Woolfson, "The Design of Coiled-Coil Structures and Assemblies", Advances in Protein Chemistry 70:79-112 (2005).
Wu et al, "Multimerization of a chimeric anti-CD20 single-chain Fv-Fc fusion protein is mediated through variable domain exchange", Protein Engineering 14(12):1025-1033 (2001).
Xiong et al, "Efficient inhibition of human B-cell lymphoma xenografts with an anti-CD20 x anti-CD3 bispecific diabody", Cancer Letters 177:29-39 (2002).
Zhu et al, "Remodeling domain interfaces to enhance heterodimer formation", Protein Science 6:781-788 (1997).

\* cited by examiner

P-Cadherin/CD3 LP-DART

P-Cadherin/CD3 LP-DART

FIG. 4
EK-DART
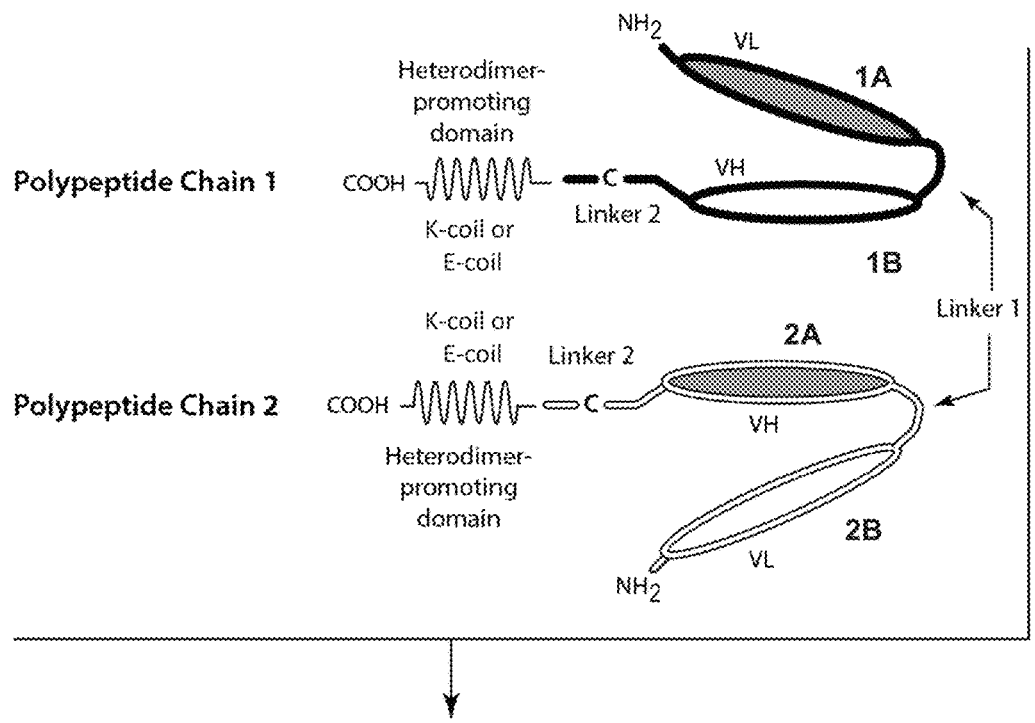
Assembled Bispecific Heterodimeric Diabody
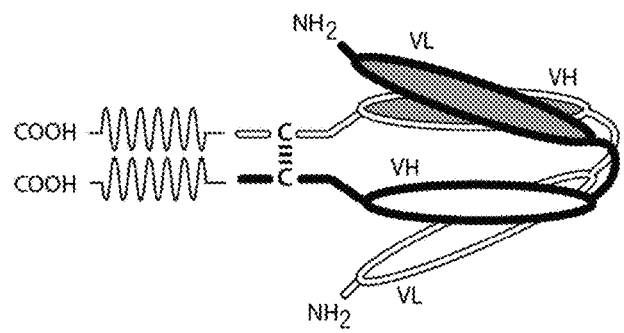

FIG. 5
LP-DART
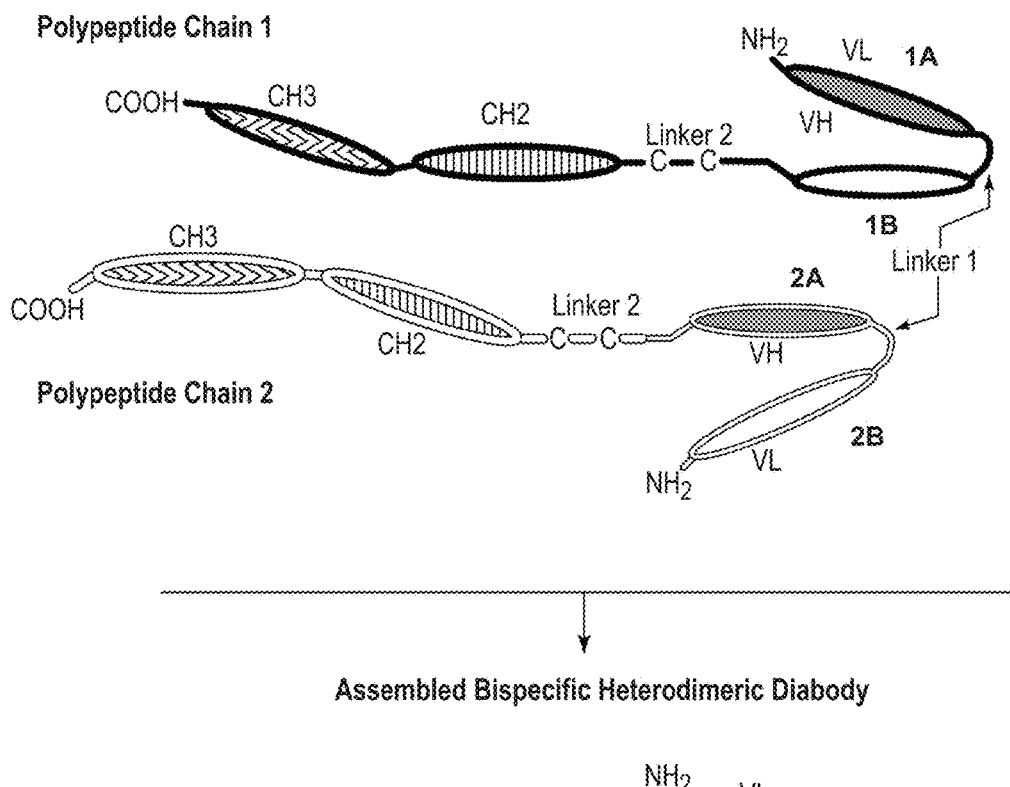
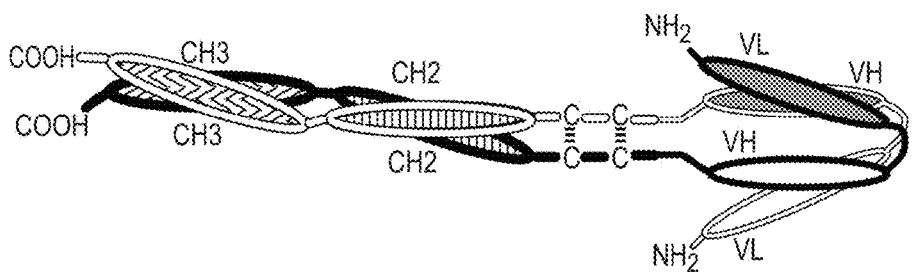
Assembled Bispecific Heterodimeric Diabody N-terminal MP3 DART

FIG. 7
C-terminal MP3 DART
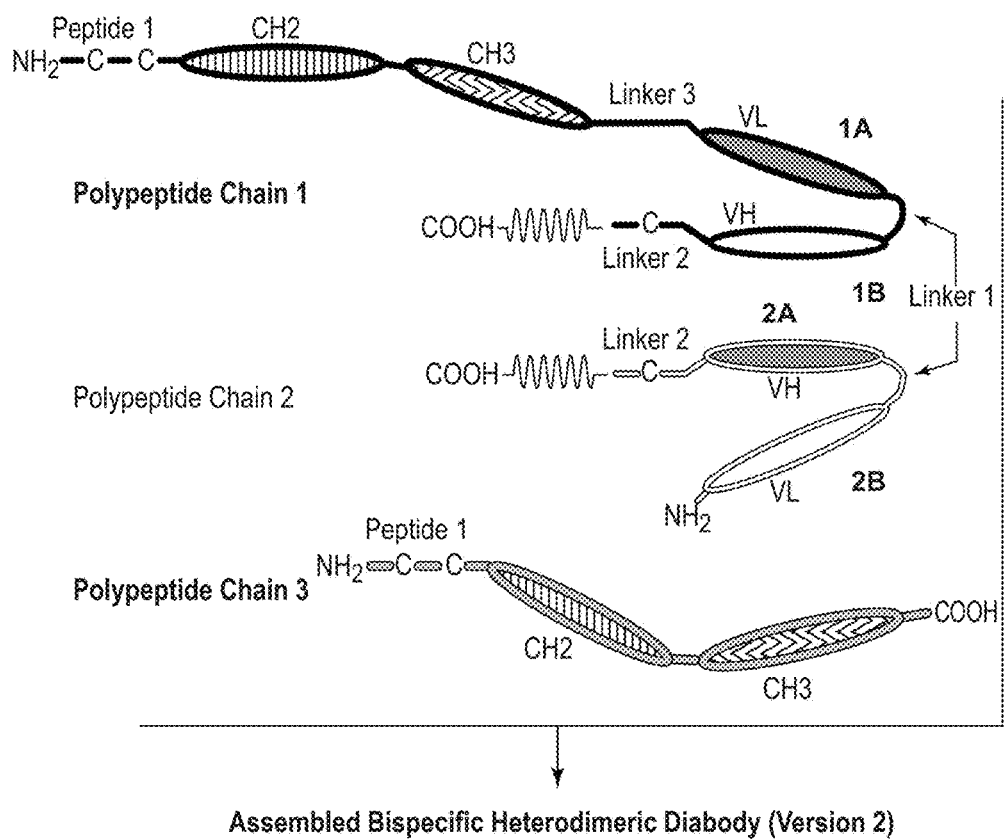
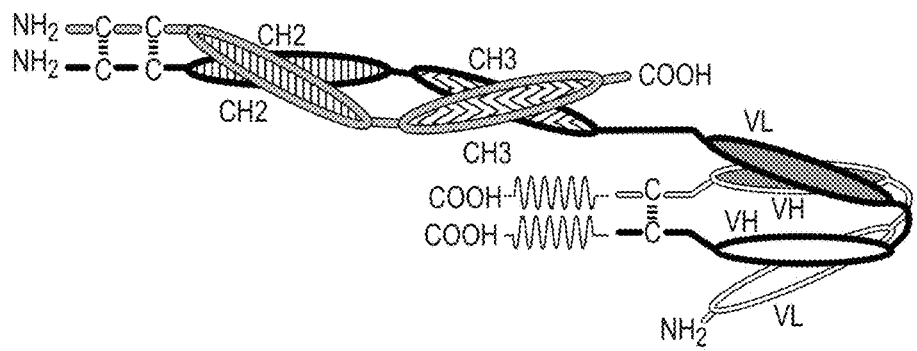

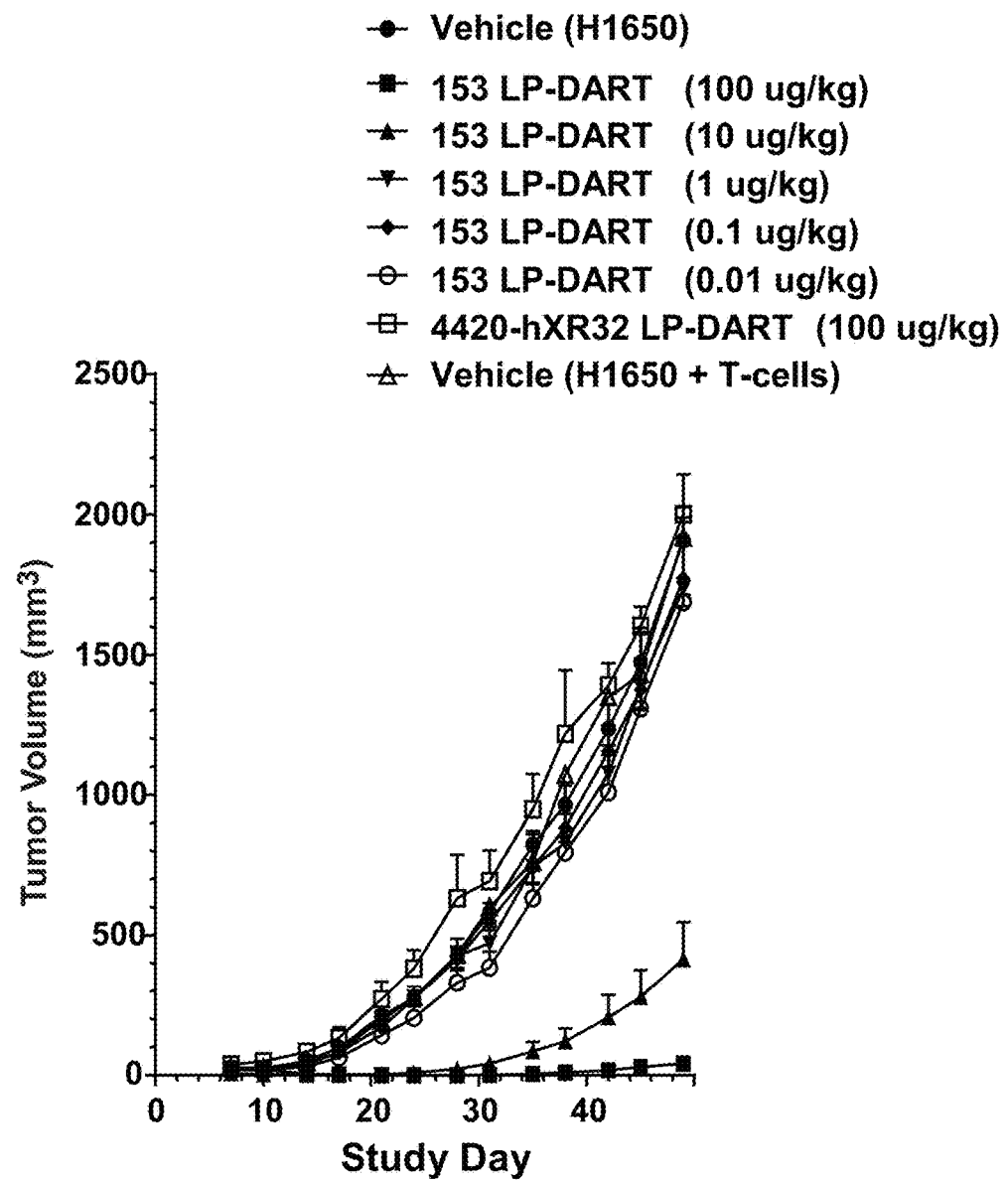

HCT-116 (colon)

SUM-149 (breast)

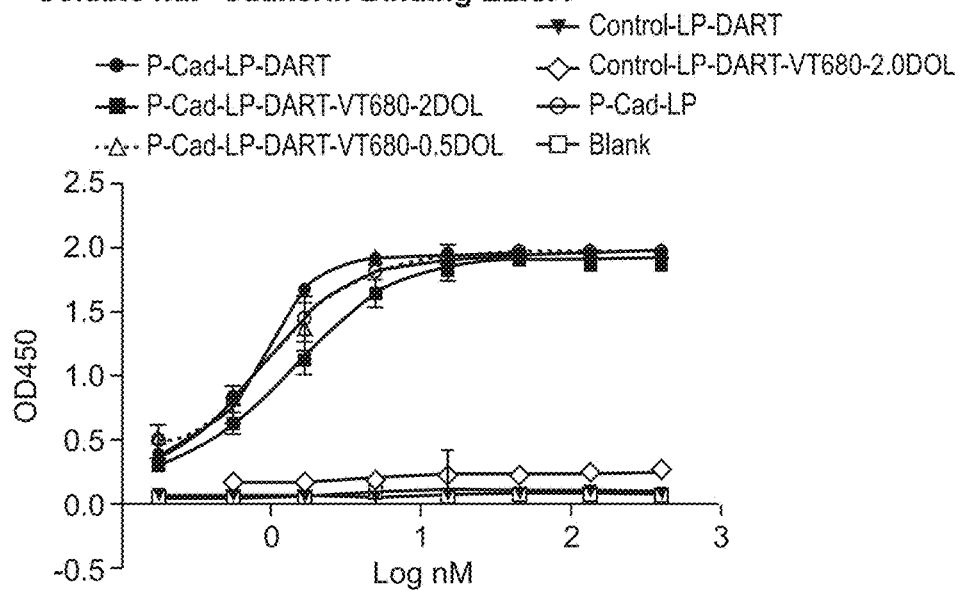
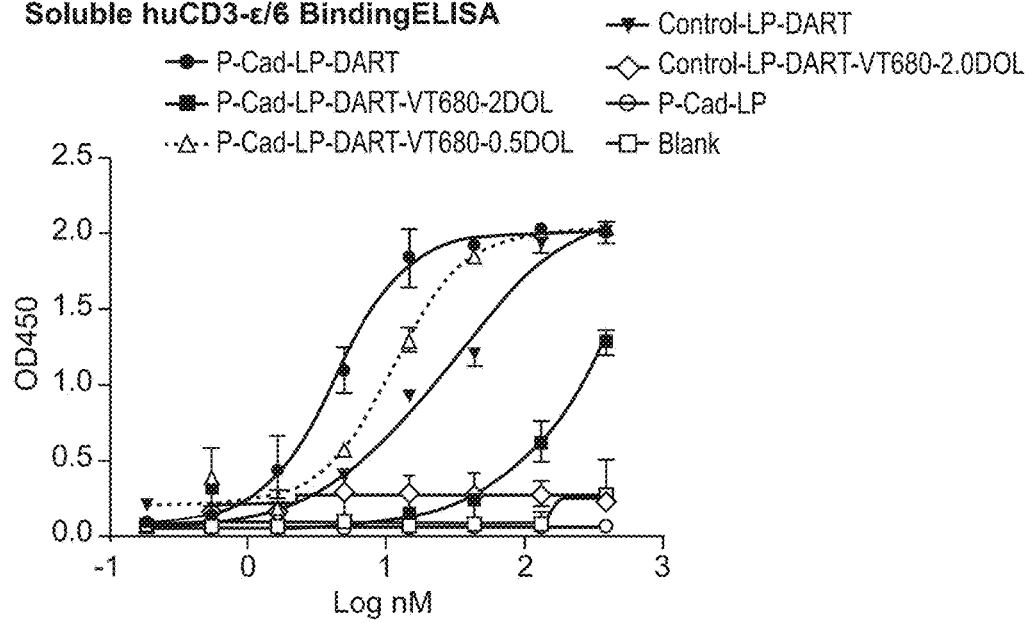

Biodistribution: *In vivo* Tumor Kinetics

Biodistribution: Whole Body Clearance

Ex-Vivo: Tumor Fluorescence

Ex-Vivo: Liver Fluorescence

Plasma Concentration Profiles in FMT Study

*Ex Vivo* Analysis of Tumor by ELISA (FMT Study)

*Ex Vivo* Analysis of Liver by ELISA (FMT Study)

Cell Test (20pM - P-Cad-LP-DART)

35 DART designed for crystallography

Crystal structure of a 35 DART

Crystal structure of a 35 DART

Voids in the heterodimer interface

FIG. 29

Modeling Five Best Disulfide Positions

VH2A

VL1A

VL2B

VH1B

Gln121(VH1B)-Gly168(VL1A)
Val129(VH1B)-Gly244(VL1A)
Val123(VH1B)-Gly168(VL1A)
Gly126(VH1B)-Ser243(VL1A)
Ala127(VH1B)-Ser232(VL1A)

Computational Disulfide Scan

| VF-DART | Chain | Variable Region | Linker 1 | Variable Region | Linker 2 |
|---|---|---|---|---|---|
| 33 | First | P-CAD 33VL SEQ ID NO:1 | Linker 1 SEQ ID NO:68 | CD3 VH SEQ ID NO:45 or 46 | Linker 2 SEQ ID NO:71 |
| 33 | Second | CD3-1-2VL SEQ ID NO:47 | Linker 1 SEQ ID NO:69 | P-CAD 33VH SEQ ID NO:2 | Linker 2 SEQ ID NO:70 |
| 34 | First | P-CAD 34VL SEQ ID NO:3 | Linker 1 SEQ ID NO:68 | CD3 VH SEQ ID NO:45 or 46 | Linker 2 SEQ ID NO:71 |
| 34 | Second | CD3-1-2VL SEQ ID NO:47 | Linker 1 SEQ ID NO:69 | P-CAD 34VH SEQ ID NO:4 | Linker 2 SEQ ID NO:70 |
| 35 | First | P-CAD 35VL SEQ ID NO:5 | Linker 1 SEQ ID NO:68 | CD3 VH SEQ ID NO:45 or 46 | Linker 2 SEQ ID NO:71 |
| 35 | Second | CD3-1-2VL SEQ ID NO:47 | Linker 1 SEQ ID NO:69 | P-CAD 35VH SEQ ID NO:6 | Linker 2 SEQ ID NO:70 |
| 153 | First | P-CAD 153VL SEQ ID NO:7 | Linker 1 SEQ ID NO:68 | CD3 VH SEQ ID NO:45 or 46 | Linker 2 SEQ ID NO:71 |
| 153 | Second | CD3-1-2VL SEQ ID NO:47 | Linker 1 SEQ ID NO:69 | P-CAD 153VH SEQ ID NO:8 | Linker 2 SEQ ID NO:70 |
| 154 | First | P-CAD 154VL SEQ ID NO:9 | Linker 1 SEQ ID NO:68 | CD3 VH SEQ ID NO:45 or 46 | Linker 2 SEQ ID NO:71 |
| 154 | Second | CD3-1-2VL SEQ ID NO:47 | Linker 1 SEQ ID NO:69 | P-CAD 154VH SEQ ID NO:10 | Linker 2 SEQ ID NO:70 |
| 163 | First | P-CAD 163VL SEQ ID NO:11 | Linker 1 SEQ ID NO:68 | CD3 VH SEQ ID NO:45 or 46 | Linker 2 SEQ ID NO:71 |
| 163 | Second | CD3-1-2VL SEQ ID NO:47 | Linker 1 SEQ ID NO:69 | P-CAD 163VH SEQ ID NO:12 | Linker 2 SEQ ID NO:70 |

| VF-DART | Chain | Variable Region | Linker 1 | Variable Region | Linker 2 |
|---|---|---|---|---|---|
| 165 | First | P-CAD 165VL<br>SEQ ID NO:13 | Linker 1<br>SEQ ID NO:68 | CD3 VH<br>SEQ ID NO:45 or 46 | Linker 2<br>SEQ ID NO:71 |
| | Second | CD3-1-2VL<br>SEQ ID NO:47 | Linker 1<br>SEQ ID NO:69 | P-CAD 165VH<br>SEQ ID NO:14 | Linker 2<br>SEQ ID NO:70 |
| 177 | First | P-CAD 177VL<br>SEQ ID NO:15 | Linker 1<br>SEQ ID NO:68 | CD3 VH<br>SEQ ID NO:45 or 46 | Linker 2<br>SEQ ID NO:71 |
| | Second | CD3-1-2VL<br>SEQ ID NO:47 | Linker 1<br>SEQ ID NO:69 | P-CAD 177VH<br>SEQ ID NO:16 | Linker 2<br>SEQ ID NO:70 |
| 178 | First | P-CAD 178VL<br>SEQ ID NO:17 | Linker 1<br>SEQ ID NO:68 | CD3 VH<br>SEQ ID NO:45 or 46 | Linker 2<br>SEQ ID NO:71 |
| | Second | CD3-1-2VL<br>SEQ ID NO:47 | Linker 1<br>SEQ ID NO:69 | P-CAD 178VH<br>SEQ ID NO:18 | Linker 2<br>SEQ ID NO:70 |
| 179 | First | P-CAD 179VL<br>SEQ ID NO:19 | Linker 1<br>SEQ ID NO:68 | CD3 VH<br>SEQ ID NO:45 or 46 | Linker 2<br>SEQ ID NO:71 |
| | Second | CD3-1-2VL<br>SEQ ID NO:47 | Linker 1<br>SEQ ID NO:69 | P-CAD 179VH<br>SEQ ID NO:20 | Linker 2<br>SEQ ID NO:70 |
| 180 | First | P-CAD 180VL<br>SEQ ID NO:21 | Linker 1<br>SEQ ID NO:68 | CD3 VH<br>SEQ ID NO:45 or 46 | Linker 2<br>SEQ ID NO:71 |
| | Second | CD3-1-2VL<br>SEQ ID NO:47 | Linker 1<br>SEQ ID NO:69 | P-CAD 180VH<br>SEQ ID NO:22 | Linker 2<br>SEQ ID NO:70 |
| 281 | First | P-CAD 281VL<br>SEQ ID NO:23 | Linker 1<br>SEQ ID NO:68 | CD3 VH<br>SEQ ID NO:45 or 46 | Linker 2<br>SEQ ID NO:71 |
| | Second | CD3-1-2VL<br>SEQ ID NO:47 | Linker 1<br>SEQ ID NO:69 | P-CAD 281VH<br>SEQ ID NO:24 | Linker 2<br>SEQ ID NO:70 |

FIG. 31A

| EK-DART | Chain | Variable Region | Linker 1 | Variable Region | Linker 2 | Coil |
|---|---|---|---|---|---|---|
| 33 | First | P-CAD33VL SEQ ID NO:1 | Linker 1 SEQ ID NO:68 | CD3 VH SEQ ID NO:45 or 46 | Linker 2 SEQ ID NO:72 | K-coil SEQ ID NO:62 |
| | Second | CD3-1-2VL SEQ ID NO:47 | Linker 1 SEQ ID NO:69 | P-CAD33VH SEQ ID NO:2 | Linker 2 SEQ ID NO:72 | E-coil SEQ ID NO:61 |
| 34 | First | P-CAD34VL SEQ ID NO:3 | Linker 1 SEQ ID NO:68 | CD3 VH SEQ ID NO:45 or 46 | Linker 2 SEQ ID NO:72 | K-coil SEQ ID NO:62 |
| | Second | CD3-1-2VL SEQ ID NO:47 | Linker 1 SEQ ID NO:69 | P-CAD34VH SEQ ID NO:4 | Linker 2 SEQ ID NO:72 | E-coil SEQ ID NO:61 |
| 35 | First | P-CAD 35VL SEQ ID NO:5 | Linker 1 SEQ ID NO:68 | CD3 VH SEQ ID NO:45 or 46 | Linker 2 SEQ ID NO:72 | K-coil SEQ ID NO:62 |
| | Second | CD3-1-2VL SEQ ID NO:47 | Linker 1 SEQ ID NO:69 | P-CAD 35VH SEQ ID NO:6 | Linker 2 SEQ ID NO:72 | E-coil SEQ ID NO:61 |
| 153 | First | P-CAD 153VL SEQ ID NO:7 | Linker 1 SEQ ID NO:68 | CD3 VH SEQ ID NO:45 or 46 | Linker 2 SEQ ID NO:72 | K-coil SEQ ID NO:62 |
| | Second | CD3-1-2VL SEQ ID NO:47 | Linker 1 SEQ ID NO:69 | P-CAD153VH SEQ ID NO:8 | Linker 2 SEQ ID NO:72 | E-coil SEQ ID NO:61 |
| 154 | First | P-CAD 154VL SEQ ID NO:9 | Linker 1 SEQ ID NO:68 | CD3 VH SEQ ID NO:45 or 46 | Linker 2 SEQ ID NO:72 | K-coil SEQ ID NO:62 |
| | Second | CD3-1-2VL SEQ ID NO:47 | Linker 1 SEQ ID NO:69 | P-CAD154VH SEQ ID NO:10 | Linker 2 SEQ ID NO:72 | E-coil SEQ ID NO:61 |
| 163 | First | P-CAD 163VL SEQ ID NO:11 | Linker 1 SEQ ID NO:68 | CD3 VH SEQ ID NO:45 or 46 | Linker 2 SEQ ID NO:72 | K-coil SEQ ID NO:62 |
| | Second | CD3-1-2VL SEQ ID NO:47 | Linker 1 SEQ ID NO:69 | P-CAD 163VH SEQ ID NO:12 | Linker 2 SEQ ID NO:72 | E-coil SEQ ID NO:61 |

FIG. 31B

| EK-DART | Chain | Variable Region | Linker 1 | Variable Region | Linker 2 | Coil |
|---|---|---|---|---|---|---|
| 165 | First | P-CAD 165VL SEQ ID NO:13 | Linker 1 SEQ ID NO:68 | CD3 VH SEQ ID NO:45 or 46 | Linker 2 SEQ ID NO:72 | K-coil SEQ ID NO:62 |
| | Second | CD3-1-2VL SEQ ID NO:47 | Linker 1 SEQ ID NO:69 | P-CAD 165VH SEQ ID NO:14 | Linker 2 SEQ ID NO:72 | E-coil SEQ ID NO:61 |
| 177 | First | P-CAD 177VL SEQ ID NO:15 | Linker 1 SEQ ID NO:68 | CD3 VH SEQ ID NO:45 or 46 | Linker 2 SEQ ID NO:72 | K-coil SEQ ID NO:62 |
| | Second | CD3-1-2VL SEQ ID NO:47 | Linker 1 SEQ ID NO:69 | P-CAD 177VH SEQ ID NO:16 | Linker 2 SEQ ID NO:72 | E-coil SEQ ID NO:61 |
| 178 | First | P-CAD 178VL SEQ ID NO:17 | Linker 1 SEQ ID NO:68 | CD3 VH SEQ ID NO:45 or 46 | Linker 2 SEQ ID NO:72 | K-coil SEQ ID NO:62 |
| | Second | CD3-1-2VL SEQ ID NO:47 | Linker 1 SEQ ID NO:69 | P-CAD 178VH SEQ ID NO:18 | Linker 2 SEQ ID NO:72 | E-coil SEQ ID NO:61 |
| 179 | First | P-CAD 179VL SEQ ID NO:19 | Linker 1 SEQ ID NO:68 | CD3 VH SEQ ID NO:45 or 46 | Linker 2 SEQ ID NO:72 | K-coil SEQ ID NO:62 |
| | Second | CD3-1-2VL SEQ ID NO:47 | Linker 1 SEQ ID NO:69 | P-CAD 179VH SEQ ID NO:20 | Linker 2 SEQ ID NO:72 | E-coil SEQ ID NO:61 |
| 180 | First | P-CAD 180VL SEQ ID NO:21 | Linker 1 SEQ ID NO:68 | CD3 VH SEQ ID NO:45 or 46 | Linker 2 SEQ ID NO:72 | K-coil SEQ ID NO:62 |
| | Second | CD3-1-2VL SEQ ID NO:47 | Linker 1 SEQ ID NO:69 | P-CAD 180VH SEQ ID NO:22 | Linker 2 SEQ ID NO:72 | E-coil SEQ ID NO:61 |
| 281 | First | P-CAD 281VL SEQ ID NO:23 | Linker 1 SEQ ID NO:68 | CD3 VH SEQ ID NO:45 or 46 | Linker 2 SEQ ID NO:72 | K-coil SEQ ID NO:62 |
| | Second | CD3-1-2VL SEQ ID NO:47 | Linker 1 SEQ ID NO:69 | P-CAD 281VH SEQ ID NO:24 | Linker 2 SEQ ID NO:72 | E-coil SEQ ID NO:61 |

FIG. 32A

| LP-DART | Chain | Variable Region | Linker 1 | Variable Region | Linker 2 | Knob or Hole |
|---|---|---|---|---|---|---|
| 33 | First | P-CAD 33VL SEQ ID NO:1 | Linker 1 SEQ ID NO:68 | CD3 VH SEQ ID NO:45 or 46 | Linker 2 SEQ ID NO:73-76 | Knob SEQ ID NO:63 |
|  | Second | CD3-1-2VL SEQ ID NO:47 | Linker 1 SEQ ID NO:69 | P-CAD 33VH SEQ ID NO:2 | Linker 2 SEQ ID NO:73-76 | Hole SEQ ID NO:64 |
| 34 | First | P-CAD 34VL SEQ ID NO:3 | Linker 1 SEQ ID NO:68 | CD3 VH SEQ ID NO:45 or 46 | Linker 2 SEQ ID NO:73-76 | Knob SEQ ID NO:63 |
|  | Second | CD3-1-2VL SEQ ID NO:47 | Linker 1 SEQ ID NO:69 | P-CAD 34VH SEQ ID NO:4 | Linker 2 SEQ ID NO:73-76 | Hole SEQ ID NO:64 |
| 35 | First | P-CAD 35VL SEQ ID NO:5 | Linker 1 SEQ ID NO:68 | CD3 VH SEQ ID NO:45 or 46 | Linker 2 SEQ ID NO:73-76 | Knob SEQ ID NO:63 |
|  | Second | CD3-1-2VL SEQ ID NO:47 | Linker 1 SEQ ID NO:69 | P-CAD 35VH SEQ ID NO:6 | Linker 2 SEQ ID NO:73-76 | Hole SEQ ID NO:64 |
| 153 | First | P-CAD 153VL SEQ ID NO:7 | Linker 1 SEQ ID NO:68 | CD3 VH SEQ ID NO:45 or 46 | Linker 2 SEQ ID NO:73-76 | Knob SEQ ID NO:63 |
|  | Second | CD3-1-2VL SEQ ID NO:47 | Linker 1 SEQ ID NO:69 | P-CAD 153VH SEQ ID NO:8 | Linker 2 SEQ ID NO:73-76 | Hole SEQ ID NO:64 |
| 154 | First | P-CAD 154VL SEQ ID NO:9 | Linker 1 SEQ ID NO:68 | CD3 VH SEQ ID NO:45 or 46 | Linker 2 SEQ ID NO:73-76 | Knob SEQ ID NO:63 |
|  | Second | CD3-1-2VL SEQ ID NO:47 | Linker 1 SEQ ID NO:69 | P-CAD 154VH SEQ ID NO:10 | Linker 2 SEQ ID NO:73-76 | Hole SEQ ID NO:64 |
| 163 | First | P-CAD 163VL SEQ ID NO:11 | Linker 1 SEQ ID NO:68 | CD3 VH SEQ ID NO:45 or 46 | Linker 2 SEQ ID NO:73-76 | Knob SEQ ID NO:63 |
|  | Second | CD3-1-2VL SEQ ID NO:47 | Linker 1 SEQ ID NO:69 | P-CAD 163VH SEQ ID NO:12 | Linker 2 SEQ ID NO:73-76 | Hole SEQ ID NO:64 |

FIG. 32B

| LP-DART | Chain | Variable Region | Linker 1 | Variable Region | Linker 2 | Knob or Hole |
|---|---|---|---|---|---|---|
| 165 | First | P-CAD 165VL SEQ ID NO:13 | Linker 1 SEQ ID NO:68 | CD3 VH SEQ ID NO:45 or 46 | Linker 2 SEQ ID NO:73-76 | Knob SEQ ID NO:63 |
| | Second | CD3-1-2VL SEQ ID NO:47 | Linker 1 SEQ ID NO:69 | P-CAD 165VH SEQ ID NO:14 | Linker 2 SEQ ID NO:73-76 | Hole SEQ ID NO:64 |
| 177 | First | P-CAD 177VL SEQ ID NO:15 | Linker 1 SEQ ID NO:68 | CD3 VH SEQ ID NO:45 or 46 | Linker 2 SEQ ID NO:73-76 | Knob SEQ ID NO:63 |
| | Second | CD3-1-2VL SEQ ID NO:47 | Linker 1 SEQ ID NO:69 | P-CAD 177VH SEQ ID NO:16 | Linker 2 SEQ ID NO:73-76 | Hole SEQ ID NO:64 |
| 178 | First | P-CAD 178VL SEQ ID NO:17 | Linker 1 SEQ ID NO:68 | CD3 VH SEQ ID NO:45 or 46 | Linker 2 SEQ ID NO:73-76 | Knob SEQ ID NO:63 |
| | Second | CD3-1-2VL SEQ ID NO:47 | Linker 1 SEQ ID NO:69 | P-CAD 178VH SEQ ID NO:18 | Linker 2 SEQ ID NO:73-76 | Hole SEQ ID NO:64 |
| 179 | First | P-CAD 179VL SEQ ID NO:19 | Linker 1 SEQ ID NO:68 | CD3 VH SEQ ID NO:45 or 46 | Linker 2 SEQ ID NO:73-76 | Knob SEQ ID NO:63 |
| | Second | CD3-1-2VL SEQ ID NO:47 | Linker 1 SEQ ID NO:69 | P-CAD 179VH SEQ ID NO:20 | Linker 2 SEQ ID NO:73-76 | Hole SEQ ID NO:64 |
| 180 | First | P-CAD 180VL SEQ ID NO:21 | Linker 1 SEQ ID NO:68 | CD3 VH SEQ ID NO:45 or 46 | Linker 2 SEQ ID NO:73-76 | Knob SEQ ID NO:63 |
| | Second | CD3-1-2VL SEQ ID NO:47 | Linker 1 SEQ ID NO:69 | P-CAD 180VH SEQ ID NO:22 | Linker 2 SEQ ID NO:73-76 | Hole SEQ ID NO:64 |
| 281 | First | P-CAD 281VL SEQ ID NO:23 | Linker 1 SEQ ID NO:68 | CD3 VH SEQ ID NO:45 or 46 | Linker 2 SEQ ID NO:73-76 | Knob SEQ ID NO:63 |
| | Second | CD3-1-2VL SEQ ID NO:47 | Linker 1 SEQ ID NO:69 | P-CAD 281VH SEQ ID NO:24 | Linker 2 SEQ ID NO:73-76 | Hole SEQ ID NO:64 |

FIG. 33A

| DART | Chain | Variable Region | Linker 1 | Variable Region |
|---|---|---|---|---|
| 33 | First | P-CAD 33VL<br>SEQ ID NO:1 | Linker 1<br>SEQ ID NO:68 | CD3 VH<br>SEQ ID NO:45 or 46 |
| 33 | Second | CD3-1-2VL<br>SEQ ID NO:47 | Linker 1<br>SEQ ID NO:69 | P-CAD 33VH<br>SEQ ID NO:2 |
| 34 | First | P-CAD 34VL<br>SEQ ID NO:3 | Linker 1<br>SEQ ID NO:68 | CD3 VH<br>SEQ ID NO:45 or 46 |
| 34 | Second | CD3-1-2VL<br>SEQ ID NO:47 | Linker 1<br>SEQ ID NO:69 | P-CAD 34VH<br>SEQ ID NO:4 |
| 35 | First | P-CAD 35VL<br>SEQ ID NO:5 | Linker 1<br>SEQ ID NO:68 | CD3 VH<br>SEQ ID NO:45 or 46 |
| 35 | Second | CD3-1-2VL<br>SEQ ID NO:47 | Linker 1<br>SEQ ID NO:69 | P-CAD 35VH<br>SEQ ID NO:6 |
| 153 | First | P-CAD 153VL<br>SEQ ID NO:7 | Linker 1<br>SEQ ID NO:68 | CD3 VH<br>SEQ ID NO:45 or 46 |
| 153 | Second | CD3-1-2VL<br>SEQ ID NO:47 | Linker 1<br>SEQ ID NO:69 | P-CAD 153VH<br>SEQ ID NO:8 |
| 154 | First | P-CAD 154VL<br>SEQ ID NO:9 | Linker 1<br>SEQ ID NO:68 | CD3 VH<br>SEQ ID NO:45 or 46 |
| 154 | Second | CD3-1-2VL<br>SEQ ID NO:47 | Linker 1<br>SEQ ID NO:69 | P-CAD 154VH<br>SEQ ID NO:10 |
| 163 | First | P-CAD 163VL<br>SEQ ID NO:11 | Linker 1<br>SEQ ID NO:68 | CD3 VH<br>SEQ ID NO:45 or 46 |
| 163 | Second | CD3-1-2VL<br>SEQ ID NO:47 | Linker 1<br>SEQ ID NO:69 | P-CAD 163VH<br>SEQ ID NO:12 |

| DART | Chain | Variable Region | Linker 1 | Variable Region |
|---|---|---|---|---|
| 165 | First | P-CAD 165VL<br>SEQ ID NO:13 | Linker 1<br>SEQ ID NO:68 | CD3 VH<br>SEQ ID NO:45 or 46 |
| | Second | CD3-1-2VL<br>SEQ ID NO:47 | Linker 1<br>SEQ ID NO:69 | P-CAD 165VH<br>SEQ ID NO:14 |
| 177 | First | P-CAD 177VL<br>SEQ ID NO:15 | Linker 1<br>SEQ ID NO:68 | CD3 VH<br>SEQ ID NO:45 or 46 |
| | Second | CD3-1-2VL<br>SEQ ID NO:47 | Linker 1<br>SEQ ID NO:69 | P-CAD 177VH<br>SEQ ID NO:16 |
| 178 | First | P-CAD 178VL<br>SEQ ID NO:17 | Linker 1<br>SEQ ID NO:68 | CD3 VH<br>SEQ ID NO:45 or 46 |
| | Second | CD3-1-2VL<br>SEQ ID NO:47 | Linker 1<br>SEQ ID NO:69 | P-CAD 178VH<br>SEQ ID NO:18 |
| 179 | First | P-CAD 179VL<br>SEQ ID NO:19 | Linker 1<br>SEQ ID NO:68 | CD3 VH<br>SEQ ID NO:45 or 46 |
| | Second | CD3-1-2VL<br>SEQ ID NO:47 | Linker 1<br>SEQ ID NO:69 | P-CAD 179VH<br>SEQ ID NO:20 |
| 180 | First | P-CAD 180VL<br>SEQ ID NO:21 | Linker 1<br>SEQ ID NO:68 | CD3 VH<br>SEQ ID NO:45 or 46 |
| | Second | CD3-1-2VL<br>SEQ ID NO:47 | Linker 1<br>SEQ ID NO:69 | P-CAD 180VH<br>SEQ ID NO:22 |
| 281 | First | P-CAD 281VL<br>SEQ ID NO:23 | Linker 1<br>SEQ ID NO:68 | CD3 VH<br>SEQ ID NO:45 or 46 |
| | Second | CD3-1-2VL<br>SEQ ID NO:47 | Linker 1<br>SEQ ID NO:69 | P-CAD 281VH<br>SEQ ID NO:24 |

UniProt|P22223|CADH3_HUMAN Cadherin-3

| | |
|---|---|
| MGLPRGPLASLLLLQVCWLQCAAS EPCRAVFREAEVTLEAGGAEQEPGQALGKVFMGCPG | 60 |

Signal Peptide, 1-24  Propeptide, 25-107

| | |
|---|---|
| QEPALFSTDNDDFTVRNGETVQERRSLKERNPLKIFPSKRILRRHKR DWVVAPISVPENG | 120 |

ECD1, 108-215

| | |
|---|---|
| KGPFPQRLNQLKSNKDRDTKIFYSITGPGADSPPEGVFAVEKETGWLLLNKPLDREEIAK | 180 |
| YELFGHAVSENGASVEDPMNISIIVTDQNDHKPKF TQDTFRGSVLEGVLPGTSVMQVTAT | 240 |

ECD2, 216-328

| | |
|---|---|
| DEDDAIYTYNGVVAYSIHSQEPKDPHDLMFTIHRSTGTISVISSGLDREKVPEYTLTIQA | 300 |
| TDMDGDSTTTAVAVVEILDANDNAPMF DPQKYEAHVPENAVGHEVQRLTVTDLDAPNSP | 360 |

ECD3, 329-440

| | |
|---|---|
| AWRATYLIMGGDDGDHFTITTHPESNQGILTTRKGLDFEAKNQHTLYVEVTNEAPFVLKL | 420 |
| PTSTATIVVHVEDVNEAPVF VPPSKVVEVQEGIPTGEPVCVYTAEDPDKENQKISYRILR | 480 |

ECD4, 441-546

| | |
|---|---|
| DPAGWLAMDPDSGQVTAVGTLDREDEQFVRNNIYEVMVLAMDNGSPPTTGTGTLLLTLID | 540 |
| VNDHGP VPEPRQITICNQSPVRQVLNITDKDLSPHTSPFQAQLTDDSDIYWTAEVNEEGD | 600 |

ECD5, 547-650

| | |
|---|---|
| TVVLSLKKFLKQDTYDVHLSLSDHGNKEQLTVIRATVCDCHGHVETCPGP WKGGFILPVL | 660 |

Transmembrane

| | |
|---|---|
| GAVLALLFLLLVLLLLVRKKRKIKEPLLLPEDDTRDNVFYYGEEGGGEEDQDYDITQLHR | 720 | and Cytoplasmic Domains, 651-829

| | |
|---|---|
| GLEARPEVVLRNDVAPTIIPTPMYRPRPANPDEIGNFIIENLKAANTDPTAPPYDTLLVF | 780 |
| DYEGSGSDAASLSSLTSSASDQDQDYDYLNEWGSRFKKLADMYGGGEDD | 829 |

(SEQ ID NO: 159)

BISPECIFIC HETERODIMERIC DIABODIES AND USES THEREOF

RELATED APPLICATIONS

This application claims the benefits of U.S. Provisional Application No. 62/019,762, filed Jul. 1, 2014, and U.S. Provisional Application No. 62/148,920, filed Apr. 17, 2015, which are hereby incorporated by referenced in their entireties.

SEQUENCE LISTING

This application is being filed electronically via EFS-Web and includes an electronically submitted sequence listing in .txt format. The .txt file contains a sequence listing entitled "PC72054A_Sequence_Listing.txt" created on Jun. 12, 2015, and having a size of 248 KB. The sequence listing contained in this .txt file is part of the specification and is incorporated herein by reference in its entirety.

FIELD OF THE INVENTION

The present invention relates to bispecific heterodimeric diabodies and uses thereof in the treatment of cancer.

BACKGROUND OF THE INVENTION

Various strategies have been developed to generate bispecific molecules capable of T cell recruitment to mediate tumor cell killing. However, most efforts to produce such molecules have been limited because of inefficient production and poor stability properties. To address these problems, an Fv-derived strategy based on a covalently linked, bispecific heterodimeric diabody structure, also known as dual-affinity re-targeting (DART®) proteins, has been developed (US Patent Application Publications Nos. 2007/0004909, 2009/0060910, and 2010/0174053).

There remains a need for bispecific heterodimeric diabodies that overcome the challenges associated with the generation of bispecific antibodies and provide highly specific and potent agents that bind to tumor cells expressing a target antigen and recruit and activate T cells through CD3 activation, resulting in an innovative and effective treatment for cancer.

SUMMARY OF THE INVENTION

The present invention provides for bispecific heterodimeric diabodies, wherein the bispecific heterodimeric diabody is capable of specific binding to an epitope of P-cadherin and to an epitope of CD3.

The present invention provides for bispecific heterodimeric diabodies, wherein the bispecific heterodimeric diabody is capable of specific binding to an epitope of P-cadherin and to an epitope of CD3, wherein the bispecific heterodimeric diabody comprises a first polypeptide chain and a second polypeptide chain, wherein: a. the first polypeptide comprises, in the N-terminal to C-terminal direction: i. a Domain 1, comprising a sub-Domain 1A and a sub-Domain 1B, and ii. a first heterodimer-promoting domain; and b. the second polypeptide chain comprises, in the N-terminal to C-terminal direction: i. a Domain 2, comprising a sub-Domain 2A and a sub-Domain 2B, and ii. a second heterodimer-promoting domain, and wherein sub-Domain 1A and sub-Domain 2A form a P-cadherin VL/VH binding domain comprising a variable heavy (VH) domain of an anti-P-cadherin antibody (P-CAD VH) and a variable light (VL) domain of an anti-P-cadherin antibody (P-CAD VL), and sub-Domain 1B and sub-Domain 2B form a CD3 VL/VH binding domain comprising a VL domain of an anti-CD3 antibody (CD3 VL) and a VH binding domain of an anti-CD3 antibody (CD3 VH); or wherein sub-Domain 1A and sub-Domain 2A form a CD3 VL/VH binding domain comprising a CD3 VL and a CD3 VH, and sub-Domain 1B and sub-Domain 2B form a P-cadherin VL/VH binding domain comprising a P-CAD VH and a P-CAD VL.

In another aspect of the invention, the sub-Domain 1A comprises a P-CAD VL or CD3 VL, and the sub-Domain 1B comprises a P-CAD VH, if the sub-Domain 1A comprises CD3 VL, or a CD3 VH, if the sub-Domain 1A comprises P-CAD VL; and wherein the sub-Domain 2B comprises a P-CAD VL or a CD3 VL depending on the VL domain selected for sub-Domain 1A, and the sub-Domain 2A comprises P-CAD VH, if the sub-Domain 2B comprises CD3 VL, or a CD3 VH, if the sub-Domain 2B comprises P-CAD VL.

In a particular aspect of the invention, the sub-Domain 1A comprises a P-CAD VL and the sub-Domain 1B comprises a CD3 VH, and the sub-Domain 2B comprises a CD3 VL and the sub-Domain 2A comprises a P-CAD VH; and wherein the P-CAD VL of the sub-Domain 1A and the P-CAD VH of the sub-Domain 2A form a VL/VH binding domain capable of specifically binding to an epitope of P-cadherin, and the CD3 VH of the sub-Domain 1B and the CD3 VL of the sub-Domain 2B form a VL/VH binding domain capable of specifically binding to an epitope of CD3.

In a particular aspect, sub-Domain 1A comprises a CD3 VL and the sub-Domain 1B comprises a P-CAD VH, and the sub-Domain 2B comprises a P-CAD VL and the sub-Domain 2A a CD3 VH; and wherein the CD3 VL of the sub-Domain 1A and the CD3 VH of the sub-Domain 2A form a VL/VH binding domain capable of specifically binding to an epitope of CD3, and the P-CAD VH of the sub-Domain 1B and the P-CAD VL of the sub-Domain 2B form a VL/VH binding domain capable of specifically binding to an epitope of P-cadherin.

In another aspect, the sub-Domain 1A comprises a VH binding domain of either an anti-P-cadherin antibody (P-CAD VH) or an anti-CD3 antibody (CD3 VH), and the sub-Domain 1B comprises a VL binding domain of either an anti-P-cadherin antibody (P-CAD VL), if the sub-Domain 1A comprises CD3 VH, or an anti-CD3 antibody (CD3 VL), if the sub-Domain 1A comprises a P-CAD VH; and wherein the sub-Domain 2B comprises a P-CAD VH or a CD3 VH depending on the VH domain selected for sub-Domain 1A, and the sub-Domain 2A comprises P-CAD VL, if the sub-Domain 2B comprises a CD3 VH, or a CD3 VL, if the sub-Domain 2B comprises a P-CAD VH.

In a particular aspect, the sub-Domain 1A comprises a P-CAD VH and the sub-Domain 1B comprises a CD3 VL, and the sub-Domain 2B comprises a CD3 VH and the sub-Domain 2A comprises a P-CAD VL; and wherein the P-CAD VH of the sub-Domain 1A and the P-CAD VL of the sub-Domain 2A form a VL/VH binding domain capable of specifically binding to an epitope of P-cadherin, and the CD3 VL of the sub-Domain 1B and the CD3 VH of the sub-Domain 2B form a VL/VH binding domain capable of specifically binding to an epitope of CD3.

In a particular aspect, the sub-Domain 1A comprises a CD3 VH and the sub-Domain 1B comprises a P-CAD VL, and the sub-Domain 2B comprises a P-CAD VH and the sub-Domain 2A comprises a CD3 VL; and wherein the CD3 VH of the sub-Domain 1A and the CD3 VL of the sub- Domain 2A form a VL/VH binding domain capable of specifically binding to an epitope of CD3, and the P-CAD VL of the sub-Domain 1B and the P-CAD VH of the sub-Domain 2B form a VL/VH binding domain capable of specifically binding to an epitope of P-cadherin.

The present invention further provides for bispecific heterodimeric diabodies wherein the first heterodimer-promoting domain and the second heterodimer-promoting domain comprise an IgG Fc region comprising a CH2 and a CH3 domain, wherein the amino acid sequence of the CH2 domain and/or the CH3 domain comprises at least one amino acid modification, as compared to a wild-type IgG Fc region, to form a knob or a hole. In one aspect, the first heterodimer-promoting domain and the second heterodimer-promoting domain are not both knobs or both holes; and/or wherein the first heterodimer-promoting domain and the second heterodimer-promoting domain form an IgG immunoglobulin Fc region. In another aspect, the IgG Fc region forming the knob comprises a sequence of SEQ ID NO: 63, and the IgG Fc region forming the hole comprises a sequence of SEQ ID NO: 64.

The present invention further provides for bispecific heterodimeric diabodies, wherein the first heterodimer-promoting domain and the second heterodimer-promoting domain comprise an E-coil region comprising glutamic acid and a negatively charged alpha-helical coil or a K-coil region comprising lysine and a positively charged helical coil; and wherein the first heterodimer-promoting domain and the second heterodimer-promoting domain are not both E-coil regions or both K-coil regions. In one aspect, the E-coil region comprises a sequence of SEQ ID NO: 61, and/or the K-coil region comprises a sequence of SEQ ID NO: 62.

The present invention further provides for bispecific heterodimeric diabodies, wherein the sub-Domain 1A and the sub-Domain 1B may be linked by a glycine-serine linker (Linker 1) and do not associate to form a VL/VH epitope binding domain, and the sub-Domain 2B and the sub-Domain 2A may be linked by a glycine-serine linker (Linker 1) and do not associate to form a VL/VH epitope binding domain. In one aspect of the invention, the glycine-serine linker (Linker 1) comprises a sequence of SEQ ID NO: 68 or SEQ ID NO: 69.

The present invention further provides for bispecific heterodimeric diabodies, wherein the first heterodimer-promoting domain comprises a cysteine linker (Linker 2) on sub-Domain 1B and/or the second heterodimer-promoting domain comprises a cysteine linker (Linker 2) on sub-Domain 2A. In one aspect, the Linker 2 of the first heterodimer-promoting domain and/or the second heterodimer-promoting domain further comprises at least one glycine residue. In another aspect, the Linker 2 of the first heterodimer-promoting domain and/or the second heterodimer-promoting domain comprises a sequence of GFNRGEC (SEQ ID NO: 70), GVEPKSC (SEQ ID NO: 71), GGCGGG (SEQ ID NO: 72), GCPPCP (SEQ ID NO: 73), GGTGGCPPCP (SEQ ID NO: 74), GEPKSSDKTHTCPPCP (SEQ ID NO: 75) or GGTGGGEPKSSDKTHTCPPCP (SEQ ID NO: 76). In another aspect, the Linker 2 of the first heterodimer-promoting domain comprises the sequence of GCPPCP (SEQ ID NO: 73), GGTGGCPPCP (SEQ ID NO: 74), GEPKSSDKTHTCPPCP (SEQ ID NO: 75) or GGTGGGEPKSSDKTHTCPPCP (SEQ ID NO: 76), and the Linker 2 of the second heterodimer-promoting domain comprises the sequence of GCPPCP (SEQ ID NO: 73), GGTGGCPPCP (SEQ ID NO: 74), GEPKSSDKTHTCPPCP (SEQ ID NO: 75) or GGTGGGEPKSSDKTHTCPPCP (SEQ ID NO: 76). In another aspect, the Linker 2 of the first heterodimer-promoting domain comprises the sequence of GGCGGG (SEQ ID NO: 72), and the Linker 2 of the second heterodimer-promoting domain comprises the sequence of GGCGGG (SEQ ID NO: 72). In another aspect, the Linker 2 of the first heterodimer-promoting domain comprises the sequence of GFNRGEC (SEQ ID NO: 70) and the Linker 2 of the second heterodimer-promoting domain comprises the sequence of GVEPKSC (SEQ ID NO: 71), or the Linker 2 of the first heterodimer-promoting domain comprises the sequence of GVEPKSC (SEQ ID NO: 71) and the Linker 2 of the second heterodimer-promoting domain comprises the sequence of GFNRGEC (SEQ ID NO: 70).

The present invention provides for bispecific heterodimeric diabodies, wherein the bispecific heterodimeric diabodies specifically bind to extracellular domain 3 (ECD3) of human P-cadherin. The present invention further provides for bispecific heterodimeric diabodies, wherein the bispecific heterodimeric diabody specifically bind to an epitope on P-cadherin but does not bind to an epitope on E-cadherin or VE-cadherin. The present invention also provides for bispecific heterodimeric diabodies, wherein the bispecific heterodimeric diabodies specifically bind to an epitope on human P-cadherin but do not bind to an epitope on mouse P-cadherin.

The present invention provides for bispecific heterodimeric diabodies, wherein the bispecific heterodimeric diabodies demonstrate an extended serum and tumor half-life. Pharmacokinetic analysis may conducted by various assays, such as ELISA. The present invention further provides for bispecific heterodimeric diabodies, wherein the bispecific heterodimeric diabodies demonstrate a lower EC50 in the presence of increased P-cadherin expression levels or increased receptor density levels. The EC50 may be determined by various in vitro and in vivo cytotoxicity assays The present invention provides for bispecific heterodimeric diabodies, comprising a P-CAD VL CDR1, a P-CAD VL CDR2, and a P-CAD VL CDR3 of a P-CAD VL comprising a sequence of SEQ ID NOS: 1, 3, 5, 7, 9, 11, 13, 15, 17, 19, 21 or 23; a CD3 VH CDR1, a CD3 VH CDR2, and a CD3 VH CDR3 of a CD3 VH comprising a sequence of SEQ ID NOS: 45 or 46; a CD3 VL CDR1, a CD3 VL CDR2, and a CD3 VL CDR3 of a CD3 VL comprising a sequence of SEQ ID NO: 47; and/or a P-CAD VH CDR1, a P-CAD VH CDR2, and a P-CAD VH CDR3 of a P-CAD VH comprising a sequence of SEQ ID NOS: 2, 4, 6, 8, 10, 12, 14, 16, 18, 20, 22 or 24.

The present invention provides for bispecific heterodimeric diabodies, comprising the P-CAD VL CDR1 comprises a sequence of SEQ ID NOS: 35 or 36, the P-CAD VL CDR2 comprises a sequence of SEQ ID NOS: 37 or 38, and the P-CAD VL CDR3 comprises a sequence of SEQ ID NOS: 39, 40, 41, 42, 43 or 44; the CD3 VH CDR1 comprises a sequence of SEQ ID NO: 48, 52 or 53, the CD3 VH CDR2 comprises a sequence of SEQ ID NOS: 49, 50 or 54 and the CD3 VH CDR3 comprises a sequence of SEQ ID NO: 51; the CD3 VL CDR1 comprises a sequence of SEQ ID NO: 55, the CD3 VL CDR2 comprises a sequence of SEQ ID NO: 56, and the CD3 VL CDR3 comprises a sequence of SEQ ID NO: 57; and/or the P-CAD VH CDR1 comprises a sequence of SEQ ID NOS: 25 or 33, the P-CAD VH CDR2 comprises a sequence of SEQ ID NOS: 26 or 34, and a P-CAD VH CDR3 comprising a sequence of SEQ ID NOS: 27, 28, 29, 30, 31 or 32.

In one aspect of the present invention, the P-CAD VL CDR1 comprises the sequence of SEQ ID NO: 35, the P-CAD VL CDR2 comprises the sequence of SEQ ID NO: 37, the P-CAD VL CDR3 comprises the sequence of SEQ ID NO: 41, the P-CAD VH CDR1 comprises the sequence of SEQ ID NO: 25, the P-CAD VH CDR2 comprises the sequence of SEQ ID NO: 26, and the P-CAD VH CDR3 comprises the sequence of SEQ ID NO: 28. In another aspect, the P-CAD VL CDR1 comprises the sequence of SEQ ID NO: 35; the P-CAD VL CDR2 comprises the sequence of SEQ ID NO: 37; and the P-CAD VL CDR3 comprises the sequence of SEQ ID NO: 42, the P-CAD VH CDR1 comprises the sequence of SEQ ID NO: 25, the P-CAD VH CDR2 comprises the sequence of SEQ ID NO: 26, and the P-CAD VH CDR3 comprises the sequence of SEQ ID NO: 29. In another aspect, the P-CAD VL CDR1 comprises the sequence of SEQ ID NO: 35; the P-CAD VL CDR2 comprises the sequence of SEQ ID NO: 37, the P-CAD VL CDR3 comprises the sequence of SEQ ID NO: 43, the P-CAD VH CDR1 comprises the sequence of SEQ ID NO: 25, the P-CAD VH CDR2 comprises the sequence of SEQ ID NO: 26, and the P-CAD VH CDR3 comprises the sequence of SEQ ID NO: 30. In another aspect, the P-CAD VL CDR1 comprises the sequence of SEQ ID NO: 35; the P-CAD VL CDR2 comprises the sequence of SEQ ID NO: 37, the P-CAD VL CDR3 comprises the sequence of SEQ ID NO: 39, the P-CAD VH CDR1 comprises the sequence of SEQ ID NO: 25, the P-CAD VH CDR2 comprises the sequence of SEQ ID NO: 26, and the P-CAD VH CDR3 comprises the sequence of SEQ ID NO: 31.

The present invention further provides for bispecific heterodimeric diabodies, comprising a P-CAD VL comprising a sequence of SEQ ID NOS: 1, 3, 5, 7, 9, 11, 13, 15, 17, 19, 21 or 23; a CD3 VH comprising a sequence of SEQ ID NOS: 45 or 46; a CD3 VL comprising the sequence of SEQ ID NO: 47; and a P-CAD VH comprising a sequence of SEQ ID NOS: 2, 4, 6, 8, 10, 12, 14, 16, 18, 20, 22 or 24. In one aspect, the P-CAD VL comprises the sequence of SEQ ID NO: 5, and the P-CAD VH comprises the sequence of SEQ ID NO: 6. In another aspect, the P-CAD VL comprises the sequence of SEQ ID NO: 7, and the P-CAD VH comprises the sequence of SEQ ID NO: 8. In another aspect, the P-CAD VL comprises the sequence of SEQ ID NO: 9 and the P-CAD VH comprises the sequence of SEQ ID NO: 10. In another aspect, the P-CAD VL comprises the sequence of SEQ ID NO: 15 and the P-CAD VH comprises the sequence of SEQ ID NO: 16.

The present invention further provides for bispecific heterodimeric diabodies capable of specific binding to an epitope of P-cadherin and to an epitope of CD3 comprising a first polypeptide chain and a second polypeptide chain, wherein the first polypeptide chain comprises a sequence of SEQ ID NO: 90 and the second polypeptide chain comprises a sequence of SEQ ID NO: 91. The present invention further provides for bispecific heterodimeric diabodies capable of specific binding to an epitope of P-cadherin and to an epitope of CD3 comprising a first polypeptide chain and a second polypeptide chain, wherein the first polypeptide chain comprises a sequence of SEQ ID NO: 92 and the second polypeptide chain comprises a sequence of SEQ ID NO: 93.

The present invention further provides for bispecific heterodimeric diabodies capable of specific binding to an epitope of P-cadherin and to an epitope of CD3 comprising a first polypeptide chain and a second polypeptide chain, wherein the first polypeptide chain comprises a sequence of SEQ ID NO: 88 and the second polypeptide chain comprises a sequence of SEQ ID NO: 89.

The present invention further provides for bispecific heterodimeric diabodies wherein the first and second polypeptide chains may be covalently bonded to one another by at least one disulfide bond.

The present invention further provides for bispecific heterodimeric diabodies capable of specific binding to an epitope of P-cadherin and to an epitope of CD3 comprising a first polypeptide chain and a second polypeptide chain, wherein the first polypeptide chain and second polypeptide chain comprises sequences as set forth in FIG. 30A, 30B, 31A, 31B, 32A or 32B. In another aspect of the invention, the bispecific heterodimeric diabodies comprise a first polypeptide chain, a second polypeptide chain and a third polypeptide chain as set forth in Table 5.

The present invention provides for bispecific heterodimeric diabodies, wherein the bispecific heterodimeric diabodies may be conjugated to a detectable label, including but not limited to, fluorophore or a radionuclide.

The present invention provides for bispecific heterodimeric diabodies that bind to P-cadherin and compete for binding to bispecific heterodimeric diabodies disclosed herein.

The present invention further provides for a pharmaceutical composition comprising a therapeutically effective amount of a bispecific heterodimeric diabody disclosed herein and a pharmaceutically acceptable carrier.

The present invention further provides for a method of treating P-cadherin associated disorders in a patient in need thereof, comprising administering to the patient a bispecific heterodimeric diabody disclosed herein or a pharmaceutical composition comprising a bispecific heterodimeric diabody disclosed herein. The present invention further provides for a method of treating a P-cadherin associated disorders in a patient in need thereof, comprising administering to the patient the bispecific heterodimeric disclosed herein or a pharmaceutical composition comprising a bispecific heterodimeric diabody disclosed herein, wherein a cytolytic T cell response is activated or induced.

The present invention further provides bispecific heterodimeric diabodies disclosed herein for use in therapy. The present invention further provides the use of bispecific heterodimeric diabodies disclosed herein in the manufacture of a medicament for use in therapy. In another aspect, the therapy is treatment of P-cadherin associated disorder. The present invention further provides bispecific heterodimeric diabodies disclosed herein for use in therapy, wherein the therapy activates or induces a cytolytic T cell response.

In one aspect, the P-cadherin associated disorder is cancer. In another aspect, the cancer is a P-cadherin expressing or P cadherin positive cancer. The cancers include, but are not limited to, breast, colorectal, ovarian, gastric, thyroid, prostate, cervical, pancreatic, lung, bladder, liver, endometrial, head and neck, testicular, and glioblastoma cancer.

The present invention further provides isolated host cells that recombinantly produce bispecific heterodimeric diabodies described herein, isolated polynucleotides comprising nucleotide sequences encoding the bispecific heterodimeric diabodies disclosed herein, and vectors comprising the polynucleotides.

The present invention further provides methods of producing bispecific heterodimeric diabodies disclosed herein, comprising culturing the host cells disclosed herein under conditions that result in production of the bispecific heterodimeric diabodies, and purifying the bispecific heterodimeric diabodies from the culture supernatant.

The present invention further provides for bispecific heterodimeric diabodies disclosed herein, wherein a crystal structure assembles into a compact spherical structure stabilized by a disulfide linkage between a pair of cysteine residues consisting of a cysteine residue at position 239 ($Cys^{239}$) of sub-Domain 1B and a cysteine residue at position 246 ($Cys^{246}$) of sub-Domain 2A; and, wherein the crystal diffracts X-rays for determination of atomic coordinates to provide resolution of better than about 2.0 Angstroms.

The present invention further provides for bispecific heterodimeric diabodies capable of specific binding to an epitope of P-cadherin and to an epitope of CD3 comprising a first polypeptide chain and a second polypeptide chain, wherein the first polypeptide chain comprises, in the N-terminal to C-terminal direction: a Domain 1, comprising a sub-Domain 1A which comprises a VL binding domain of an anti-CD3 antibody (CD3 VL) comprising a sequence of SEQ ID NO: 47, and a sub-Domain 1B which comprises a VH binding domain of either an anti-P-cadherin antibody (P-CAD VH) comprising a sequence of SEQ ID NO: 6, wherein the sub-Domain 1A and sub-Domain 1B may be covalently linked by a glycine-serine linker (Linker 1) and do not associate to form a VL/VH epitope binding domain; and the second polypeptide chain comprises, in the N-terminal to C-terminal direction: a Domain 2, comprising a sub-Domain 2B which comprises a P-CAD VL comprising a sequence of SEQ ID NO: 5, and a sub-Domain 2A which comprises a CD3 VH comprising a sequence of SEQ ID NO: 45, wherein the sub-Domain 2B and sub-Domain 2A may be covalently linked by a glycine-serine linker (Linker 1) and do not associate to form a VL/VH epitope binding domain; and wherein a crystal structure assembles into a compact spherical structure stabilized by a disulfide linkage between a pair of cysteine residues comprising a cysteine residue at position 239 ($Cys^{239}$) of sub-Domain 1B and a cysteine residue at position 246 ($Cys^{246}$) of sub-Domain 2A; and, wherein the crystal diffracts X-rays for determination of atomic coordinates to provide resolution of better than about 2.0 Angstroms.

In another aspect, the bispecific heterodimeric diabodies described herein contain two antigen binding sites separated from each other by about 40 Angstroms and the binding sites may be located on the orthogonally opposite sides of the bispecific heterodimeric diabody.

The present invention further provides methods of identifying additional locations for cysteine residues to form a disulfide linkage within bispecific heterodimeric diabodies based on the crystal structures disclosed herein, wherein the crystal structure is analyzed for a pair of amino acid residue locations for substitution with a pair of cysteine residues that form a disulfide linkage. In a particular aspect of the present invention, the pair of amino acid residue locations for substitution with a pair of cysteine residues that form a disulfide linkage may be selected from the group consisting of amino acid locations $Gln^{121}$(VH1B)$Gly^{160}$(VL1A), $Val^{129}$(VH1B)$Gly^{244}$(VL1A), $Val^{123}$(VH1B)$Gly^{160}$(VL1A), $Gly^{128}$(VH1B)$Ser^{242}$(VL1A), and $Ala^{127}$(VH1B)$Ser^{242}$(VL1A). The disulfide linkage may reduce solvent accessibility and reduce the length of linkers.

The present invention further provides methods of engineering bispecific heterodimeric diabody variants in an attempt to form a more stable interdomain association, wherein the engineering is through amino acid site-directed mutagenesis in the interdomain interface based on the crystal structure disclosed herein, wherein the amino acid site-directed mutagenesis fills up large interior voids/holes. In a particular aspect of the present invention, the site-directed mutagenesis may increase amino acid side chain volumes by replacing small amino acids for amino acids with bulky aromatic side-chains. In another aspect of the invention, the small amino acids may be selected from the group consisting of amino acids at positions $Ala^{44}$(VL1A), $Val^{213}$(VH2A), $Leu^{238}$(VH2A), or $Met^{231}$(VL2B). In another aspect of the invention, the amino acids with bulky aromatic side-chains may be selected from the group consisting of phenylalanine, tyrosine, or tryptophan.

The present invention further provides for antibodies that binds to P-cadherin, comprising a CDR1, a CDR2, and a CDR3 of a light chain variable region (VL) comprising the sequence of SEQ ID NOS: 1, 3, 5, 7, 9, 11, 13, 15, 17, 19, 21 or 23 and/or a CDR1, a CDR2, and a CDR3 of a heavy chain variable region (VH) comprising the sequence of SEQ ID NOS: 2, 4, 6, 8, 10, 12, 14, 16, 18, 20, 22 or 24.

In another aspect of the invention, the antibodies disclosed herein comprise a VL CDR1 comprising the sequence of SEQ ID NO: 35 or 36, a VLCDR2 comprising the sequence of SEQ ID NO: 37 or 38, a VL CDR3 comprising the sequence of SEQ ID NO: 39, 40, 41, 42, 43 or 44, a VH CDR1 comprising the sequence of SEQ ID NO: 25 or 33, a VH CDR2 comprising the sequence of SEQ ID NO: 26 or 34, and a VH CDR3 comprising the sequence of SEQ ID NO: 27, 28, 29, 30, 31 or 32.

In another aspect of the invention, the antibodies disclosed herein comprise a VL CDR1 comprising the sequence of SEQ ID NO: 35 or 36, a VL CDR2 comprising the sequence of SEQ ID NO: 37 or 38, a VL CDR3 comprising the sequence of SEQ ID NO: 39, 40, 41, 42, 43 or 44, a VH CDR1 comprising the sequence of SEQ ID NO: 25, a VH CDR2 comprising the sequence of SEQ ID NO: 26, and a VH CDR3 comprising the sequence of SEQ ID NO: 27, 28, 29, 30, 31 or 32.

In another aspect of the invention, the antibodies disclosed herein comprise a VL CDR1 comprising the sequence of SEQ ID NO: 35, a VL CDR2 comprising the sequence of SEQ ID NO: 37, a VL CDR3 comprising the sequence of SEQ ID NO: 42, a VH CDR1 comprising the sequence of SEQ ID NO: 25, a VH CDR2 comprising the sequence of SEQ ID NO: 26, and a VH CDR3 comprising the sequence of SEQ ID NO: 29.

The present invention further provides for antibodies that binds to P-cadherin, comprising a light chain variable region comprising the sequence of SEQ ID NOS: 1, 3, 5, 7, 9, 11, 13, 15, 17, 19, 21 and 23, and/or a heavy chain variable region comprising the sequence of SEQ ID NOS: 2, 4, 6, 8, 10, 12, 14, 16, 18, 20, 22 or 24. In another aspect of the invention, the antibodies disclosed herein comprise a light chain variable region amino acid comprising the sequence of SEQ ID NO: 5, and/or a heavy chain variable region comprising the sequence of SEQ ID NO: 6. In another aspect of the invention, the antibodies disclosed herein comprise a light chain variable region comprising the sequence of SEQ ID NO: 7, and/or a heavy chain variable region comprising the sequence of SEQ ID NO: 8. In another aspect of the invention, the antibodies disclosed herein comprise a light chain variable region comprising the sequence of SEQ ID NO: 9 and/or a heavy chain variable region comprising the sequence of SEQ ID NO: 10. In another aspect of the invention, the antibodies disclosed herein comprise a light chain variable region comprising the sequence of SEQ ID NO: 15 and/or a heavy chain variable region comprising the sequence of SEQ ID NO: 16.

The present invention further provides for antibodies that bind to P-cadherin and compete for binding to P-cadherin with antibodies disclosed herein.

The present invention further provides for pharmaceutical compositions comprising a therapeutically effective amount of an antibody disclosed herein and a pharmaceutically acceptable carrier.

The present invention further provides a method of treating P-cadherin associated disorder in a patient in need thereof, comprising administering to the patient an antibody disclosed herein or a pharmaceutical composition comprising an antibody disclosed herein. The present invention further provides antibodies disclosed herein for use in therapy. The present invention further provides the use of antibodies disclosed herein in the manufacture of a medicament for use in therapy.

In one aspect, the P-cadherin associated disorder is cancer. In another aspect, the cancer is a P-cadherin expressing or P cadherin positive cancer. The cancers include, but are not limited to, breast, colorectal, ovarian, gastric, thyroid, prostate, cervical, pancreatic, lung, bladder, liver, endometrial, head and neck, testicular, and glioblastoma cancer.

The present invention further provides nucleic acids that encode the antibodies disclosed herein. In another aspect of the invention, the nucleic acids may comprise a sequence that is selected from the group consisting of SEQ ID NOS: 98, 100, 102, 104, 106, 108, 110, 112, 114 and 116. In a further aspect of the invention, the nucleic acids may comprise a sequence that is selected from the group consisting of SEQ ID NOS: 97, 99, 101, 103, 105, 107, 109, 111, 113 and 115. The present invention further provides vectors comprising nucleic acids disclosed herein and host cells comprising vectors disclosed herein.

The present invention further provides for bispecific heterodimeric diabodies or antibodies disclosed herein, wherein the P-CAD VL comprises a P-CAD VL CDR1 sequence comprising $X_{L1.1}$-$X_{L1.2}$-$X_{L1.3}$-$X_{L1.4}$-$XL_{1.5}$-$X_{L1.6}$-$X_{L1.7}$-$X_{L1.8}$-$X_{L1.9}$-$X_{L1.10}$-$X_{L1.11}$-$X_{L1.2}$-$X_{L1.13}$, wherein $X_{L1.1}$ to $X_{L1.13}$ each independently is an amino acid residue according to column 3 of Table 57, Table 58, or Table 59; a P-CAD VL CDR2 sequence comprising $X_{L2.1}$-$X_{L2.2}$-$X_{L2.3}$-$X_{L2.4}$-$X_{L2.5}$-$X_{L2.6}$-$X_{L2.7}$, wherein $X_{L2.1}$ to $X_{L2.7}$ each independently is an amino acid residue according to column 3 of Table 60, Table 61, or Table 62; and a P-CAD VL CDR3 sequence comprising $X_{L3.1}$-$X_{L3.2}$-$X_{L3.3}$-$X_{L3.4}$-$X_{L3.5}$-$X_{L3.6}$-$X_{L3.7}$-$X_{L3.8}$-$X_{L3.9}$-$X_{L3.10}$-$X_{L3.11}$, wherein $X_{L3.1}$ to $X_{L3.11}$ each independently is an amino acid residue according to column 3 of Table 63, Table 64, or Table 65; and the P-CAD VH comprises: a P-CAD VH CDR1 sequence comprising $X_{H1.1}$-$X_{H1.2}$-$X_{H1.3}$-$X_{H1.4}$-$X_{H1.5}$-$X_{H1.6}$-$X_{H1.7}$-$X_{H1.8}$-$X_{H1.9}$-$X_{H1.10}$ or $X_{H1.5}$, $X_{H1.6}$-$X_{H1.7}$-$X_{H1.8}$-$X_{H1.9}$-$X_{H1.10}$, wherein $X_{H1.1}$ to $X_{H1.10}$ each independently is an amino acid residue according to column 3 of Table 48, Table 49, or Table 50; a P-CAD VH CDR2 sequence comprising $X_{H2.1}$-$X_{H2.2}$-$X_{H2.3}$-$X_{H2.4}$-$X_{H2.5}$-$X_{H2.6}$-$X_{H2.7}$-$X_{H2.8}$-$X_{H2.9}$-$X_{H2.10}$-$X_{H2.11}$-$X_{H2.12}$-$X_{H2.13}$-$X_{H2.14}$-$X_{H2.15}$-$X_{H2.16}$-$X_{H2.17}$ or $X_{H2.1}$-$X_{H2.2}$-$X_{H2.3}$-$X_{H2.4}$-$X_{H2.5}$-$X_{H2.6}$-$X_{H2.7}$-$X_{H2.8}$-$X_{H2.9}$-$X_{H2.10}$, wherein $X_{H2.1}$ to $X_{H2.17}$ each independently is an amino acid residue according to column 3 of Table 51, Table 52, or Table 53; and a P-CAD VH CDR3 sequence comprising $X_{H3.1}$-$X_{H3.2}$-$X_{H3.3}$-$X_{H3.4}$-$X_{H3.5}$-$X_{H3.6}$-$X_{H3.7}$-$X_{H3.8}$-$X_{H3.9}$, wherein $X_{H3.1}$ to $X_{H3.9}$ each independently is an amino acid residue according to column 3 of Table 54, Table 55, or Table 56.

In one aspect, $X_{L1.1}$ to $X_{L1.13}$ each independently is an amino acid residue according to column 3 of Table 57. In another aspect, $X_{L1.1}$ to $X_{L1.13}$ each independently is an amino acid residue according to column 3 of Table 58. In another aspect, $X_{L1.1}$ to $X_{L1.13}$ each independently is an amino acid residue according to column 3 of Table 59. In another aspect, $X_{L2.1}$ to $X_{L2.7}$ each independently is an amino acid residue according to column 3 of Table 60. In another aspect, $X_{L2.1}$ to $X_{L2.7}$ each independently is an amino acid residue according to column 3 of Table 61. In another aspect, $X_{L2.1}$ to $X_{L2.7}$ each independently is an amino acid residue according to column 3 of, or Table 62. In another aspect, $X_{L3.1}$ to $X_{L3.11}$ each independently is an amino acid residue according to column 3 of Table 63. In another aspect, $X_{L3.1}$ to $X_{L3.11}$ each independently is an amino acid residue according to column 3 of Table 64. In another aspect, $X_{L3.1}$ to $X_{L3.11}$ each independently is an amino acid residue according to column 3 of or Table 65.

In another aspect, $X_{H1.1}$ to $X_{H1.10}$ each independently is an amino acid residue according to column 3 of Table 48. In another aspect, $X_{H1.1}$ to $X_{H1.10}$ each independently is an amino acid residue according to column 3 of Table 49. In another aspect, $X_{H1.1}$ to $X_{H1.10}$ each independently is an amino acid residue according to column 3 of Table 50. In another aspect, $X_{H2.1}$ to $X_{H2.17}$ each independently is an amino acid residue according to column 3 of Table 51. In another aspect, $X_{H2.1}$ to $X_{H2.17}$ each independently is an amino acid residue according to column 3 of Table 52. In another aspect, $X_{H2.1}$ to $X_{H2.17}$ each independently is an amino acid residue according to column 3 of Table 53. In another aspect, $X_{H3.1}$ to $X_{H3.9}$ each independently is an amino acid residue according to column 3 of Table 54. In another aspect, $X_{H3.1}$ to $X_{H3.9}$ each independently is an amino acid residue according to column 3 of Table 55. In another aspect, $X_{H3.1}$ to $X_{H3.9}$ each independently is an amino acid residue according to column 3 of Table 56.

The present invention further provides for bispecific heterodimeric diabodies or antibodies disclosed herein, wherein the P-CAD VL comprises a P-CAD VL CDR1 sequence comprising $X_{L1.1}$-$X_{L1.2}$-$X_{L1.3}$-$X_{L1.4}$-$X_{L1.5}$-$X_{L1.6}$-$X_{L1.7}$-$X_{L1.8}$-$X_{L1.9}$-$X_{L1.10}$-$X_{L1.11}$-$X_{L1.2}$-$X_{L1.13}$, wherein $X_{L1.1}$ to $X_{L1.13}$ each independently is an amino acid residue according to column 3 or column 4 of Table 69; a P-CAD VL CDR2 sequence comprising $X_{L2.1}$-$X_{L2.2}$-$X_{L2.3}$-$X_{L2.4}$-$X_{L2.5}$-$X_{L2.6}$-$X_{L2.7}$, wherein $X_{L2.1}$ to $X_{L2.7}$ each independently is an amino acid residue according to column 3 or column 4 of Table 70; and a P-CAD VL CDR3 sequence comprising $X_{L3.1}$-$X_{L3.2}$-$X_{L3.3}$-$X_{L3.4}$-$X_{L3.5}$-$X_{L3.6}$-$X_{L3.7}$-$X_{L3.8}$-$X_{L3.9}$-$X_{L3.10}$-$X_{L3.11}$, wherein $X_{L3.1}$ to $X_{L3.11}$ each independently is an amino acid residue according to column 3 or column 4 of Table 71; and the P-CAD VH comprises a P-CAD VH CDR1 sequence comprising $X_{H1.1}$-$X_{H1.2}$-$X_{H1.3}$-$X_{H1.4}$-$X_{H1.5}$-$X_{H1.6}$-$X_{H1.7}$-$X_{H1.8}$-$X_{H1.9}$-$X_{H1.10}$ or $X^{H1.5}$, $X_{H1.6}$-$X_{H1.7}$-$X_{H1.8}$-$X_{H1.9}$-$X_{H1.10}$, wherein $X_{H1.1}$ to $X_{H1.10}$ each independently is an amino acid residue according to column 3 or column 4 of Table 66; a P-CAD VH CDR2 sequence comprising $X_{H2.1}$-$X_{H2.2}$-$X_{H2.3}$-$X_{H2.4}$-$X_{H2.5}$-$X_{H2.6}$-$X_{H2.7}$-$X_{H2.8}$-$X_{H2.9}$-$X_{H2.10}$-$X_{H2.11}$-$X_{H2.12}$-$X_{H2.13}$-$X_{H2.14}$-$X_{H2.15}$-$X_{H2.16}$-$X_{H2.17}$ or $X_{H2.1}$-$X_{H2.2}$-$X_{H2.3}$-$X_{H2.4}$-$X_{H2.5}$-$X_{H2.6}$-$X_{H2.7}$-$X_{H2.8}$-$X_{H2.9}$-$X_{H2.10}$, wherein $X_{H2.1}$ to $X_{H2.17}$ each independently is an amino acid residue according to column 3 or column 4 of Table 67, and a P-CAD VH CDR3 sequence comprising $X_{H3.1}$-$X_{H3.2}$-$X_{H3.3}$-$X_{H3.4}$-$X_{H3.5}$-$X_{H3.6}$-$X_{H3.7}$-$X_{H3.8}$-$X_{H3.9}$, wherein $X_{H3.1}$ to $X_{H3.9}$ each independently is an amino acid residue according to column 3 or column 4 of Table 68.

In one aspect, $X_{L1.1}$ to $X_{L1.13}$ each independently is an amino acid residue according to column 3 of Table 69. In another aspect, $X_{L1.1}$ to $X_{L1.13}$ each independently is an amino acid residue according to column 4 of Table 69. In another aspect, $X_{L2.1}$ to $X_{L2.7}$ each independently is an amino acid residue according to column 3 of Table 70. In another aspect, $X_{L2.1}$ to $X_{L2.7}$ each independently is an amino acid residue according to column 4 of Table 70. In another aspect, $X_{L3.1}$ to $X_{L3.11}$ each independently is an amino acid residue according to column 3 of Table 71. In another aspect, $X_{L3.1}$ to $X_{L3.11}$ each independently is an amino acid residue according to column 4 of Table 71. In another aspect, $X_{H1.1}$ to $X_{H1.10}$ each independently is an amino acid residue according to column 3 of Table 66. In another aspect, $X_{H1.1}$ to $X_{H1.10}$ each independently is an amino acid residue according to column 4 of Table 66. In another aspect, $X_{H2.1}$ to $X_{H2.17}$ each independently is an amino acid residue according to column 3 of Table 67. In another aspect, $X_{H2.1}$ to $X_{H2.17}$ each independently is an amino acid residue according to column 4 of Table 67. In another aspect, $X_{H3.1}$ to $X_{H3.9}$ each independently is an amino acid residue according to column 3 of Table 68. In another aspect, $X_{H3.1}$ to $X_{H3.9}$ each independently is an amino acid residue according to column 4 of Table 68.

Further, the present invention provides for $X_{H1.8}$ is G, $X_{H2.5}$ is Y, $X_{H3.1}$ is I, $X_{H3.7}$ is F, $X_{L3.3}$ is W, $X_{H2.6}$ is N, $X_{H2.16}$ is Q, $X_{H3.5}$ is N, $X_{H3.9}$ is I, $X_{L1.8}$ is G, $X_{L2.2}$ is N, $X_{L2.3}$ is N, $X_{L3.2}$ is T, and/or $X_{L3.4}$ is D. The present invention also provides for any combination of the aspects described herein.

BRIEF DESCRIPTION OF DRAWINGS

FIG. 4 provides a schematic representation of an assembled EK-DART bispecific heterodimeric diabody having a first polypeptide chain (1) wherein a first heterodimer-promoting domain comprises a glutamic acid-rich region that forms a negatively charged alpha-helical coil (E-coil), and a second polypeptide chain (2) wherein a second heterodimer-promoting domain comprises a lysine rich region that forms a positively charged helical coil (K-coil).

FIG. 5 provides a schematic representation of an assembled LP-DART bispecific heterodimeric diabody having a first heterodimer-promoting domain and a second heterodimer-promoting domain comprising an Fc region optimized to associate via a "knob-in-hole" association.

FIG. 7 provides the structures of an alternative bispecific heterodimeric diabody having an Fc domain termed MP3-DART. The bispecific heterodimeric diabody is attached to the C-terminal side of the Fc domain and is thus termed "C-terminal MP3 DART." The C-terminal MP3-DART comprises a first, second and third polypeptide chain which are schematically represented. The final structure of the C-terminal MP3-DART is represented.

FIG. 16 demonstrates the in vivo ability of 153 LP-DART to decrease tumor volume in murine H1650 lung cancer model.

FIGS. 21A-21D provide in vitro assays to evaluate the properties of fluorophore Labeled 153 LP-DART and T cells.

FIG. 29 provides a graphical depiction of the crystal structure of a crystallography 35 DART protein with various disulfide bond locations (Cys-Cys sites) to reduce solvent accessibility of the disulfide bond, as well as, to reduce the length of linkers.

FIGS. 30A and 30B provide amino acid sequences for first and second polypeptide chains of VF-DART bispecific heterodimeric diabodies of the present invention.

FIGS. 31A and 31B provide amino acid sequences for first and second polypeptide chains of EK-DART bispecific heterodimeric diabodies of the present invention.

FIGS. 32A and 32B provide amino acid sequences for first and second polypeptide chains of LP-DART bispecific heterodimeric diabodies of the present invention.

FIGS. 33A and 33B provide amino acid sequences for first and second polypeptide chains of DART bispecific heterodimeric diabodies of the present invention.

FIG. 35 provides the full length P-Cadherin epitope sequence (UniProt P22223, CADH3, Human Cadherin-3).

DETAILED DESCRIPTION

Figure 1A:
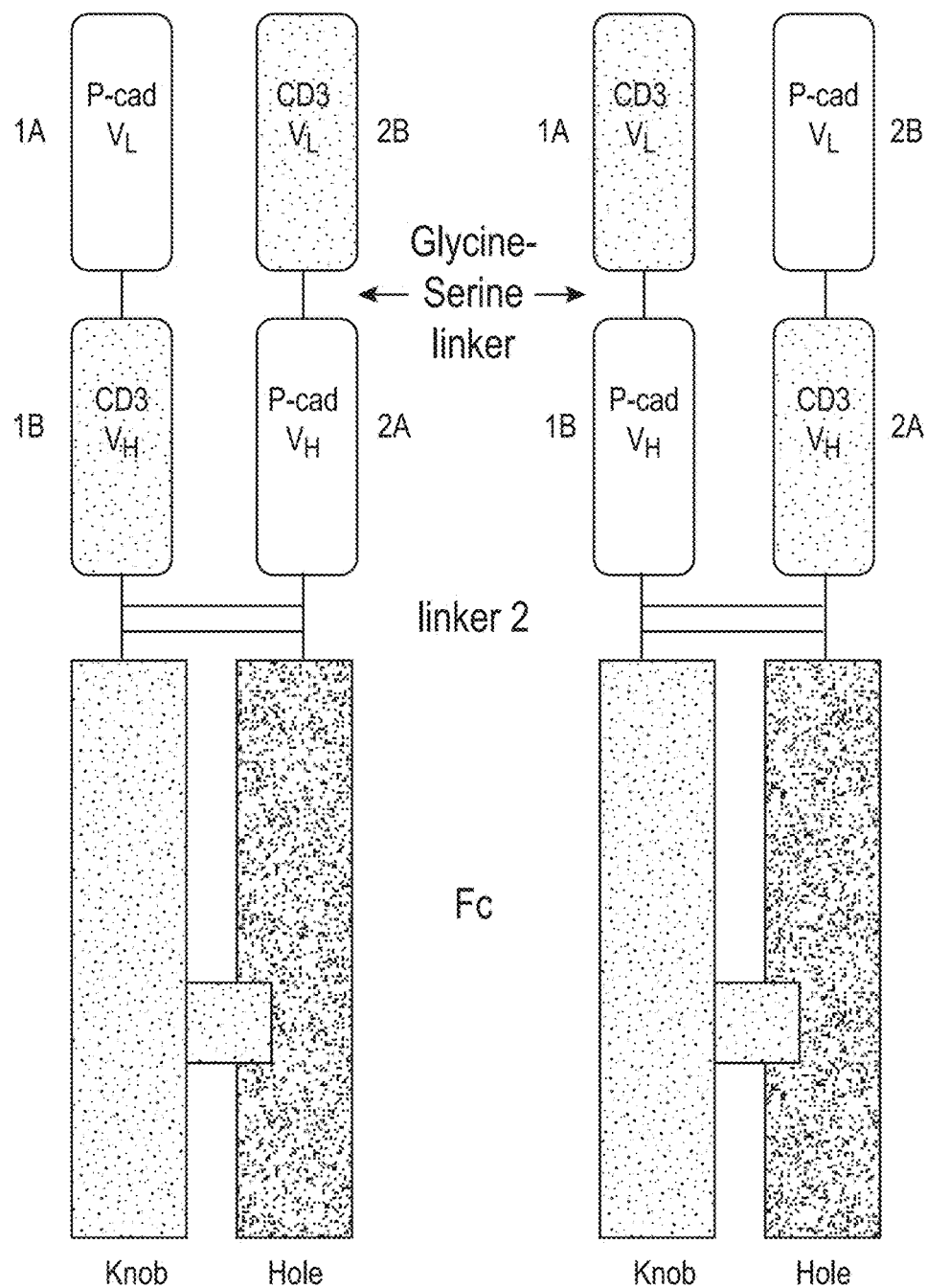
FIGS. 1A and 1B provide schematics of four alternative representations of LP-DART P-cadherin/CD3 bispecific heterodimeric diabodies having a first heterodimer-promoting domain and second heterodimer-promoting domain comprising an Fc region optimized to associate via a "knob-in-hole" association.

The present invention describes novel bispecific heterodimeric diabodies comprising an antigen binding domain that specifically binds P-cadherin, and an antigen binding domain that specifically binds CD3 for the recruitment of and activation of cytolytic T cells. The bispecific heterodimeric diabodies may further comprise a Fc domain. Moreover, it is demonstrated herein that the bispecific heterodimeric diabodies successfully direct and activate T cell cytotoxicity to tumor cells expressing P-cadherin. Further, the bispecific heterodimeric diabodies of the present invention have enhanced pharmacokinetic properties to extend in vivo half-life, and were designed to engage and activate polyclonal T cell populations via the CD3 complex in the presence of P-cadherin expressing tumors.

The present invention describes the isolation and characterization of fully human single-chain antibody binding domains against P-cadherin derived from human phage display libraries. The invention further provides covalently linking these P-cadherin binding domains to antigen binding domains of anti-CD3 antibodies in the previously described DART format (Moore et al., Blood, 117(17): 4542-4551, 2011) to create bispecific heterodimeric diabodies that are capable of simultaneous binding to P-cadherin and CD3.

Further, in an aspect of the invention, the anti-P-cadherin/anti-CD3 DART proteins, also known as bispecific heterodimeric diabodies, successfully direct and activate T cell cytotoxicity of cells expressing P-cadherin.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The practice of the present invention employs, unless otherwise indicated, conventional techniques of molecular biology (including recombinant techniques), microbiology, cell biology, biochemistry, nucleic acid chemistry, and immunology, which are within the skill of the art. Such techniques are explained fully in the literature, such as, Current Protocols in Immunology (J. E. Coligan et al., eds., 1999, including supplements through 2001); Current Protocols in Molecular Biology (F. M. Ausubel et al., eds., 1987, including supplements through 2001); Molecular Cloning: A Laboratory Manual, third edition (Sambrook and Russel, 2001).

P-cadherin (Cadherin-3, CDH3) belongs to the classical cadherin superfamily of transmembrane glycoproteins that regulate calcium-dependent cell-cell adhesion during development and tissue homeostasis (Gumbiner et al., J. Cell Biol., 148: 399-403, (2000)). The cadherin intracellular domains directly interact with cytoplasmic catenins that link to the actin cytoskeletal network, providing the molecular basis for stable cell interactions. The cadherin/catenin complex, as well as the signaling pathways controlled by this structure, represent a major regulatory mechanism that guide cell fate decisions, through its influence on cell growth, differentiation, motility, and survival (Cavallaro et al, 2011). Classical cadherins include the E-cadherin (CDH1), N-cadherin (CDH2) and P-cadherin (CDH3). P-cadherin expression in normal tissues is low and is restricted primarily to myoepithelial cells and the basal layers of stratified epithelium. Increased expression of P-cadherin has been reported in various tumors, including breast, gastric, endometrial, pancreatic and colorectal cancers and is a good prognosticator of poor survival of patients with advanced disease (Hardy et al, 2002; Imai et al, 2008; Parades et al, 2005; Stefansson et al, 2004; Taniuchi et al, 2005). Gene expression profiling and immunohistochemistry analyses further suggested lung (including but not limited to non-small cell lung and small cell lung cancers), ovarian, head and neck, thyroid and bladder cancers.

CD3 (cluster of differentiation 3) is a T cell co-receptor protein complex that comprising four distinct chains ε, δ, γ and ζ that form εδ, εγ and ζζ dimers.

These dimers associate with a molecule known as the T cell receptor (TCR) and generate an activation signal in T lymphocytes. The TCR and CD3 molecules together comprise the TCR complex. It is well known that anti-CD3 antibodies elicit the generation of cytotoxic T cells through the activation of endogenous lymphokine production and are capable of selectively killing tumor targets (Yun et al., Cancer Research, 49: 4770-4774 (1989)).

More specifically, T cells express TCR complexes that are able to induce antigen specific immune responses (Smith-Garvin et al, 2009). Antigens are peptides expressed by tumor cells and virally infected cells capable of stimulating immune responses. Intracellularly expressed antigens are bound to major histocompatibility class I (MHC class I)

molecules and transported to the surface where they are exposed to T cells. If the binding affinity of the TCR to the MHC class I in complex with the antigen is sufficient the formation of an immune synapse will be initiated. Signaling through the immune synapse is mediated through the CD3 co-receptors that form εδ, εγ and ζζ dimers. These dimers associate with the TCR and generate an activation signal in T lymphocytes. This signaling cascade directs T cell mediated killing of the cell expressing the antigen. Cytotoxicity is mediated by release and transfer of granzyme B and perforin from the T cell to the target cell.

Without being bound by theory, it is believed that the bispecific heterodimer diabodies of the present invention may allow the T cell to circumvent the need for the interaction of the TCR and MHC class I in complex with antigen, and instead redirects T cells to target cells through direct co-engagement of CD3 (such as CD3 epsilon) expressed on the T cell and P-cadherin expressed on the tumor.

"Effector function" as used herein is meant as the capacity to support a biochemical event that results from the interaction of an anti-CD3 binding domain of a bispecific heterodimeric diabody with a cytotoxic T cell.

As used herein, the terms "antibody" and "antibodies" refer to monoclonal antibodies, multispecific antibodies, human antibodies, humanized antibodies, synthetic antibodies, chimeric antibodies, polyclonal antibodies, camelized antibodies, single-chain Fvs (scFv), single chain antibodies, Fab fragments, F(ab') fragments, disulfide-linked bispecific Fvs (sdFv), intrabodies, and anti-idiotypic (anti-Id) antibodies (including, e.g. anti-Id and anti-anti-Id antibodies to antibodies of the invention), and epitope-binding fragments or binding domains of any of the above. In particular, antibodies include immunoglobulin molecules and immunologically active fragments of immunoglobulin molecules, i.e., molecules that contain an antigen binding site. Immunoglobulin molecules can be of any type (e.g. IgG, IgE, IgM, IgD, IgA and IgY), class (e.g. $IgG_1$, $IgG_2$, $IgG_3$, $IgG_4$, $IgA_1$ and $IgA_2$) or subclass.

As used herein, the term "bispecific heterodimeric diabody" refers to a complex of two or more polypeptide chains or proteins, each comprising at least one antibody VL and one antibody VH domain or fragment thereof, wherein both antibody binding domains are comprised within a single polypeptide chain and wherein the VL and VH domains in each polypeptide chain are from different antibodies.

As used herein, the terms "immunospecifically binds," "immunospecifically recognizes," "specifically binds," "specifically recognizes" and analogous terms refer to molecules e.g. binding domains, that specifically bind to an antigen (e.g. epitope or immune complex) and do not specifically bind to another molecule. A molecule that specifically binds to an antigen may bind to other peptides or polypeptides with lower affinity as determined by assays known in the art e.g. immunoassays, BIACORE®, or other assays. Preferably, molecules that specifically bind an antigen do not cross-react with other proteins.

As used herein, the terms "heavy chain", "light chain", "variable region" or "variable domain", "framework region", "constant domain", and the like, have their ordinary meaning in the immunology art and refer to domains in naturally occurring immunoglobulins and the corresponding domains of recombinant binding proteins (e.g. humanized antibodies, single chain antibodies, chimeric antibodies, etc.). The basic structural unit of naturally occurring immunoglobulins is a tetramer having two light chains and two heavy chains, usually expressed as a glycoprotein of about 150,000 Da. The amino-terminal (N-terminal) portion of each chain includes a variable region of about 100 to 110 or more amino acids primarily responsible for antigen recognition. The carboxy-terminal (C-terminal) portion of each chain defines a constant region. Each light chain is comprised a light chain variable domain (VL) and a light chain constant domain (CL). Each heavy chain is comprised of a heavy chain variable region (VH) and a heavy chain constant region, having CH1, hinge, CH2 and CH3 domains. The variable regions of an IgG molecule comprise regions of hypervariability, termed the complementarity determining regions (CDRs), which contain the residues in contact with antigen, and non-CDR segments, termed framework regains (FR), which generally maintain the structure and determine the positioning of the CDR loops (although certain framework residues may also contact antigen). Each VH and VL comprises three CDRs and four FRs, arranged from amino-terminus to carboxy-terminus in the following structure: n-FR1, CDR1, FR2, CDR2, FR3, CDR3, FR4-c. Immunoglobulin molecules can be of any type (e.g., IgG, IgE, IgM, IgD, IgA and IgY) and class (e.g., IgGI, IgG2, IgG 3, IgG4, IgAI and IgA2) or subclass.

The "hinge region" or "hinge domain" is generally defined as stretching from Glu216 to Pro230 of human IgG-1. Hinge regions of other IgG isotypes may be aligned with the IgG1 sequence by placing the first and last cysteine residues forming inter-heavy chain S—S binds in the same positions.

As used herein, the term "Fc region," "Fc domain" or analogous terms are used to define a C-terminal region of an IgG heavy chain. The Fc region of an IgG comprises two constant domains, CH2 and CH3. The CH2 domain of a human IgG Fc region usually extends from amino acids 231 to amino acid 341 according to the numbering system of Kabat. The CH3 domain of a human IgG Fc region usually extends from amino acids 342 to 447 according to the numbering system of Kabat. The CH2 domain of a human IgG Fc region (also referred to as "Cγ 2" domain) is unique in that it is not closely paired with another domain. Rather, two N-linked branched carbohydrate chains are interposed between the two CH2 domains of an intact native IgG.

When referring to binding proteins, binding domains, or antibodies (as broadly defined herein), the assignment of amino acids to each domain is in accordance with the definitions of Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., 1989, Nature 342:877-883. Other approaches to CDR identification include the "AbM definition," which is a compromise between Kabat and Chothia and is derived using Oxford Molecular's AbM antibody modeling software (Accelrys, San Diego, Calif.), or the "contact definition" of CDRs based on observed antigen contacts, set forth in MacCallum et al., 1996, J. Mol. Biol., 262:732-745. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but may nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given aspect containing more than one CDR, the CDRs may be defined in accordance with any of Kabat, Chothia, extended, AbM, contact, and/or conformational definitions.

A humanized antibody refers to forms of non-human (e.g. murine) antibodies that are chimeric immunoglobulins, immunoglobulin chains, or fragments thereof (such as Fv, Fab, Fab', F(ab')$_2$ or other antigen-binding subsequences or binding domains of antibodies) that contain minimal sequences derived from non-human immunoglobulins. Preferably, humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and capacity.

The term "monoclonal antibody" refers to an antibody that is derived from a single clone, including any eukaryotic, prokaryotic, or phage clone, and not the method by which it is produced. Monoclonal antibodies from which binding domains of the bispecific heterodimeric diabodies of the invention can be prepared using a wide variety of techniques known in the art including the use of hybridoma, recombinant, and phage display technologies, or a combination thereof. For example, monoclonal antibodies can be produced using hybridoma techniques including those known in the art.

Antibodies can also be generated using various phage display methods known in the art. In phage display methods, functional antibody domains are displayed on the surface of phage particles which carry the polynucleotide sequences encoding them. In a particular aspect, such phage can be utilized to display antigen binding domains, such as Fab and Fv or disulfide-bond stabilized Fv, expressed from a repertoire or combinatorial antibody library (e.g. human or murine). Phage expressing an antigen binding domain that binds the antigen of interest can be selected or identified with antigen, e.g. using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkmann et al. (1995) "Phage Display Of Disulfide-Stabilized Fv Fragments," J. Immunol. Methods, 182:41-50.

The functional characteristics of the multiple IgG isotypes, and domains thereof, are well known in the art. The amino acid sequences of IgG1, IgG2, IgG3 and IgG4 are known in the art. Selection and/or combinations of two or more domains from specific IgG isotypes for use in the methods of the invention may be based on any known parameter of the parent isotypes including affinity to FcγR. For example, use of regions or domains from IgG isotypes that exhibit limited or no binding to FcγRIIB, e.g. IgG2 or IgG4, may find particular use where a bispecific heterodimeric diabody is desired to be engineered to maximize binding to an activating receptor and minimize binding to an inhibitory receptor. Similarly, use of Fc regions or domains from IgG isotypes known to preferentially bind C1q or FcγRIIIA, e.g. IgG3 may be combined with Fc amino acid modifications known in the art to enhance antibody-dependent cell mediated cytotoxicity (ADCC) and/or complement dependent cytotoxicity (CDC), to engineer a bispecific heterodimeric diabody molecule such that effector function activity, e.g. complement activation or ADCC, is maximized. In a similar fashion, mutations may be made in the Fc regions or domains of IgG isotypes that minimize or eliminate the effector function of the Fc region.

The term "epitope" refers to that portion of a molecule capable of being recognized by and bound by an antibody at one or more of the antibody's antigen-binding regions. Epitopes often consist of a chemically active surface grouping of molecules such as amino acids or sugar side chains and have specific three-dimensional structural characteristics as well as specific charge characteristics. The term "antigenic epitope" as used herein, is defined as a portion of a polypeptide to which an antibody can specifically bind as determined by any method well known in the art, for example, by conventional immunoassays. A "nonlinear epitope" or "conformational epitope" comprises noncontiguous polypeptides (or amino acids) within the antigenic protein to which an antibody specific to the epitope binds. Once a desired epitope on an antigen is determined, it is possible to generate antibodies to that epitope, e.g. using the techniques described herein. During the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another e.g. the antibodies compete for binding to the antigen.

One method is to identify the epitope to which antibodies bind, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. Epitope mapping is commercially available from various sources, for example, Pepscan Systems (Edelhertweg 15, 8219 PH Lelystad, The Netherlands). In an additional example, mutagenesis of an antigen binding domain, domain swapping experiments and alanine scanning mutagenesis can be performed to identify residues required, sufficient, and/or necessary for epitope binding. The binding affinity and the off-rate of an antigen-binding domain interaction can be determined by competitive binding assays. One example of a competitive binding assay is a radioimmunoassay comprising the incubation of labeled antigen, and the detection of the molecule bound to the labeled antigen. The affinity of the molecule of the present invention for an antigen and the binding off-rates can be determined from the saturation data by Scatchard analysis.

The affinities and binding properties of the molecules of the invention for an antigen may be initially determined using in vitro assays (biochemical or immunological based assays) known in the art for antigen-binding domain, including but not limited to enzyme-linked immunosorbent assay (ELISA) assay, surface plasmon resonance (SPR) assay, Bio-Layer Interferometry, or immunoprecipitation assays. The molecules of the invention may have similar binding properties in in vivo models (such as those described and disclosed herein) as those in in vitro based assays. However, the present invention does not exclude molecules of the invention that do not exhibit the desired phenotype in in vitro based assays but do exhibit the desired phenotype in in vivo.

The term "binding affinity ($K_D$)" as used herein, is intended to refer to the dissociation rate of a particular antigen-antibody interaction. The $K_D$ is the ratio of the rate of dissociation, also called the "off-rate ($k_{off}$)", to the association rate, or "on-rate ($k_{on}$)". Thus, $K_D$ equals $k_{off}/k_{on}$ and is expressed as a molar concentration (M). It follows that the smaller the $K_D$, the stronger the affinity of binding. Therefore, a $K_D$ of 1 μM indicates weak binding affinity compared to a $K_D$ of 1 nM. $K_D$ values for antibodies can be determined using methods well established in the art. One method for determining the $K_D$ of an antibody is by using surface plasmon resonance (SPR), typically using a biosensor system such as a BIACORE® system. BIAcore kinetic analysis comprises analyzing the binding and dissociation of an antigen from chips with immobilized molecules (e.g. molecules comprising epitope binding domains), on their surface. Another method for determining the $K_D$ of an antibody is by using Bio-Layer Interferometry, typically using OCTET® technology (Octet QK$^e$ system, ForteBio).

As used herein, the terms "nucleic acids" and "nucleotide sequences" include DNA molecules (e.g. cDNA or genomic DNA), RNA molecules (e.g. mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

The present invention also includes polynucleotides that encode the bispecific heterodimeric diabodies of the invention, including the polypeptides and binding regions of the antibodies. The polynucleotides encoding the molecules of the invention may be obtained, and the nucleotide sequence of the polynucleotides determined, by any method known in the art.

The polynucleotides that encode the bispecific heterodimeric diabodies of the present invention may include the following: only the coding sequence for the variant, the coding sequence for the variant and additional coding sequences such as a functional polypeptide, or a signal or secretory sequence or a pro-protein sequence; the coding sequence for the antibody and non-coding sequence, such as introns or non-coding sequence 5' and/or 3' of the coding sequence for the antibody. The term "polynucleotide encoding a bispecific heterodimeric diabody" encompasses a polynucleotide which includes additional coding sequence for the variant but also a polynucleotide which includes additional coding and/or non-coding sequence. It is known in the art that a polynucleotide sequence that is optimized for a specific host cell/expression system can readily be obtained from the amino acid sequence of the desired protein (see GENEART® AG, Regensburg, Germany).

As used herein, the term "cancer" refers to a neoplasm or tumor resulting from abnormal uncontrolled growth of cells. In some aspects, cancer refers to a benign tumor, which has remained localized. In other aspects, cancer refers to a malignant tumor, which has invaded and destroyed neighboring body structures and spread to distant sites. In some aspects, the cancer is associated with a specific cancer antigen.

As used herein, a "therapeutically effective amount" refers to that amount of the therapeutic agent sufficient to treat or manage a disease or disorder. A therapeutically effective amount may refer to the amount of therapeutic agent sufficient to delay or minimize the onset of disease, e.g. delay or minimize the spread of cancer. A therapeutically effective amount may also refer to the amount of the therapeutic agent that provides a therapeutic benefit in the treatment or management of a disease. Further, a therapeutically effective amount with respect to a therapeutic agent of the invention means the amount of therapeutic agent alone, or in combination with other therapies, that provides a therapeutic benefit in the treatment or management of a disease.

As used herein, the terms "prophylactic agent" and "prophylactic agents" refer to any agent(s) which can be used in the prevention of a disorder, or prevention of recurrence or spread of a disorder. A prophylactically effective amount may refer to the amount of prophylactic agent sufficient to prevent the recurrence or spread of hyperproliferative disease, particularly cancer, or the occurrence of such in a patient, including but not limited to those predisposed to hyperproliferative disease, for example those genetically predisposed to cancer or previously exposed to carcinogens. A prophylactically effective amount may also refer to the amount of the prophylactic agent that provides a prophylactic benefit in the prevention of disease. Further, a prophylactically effective amount with respect to a prophylactic agent of the invention means that amount of prophylactic agent alone, or in combination with other agents, that provides a prophylactic benefit in the prevention of disease.

As used herein, the terms "prevent", "preventing" and "prevention" refer to the prevention of the recurrence or onset of one or more symptoms of a disorder in a subject as result of the administration of a prophylactic or therapeutic agent.

As used herein, the term "in combination" refers to the use of more than one prophylactic and/or therapeutic agents. The use of the term "in combination" does not restrict the order in which prophylactic and/or therapeutic agents are administered to a subject with a disorder. In other words, the combination therapy may be done by separately, sequentially, or simultaneously treating with the therapeutic agents.

Recombinant Expression of Molecules of the Invention

Once a nucleic acid sequence encoding molecules of the invention (i.e. binding domains) has been obtained, the vector for the production of the molecules may be produced by recombinant DNA technology using techniques well known in the art.

The polynucleotides encoding the bispecific heterodimeric diabody binding domains of the present invention may include an expression control polynucleotide sequence operably linked to the antibody coding sequences, including naturally-associated or heterologous promoter regions known in the art. The expression control sequences may be eukaryotic promoter systems in vectors capable of transforming or transfecting eukaryotic host cells, but control sequences for prokaryotic hosts may also be used. Once the vector has been incorporated into the appropriate host cell line, the host cell is propagated under conditions suitable for expressing the nucleotide sequences, and, as desired, for the collection and purification of the antibodies. Eukaryotic cell lines include the CHO cell lines, various COS cell lines, HeLa cells, myeloma cell lines, transformed B-cells, or human embryonic kidney cell lines.

Bispecific Heterodimeric Diabodies

As stated previously, bispecific heterodimeric diabody refers to a complex of two or more polypeptide chains or proteins, each comprising at least one antibody VL domain and one antibody VH domain or fragment thereof, wherein both antibody binding domains are comprised within a single polypeptide chain and wherein the VL and VH domains in each polypeptide chain are from different antibodies. In specific aspects, bispecific heterodimeric diabody includes dimers or tetramers of polypeptide chains containing both a VL and VH domain. The individual polypeptide chains comprising the multimeric proteins may be covalently joined to at least one other peptide of the multimer by interchain disulfide bonds.

Bispecific heterodimeric diabodies of the present invention are comprised of anti-P-cadherin (P-CAD) binding domains covalently linked to anti-CD3 (CD3) binding domains utilizing a Dual-Affinity Re-Targeting (DART®) platform technology (US Patent Application Publications Nos. 2007/0004909, 2009/0060910 and 2010/0174053). The DART technology provides a covalent linkage which results in a molecule that may have superior stability, optimal heavy and light chain pairing and antigen recognition. Moreover, the minimal linker size and content may decrease the potential for immunogenicity. The DART proteins of the present invention simultaneously target T cells (CD3) and tumor cells (P-CAD) and successfully direct and activate T cell cytoxicity to tumor cells expressing P-cadherin.

Each polypeptide chain of the bispecific heterodimeric diabody comprises a VL domain and a VH domain, which may be covalently linked (Linker 1) such that the antibody binding domains are constrained from self-assembly. In addition, each polypeptide chain comprises a heterodimerization domain, which promotes heterodimerization of the multiple polypeptide chains and reduces the probability of homodimerization of the different polypeptide chains. The heterodimerization domain may be located at the N-terminus of the polypeptide chain or the C-terminus. The heterodimerization domain may comprise a cysteine linker (Linker 2) that is 1, 2, 3, 4, 5, 6, or more amino acid residues in length. Interaction of two of the polypeptide chains may produce two VL/VH pairings, forming two epitope binding domains, i.e., a bivalent molecule. Neither the VH or VL domain is constrained to any position within the polypeptide chain, i.e. restricted to the amino or carboxy terminus, nor are the domains restricted in their relative positions to one another, i.e. the VL domain may be N-terminal to the VH domain and vice versa. The only restriction is that a complimentary polypeptide chain be available in order to form a functional diabody. Where the VL and VH domains are derived from antibodies specific for different antigens, formation of a functional bispecific heterodimeric diabody requires the interaction of two different polypeptide chains, i.e. formation of a heterodimer. In contrast, where two differing polypeptide chains are free to interact, e.g. in a recombinant expression system, one comprising a VLA and a VHB (A, being a first epitope and B, being a second epitope) and the other comprising a VLB and a VHA, two differing binding sites may form: VLA-VHA and VLB-VHB. For all bispecific heterodimeric diabody polypeptide chain pairs, misalignment or mis-binding of the two chains is a possibility, e.g. interaction of VL-VL or VH-VH domains. However, purification of functional bispecific heterodimeric diabodies is easily managed based on the immunospecificity of the properly dimerized binding site using any affinity based method known in the art or exemplified herein, e.g. affinity chromatography.

The bispecific heterodimeric diabodies of the invention may simultaneously bind two separate and distinct epitopes. In certain aspects, at least one epitope binding site is specific for the CD3 determinant expressed on an immune effector cell e.g. expressed on T lymphocytes. In one aspect, the bispecific heterodimeric diabody molecule binds to the effector cell determinant and also activates the effector cell. In one aspect, the epitope-binding domain is capable of binding the P-cadherin tumor-associated antigen that is associated with breast, colorectal, ovarian, gastric, thyroid, prostate, cervical, pancreatic, lung (including but not limited to non-small cell lung cancer and small cell lunch cancer), bladder, liver, endometrial, head and neck, testicular, and glioblastoma cancer.

The bispecific heterodimeric diabodies of the present invention comprise antigen binding domains generally derived from immunoglobulins or antibodies. The antibodies from which the binding domains used in the methods of the invention are derived may be from any animal origin including birds and mammals (e.g. human, non-human primate, murine, donkey, sheep, rabbit, goat, guinea pig, camel, horse, or chicken). Preferably, the antibodies are human or humanized monoclonal antibodies. As used herein, "human" antibodies include antibodies having the amino acid sequence of a human immunoglobulin and include antibodies isolated from human immunoglobulin libraries or libraries of synthetic human immunoglobulin coding sequences or from mice that express antibodies from human genes.

The bispecific heterodimeric diabodies of the present invention may be characterized in a variety of ways. In particular, molecules of the invention may be assayed for the ability to immunospecifically bind to an antigen. Molecules that have been identified to immunospecifically bind to an antigen can then be assayed for their specificity and affinity for the antigen.

The bispecific heterodimeric diabodies of the present invention may be produced using a variety of methods well known in the art, including de novo protein synthesis and recombinant expression of nucleic acids encoding the binding proteins. The desired nucleic acid sequences may be produced by recombinant methods (e.g. PCR mutagenesis of an earlier prepared variant of the desired polynucleotide) or by solid-phase DNA synthesis. Usually recombinant expression methods are used. In one aspect, the invention provides a polynucleotide that comprises a sequence encoding an anti-CD3 VH and/or VL; in another aspect, the invention provides a polynucleotide that comprises a sequence encoding an anti-P-cadherin VH and/or VL. Because of the degeneracy of the genetic code, a variety of nucleic acid sequences encode each immunoglobulin amino acid sequence, and the present invention includes all nucleic acids encoding the binding proteins described herein.

Linkers/Peptides

The polypeptide chains of the bispecific heterodimeric diabodies may be comprise various linkers and peptides. The linkers and peptides may be 0, 1, 2, 3, 4, 5, 6, 7, 8, 9 or more amino acids. In certain aspects, the polypeptide chains of the bispecific heterodimeric diabodies may comprise a glycine-serine linker (Linker 1). In another aspect the Linker 1 may comprise, but is not limited to, the sequences of GGGSGGGG (SEQ ID NO: 68) and GGGGSGGGG (SEQ ID NO 69).

In certain aspects, the polypeptide chains of the bispecific heterodimeric diabodies may comprise a cysteine linker (Linker 2). In another aspect, the Linker 2 may further comprise at least one glycine residue. In one aspect, the Linker 2 may comprise, but is not limited to, the sequences selected of GFNRGEC (SEQ ID NO: 70), GVEPKSC (SEQ ID NO: 71), and GGCGGG (SEQ ID NO: 72). In certain aspects, the Linker 2 may comprise a truncated IgG1 hinge region having the sequence CPPCP (SEQ ID NO 60) and at least one glycine residue. In another aspect, the Linker 2 may comprise, but is not limited to, the sequences of GCPPCP (SEQ ID NO: 73), GGTGGCPPCP (SEQ ID NO: 74), GEPKSSDKTHTCPPCP (SEQ ID NO: 75) and GGTGGGEPKSSDKTHTCPPCP (SEQ ID NO: 76).

In certain aspects, the polypeptide chains of the bispecific heterodimeric diabodies may comprise a Linker 3. In one aspect, the Linker 3 may comprise, but is not limited to, the sequence of KAPSSSPME (SEQ ID NO 77).

In certain aspects, the polypeptide chains of the bispecific heterodimeric diabodies may comprise a Peptide 1. In certain aspects, the Peptide 1 may comprise a truncated IgG1 hinge region having the sequence CPPCP (SEQ ID NO 60). In one aspect, the Peptide 1 may comprise, but is not limited to, the sequence of DKTHTCPPCP (SEQ ID NO 96).

VF-DART

Figure 2:
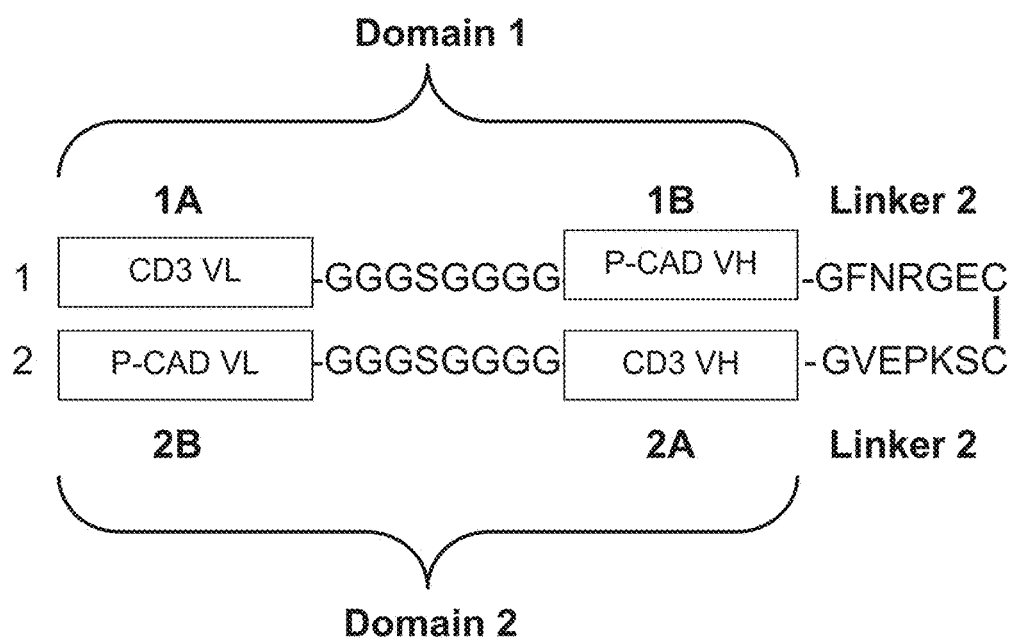
FIG. 2 provides a schematic representation of a VF-DART bispecific heterodimeric diabody that simultaneously targets and activates T cells (via CD3 antigen) and tumor cells (via P-cadherin antigen) having a first polypeptide chain (1) wherein a first heterodimer-promoting domain comprises a C-terminal peptide that forms a disulfide bond for stability with a C-terminal peptide of a second heterodimer-promoting domain of a second polypeptide chain (2) via a cysteine linker (Linker 2) having sequences, for example, GFNRGEC (SEQ ID NO: 70) or GVEPKSC (SEQ ID NO 71). The polypeptide chains of the bispecific heterodimeric diabodies may comprise a glycine-serine linker (Linker 1) having a sequence GGGSGGGG (SEQ ID NO: 68) as depicted herein.
Figure 3:
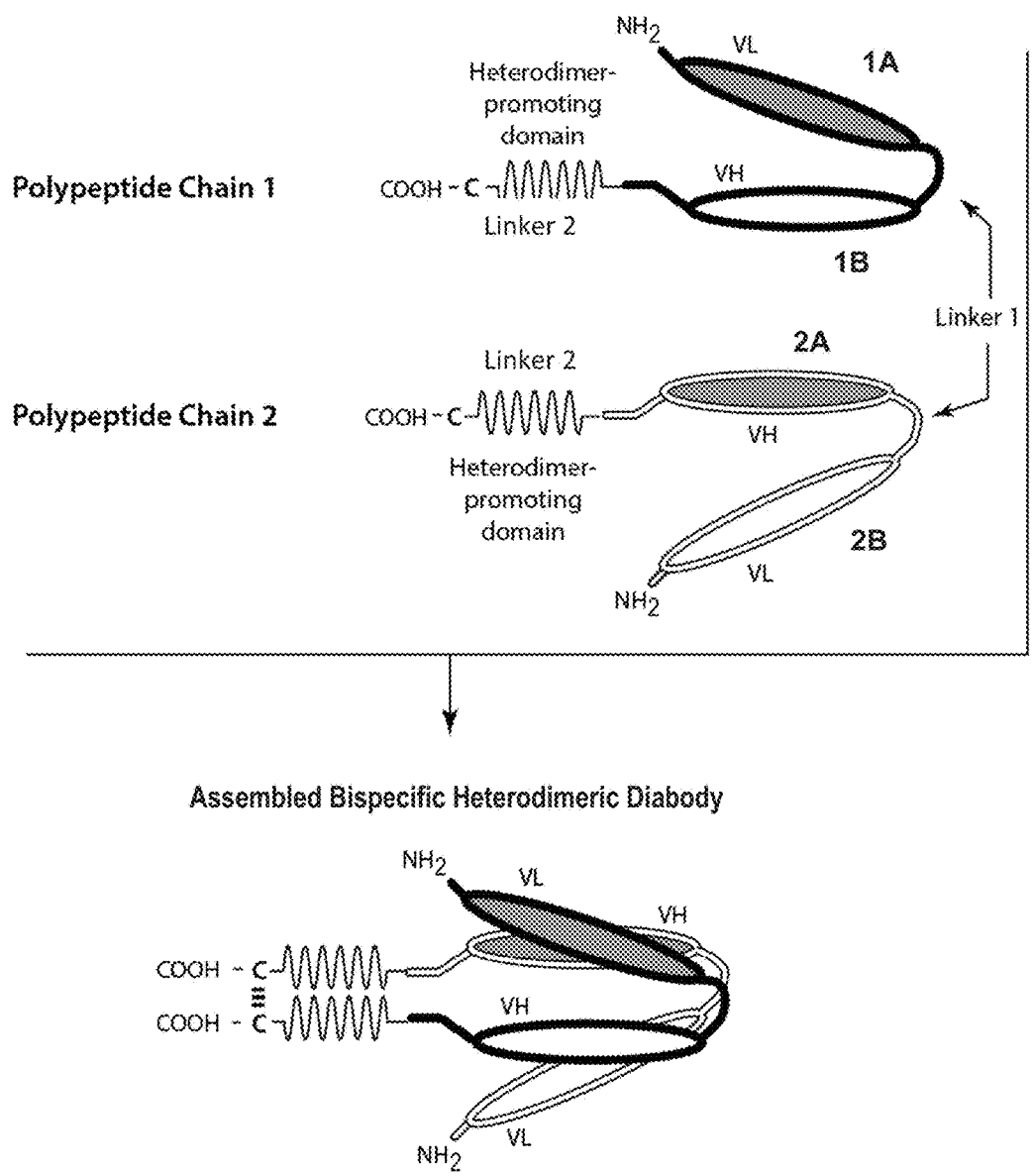
FIG. 3 provides a schematic representation of an assembled VF-DART bispecific heterodimeric diabody having a first polypeptide chain (1) and second polypeptide chain (2) wherein a first heterodimer-promoting domain (such as SEQ ID NO: 70 or SEQ ID NO: 71, described in detail below) and a second heterodimer-promoting domain (such as SEQ ID NO: 71 or SEQ ID NO: 70, depending on the selection of the first heterodimer promoting domain) comprise a cysteine residue.

In an aspect of the present invention, a bispecific heterodimeric diabody, known as a VF-DART, as shown in FIGS. 2 and 3, comprises a first polypeptide chain (1) and a second polypeptide chain (2).

In one aspect, the first polypeptide chain (1) may comprise: a Domain 1, comprising (i) a sub-Domain 1A which comprises a VL binding region of either an anti-P-cadherin antibody (P-CAD VL) or an anti-CD3 antibody (CD3 VL), (ii) a sub-Domain 1B which comprises a VH binding region of either an anti-P-cadherin antibody (P-CAD VH), if such sub-Domain 1A comprises a CD3 VL, or an anti-CD3 antibody (CD3 VH), if the sub-Domain 1A comprises a P-CAD VL, and the sub-Domain 1A and sub-Domain 1B may be covalently linked by a glycine-serine linker (Linker 1) such that the sub-Domain 1B and sub-Domain 1A do not associate to form an epitope binding site; and may comprise a first heterodimer promoting domain comprising a cysteine linker (Linker 2) on the sub-Domain 1B.

In another aspect, the first polypeptide chain (1) may comprise: a Domain 1, comprising (i) a sub-Domain 1A which comprises a P-CAD VH or a CD3 VH, (ii) a sub-Domain 1B which comprises either a P-CAD VL, if the sub-Domain 1A comprises a CD3 VH, or a CD3 VL, if the sub-Domain 1A comprises a P-CAD VH, the sub-Domain 1A and sub-Domain 1B may be covalently linked by a glycine-serine linker (Linker 1) such that the sub-Domain 1B and sub-Domain 1A do not associate to form an epitope binding site; and may comprise a first heterodimer promoting domain comprising a cysteine linker (Linker 2) on the sub-Domain 1B.

In one aspect, the first polypeptide chain (1) may comprise: a Domain 1, comprising (i) a sub-Domain 1A which comprises a P-CAD VL and (ii) a sub-Domain 1B which comprises a CD3 VH. In another aspect, the first polypeptide chain (1) may comprise: a Domain 1, comprising (i) a sub-Domain 1A which comprises a CD3 VL and (ii) a sub-Domain 1B which comprises a P-CAD VH. In a further aspect, the first polypeptide chain (1) may comprise: a Domain 1, comprising (i) a sub-Domain 1A which comprises a P-CAD VH and (ii) a sub-Domain 1B which comprises a CD3 VL. In another aspect, the first polypeptide chain (1) may comprise: a Domain 1, comprising (i) a sub-Domain 1A which comprises a CD3 VH and (ii) a sub-Domain 1B which comprises a P-CAD VL.

In one aspect, the second polypeptide chain (2) may comprise: a Domain 2, comprising (i) a sub-Domain 2B, which comprises a VL binding region of either an anti-P-cadherin antibody (P-CAD VL) or an anti-CD3 antibody (CD3 VL) depending on the VL domain selected for sub-Domain 1A, (ii) a sub-Domain 2A which comprises a VH binding region of either an anti-P-cadherin antibody (P-CAD VH), if such sub-Domain 2B comprises a CD3 VL, or an anti-CD3 antibody (CD3 VH), if such sub-Domain 2B comprises a P-CAD VL, and the sub-Domain 2B and sub-Domain 2A may be covalently linked by a glycine-serine linker (Linker 1) such that the sub-Domain 2B and sub-Domain 2A do not associate to form an epitope binding site; and may comprise a second heterodimer promoting domain comprising a cysteine linker (Linker 2) on the sub-Domain 2A.

In another aspect, the second polypeptide chain (2) may comprise: a Domain 2, comprising (i) a sub-Domain 2B which comprises a P-CAD VH or a CD3 VH, (ii) a sub-Domain 2A which comprises either a P-CAD VL, if such sub-Domain 2B comprises a CD3 VH, or a CD3 VL, if such sub-Domain 2B comprises a P-CAD VH, and the sub-Domain 2B and sub-Domain 2A may be covalently linked by a glycine-serine linker (Linker 1) such that the sub-Domain 2B and sub-Domain 2A do not associate to form an epitope binding site; and may comprise a second heterodimer promoting domain comprising a cysteine linker (Linker 2) on the sub-Domain 2A.

In one aspect, the second polypeptide chain (2) may comprise: a Domain 2, comprising (i) a sub-Domain 2B which comprises a P-CAD VL and (ii) a sub-Domain 2A which comprises a CD3 VH. In another aspect, the second polypeptide chain (2) may comprise: a Domain 2, comprising (i) a sub-Domain 2B which comprises a CD3 VL and (ii) a sub-Domain 2A which comprises a P-CAD VH. In a further aspect, the second polypeptide chain (2) may comprise: a Domain 2, comprising (i) a sub-Domain 2B which comprises a P-CAD VH and (ii) a sub-Domain 2A which comprises a CD3 VL. In another aspect, the second polypeptide chain (2) may comprise: a Domain 2, comprising (i) a sub-Domain 2B which comprises a CD3 VH and (ii) a sub-Domain 2A which comprises a P-CAD VL.

In another aspect of the VF-DART, the sub-Domain 1A and the sub-Domain 2A may associate to form a first binding site, having a VL/VH binding domain, that binds to an epitope on CD3 or P-cadherin, and the sub-Domain 1B and the sub-Domain 2B may associate to form a second binding site, having a VL/VH binding domain, that binds to an epitope on P-cadherin or CD3.

The first polypeptide chain (1) and second polypeptide chain (2) may be covalently bonded to one another, for example at the cysteine residues located within the first and second heterodimer promoting domain. In one aspect, the cysteine residue in Linker 2 of the first heterodimer promoting domain and the cysteine residue in the Linker 2 of the second heterodimer promoting domain may be linked by at least one disulfide bond.

In an aspect of the present invention, the CD3 VL may comprise the sequence of SEQ ID NO: 47 and the CD3 VH may be a sequence selected from the group consisting of SEQ ID NOS: 45 and 46. In another aspect, the P-CAD VL may be a sequence selected from the group consisting of SEQ ID NOS: 1, 3, 5, 7, 9, 11, 13, 15, 17, 19, 21, and 23 and the P-CAD VH may be a sequence selected from the group consisting of SEQ ID NOS: 2, 4, 6, 8, 10, 12, 14, 16, 18, 20, 22, and 24. In one aspect, the glycine-serine linker (Linker 1) may comprise a sequence selected from the group consisting of GGGSGGGG (SEQ ID NO: 68) and GGGGSGGGG (SEQ ID NO 69). In an aspect of the present invention, the cysteine linker (Linker 2) of the first heterodimer promoting domain may comprise the sequence of GFNRGEC (SEQ ID NO: 70) and the cysteine linker (Linker 2) of the second heterodimer promoting domain may comprise the sequence of GVEPKSC (SEQ ID NO: 71). In another aspect of the present invention, the cysteine linker (Linker 2) of the first heterodimer promoting domain may comprise the sequence of GVEPKSC (SEQ ID NO: 71) and the cysteine linker (Linker 2) of the second heterodimer promoting domain may comprise the sequence of GFNRGEC (SEQ ID NO: 70).

The sequences for the first and second polypeptide chains of VF-DART proteins with the various P-cadherin and CD3 antibodies described herein are provided in FIGS. 30A and 30B.

EK-DART Containing E/K Coil Regions

Heterodimer formation of the two different polypeptide chains of a bispecific heterodimeric diabody may also be promoted by the use of domains that have affinity for the opposite member and repulsion towards itself. An example of such a domain is a coiled-coil domain. For example, a first polypeptide chain (1) may include a first heterodimer promoting domain having a glutamic acid-rich region that forms a negatively charged alpha-helical coil (E-coil), and a second polypeptide chain (2) may include a second heterodimer promoting domain having a lysine rich region that forms a positively charged helical coil (K-coil), allowing for an electrostatic interaction to promote heterodimer formation. Homodimer formation may be reduced as an E-coil would have repulsive force for another E-coil-containing polypeptide and vice-versa for the K-coil.

In an aspect of the present invention, a bispecific heterodimeric diabody, known as an EK-DART, as shown in FIG. 4, comprises a first polypeptide chain (1) and a second polypeptide chain (2).

In one aspect, the first polypeptide chain (1) may comprise: a Domain 1, comprising (i) a sub-Domain 1A which comprises a VL binding region of either an anti-P-cadherin antibody (P-CAD VL) or an anti-CD3 antibody (CD3 VL), (ii) a sub-Domain 1B which comprises a VH binding region of either an anti-P-cadherin antibody (P-CAD VH), if the sub-Domain 1A comprises a CD3 VL, or an anti-CD3 antibody (CD3 VH), if the sub-Domain 1A comprises a P-CAD VL, and the sub-Domain 1A and sub-Domain 1B may be covalently linked by a glycine-serine linker (Linker 1) such that the sub-Domain 1A and sub-Domain 1B do not associate to form an epitope binding site; and may comprise a first heterodimer promoting domain comprising (i) a cysteine linker (Linker 2) on the sub-Domain 1B, and (ii) an E-coil region covalently linked to the Linker 2.

In another aspect, the first polypeptide chain (1) may comprise: a Domain 1, comprising (i) a sub-Domain 1A which comprises a P-CAD VH or a CD3 VH, (ii) a sub-Domain 1B which comprises either a P-CAD VL, if the sub-Domain 1A comprises a CD3 VH, or a CD3 VL, if the sub-Domain 1A comprises a P-CAD VH, and the sub-Domain 1A and sub-Domain 1B may be covalently linked by a glycine-serine linker (Linker 1) such that the sub-Domain 1A and sub-Domain 1B do not associate to form an epitope binding site; and may comprise a first heterodimer promoting domain comprising (i) a cysteine linker (Linker 2) on the sub-Domain 1B, and (ii) an E-coil region covalently linked to the Linker 2.

In one aspect, the first polypeptide chain (1) may comprise: a Domain 1, comprising (i) a sub-Domain 1A which comprises a P-CAD VL and (ii) a sub-Domain 1B which comprises a CD3 VH. In another aspect, the first polypeptide chain (1) may comprise: a Domain 1, comprising (i) a sub-Domain 1A which comprises a CD3 VL and (ii) a sub-Domain 1B which comprises a P-CAD VH. In a further aspect, the first polypeptide chain (1) may comprise: a Domain 1, comprising (i) a sub-Domain 1A which comprises a P-CAD VH and (ii) a sub-Domain 1B which comprises a CD3 VL. In another aspect, the first polypeptide chain (1) may comprise: a Domain 1, comprising (i) a sub-Domain 1A which comprises a CD3 VH and (ii) a sub-Domain 1B which comprises a P-CAD VL.

In one aspect, the second polypeptide chain (2) may comprise: a Domain 2, comprising (i) a sub-Domain 2B which comprises a VL binding region of either an anti-P-cadherin antibody (P-CAD VL) or an anti-CD3 antibody (CD3 VL) depending on the VL domain selected for sub-Domain 1A, (ii) a sub-Domain 2A which comprises a VH binding region of either an anti-P-cadherin antibody (P-CAD VH), if the sub-Domain 2B comprises a CD3 VL, or an anti-CD3 antibody (CD3 VH), if the sub-Domain 2B comprises a P-CAD VL, and the sub-Domain 2B and sub-Domain 2A may be covalently linked by a glycine-serine linker (Linker 1) such that the sub-Domain 2B and sub-Domain 2A do not associate to form an epitope binding site; and may comprise a second heterodimer promoting domain comprising (i) a cysteine linker (Linker 2) on the sub-Domain 2A and (ii) a K-coil region covalently linked to the Linker 2.

In another aspect, the second polypeptide chain (2) may comprise: a Domain 2, comprising (i) a sub-Domain 2B which comprises a P-CAD VH or a CD3 VH, (ii) a sub-Domain 2A which comprises either a P-CAD VL, if the sub-Domain 2B comprises a CD3 VH, or a CD3 VL, if the sub-Domain 2B comprises a P-CAD VH, and the sub-Domain 2B and sub-Domain 2A may be covalently linked by a glycine-serine linker (Linker 1) such that the sub-Domain 2B and sub-Domain 2A do not associate to form an epitope binding site; and may comprise a second heterodimer promoting domain comprising (i) a cysteine linker (Linker 2) on the sub-Domain 2A and (ii) a K-coil region covalently linked to the Linker 2.

In one aspect, the second polypeptide chain (2) may comprise: a Domain 2, comprising (i) a sub-Domain 2B which comprises a P-CAD VL and (ii) a sub-Domain 2A which comprises a CD3 VH. In another aspect, the second polypeptide chain (2) may comprise: a Domain 2, comprising (i) a sub-Domain 2B which comprises a CD3 VL and (ii) a sub-Domain 2A which comprises a P-CAD VH. In a further aspect, the second polypeptide chain (2) may comprise: a Domain 2, comprising (i) a sub-Domain 2B which comprises a P-CAD VH and (ii) a sub-Domain 2A which comprises a CD3 VL. In another aspect, the second polypeptide chain (2) may comprise: a Domain 2, comprising (i) a sub-Domain 2B which comprises a CD3 VH and (ii) a sub-Domain 2A which comprises a P-CAD VL.

In another aspect of the EK-DART, the sub-Domain 1A and the sub-Domain 2A may associate to form a first binding site, having a VL/VH binding domain region, that binds to an epitope on CD3 or P-cadherin, and the sub-Domain 1B and the sub-Domain 2B may associate to form a second binding site, having a VL/VH binding domain region, that binds to an epitope on P-cadherin or CD3.

The first polypeptide chain (1) and second polypeptide chain (2) may be covalently bonded to one another, for example at the cysteine residues located within the first and second heterodimer promoting domain. In one aspect, the cysteine residue in Linker 2 of the first heterodimer promoting domain and the cysteine residue in the Linker 2 of the second heterodimer promoting domain may be linked by at least one disulfide bond.

In an aspect of the present invention, the CD3 VL may comprise the sequence of SEQ ID NO: 47 and the CD3 VH may be a sequence selected from the group consisting of SEQ ID NOS: 45 and 46. In another aspect, the P-CAD VL may be a sequence selected from the group consisting of SEQ ID NOS: 1, 3, 5, 7, 9, 11, 13, 15, 17, 19, 21, and 23 and the P-CAD VH may be a sequence selected from the group consisting of SEQ ID NOS: 2, 4, 6, 8, 10, 12, 14, 16, 18, 20, 22, and 24. In one aspect, the glycine-serine linker (Linker 1) may comprise a sequence selected from the group consisting of GGGSGGGG (SEQ ID NO: 68) and GGGGSGGGG (SEQ ID NO 69). In an aspect of the invention, the cysteine linker (Linker 2) of the first heterodimer promoting domain and the second heterodimer domain may comprise the sequence of GGCGGG (SEQ ID NO: 72). In one aspect, first heterodimer promoting domain further comprises a glutamic acid-rich region (E-coil) comprising the sequence of EVAALEKEVAALEKEVAALEKEVAALEK (SEQ ID NO: 61). In another aspect, the second heterodimer promoting domain further comprises a lysine rich region (K-coil) comprising the sequence of KVAALKEKVAALKEKVAALKEKVAALKE (SEQ ID NO: 62).

Table 1 and FIGS. 31A and 31B provide the sequences for the first and second polypeptide chains of EK-DART proteins with the various P-cadherin and CD3 antibodies described herein.

TABLE 1

Sequences of the first and second polypeptide chains of EK-DART proteins.

| | EK-DART Sequence |
|---|---|
| 35 | P-CAD 35VL X CD3-1VH-K-COIL SEQ ID NO: 80<br>QSVLTQPPSVSAAPGQKVTISCSGSSSNIGNNYVSWYQQLPGTAPKLLIYDNNKRPSGIPD<br>RFSGSKSGTSATLGITGLQTGDEADYYCGTWDSSLSAVVFGGGTKLTVLGGGSGGGGEV<br>QLVESGGGLVQPGGSLRLSCAASGFTFSTYAMNWVRQAPGKGLEWVGRIRSKYNNYATY<br>YADSVKGRFTISRDDSKNSLYLQMNSLKTEDTAVYYCVRHGNFGNSYVSWFAYWGQGTL<br>VTVSSGGCGGGKVAALKEKVAALKEKVAALKEKVAALKE<br>CD3-1-2VL X P-CAD 35VH-E-COIL SEQ ID NO: 81<br>QAVVTQEPSLTVSPGGTVTLTCRSSTGAVTTSNYANWVQQKPGQAPRGLIGGTNKRAPW<br>TPARFSGSLLGGKAALTITGAQAEDEADYYCALWYSNLWVFGGGTKLTVLGGGSGGGG<br>EVQLVQSGAEVKKPGASVKVSCKASGYTFTSYGISWVRQAPGQGLEWMGWISAYNGNTN<br>YAQKLQGRVTMTTDTSTSTAYMELRSLRSDDTAVYYCATIDTASAFDIWGQGTMVTVSSG<br>GCGGGEVAALEKEVAALEKEVAALEKEVAALEK |
| 153 | P-CAD 153VL X CD3-2VH-K-COIL SEQ ID NO: 82<br>QSVLTQPPSVSAAPGQKVTISCSGSSSNIGNNYVSWYQQLPGTAPKLLIYDNNKRPSGIPD<br>RFSGSKSGTSATLGITGLQTGDEADYYCGTWDSSLSGVVFGGGTKLTVLGGGSGGGGEV<br>QLVESGGGLVQPGGSLRLSCAASGFTFNTYAMNWVRQAPGKGLEWVARIRSKYNNYATY<br>YADSVKDRFTISRDDSKNSLYLQMNSLKTEDTAVYYCVRHGNFGNSYVSWFAYWGQGTL<br>VTVSSGGCGGGKVAALKEKVAALKEKVAALKEKVAALKE<br>CD3-1-2VL X P-CAD 153VH-E-COIL SEQ ID NO: 83<br>QAVVTQEPSLTVSPGGTVTLTCRSSTGAVTTSNYANWVQQKPGQAPRGLIGGTNKRAPW<br>TPARFSGSLLGGKAALTITGAQAEDEADYYCALWYSNLWVFGGGTKLTVLGGGSGGGG<br>EVQLVQSGAEVKKPGASVKVSCKASGYTFTSYGISWVRQAPGQGLEWMGWISAYNGNTN<br>YAQKLQGRVTMTTDTSTSTAYMELRSLRSDDTAVYYCATIDTANAFGIWGQGTMVTVSSG<br>GCGGGEVAALEKEVAALEKEVAALEKEVAALEK |
| 154 | P-CAD 154VL X CD3-2VH-K-COIL SEQ ID NO: 84<br>QSVLTQPPSVSAAPGQKVTISCSGSSSNIGNNYVSWYQQLPGTAPKLLIYDNNKRPSGIPD<br>RFSGSKSGTSATLGITGLQTGDEADYYCGTWDSSLSSYVFGTGTKVTVLGGGSGGGGEV<br>QLVESGGGLVQPGGSLRLSCAASGFTFNTYAMNWVRQAPGKGLEWVARIRSKYNNYATY<br>YADSVKDRFTISRDDSKNSLYLQMNSLKTEDTAVYYCVRHGNFGNSYVSWFAYWGQGTL<br>VTVSSGGCGGGKVAALKEKVAALKEKVAALKEKVAALKE<br>CD3-1-2VL X P-CAD 154VH-E-COIL SEQ ID NO: 85<br>QAVVTQEPSLTVSPGGTVTLTCRSSTGAVTTSNYANWVQQKPGQAPRGLIGGTNKRAPW<br>TPARFSGSLLGGKAALTITGAQAEDEADYYCALWYSNLWVFGGGTKLTVLGGGSGGGG<br>EVQLVQSGAEVKKPGASVKVSCKASGYTFTSYGISWVRQAPGQGLEWMGWISAYNGNTN<br>YAQKLQGRVTMTTDTSTSTAYMELRSLRSDDTAVYYCATIDTATAFDIWGQGTMVTVSSG<br>GCGGGEVAALEKEVAALEKEVAALEKEVAALEK |
| 177 | P-CAD 177VL X CD3-1VH-K-COIL SEQ ID NO: 86<br>QSVLTQPPSVSAAPGQKVTISCSGSSSNIGNNYVSWYQQLPGTAPKLLIYDNNKRPSGIPD<br>RFSGSKSGTSATLGITGLQTGDEADYYCGTWDSSLSAYVFGTGTKVTVLGGGSGGGGEV<br>QLVESGGGLVQPGGSLRLSCAASGFTFSTYAMNWVRQAPGKGLEWVGRIRSKYNNYATY<br>YADSVKGRFTISRDDSKNSLYLQMNSLKTEDTAVYYCVRHGNFGNSYVSWFAYWGQGTL<br>VTVSSGGCGGGKVAALKEKVAALKEKVAALKEKVAALKE<br>CD3-1-2VL X P-CAD 177VH-E-COIL SEQ ID NO: 87<br>QAVVTQEPSLTVSPGGTVTLTCRSSTGAVTTSNYANWVQQKPGQAPRGLIGGTNKRAPW<br>TPARFSGSLLGGKAALTITGAQAEDEADYYCALWYSNLWVFGGGTKLTVLGGGSGGGG<br>EVQLVQSGAEVKKPGASVKVSCKASGYTFTSYGISWVRQAPGQGLEWMGWISAYNGNTN |

TABLE 1-continued

Sequences of the first and second polypeptide
chains of EK-DART proteins.

EK-DART Sequence

YAQKLQGRVTMTTDTSTSTAYMELRSLRSDDTAVYYCATIDTANAFDIWGQGTMVTVSSG
GCGGGEVAALEKEVAALEKEVAALEKEVAALEK

Bispecific Heterodimeric Diabodies Comprising Fc Regions or Portions Thereof

The invention encompasses bispecific heterodimeric diabodies comprising Fc regions or domains, or portions thereof. In certain aspects, the Fc region, or portion(s) thereof, comprises one or more constant domain(s) of the Fc region of IgG1, IgG2, IgG3 or IgG4 (e.g. a CH2 or CH3 domain). In other aspects, the invention encompasses molecules comprising an Fc region or portion thereof, wherein the Fc region or portion thereof comprises at least one amino acid modification (e.g. substitution) relative to a comparable wild-type Fc region or portion thereof. Variant Fc regions are well known in the art, and are primarily used to alter the phenotype of the antibody comprising the variant Fc region as assayed in any of the binding activity or effector function assays well known in the art, e.g. ELISA, SPR analysis, or ADCC. Such variant Fc regions, or portions thereof, may extend the plasma half-life and stability exhibited by a diabody molecule of the invention comprising an Fc region or portion thereof. In other aspects, the invention encompasses the use of any Fc variant known in the art.

In certain aspects, one or more modifications to the amino acids of the Fc region reduce the affinity and avidity of the Fc region and, thus, the diabody molecule of the invention, for one or more FcγR receptors. In a specific aspect, the invention encompasses diabodies comprising a variant Fc region, or portion thereof, wherein the variant Fc region comprises at least one amino acid modification relative to a wild type Fc region which variant Fc region only binds one FcγR, wherein the FcγR is FcγRIIIA. In another specific aspect, the invention encompasses diabodies comprising a variant Fc region, or portion thereof, wherein the variant Fc region comprises at least one amino acid modification relative to a wild type Fc region, which variant Fc region only binds one FcγR, wherein the FcγR is FcγRIIA. In another specific aspect, the invention encompasses diabodies comprising a variant Fc region or portion thereof, wherein the variant Fc region comprises at least one amino acid modification relative to a wild type Fc region, which variant Fc region only binds one FcγR, wherein the FcγR is FcγRIIB. In certain aspects, the invention encompasses molecules comprising a variant Fc region wherein the variant confers or mediates decreased ADCC activity (or other effector function) and/or an increased binding to FcγRIIB (CD32B), relative to a molecule comprising no Fc region or comprising a wild-type Fc region, as measured using methods known to one skilled in the art and described herein.

The invention also encompasses the use of an Fc region comprising domains or regions from two or more IgG isotypes. As known in the art, amino acid modification of the Fc region may profoundly affect Fc-mediated effector function and/or binding activity. However, these alterations in functional characteristics may be further refined and/or manipulated when implemented in the context of selected IgG isotypes. Similarly, the native characteristics of the isotype Fc may be manipulated by one or more amino acid modifications. The multiple IgG isotypes (i.e., IgG1, IgG2, IgG3 and IgG4) exhibit differing physical and functional properties including serum half-life, complement fixation, FcγR binding affinities and effector function activities (e.g. ADCC, CDC) due to differences in the amino acid sequences of their hinge and/or Fc regions. In certain aspects, the amino acid modification and IgG Fc region are independently selected based on their respective, separate binding and/or effector function activities in order to engineer a diabody with desired characteristics. In most aspects, the amino acid modifications and IgG hinge/Fc regions have been separately assayed for binding and/or effector function activity as described herein or known in the art in the context of an IgG1. In certain aspects, the amino acid modification and IgG hinge/Fc region display similar functionality, e.g. decreased ADCC activity (or other effector function) and/or an increased binding to FcγRIIB in the context of the diabody molecule or other Fc-containing molecule (e.g. and immunoglobulin). In other aspects, the invention encompasses variant Fc regions comprising combinations of amino acid modifications known in the art and selected IgG regions that exhibit novel properties, which properties were not detectable when the modifications and/or regions were independently assayed as described herein.

LP-DART

Figure 1B:
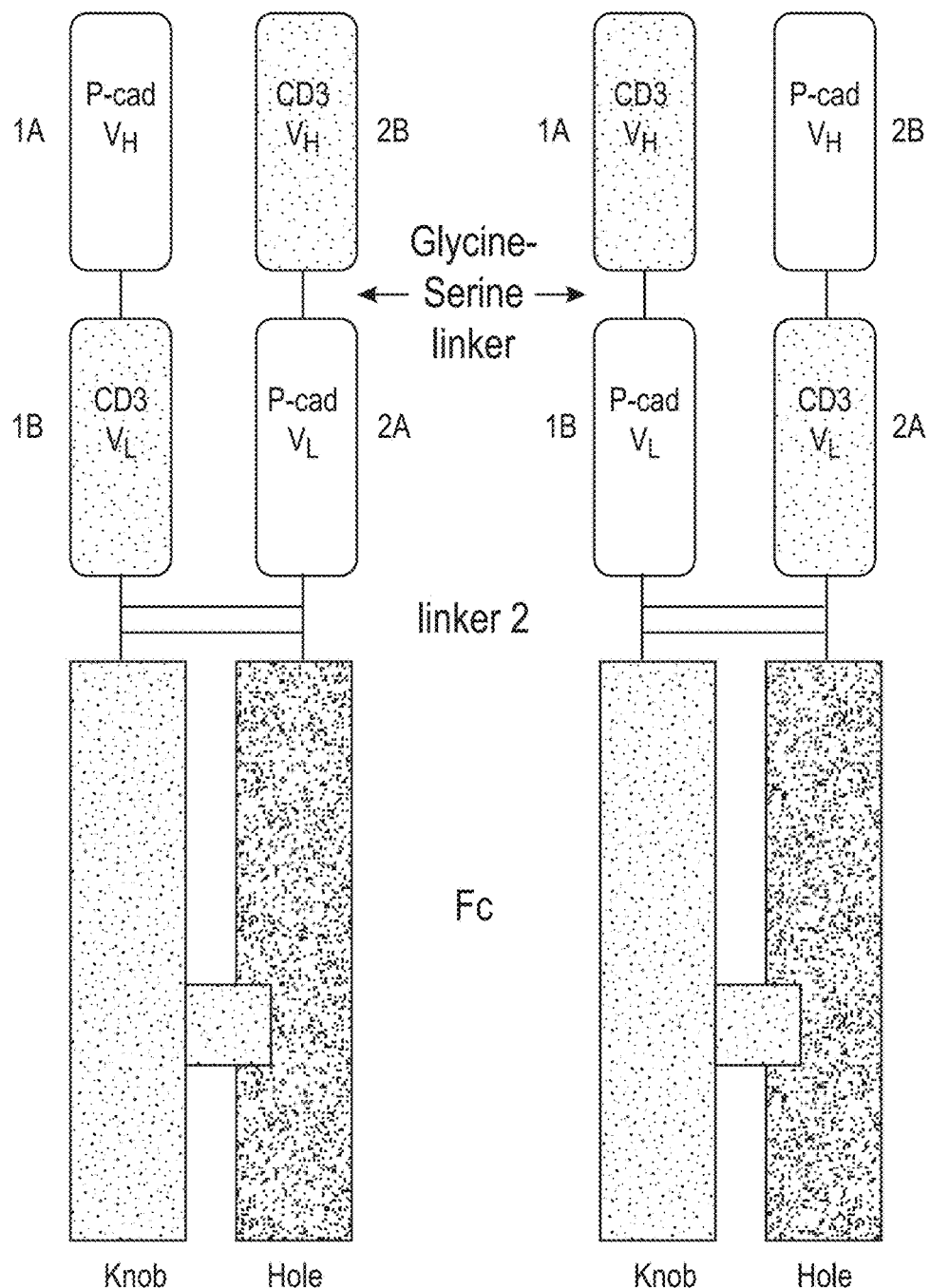

In an aspect of the present invention, a bispecific heterodimeric diabody having an Fc region, termed LP-DART, is shown in FIGS. 1 and 5. An LP-DART may be comprised of two scFv domains that bind a target antigen and CD3, which is fused to a Fc domain of IgG. In one aspect of the invention, the bispecific heterodimeric diabody may be comprised of two scFv domains that bind P-cadherin and CD3 epsilon, which is fused to a Fc domain of IgG1. In particular, FIGS. 1A and 1B show four alternative representations of anti-P-cadherin/anti-human CD3 LP-DART and FIG. 5 shows a general schematic of an assembled LP-DART. The LP-DART is similar to the structure described above for the VF-DART or EK-DART, except the first and second heterodimer promoting domains comprise an immunoglobulin Fc region having CH2 and/or CH3 domains of an immunoglobulin Fc region, wherein the CH2 and/or CH3 domains have been altered to comprise a knob (protuberance) or a hole (cavity). Modifications to the Fc portion of the LP-DART are described below.

In an aspect of the present invention, a LP-DART bispecific heterodimeric diabody, as shown in FIGS. 1A, 1B and 5, comprises a first polypeptide chain (1) and a second polypeptide chain (2).

In one aspect, the first polypeptide chain (1) may comprise: a Domain 1, comprising (i) a sub-Domain 1A which comprises a VL binding region of either an anti-P-cadherin antibody (P-CAD VL) or an anti-CD3 antibody (CD3 VL), (ii) a sub-Domain 1B which comprises a VH binding region of either an anti-P-cadherin antibody (P-CAD VH), if such sub-Domain 1A comprises a CD3 VL, or an anti-CD3 antibody (CD3 VH), if such sub-Domain 1A comprises a P-CAD VL, and the sub-Domain 1A and sub-Domain 1B may be covalently linked by a glycine-serine linker (Linker 1) such that the sub-Domain 1A and sub-Domain 1B do not associate to form an epitope binding site; and may comprise a first heterodimer promoting domain comprising (i) a cysteine linker (Linker 2) on the sub-Domain 1B and (ii) a Fc region having a CH2 and/or CH3 domain altered to comprise a knob Fc chain (protuberance) or a hole Fc chain (cavity) covalently linked to the Linker 2.

In another aspect, the first polypeptide chain (1) may comprise: a Domain 1, comprising (i) a sub-Domain 1A which comprises a P-CAD VH or a CD3 VH, (ii) a sub-Domain 1B which comprises either a P-CAD VL, if such sub-Domain 1A comprises a CD3 VH, or a CD3 VL, if such sub-Domain 1A comprises a P-CAD VH, and the sub-Domain 1A and sub-Domain 1B may be covalently linked by a glycine-serine linker (Linker 1) such that the sub-Domain 1A and sub-Domain 1B do not associate to form an epitope binding site; and may comprise a first heterodimer promoting domain comprising (i) a cysteine linker (Linker 2) on the sub-Domain 1B and (ii) a Fc region having a CH2 and/or CH3 domain altered to comprise a knob Fc chain (protuberance) or a hole Fc chain (cavity) covalently linked to the Linker 2.

In one aspect, the first polypeptide chain (1) may comprise: a Domain 1, comprising (i) a sub-Domain 1A which comprises a P-CAD VL and (ii) a sub-Domain 1B which comprises a CD3 VH. In another aspect, the first polypeptide chain (1) may comprise: a Domain 1, comprising (i) a sub-Domain 1A which comprises a CD3 VL and (ii) a sub-Domain 1B which comprises a P-CAD VH. In a further aspect, the first polypeptide chain (1) may comprise: a Domain 1, comprising (i) a sub-Domain 1A which comprises a P-CAD VH and (ii) a sub-Domain 1B which comprises a CD3 VL. In another aspect, the first polypeptide chain (1) may comprise: a Domain 1, comprising (i) a sub-Domain 1A which comprises a CD3 VH and (ii) a sub-Domain 1B which comprises a P-CAD VL.

In one aspect, the second polypeptide chain (2) may comprise: a Domain 2, comprising (i) a sub-Domain 2B which comprises a VL binding region of either an anti-P-cadherin antibody (P-CAD VL) or an anti-CD3 antibody (CD3 VL) depending on the VL domain selected for sub-Domain 1A, (ii) a sub-Domain 2A which comprises a VH binding region of either an anti-P-cadherin antibody (P-CAD VH), if such sub-Domain 2B comprises a CD3 VL, or an anti-CD3 antibody (CD3 VH), if such sub-Domain 2B comprises a P-CAD VL, and the sub-Domain 2B and sub-Domain 2A may be covalently linked by a glycine-serine linker (Linker 1) such that the sub-Domain 2B and sub-Domain 2A do not associate to form an epitope binding site; and may comprise a second heterodimer promoting domain comprising (i) cysteine linker (Linker 2) on the sub-Domain 2A and (ii) a Fc region having a CH2 and/or CH3 domain altered to comprise either a knob Fc chain (protuberance), if such first heterodimer region comprises a hole Fc chain (cavity), or a hole Fc chain (cavity), if such first heterodimer region comprises a knob Fc chain (protuberance), covalently linked to the Linker 2.

In another aspect, the second polypeptide chain (2) may comprise: a Domain 2, comprising (i) a sub-Domain 2B which comprises a P-CAD VH or a CD3 VH, (ii) a sub-Domain 2A which comprises either a P-CAD VL, if such sub-Domain 2B comprises a CD3 VH, or a CD3 VL, if such sub-Domain 2B comprises a P-CAD VH, and the sub-Domain 2B and sub-Domain 2A may be covalently linked by a glycine-serine linker (Linker 1) such that the sub-Domain 2B and sub-Domain 2A do not associate to form an epitope binding site; and may comprise a second heterodimer promoting domain comprising (i) a cysteine linker (Linker 2) on the sub-Domain 2A and (ii) a Fc region having a CH2 and/or CH3 domain altered to comprise either a knob Fc chain (protuberance), if such first heterodimer region comprises a hole Fc chain (cavity), or a hole Fc chain (cavity), if such first heterodimer region comprises a knob Fc chain (protuberance), covalently linked to the Linker 2.

In one aspect, the second polypeptide chain (2) may comprise: a Domain 2, comprising (i) a sub-Domain 2B which comprises a P-CAD VL and (ii) a sub-Domain 2A which comprises a CD3 VH. In another aspect, the second polypeptide chain (2) may comprise: a Domain 2, comprising (i) a sub-Domain 2B which comprises a CD3 VL and (ii) a sub-Domain 2A which comprises a P-CAD VH. In a further aspect, the second polypeptide chain (2) may comprise: a Domain 2, comprising (i) a sub-Domain 2B which comprises a P-CAD VH and (ii) a sub-Domain 2A which comprises a CD3 VL. In another aspect, the second polypeptide chain (2) may comprise: a Domain 2, comprising (i) a sub-Domain 2B which comprises a CD3 VH and (ii) a sub-Domain 2A which comprises a P-CAD VL.

In another aspect of the LP-DART, the sub-Domain 1A and the sub-Domain 2A may associate to form a first binding site, having a VL/VH binding domain region, that binds to an epitope on CD3 or P-cadherin, and the sub-Domain 1B and the sub-Domain 2B may associate to form a second binding site, having a VL/VH binding domain region, that binds to an epitope on P-cadherin or CD3.

The first polypeptide chain (1) and second polypeptide chain (2) may be covalently bonded to one another, for example at the cysteine residues located within the first and second heterodimer promoting domain. In one aspect, the cysteine residue in Linker 2 of the first heterodimer promoting domain and the cysteine residue in the Linker 2 of the second heterodimer promoting domain may be linked by at least one disulfide bond.

In an aspect of the present invention, the CD3 VL may comprise the sequence of SEQ ID NO: 47 and the CD3 VH may be a sequence selected from the group consisting of SEQ ID NOS: 45 and 46. In another aspect, the P-CAD VL may be a sequence selected from the group consisting of SEQ ID NOS: 1, 3, 5, 7, 9, 11, 13, 15, 17, 19, 21, and 23 and the P-CAD VH may be a sequence selected from the group consisting of SEQ ID NOS: 2, 4, 6, 8, 10, 12, 14, 16, 18, 20, 22, and 24. In one aspect, the glycine-serine linker (Linker 1) may comprise a sequence selected from the group consisting of GGGSGGGG (SEQ ID NO: 68) and GGGGSGGGG (SEQ ID NO 69).

In another aspect of the invention, the cysteine linker (Linker 2) may comprise a truncated IgG1 hinge region having the sequence CPPCP (SEQ ID NO 60) and at least one glycine residue preceding the hinge region. In one aspect, the Linker 2 may comprise a sequence selected from the group consisting of GCPPCP (SEQ ID NO: 73), GGTGGCPPCP (SEQ ID NO 74), GEPKSSDKTHTCPPCP (SEQ ID NO 75) and GGTGGGEPKSSDKTHTCPPCP (SEQ ID NO 76).

In one aspect, the first heterodimer promoting domain may comprise a Fc region having a CH2 and/or CH3 domain altered to comprise either a knob Fc chain (protuberance) comprising a sequence of SEQ ID NO: 63, or a hole Fc chain (cavity) comprising a sequence of SEQ ID NO: 64. In another aspect, the second heterodimer promoting domain may comprise a Fc region having a CH2 and/or CH3 domain altered to comprise either a knob Fc chain (protuberance) comprising a sequence of SEQ ID NO: 63, if such first heterodimer region comprises a hole Fc chain (cavity), or a hole Fc chain (cavity) comprising a sequence of SEQ ID NO: 64, if such first heterodimer region comprises a knob Fc chain (protuberance).

Table 2 and FIGS. 32A and 32B provide the amino acid sequences for the first and second polypeptide chains of LP-DART proteins with the various P-cadherin and CD3 antibodies described herein. SEQ ID NOs 117-124 provide the corresponding nucleotide sequences are referenced in parenthesis.

TABLE 2

Sequences of the first and second polypeptide chains of LP-DART proteins.

LP-DART Sequence

| | |
|---|---|
| 35 | P-CAD 35VL x CD3-1VH-Knob, SEQ ID NO: 88<br>QSVLTQPPSVSAAPGQKVTISCSGSSSNIGNNYVSWYQQLPGTAPKLLIYDNNKRPSGIPD<br>RFSGSKSGTSATLGITGLQTGDEADYYCGTWDSSLSAVVFGGGTKLTVLGGGSGGGEV<br>QLVESGGGLVQPGGSLRLSCAASGFTFSTYAMNWVRQAPGKGLEWVGRIRSKYNNYATY<br>YADSVKGRFTISRDDSKNSLYLQMNSLKTEDTAVYYCVRHGNFGNSYVSWFAYWGQGTL<br>VTVSSGCPPCPAPEAAGAPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIEKTISKAK<br>GQPREPQVCTLPPSREEMTKNQVSLWCLVKGFYPSDIAVEWESNGQPENNYKTTPPVLD<br>SDGSFFLYSKLTVDKSRWQQGNVFSCSVMHEALHNHYTQKSLSLSPG (SEQ ID NO: 117)<br>CD3-1-2VL x P-CAD 35VH-Hole, SEQ ID NO: 89<br>QAVVTQEPSLTVSPGGTVTLTCRSSTGAVTTSNYANWVQQKPGQAPRGLIGGTNKRAPW<br>TPARFSGSLLGGKAALTITGAQAEDEADYYCALWYSNLWVFGGGTKLTVLGGGSGGGG<br>EVQLVQSGAEVKKPGASVKVSCKASGYTFTSYGISWVRQAPGQGLEWMGWISAYNGNTN<br>YAQKLQGRVTMTTDTSTSTAYMELRSLRSDDTAVYYCATIDTASAFDIWGQGTMVTVSSG<br>CPPCPAPEAAGAPSVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPIEKTISKAKGQPREP<br>QVYTLPPCREEMTKNQVSLSCAVKGFYPSDIAVEWESNGQPENNYKTTPPVLDSDGSFFL<br>VSKLTVDKSRWQQGNVFSCSVMHEALHNHYTQKSLSLSPG (SEQ ID NO: 118) |
| 153 | P-CAD 153VL x CD3-1VH-Knob (153 LP-DART B), SEQ ID NO: 90<br>QSVLTQPPSVSAAPGQKVTISCSGSSSNIGNNYVSWYQQLPGTAPKLLIYDNNKRPSGIPD<br>RFSGSKSGTSATLGITGLQTGDEADYYCGTWDSSLSGVVFGGGTKLTVLGGGSGGGEV<br>QLVESGGGLVQPGGSLRLSCAASGFTFSTYAMNWVRQAPGKGLEWVGRIRSKYNNYATY<br>YADSVKGRFTISRDDSKNSLYLQMNSLKTEDTAVYYCVRHGNFGNSYVSWFAYWGQGTL<br>VTVSSGCPPCPAPEAAGAPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIEKTISKAK<br>GQPREPQVCTLPPSREEMTKNQVSLWCLVKGFYPSDIAVEWESNGQPENNYKTTPPVLD<br>SDGSFFLYSKLTVDKSRWQQGNVFSCSVMHEALHNHYTQKSLSLSPG (SEQ ID NO: 119)<br>CD3-1-2VL x P-CAD 153VH-Hole (153 LP-DART A), SEQ ID NO: 91<br>QAVVTQEPSLTVSPGGTVTLTCRSSTGAVTTSNYANWVQQKPGQAPRGLIGGTNKRAPW<br>TPARFSGSLLGGKAALTITGAQAEDEADYYCALWYSNLWVFGGGTKLTVLGGGSGGGG<br>EVQLVQSGAEVKKPGASVKVSCKASGYTFTSYGISWVRQAPGQGLEWMGWISAYNGNTN<br>YAQKLQGRVTMTTDTSTSTAYMELRSLRSDDTAVYYCATIDTANAFGIWGQGTMVTVSSG<br>CPPCPAPEAAGAPSVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPIEKTISKAKGQPREP<br>QVYTLPPCREEMTKNQVSLSCAVKGFYPSDIAVEWESNGQPENNYKTTPPVLDSDGSFFL<br>VSKLTVDKSRWQQGNVFSCSVMHEALHNHYTQKSLSLSPG (SEQ ID NO: 120) |
| 154 | P-CAD 154VL x CD3-1VH-Knob, SEQ ID NO: 92<br>QSVLTQPPSVSAAPGQKVTISCSGSSSNIGNNYVSWYQQLPGTAPKLLIYDNNKRPSGIPD<br>RFSGSKSGTSATLGITGLQTGDEADYYCGTWDSSLSSYVFGTGTKVTVLGGGSGGGEV<br>QLVESGGGLVQPGGSLRLSCAASGFTFSTYAMNWVRQAPGKGLEWVGRIRSKYNNYATY<br>YADSVKGRFTISRDDSKNSLYLQMNSLKTEDTAVYYCVRHGNFGNSYVSWFAYWGQGTL<br>VTVSSGCPPCPAPEAAGAPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIEKTISKAK<br>GQPREPQVCTLPPSREEMTKNQVSLWCLVKGFYPSDIAVEWESNGQPENNYKTTPPVLD<br>SDGSFFLYSKLTVDKSRWQQGNVFSCSVMHEALHNHYTQKSLSLSPG (SEQ ID NO: 121)<br>CD3-1-2VL x P-CAD 154VH-Hole, SEQ ID NO: 93<br>QAVVTQEPSLTVSPGGTVTLTCRSSTGAVTTSNYANWVQQKPGQAPRGLIGGTNKRAPW<br>TPARFSGSLLGGKAALTITGAQAEDEADYYCALWYSNLWVFGGGTKLTVLGGGSGGGG<br>EVQLVQSGAEVKKPGASVKVSCKASGYTFTSYGISWVRQAPGQGLEWMGWISAYNGNTN<br>YAQKLQGRVTMTTDTSTSTAYMELRSLRSDDTAVYYCATIDTATAFDIWGQGTMVTVSSG<br>CPPCPAPEAAGAPSVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPIEKTISKAKGQPREP<br>QVYTLPPCREEMTKNQVSLSCAVKGFYPSDIAVEWESNGQPENNYKTTPPVLDSDGSFFL<br>VSKLTVDKSRWQQGNVFSCSVMHEALHNHYTQKSLSLSPG (SEQ ID NO: 122) |
| 177 | P-CAD 177VL x CD3-1VH-Knob, SEQ ID NO: 94<br>QSVLTQPPSVSAAPGQKVTISCSGSSSNIGNNYVSWYQQLPGTAPKLLIYDNNKRPSGIPD<br>RFSGSKSGTSATLGITGLQTGDEADYYCGTWDSSLSAYVFGTGTKVTVLGGGSGGGEV<br>QLVESGGGLVQPGGSLRLSCAASGFTFSTYAMNWVRQAPGKGLEWVGRIRSKYNNYATY<br>YADSVKGRFTISRDDSKNSLYLQMNSLKTEDTAVYYCVRHGNFGNSYVSWFAYWGQGTL<br>VTVSSGCPPCPAPEAAGAPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIEKTISKAK<br>GQPREPQVCTLPPSREEMTKNQVSLWCLVKGFYPSDIAVEWESNGQPENNYKTTPPVLD<br>SDGSFFLYSKLTVDKSRWQQGNVFSCSVMHEALHNHYTQKSLSLSPG (SEQ ID NO: 123)<br>CD3-1-2VL x P-CAD 177VH-Hole, SEQ ID NO: 95<br>QAVVTQEPSLTVSPGGTVTLTCRSSTGAVTTSNYANWVQQKPGQAPRGLIGGTNKRAPW<br>TPARFSGSLLGGKAALTITGAQAEDEADYYCALWYSNLWVFGGGTKLTVLGGGGSGGGG |

TABLE 2-continued

Sequences of the first and second polypeptide chains of LP-DART proteins.

LP-DART Sequence

```
EVQLVQSGAEVKKPGASVKVSCKASGYTFTSYGISWVRQAPGQGLEWMGWISAYNGNTN
YAQKLQGRVTMTTDTSTSTAYMELRSLRSDDTAVYYCATIDTANAFDIWGQGTMVTVSSG
CPPCPAPEAAGAPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREP
QVYTLPPCREEMTKNQVSLSCAVKGFYPSDIAVEWESNGQPENNYKTTPPVLDSDGSFFL
VSKLTVDKSRWQQGNVFSCSVMHEALHNHYTQKSLSLSPG (SEQ ID NO: 124)
```

Effector Null Mutations in Human IgG1 CH2-CH3 and Removal of C-Terminal Lys.

The Fc region of human IgG1 was modified to remove the C-terminal lysine residue often cleaved post-translationally, as well as, introducing mutations L234A, L235A and G237A using standard primer-directed PCR mutagenesis to oblate effector function due to binding to FcγRIII (effector null phenotype).

Knobs-in-Holes Mutations in Human IgG1 CH2-CH3

'Knobs-in-holes' is an effective design strategy known in the art for engineering antibody heavy chain homodimers for heterodimerization. In this approach a 'knob' variant was obtained by replacement of a small amino acid with a larger one in one chain of the Fc region of IgG1 e.g. Y349C and T366W. The 'knob' was designed to insert into a 'hole' in the CH3 domain of the complimentary chain of the Fc region created by replacement of a large residue with a smaller one e.g. S354C, T366S, L368A and Y407V.

The knob-in-hole designation is analogous to the protuberance and cavity designation and may be used interchangeably.

A "protuberance" or "knob" refers to at least one amino acid side chain which projects from the interface of the first polypeptide and is therefore positionable in a compensatory cavity in the adjacent interface (i.e. the interface of the second polypeptide) so as to stabilize the heterodimer, and thereby favor heterodimer formation over homodimer formation, for example. The protuberance may exist in the original interface or may be introduced synthetically (e.g. by altering nucleic acid encoding the interface). Normally, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. The upper limit for the number of original residues which are replaced is the total number of residues in the interface of the first polypeptide.

Certain import residues for the formation of a protuberance are generally naturally occurring amino acid residues and are preferably selected from arginine (R), phenylalanine (F), tyrosine (Y) and tryptophan (W).

A "cavity" or "hole" refers to at least one amino acid side chain which is recessed from the interface of the second polypeptide and therefore accommodates a corresponding protuberance on the adjacent interface of the first polypeptide. The cavity may exist in the original interface or may be introduced synthetically (e.g. by altering nucleic acid encoding the interface). Normally, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. The upper limit for the number of original residues which are replaced is the total number of residues in the interface of the second polypeptide.

Certain import residues for the formation of a cavity are usually naturally occurring amino acid residues and are preferably selected from alanine (A), serine (S), threonine (T) and valine (V).

An "original" amino acid residue is one which is replaced by an "import" residue which can have a smaller or larger side chain volume than the original residue. The import amino acid residue can be a naturally occurring or non-naturally occurring amino acid residue, but preferably is the former. "Naturally occurring" amino acid residues are those residues encoded by the genetic code. By "non-naturally occurring" amino acid residue is meant a residue which is not encoded by the genetic code, but which is able to covalently bind adjacent amino acid residue(s) in the polypeptide chain. Examples of non-naturally occurring amino acid residues are norleucine, ornithine, norvaline, homoserine and other amino acid residue analogues such as those described in Ellman et al., Meth. Enzym. 202:301-336 (1991), for example. The method of the instant invention involves replacing at least one original amino acid residue, but more than one original residue can be replaced. Normally, no more than the total residues in the interface of the first or second polypeptide may comprise original amino acid residues which are replaced.

The protuberance or knob is "positionable" in the cavity or hole which means that the spatial location of the protuberance and cavity on the interface of the first polypeptide and second polypeptide respectively and the sizes of the protuberance and cavity are such that the protuberance may be located in the cavity without significantly perturbing the normal association of the first and second polypeptides at the interface. Since protuberances such as Tyr, Phe and Trp do not typically extend perpendicularly from the axis of the interface, the alignment of a protuberance with a corresponding cavity relies on modeling the protuberance/cavity pair based upon a three-dimensional structure such as that obtained by X-ray crystallography or nuclear magnetic resonance (NMR). This can be achieved using widely accepted techniques in the art.

Therefore, to favor heterodimerization of the resultant Fc regions, complimentary mutations were introduced such that each Fc chain would carry one set of mutations, Y349C and T366W for the knob (or protuberance) Fc chain (SEQ ID NO: 63), or S354C, T366S, L368A and Y407V for the hole (or cavity) Fc chain (SEQ ID NO: 64), as provided in Table 3. When co-transfected into a suitable mammalian host the DNA encoding the amino acid sequences of SEQ ID NOS: 63 and 64 produce an Fc region that is predominantly bispecific heterodimeric possessing one knob (or protuberance) Fc chain associated with one hole (or cavity) Fc chain.

In another aspect of the present invention, a C-terminal MP3-DART, as shown in FIG. 7, may comprise, in an

TABLE 3

Sequences of Fc regions.

| SEQ ID NO: | Sequence |
|---|---|
| SEQ ID NO: 63<br>Knob Fc chain<br>Mutations | APEAAGAPSVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPIEKTISKAKG<br>QPREPQVCTLPPSREEMTKNQVSLWCLVKGFYPSDIAVEWESNGQPENNYKTTP<br>PVLDSDGSFFLYSKLTVDKSRWQQGNVFSCSVMHEALHNHYTQKSLSLSPG |
| SEQ ID NO: 64<br>Hole Fc chain<br>Mutations | APEAAGAPSVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPIEKTISKAKG<br>QPREPQVYTLPPCREEMTKNQVSLSCAVKGFYPSDIAVEWESNGQPENNYKTTP<br>PVLDSDGSFFLVSKLTVDKSRWQQGNVFSCSVMHEALHNHYTQKSLSLSPG |

Using overlapping primer extension PCR, a 5' BspEI restriction enzyme recognition sequence TCCGGA (SEQ ID NO 67) was introduced for use in subcloning the knob (protuberance) and hole (cavity) Fc chains to each DART chain containing a 3' BspEI site. This restriction site codes for an in-frame insertion of the amino acids serine and glycine (ser-gly) at the DART-Fc junction. Anti-P-cadherin/anti-CD3 LP-DART proteins were constructed as described in Example 6.

The anti-P-cadherin/anti-CD3 LP-DART proteins of the present invention are stable against aggregation in thermal stability studies and, potent bispecific diabody-Fc fusions targeting both human CD3 and P-Cadherin. The knob-in-hole Fc domain allows for improved expression in CHO cells and improved purification resulting in high purity of desired heterodimer. The mutations engineered within the Fc domain abrogate FcγR binding thus potentially avoiding ADCC mediated T cell depletion. Further, the incorporation of the Fc domain to a DART protein enhances stability of the molecule as shown by differential scanning calorimetry (DSC) and forced aggregation assays when compared to clinically approved monoclonal antibodies. Additionally, the Fc domain improves the pharmacokinetic profile.

MP3 DART

Figure 6:
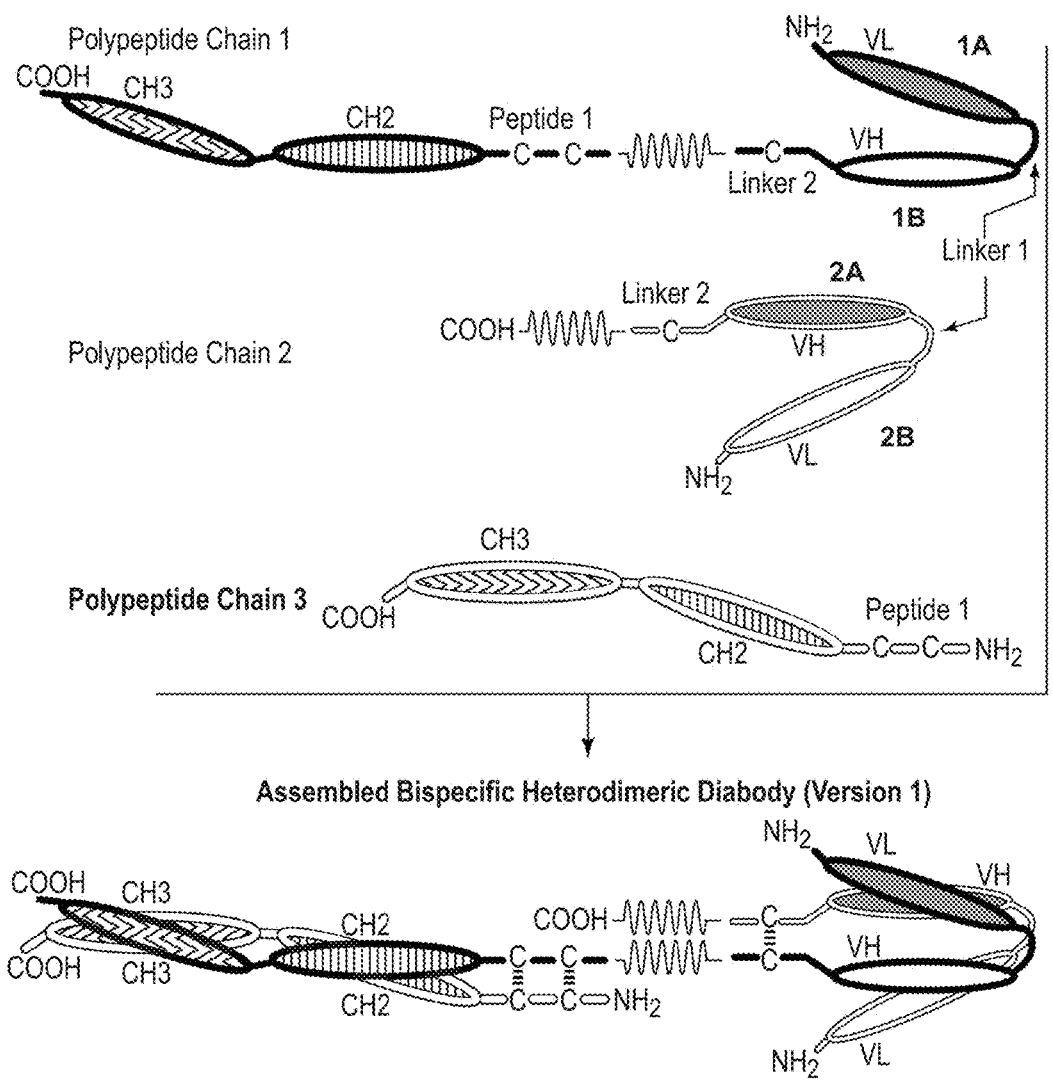
FIG. 6 provides the structures of an alternative bispecific heterodimeric diabody having an Fc domain termed MP3-DART. The bispecific heterodimeric diabody is attached to the N-terminal side of the Fc domain and is thus termed "N-terminal MP3-DART." The N-terminal MP3-DART comprises a first, second and third polypeptide chain which are schematically represented. The final structure of the N-terminal MP3-DART is represented.

FIGS. 6 and 7 are schematic representations of an N-terminal MP3-DART and a C-terminal MP3-DART bispecific heterodimeric diabody, respectively. Such MP3-DART proteins are composed of three polypeptide chains: a first polypeptide chain (1), a second polypeptide chain (2) and a third polypeptide chain (3).

In an aspect of the present invention, an N-terminal MP3-DART, as shown in FIG. 6, may comprises, in an N-terminal to C-terminal orientation, the first polypeptide chain (1) comprising: a Domain 1, comprising (i) a sub-Domain 1A which comprises a VL binding region of either an anti-P-cadherin antibody (P-CAD VL) or an anti-CD3 antibody (CD3 VL), (ii) a sub-Domain 1B which comprises a VH binding region of either an anti-P-cadherin antibody (P-CAD VH), if such sub-Domain 1A comprises a CD3 VL, or an anti-CD3 antibody (CD3 VH), if such sub-Domain 1A comprises a P-CAD VL, and the sub-Domain 1A and sub-Domain 1B may be covalently linked by a glycine-serine linker (Linker 1) such that the sub-Domain 1A and sub-Domain 1B do not associate to form an epitope binding site; and may comprise a first heterodimer promoting domain comprising (i) a cysteine linker (Linker 2) on the sub-Domain 1B, (ii) a cysteine Peptide 1 on the Linker 2 and (iii) a Fc region having a CH2 and/or CH3 domain of an IgG domain covalently linked to the Peptide 1.

In another aspect of the present invention, a C-terminal MP3-DART, as shown in FIG. 7, may comprise, in an N-terminal to C-terminal orientation, the first polypeptide chain (1) comprising: a first heterodimer promoting domain, comprising (i) a cysteine Peptide 1, (ii) a Fc region having CH2 and/or CH3 domain of an IgG Fc domain, and (iii) a Linker 3 on the Fc region; and a Domain 1, comprising (i) a sub-Domain 1A which comprises a VL binding region of either an anti-P-cadherin antibody (P-CAD VL) or an anti-CD3 antibody (CD3 VL), (ii) a sub-Domain 1B which comprises a VH binding region of either an anti-P-cadherin antibody (P-CAD VH), if such sub-Domain 1A comprises a CD3 VL, or an anti-CD3 antibody (CD3 VH), if such sub-Domain 1A comprises a P-CAD VL, and the sub-Domain 1A and sub-Domain 1B may be covalently linked by a glycine-serine linker (Linker 1) such that the sub-Domain 1A and sub-Domain 1B do not associate to form an epitope binding site, and (iv) a cysteine linker (Linker 2) on the sub-Domain 1B.

In another aspect, the first polypeptide chain (1) of the N-terminal MP3-DART or C-terminal MP3-DART, may comprises: a Domain 1, comprising (i) a sub-Domain 1A which comprises a P-CAD VH or a CD3 VH, (ii) a sub-Domain 1B which comprises either a P-CAD VL, if such sub-Domain 1A comprises a CD3 VH, or a CD3 VL, if such sub-Domain 1A comprises a P-CAD VH.

In one aspect, the first polypeptide chain (1) of the N-terminal MP3-DART or C-terminal MP3-DART may comprise: a Domain 1, comprising (i) a sub-Domain 1A which comprises a P-CAD VL and (ii) a sub-Domain 1B having a CD3 VH. In another aspect, the first polypeptide chain (1) may comprise: a Domain 1, comprising (i) a sub-Domain 1A which comprises a CD3 VL and (ii) a sub-Domain 1B which comprises a P-CAD VH. In a further aspect, the first polypeptide chain (1) may comprise: a Domain 1, comprising (i) a sub-Domain 1A which comprises a P-CAD VH and (ii) a sub-Domain 1B which comprises a CD3 VL. In another aspect, the first polypeptide chain (1) may comprise: a Domain 1, comprising (i) a sub-Domain 1A having a CD3 VH and (ii) a sub-Domain 1B which comprises a P-CAD VL.

In one aspect, the second polypeptide chain (2) of an N-terminal MP3-DART or C-terminal MP3-DART may comprise: a Domain 2, comprising (i) a sub-Domain 2B which comprises a VL binding region of either an anti-P-cadherin antibody (P-CAD VL) or an anti-CD3 antibody (CD3 VL) depending upon the VL domain selected for the first polypeptide chain of the MP3-DART, (ii) a sub-Domain 2A which comprises a VH binding region of either an anti-P-cadherin antibody (P-CAD VH), if such sub-Domain 2B comprises a CD3 VL, or an anti-CD3 antibody (CD3

VH), if such sub-Domain 2B comprises a P-CAD VL, and the sub-Domain 2B and sub-Domain 2A may be covalently linked by a glycine-serine linker (Linker 1) such that the sub-Domain 2B and sub-Domain 2A do not associate to form an epitope binding site; and may comprise a second heterodimer promoting domain comprising a cysteine linker (Linker 2) on sub-Domain 2A.

In another aspect, the second polypeptide chain (2) may comprise: a Domain 2, comprising (i) a sub-Domain 2B which comprises a P-CAD VH or a CD3 VH, (ii) a sub-Domain 2A which comprises either a P-CAD VL, if such sub-Domain 2B comprises a CD3 VH, or a CD3 VL, if such sub-Domain 2B comprises a P-CAD VH.

In one aspect, the second polypeptide chain (2) may comprise: a Domain 2, comprises (i) a sub-Domain 2B which comprises a P-CAD VL and (ii) a sub-Domain 2A having a CD3 VH. In another aspect, the second polypeptide chain (2) may comprise: a Domain 2, comprising (i) a sub-Domain 2B which comprises a CD3 VL and (ii) a sub-Domain 2A which comprises a P-CAD VH. In a further aspect, the second polypeptide chain (2) may comprise: a Domain 2, comprising (i) a sub-Domain 2B which comprises a P-CAD VH and (ii) a sub-Domain 2A which comprises a CD3 VL. In another aspect, the second polypeptide chain (2) may comprise: a Domain 2, comprising (i) a sub-Domain 2B which comprises a CD3 VH and (ii) a sub-Domain 2A which comprises a P-CAD VL.

In one aspect, the third polypeptide chain (3) of an N-terminal MP3-DART or C-terminal MP3-DART, in an N-terminal to C-terminal orientation, may comprise: a third heterodimer promoting domain comprising (i) a cysteine Peptide 1 and (ii) a Fc region having a CH2 and/or CH3 domain of an IgG Fc domain.

In one aspect of the invention, the sub-Domain 1A and the sub-Domain 2A may associate to form a first binding site, having a VL/VH region, that binds to an epitope on CD3 or P-cadherin, and the sub-Domain 1B and the sub-Domain 2B may associate to form a second binding site, having a VL/VH region, that binds to an epitope on P-cadherin or CD3.

The first polypeptide chain (1) and second polypeptide chain (2) may be covalently bonded to one another, for example at the cysteine residues located within the first and second heterodimer promoting domains. In one aspect, the cysteine residue in Linker 2 on the first heterodimer promoting domain and the cysteine residue in the Linker 2 on the second heterodimer promoting region may be linked by at least one disulfide bond.

The first heterodimer promoting domain of the first polypeptide chain (1) and the third heterodimer promoting domain of the third polypeptide chain (3) may associate with one another to form an immunoglobulin Fc region. The first polypeptide chain (1) and third polypeptide chain (3) may be covalently bonded to one another, for example at cysteine residues located within the first and third heterodimer promoting domains. In another aspect, the cysteine residue in Peptide 1 on the first heterodimer promoting domain and the cysteine residue in the Peptide 1 on the third heterodimer promoting domain may be linked by at least one disulfide bond.

In an aspect of the present invention, the CD3 VL may comprise the sequence of SEQ ID NO: 47 and the CD3 VH may be a sequence selected from the group consisting of SEQ ID NOS: 45 and 46. In another aspect, the P-CAD VL may be a sequence selected from the group consisting of SEQ ID NOS: 1, 3, 5, 7, 9, 11, 13, 15, 17, 19, 21, and 23 and the P-CAD VH may be a sequence selected from the group consisting of SEQ ID NOS: 2, 4, 6, 8, 10, 12, 14, 16, 18, 20, 22, and 24. In one aspect, the glycine-serine linker (Linker 1) may comprise a sequence selected from the group consisting of GGGSGGGG (SEQ ID NO: 68) and GGGGSGGGG (SEQ ID NO 69).

In an aspect of the present invention, the cysteine linker (Linker 2) may comprise a sequence selected from the group consisting of GFNRGEC (SEQ ID NO: 70) and GVEPKSC (SEQ ID NO: 71). In another aspect the cysteine linker (Linker 2) of the first heterodimer promoting domain may comprise the sequence of GFNRGEC (SEQ ID NO: 70) and the cysteine linker (Linker 2) of the second heterodimer promoting domain may comprise the sequence of GVEPKSC (SEQ ID NO: 71).

In certain aspects, the Linker 3 of the third heterodimer promoting region may comprise the sequence of KAPSSSPME (SEQ ID NO 77).

In certain aspects, the Peptide 1 on the first and third heterodimer promoting regions may comprise a truncated IgG1 hinge region having the sequence CPPCP (SEQ ID NO 60). In one aspect, the Peptide 1 may comprise, but is not limited to, the sequence of DKTHTCPPCP (SEQ ID NO 96).

The knob and hole strategy described herein may be utilized in the MP3-DART constructs to ensure proper pairing of the first and third polypeptide chains. Similar to the LP-DART described herein, the Fc region of human IgG1 may be modified to remove the C-terminal lysine residue often cleaved post-translationally, as well as, to introduce mutations L234A, L235A and G237A mutations to oblate effector function due to binding to FcγRIII (effector null phenotype). In one aspect a knob is created by modifying a native IgG Fc region to contain the modification T366W. In another aspect a hole is created by modifying a native IgG Fc region to contain the modification T366S, L368A and Y407V. Preferably the first polypeptide chain comprises the knob and the third polypeptide chain comprises the hole. To aid in purifying the MP3-DART™ from any homodimer of the third polypeptide chain, the protein A binding site of the CH2 and CH3 domains of the third polypeptide chain is preferably mutated by amino acid substitution at position 435 (H435R). Thus, any homodimer of the third polypeptide chain does not bind to protein A, whereas the MP3-DART™ retains its ability to bind protein A via the protein A binding site on the first polypeptide chain. Therefore, the knob (or protuberance) Fc chain may have the sequences of SEQ ID NO: 65 and the hole (or cavity) Fc chain may have sequence of SEQ ID NO: 66, as provided in Table 4.

TABLE 4

Sequences of Fc regions.

| SEQ ID NO: | Sequence |
|---|---|
| SEQ ID 65<br>Knob Fc chain<br>Mutations | APEAAGAPSVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPIEKTISKAKG<br>QPREPQVYTLPPSREEMTKNQVSLSCAVKGFYPSDIAVEWESNGQPENNYKTTP<br>PVLDSDGSFFLVSKLTVDKSRWQQGNVFSCSVMHEALHNRYTQKSLSLSPGK |
| SEQ ID 66<br>Hole Fc chain<br>mutations | APEAAGAPSVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPIEKTISKAKG<br>QPREPQVYTLPPSREEMTKNQVSLWCLVKGFYPSDIAVEWESNGQPENNYKTTP<br>PVLDSDGSFFLYSKLTVDKSRWQQGNVFSCSVMHEALHNHYTQKSLSLSPGK |

Table 5 describes the first (1), second (2) and third (3) polypeptide chains of exemplary N-terminal MP3-DART and C-terminal MP3-DART proteins that were constructed with the various P-cadherin and CD3-1 antibodies described herein. SEQ ID NOs.125-158 provide the amino acid and nucleotide sequences (referenced in parenthesis) for polypeptide chains 1, 2 and 3 for the N-terminal and C-terminal MP3-DART bispecific heterodimeric diabodies described in Table 5.

TABLE 5

First, second and third polypeptide chains of MP3- DART proteins.

| | First polypeptide chain (1) sequences | Second polypeptide chain (2) sequences | Third polypeptide chain (3) sequences |
|---|---|---|---|
| C-terminal MP3-DART P-CAD 35 VH and VL | P-CAD 35VLXCD3-1VH SEQ ID NO: 127 (SEQ ID NO: 128) | CD3-1-2VLXP-CAD 35VH SEQ ID NO: 129 (SEQ ID NO: 130) | SEQ ID NO: 125 (SEQ ID NO: 126) |
| C-terminal MP3-DART P-CAD153 VH and VL | P-CAD 153VLXCD3-1VH SEQ ID NO: 131 (SEQ ID NO: 132) | CD3-1-2VLXP-CAD 153VH SEQ ID NO: 133 (SEQ ID NO: 134) | SEQ ID NO: 125 (SEQ ID NO: 126) |
| C-terminal MP3-DART P-CAD154 VH and VL | P-CAD 154VLXCD3-1VH SEQ ID NO: 135 (SEQ ID NO: 136) | CD3-1-2VLXP-CAD 154VH SEQ ID NO: 137 (SEQ ID NO: 138) | SEQ ID NO: 125 (SEQ ID NO: 126) |
| C-terminal MP3-DART P-CAD177 VH and VL | P-CAD 177VLXCD3-1VH SEQ ID NO: 139 (SEQ ID NO: 140) | CD3-1-2VLXP-CAD 177VH SEQ ID NO: 141 (SEQ ID NO: 142) | SEQ ID NO: 125 (SEQ ID NO: 126) |
| N-terminal MP3-DART P-CAD 35 VH and VL | P-CAD 35VLXCD3-1VH SEQ ID NO: 143 (SEQ ID NO: 144) | CD3-1-2VLXP-CAD 35VH SEQ ID NO: 145 (SEQ ID NO: 146) | SEQ ID NO: 125 (SEQ ID NO: 126) |
| N-terminal MP3-DART P-CAD 153 VH and VL | P-CAD 153VLXCD3-1VH SEQ ID NO: 147 (SEQ ID NO: 148) | CD3-1-2VLXP-CAD 153VH SEQ ID NO: 149 (SEQ ID NO: 150) | SEQ ID NO: 125 (SEQ ID NO: 126) |
| N-terminal MP3-DART P-CAD 154 VH and VL | P-CAD 154VLXCD3-1VH SEQ ID NO: 151 (SEQ ID NO: 152) | CD3-1-2VLXP-CAD 154VH SEQ ID NO: 153 (SEQ ID NO: 154) | SEQ ID NO: 125 (SEQ ID NO: 126) |
| N-terminal MP3 DART P-CAD 177 VH and VL | P-CAD 177VLXCD3-1VH SEQ ID NO: 155 (SEQ ID NO: 156) | CD3-1-2VLXP-CAD 177VH SEQ ID NO: 157 (SEQ ID NO: 158) | SEQ ID NO: 125 (SEQ ID NO: 126) |

Engineered Cysteine Residues

In certain aspects, each polypeptide chain of the bispecific heterodimeric diabody may be engineered to comprise at least one cysteine residue that may interact with a counterpart cysteine residue on another polypeptide chain of the invention to form an inter-chain disulfide bond. The inter-chain disulfide bonds may serve to stabilize the diabody molecule, improving expression and recovery in recombinant systems, resulting in a stable and consistent formulation, as well as, improving the stability of the isolated and/or purified product in vivo. The cysteine residue or residues may be introduced as a single amino acid or as part of larger amino-acid sequence, e.g. hinge region, in any portion of the polypeptide chain. In a specific aspect, at least one cysteine residue is engineered to occur at the C-terminus of the polypeptide chain.

Cancer Treatment

The invention encompasses methods and compositions for treatment, prevention or management of cancer in a subject, comprising administering to the subject a therapeutically effective amount of a bispecific heterodimeric diabody engineered in accordance with the invention, which molecule further binds a cancer antigen. Molecules of the invention may be particularly useful for the prevention, inhibition, reduction of growth and/or regression of primary tumors and metastasis of cancer cells. Although not intending to be bound by a particular mechanism of action, molecules of the invention may mediate effector function which may result in tumor clearance, tumor reduction or a combination thereof.

Accordingly, the invention provides methods of preventing or treating cancer characterized by a P-cadherin cancer antigen by engineering the bispecific heterodimeric diabody to immunospecifically recognize the P-cadherin cancer antigen and a CD3 antigen on T cells. The bispecific heterodimeric diabodies that have been engineered according to the invention are useful for prevention or treatment of cancer, since they have a cytotoxic activity by anti-CD3 induced activated killer T cells.

Therefore an aspect of the present invention provides a method of treating P-cadherin positive cancer in a patient in need thereof, wherein the cancer is selected from the group consisting of breast, colorectal, ovarian, gastric, thyroid, prostate, cervical, pancreatic, lung (including but not limited to non-small cell lung cancer and small cell lunch cancer), bladder, liver, endometrial, head and neck, testicular, and glioblastoma cancer.

The invention also provides a bispecific heterodimeric diabody of the invention for use in the method of treating cancer defined herein. In addition, the invention provides the use of a bispecific heterodimeric diabody of the invention in the manufacture of a medicament for the treatment of cancer as defined herein.

In a specific aspect, a bispecific heterodimeric diabody of the invention inhibits or reduces the growth of cancer cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth of cancer cells in the absence of the bispecific heterodimeric diabody of the invention.

In a specific aspect, a bispecific heterodimeric diabody of the invention kills cells or inhibits or reduces the growth of cancer cells at least 5%, at least 10%, at least 20%, at least 25%, at least 30%, at least 35%, at least 40%, at least 45%, at least 50%, at least 60%, at least 70%, at least 75%, at least 80%, at least 85%, at least 90%, at least 95%, or at least 100% better than in the absence of the bispecific heterodimeric diabody of the invention.

The invention further encompasses administering the molecules of the invention in combination with other therapies known to those skilled in the art for the treatment or prevention of cancer including but not limited to, current standard and experimental chemotherapies, biological therapies, immunotherapies, radiation therapies, or surgery. In some aspects, the molecules of the invention may be administered in combination with a therapeutically or prophylactically effective amount of one or more agents, therapeutic antibodies or other agents known to those skilled in the art for the treatment and/or prevention of cancer.

Accordingly, methods for treating cancer include administering to a patient in need thereof an effective amount of a bispecific heterodimeric diabody of the present invention in combination with a chemotherapeutic agent. Such combination treatment may be administered separately, sequentially, or simultaneously. Suitable chemotherapeutic agents include, but are not limited to, 5-fluorouracil, asparaginase, BCNU, bleomycin, calicheamicin, camptothecins, carboplatin, cisplatin, cyclophosphamide, cytarabine, cytoxan, dacarbazine, dactinomycin, daunorubicin, docetaxel, doxorubicin, etoposide, hydroxyurea, idarubicin, ifosfamide, irinotecan, L-asparaginase, mercaptopurine, methotrexate, mitomycin, mitoxantrone, nitrogen mustards, nitrosoureas, paclitaxel, plicamycin, procarbizine, taxol, thioguanine, topotecan, vinblastine, vincristine, and vinorelbine, The dosage amounts and frequencies of administration provided herein are encompassed by the terms therapeutically effective and prophylactically effective. The dosage and frequency further may vary according to factors specific for each patient depending on the specific therapeutic or prophylactic agents administered, the severity and type of cancer, the route of administration, as well as age, body weight, response, and the past medical history of the patient. Suitable regimens may be selected by one skilled in the art by considering such factors and by following, for example, dosages reported in the literature and recommended in the Physician's Desk Reference ($56^{th}$ ed., 2002).

The bispecific heterodimeric diabodies of the present invention may be in the form of a pharmaceutical composition for administration that are formulated to be appropriate for the selected mode of administration, and pharmaceutically acceptable diluent or excipients, such as buffers, surfactants, preservatives, solubilizing agents, isotonicity agents, stabilizing agents, carriers, and the like. Remington's Pharmaceutical Sciences, Mack Publishing Co., Easton Pa., $18^{th}$ ed., 1995, provides a compendium of formulation techniques as are generally known to practitioners.

These pharmaceutical compositions may be administered by any means known in the art that achieve the generally intended purpose to treat cancer. The route of administration may be parenteral, defined herein as referring to modes of administration that include but not limited to intravenous, intramuscular, intraperitoneal, subcutaneous, and intraarticular injection and infusion. The dosage administered may be dependent upon the age, health, and weight of the recipient, kind of concurrent treatment, if any, frequency of treatment, and the nature of the effect desired.

Compositions within the scope of the invention include all compositions wherein a bispecific heterodimeric diabody is present in an amount that is effective to achieve the desired medical effect for treating cancer. While individual needs may vary from one patient to another, the determination of the optimal ranges of effective amounts of all of the components is within the ability of the clinician of ordinary skill.

The present invention provides kits that may be used in the above methods. In one aspect, a kit comprises a bispecific heterodimeric diabody of the invention. In another aspect, a kit further comprises one or more other prophylactic or therapeutic agents useful for the treatment of cancer, in one or more containers. In certain aspects, the other prophylactic or therapeutic agent is a chemotherapeutic. In other aspects, the prophylactic or therapeutic agent is a biological or hormonal therapeutic.

Several aspects of the pharmaceutical compositions, prophylactic, or therapeutic agents of the invention are preferably tested in vitro, in a cell culture system, and in an animal model organism, such as a rodent animal model system, for the desired therapeutic activity prior to use in humans.

Toxicity and efficacy of the prophylactic and/or therapeutic protocols of the instant invention maybe determined by standard pharmaceutical procedures in cell cultures or experimental animals, e.g. for determining the $LD_{50}$ (the dose lethal to 50% of the population) and the $ED_{50}$ (the dose therapeutically effective in 50% of the population). The dose ratio between toxic and therapeutic effects is the therapeutic index and it may be expressed as the ratio $LD_{50}/ED_{50}$. Prophylactic and/or therapeutic agents that exhibit large therapeutic indices are preferred.

Further, any assays known to those skilled in the art may be used to evaluate the prophylactic and/or therapeutic utility of the therapies or combinatorial therapies disclosed herein for treatment or prevention of cancer.

Biological Deposits

Representative materials of the present invention were deposited in the American Type Culture Collection, 10801 University Boulevard, Manassas, Va. 20110-2209, USA (ATCC) on Dec. 20, 2013. Vector 153 LP-DART A having ATCC Accession No. PTA-120809 comprises a recombinant human DNA insert encoding P-cadherin LP-DART (Fc-fusion diabody) Chain A, and vector 153 LP-DART B having ATCC Accession No. PTA-120810 comprises a recombinant human DNA insert encoding P-cadherin LP- DART (Fc-fusion diabody) Chain B. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer Inc and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The following examples of specific aspects for carrying out the present invention are offered for illustrative purposes only, and are not intended to limit the scope of the present invention in any way.

Example 1

Generation of P-Cadherin Antibodies and Bispecific Heterodimeric Diabodies

Bispecific heterodimeric diabodies were constructed to assess the recombinant production, purification and binding characteristics of each. The affinity purified bispecific heterodimeric diabodies were produced by the recombinant expression systems described herein. ELISA and SPR analysis further revealed that the covalent bispecific heterodimeric diabodies exhibited affinity for both target antigens, P-cadherin and CD-3, and could bind both antigens simultaneously.

A. Phage Display

Single chain fragment variable (scFv) moieties that bind to the extracellular domain (ECD) of P-cadherin were identified with a phage display library composed of scFv derived from non-immunized human donors utilizing techniques known in the art. The binding of the scFvs expressed on the surface of phage was measured on P-cadherin protein constructs and P-cadherin-expressing cells by standard ELISA techniques.

B. Sequencing Analysis

ScFv fragments were sequenced with primers 5' GGAGATTTTCAACGTGAA 3' (SEQ ID NO: 58) and 5' CTCTTCTGAGATGAGTTTTTG 3' (SEQ ID NO: 59) as either unpurified bacterial glycerol stock or as purified plasmid using conventional methods.

C. Conversion to DART

ScFv fragments that demonstrated strong recombinant P-cadherin or cell surface binding (>3× background or negative cell binding) were selected for subcloning into DART proteins. DART design and cloning methods were previously described (Johnson et al, J Mol Biol, 399:436-449, 2010; Moore et al, Blood, 117(17):4542-51, 2011). Methods for adapting novel anti-P-cadherin scFv from the phage display library are as follows: fragments were amplified by standard polymerase chain reaction (PCR) with primers incorporating BamHI/BspEI for VH and BssHII/BamHI for VL. Fragments were cut with corresponding restriction enzymes according to manufacturer's specifications (New England Biolabs).

To generate a DART expression vector, anti-P-cadherin VH (P-CAD VH) or VL (P-CAD VL) scFv were gel purified (QIAGEN® Gel Purification Kit) and ligated separately into mammalian expression vectors containing either the anti-CD3 VL (CD3 VL) or VH (CD3 VH) scFv.

For the generation of a VF-DART, as shown in FIGS. 2 and 3, the DART expression vector further comprised a first and second heterodimer promoting domain each having a cysteine linker (Linker 2), such as GFNRGEC (SEQ ID NO: 70) or GVEPKSC (SEQ ID NO: 77).

To generate an EK-DART, as shown in FIG. 4, the DART expression vector further comprised a first and second heterodimer promoting domain each having a cysteine linker (Linker 2), such as GGCGGG (SEQ ID NO: 72), and either an E-coil domain (SEQ ID NO: 61) or a K-coil domain (SEQ ID NO: 62).

To generate a LP-DART, as shown in FIGS. 1 and 5, the DART expression vectors further comprised a first and second heterodimer promoting domain each having a cysteine linker (Linker 2), such as GCPPCP (SEQ ID NO: 73), GGTGGCPPCP (SEQ ID NO 74), GEPKSSDKTHTCPPCP (SEQ ID NO 75), or GGTGGGEPKSSDKTHTCPPCP (SEQ ID NO 76), and either a "knob" Fc chain (SEQ ID NO: 63) or a "hole" Fc chain (SEQ ID NO: 64).

In addition to novel anti-P-cadherin scFv from the phage display library, the VH and VL domains from the anti-P-cadherin clinical mAb PF-03732010 (Zhang et al, Clin Cancer Res. 16(21), 5177-5188, 2010) were also sub-cloned into the various DART expression vectors described above to act as a positive control.

The DART proteins were then transiently expressed in mammalian cells by co-transfecting expression vectors into HEK 293 cells. DART proteins retaining P-cadherin affinity were affinity purified using anti-coiled-coil mAb 15F1 coupled to CNBr-activated sepharose 4B (GE Healthcare, Piscataway, N.J.). The biochemical properties of the purified DART proteins were assessed by SDS-PAGE and SEC.

Table 6 provides the VL and VH amino acid sequences for the anti-P-cadherin scFv clones generated by the techniques described herein. CDRs for clones 20 and 30 are underlined according to Kabat. SEQ ID NOs 97-116 provide the corresponding nucleotide sequences referenced in parenthesis.

TABLE 6

P-CAD VL and VH sequences.

| SEQ ID NO.<br>P-CAD Clone # | SEQUENCE |
|---|---|
| SEQ ID NO: 1<br>P-CAD 33 VL | QSVLTQPPSVSAAPGQKVTISCSGSSSNIGNNYVSWYQQLPGTAPKLLIYDNNKR<br>PSGIPDRFSGSKSGTSATLGITGLQTGDEADYYCGTWDSSLSAYVFGTGTKVTVL |
| SEQ ID NO: 2<br>P-CAD 33 VH | QMQLVQSGAEVKKPGASVKVSCKASGYTFTSYGISWVRQAPGQGLEWMGWISA<br>YNGNTNYAQKLQGRVTMTTDTSTSTAYMELRSLRSDDTAVYYCALIGSGVAFDIW<br>GQGTMVTVSS |
| SEQ ID NO: 3<br>P-CAD 34 VL | QSVVTQPPSVSAAPGQKVTISCSGSSSNIGNNYVSWYQQLPGTAPKLLIYDNNKR<br>PSGIPDRFSGSKSGTSATLGITGLQTGDEADYYCGTWDSSLSAWVFGGGTKLTVL |
| SEQ ID NO: 4<br>P-CAD 34 VH | EVQLVQSGAEVKKPGASVKVSCKASGYTFTSYGISWVRQAPGQGLEWMGWISAY<br>NGNTNYAQKLQGRVTMTTDTSTSTAYMELRSLRSDDTAVYYCATIDTASAFDIWG<br>QGTMVTVSS |
| SEQ ID NO: 5<br>P-CAD 35 VL<br>(SEQ ID NO: 97) | QSVLTQPPSVSAAPGQKVTISCSGSSSNIGNNYVSWYQQLPGTAPKLLIYDNNKR<br>PSGIPDRFSGSKSGTSATLGITGLQTGDEADYYCGTWDSSLSAVVFGGGTKLTVL |
| SEQ ID NO: 6<br>P-CAD 35 VH<br>(SEQ ID NO: 98) | EVQLVQSGAEVKKPGASVKVSCKASGYTFTSYGISWVRQAPGQGLEWMGWISAY<br>NGNTNYAQKLQGRVTMTTDTSTSTAYMELRSLRSDDTAVYYCATIDTASAFDIWG<br>QGTMVTVSS |
| SEQ ID NO: 7<br>P-CAD 153 VL<br>(SEQ ID NO: 99) | QSVLTQPPSVSAAPGQKVTISCSGSSSNIGNNYVSWYQQLPGTAPKLLIYDNNKR<br>PSGIPDRFSGSKSGTSATLGITGLQTGDEADYYCGTWDSSLSGVVFGGGTKLTVL |
| SEQ ID NO: 8<br>P-CAD 153 VH<br>(SEQ ID NO: 100) | EVQLVQSGAEVKKPGASVKVSCKASGYTFTSYGISWVRQAPGQGLEWMGWISAY<br>NGNTNYAQKLQGRVTMTTDTSTSTAYMELRSLRSDDTAVYYCATIDTANAFGIWG<br>QGTMVTVSS |
| SEQ ID NO: 9<br>P-CAD 154 VL<br>(SEQ ID NO: 101) | QSVLTQPPSVSAAPGQKVTISCSGSSSNIGNNYVSWYQQLPGTAPKLLIYDNNKR<br>PSGIPDRFSGSKSGTSATLGITGLQTGDEADYYCGTWDSSLSSYVFGTGTKVTVL |
| SEQ ID NO: 10 P-<br>CAD 154 VH<br>(SEQ ID NO: 102) | EVQLVQSGAEVKKPGASVKVSCKASGYTFTSYGISWVRQAPGQGLEWMGWISAY<br>NGNTNYAQKLQGRVTMTTDTSTSTAYMELRSLRSDDTAVYYCATIDTATAFDIWG<br>QGTMVTVSS |
| SEQ ID NO: 11<br>P-CAD 163 VL<br>(SEQ ID NO: 103) | QSVLTQPPSVSAAPGQKVTISCSGSSSNIGNNYVSWYQQLPGTAPKLLIYDNNKR<br>PSGIPDRFSGSKSGTSATLGITGLQTGDEADYYCGTWDSSLSAYVFGTGTKVTVL |
| SEQ ID NO: 12<br>P-CAD 163 VH<br>(SEQ ID NO: 104) | EVQLVQSGAEVKKPGASVKVSCKASGYTFTSYGFSWMRQAPGQGLEWMGWISA<br>YNGNTNYAQKLQGRVTMTTDTSTSTAYMELRSLRSDDTAVYYCATIDTASAFDIW<br>GQGTMVTVSS |
| SEQ ID NO: 13<br>P-CAD 165 VL<br>(SEQ ID NO: 105) | QSVLTQPPSVSAAPGQKVTISCSGSSSNIGNNYVSWYQQLPGTAPKLLIYDNNKR<br>PSGIPDRFSGSKSGTSATLGITGLQAGDEADYYCGTWDSSLSAYVFGTGTKVTVL |
| SEQ ID NO: 14<br>P-CAD 165 VH<br>(SEQ ID NO: 106) | EVQLVQSGAEVKKPGASVKVSCKASGYTFTSYGISWVRQAPGQGLEWMGWISAY<br>NGNTNYAQKLQGRVTMTTDTSTSTAYMELRSLRSDDTAVYYCATIDTANAFDIWG<br>QGTMVTVSS |
| SEQ ID NO: 15<br>P-CAD 177 VL<br>(SEQ ID NO: 107) | QSVLTQPPSVSAAPGQKVTISCSGSSSNIGNNYVSWYQQLPGTAPKLLIYDNNKR<br>PSGIPDRFSGSKSGTSATLGITGLQTGDEADYYCGTWDSSLSAYVFGTGTKVTVL |

TABLE 6-continued

P-CAD VL and VH sequences.

| SEQ ID NO. P-CAD Clone # | SEQUENCE |
|---|---|
| SEQ ID NO: 16 P-CAD 177 VH (SEQ ID NO: 108) | EVQLVQSGAEVKKPGASVKVSCKASGYTFTSYGISWVRQAPGQGLEWMGWISAY NGNTNYAQKLQGRVTMTTDTSTSTAYMELRSLRSDDTAVYYCATIDTANAFDIWG QGTMVTVSS |
| SEQ ID NO: 17 P-CAD 178 VL (SEQ ID NO: 109) | QSVLTQPPSVSAAPGQKVTISCSGSSSNIGNNYVSWYQQLPGTAPKLLIYDNNKR PSGIPDRFSGSKSGTSATLGITGLQTGDEADYYCGTWDSSLSAVVFGGGTKLTVL |
| SEQ ID NO: 18 P-CAD 178 VH (SEQ ID NO: 110) | EVQLVQSGAEVKKPGASVKVSCKASGYTFTSYGISWVRQAPGQGLEWMGWISAY NGNTNYAQKLQGRVTMTTDTSTSTAYMELRSLRSDDTAVYYCATIDTANAFDIWG QGTMVTVSS |
| SEQ ID NO: 19 P-CAD 179 VL (SEQ ID NO: 111) | QSVLTQPPSVSAAPGQKVTISCSGSRSNIGNNYVSWYQQLPGTAPKLLIYDSNKR PSGIPDRFSGSKSGTSATLGITGLQTGDEADYYCGTWDSSLSSWVFGGGTKLTVL |
| SEQ ID NO: 20 P-CAD 179 VH (SEQ ID NO: 112) | EVQLVQSGAEVKKPGASVKVSCKASGYTFTSYGISWVRQAPGQGLEWMGWISAY NGNTNYAQKLQGRVTMTTDTSTSTAYMELRSLRSDDTAVYYCATIDTANAFDIWG QGTMVTVSS |
| SEQ ID NO: 21 P-CAD 180 VL (SEQ ID NO: 113) | QSVVTQPPSVSAAPGQKVTISCSGSSSNIGNNYVSWYQQLPGTAPKLLIYDNNKR PSGIPDRFSGSKSGTSATLGITGLQTGDEADYYCGTWDSSLSAYVFGTGTKVTVL |
| SEQ ID NO: 22 P-CAD 180 VH (SEQ ID NO: 114) | EVQLVQSGAEVKKPGASVKVSCKASGYTFTSYGISWVRQAPGQGLEWMGWISAY NGNTNYAQKLQGRVTMTTDTSTSTAYMELRSLRSDDTAVYYCATIDTANAFDIWG QGTMVTVSS |
| SEQ ID NO: 23 P-CAD 281 VL (SEQ ID NO: 115) | QSVVTQPPSVSAAPGQKVTISCSGSSSNIGNNYVSWYQQLPGTAPKLLIYDNNKR PSGIPDRFSGSKSGTSATLGITGLQTGDEADYYCGTWDSSLSAWVFGGGTKLTVL |
| SEQ ID NO: 24 P-CAD 281 VH (SEQ ID NO: 116) | EVQLVQSGAEVKKPGASVKVSCKASGYTFTSYGISWVRQAPGQGLEWMGWISAY NGNTNYAQKLQGRVTMTTDTSTSTAYMELRSLRSDDTAVYYCATINAPNNFDIWG QGTMVTVSS |
| SEQ ID NO: 236 P-CAD 20 VL | AIQMTQSPSSLSASVGDRVTITCRASQSIGKYLNWYQQIPGKAPKLLIYTASTLQTG VPSRFSGSGSGTDFTLTIVSLQPEDFATYYCQQSFNTPRTFGQGTKVEIK |
| SEQ ID NO: 237 P-CAD 20 VH | EVQLVQSGAEVKKPGASVKVSCKASGYTFTGYYMHWVRQAPGQGLEWMGRINP NSGGTNYAQKFQGRVTMTRDTSISTAYMELSRLRSDDTAVYYCAKGSGSGAFDI WGQGTMVTVSS |
| SEQ ID NO: 238 P-CAD 30 VL | DIVMTQSPLSLPVTLGQPASISCRSSQSLVHSDGNTYLHWFQQRPGQSPRRLIYK VSNRDSGVPDRFSGSGSGTDFTLKISRVEAEDVGVYYCMQGTHWPPLFGQGTKV EIK |
| SEQ ID NO: 239 P-CAD 30 VH | EVQLVESGGGVVQPGRSLRLSCAASGFTFSSYGMHWVRQAPGKGLEWVAVISY DGSNKYYADSVKGRFTISRDNSKNTLYLQMNSLRAEDTAVYYCAKSSSDRTFDYW GQGTLVTVSS |

Tables 7a and 7b provide the CDR sequences for the anti-P-cadherin VH scFv clones generated, using the Kabat and AbM numbering designations, respectively.

TABLE 7a

P-CAD VH CDR sequences using Kabat numbering.

| P-CAD scFv Clone # | P-CAD VH CDR1 | P-CAD VH CDR2 | P-CAD VH CDR3 |
|---|---|---|---|
| 33 | SYGIS SEQ ID NO: 25 | WISAYNGNTNYAQKLQG SEQ ID NO: 26 | IGSGVAFDI SEQ ID NO: 27 |
| 34 | SYGIS SEQ ID NO: 25 | WISAYNGNTNYAQKLQG SEQ ID NO: 26 | IDTASAFDI SEQ ID NO: 28 |
| 35 | SYGIS SEQ ID NO: 25 | WISAYNGNTNYAQKLQG SEQ ID NO: 26 | IDTASAFDI SEQ ID NO: 28 |

TABLE 7a-continued

P-CAD VH CDR sequences using Kabat numbering.

| P-CAD scFv Clone # | P-CAD VH CDR1 | P-CAD VH CDR2 | P-CAD VH CDR3 |
|---|---|---|---|
| 153 | SYGIS SEQ ID NO: 25 | WISAYNGNTNYAQKLQG SEQ ID NO: 26 | IDTANAFGI SEQ ID NO: 29 |
| 154 | SYGIS SEQ ID NO: 25 | WISAYNGNTNYAQKLQG SEQ ID NO: 26 | IDTATAFDI SEQ ID NO: 30 |
| 163 | SYGIS SEQ ID NO: 25 | WISAYNGNTNYAQKLQG SEQ ID NO: 26 | IDTASAFDI SEQ ID NO: 28 |

TABLE 7a-continued

P-CAD VH CDR sequences using Kabat numbering.

| P-CAD scFv Clone # | P-CAD VH CDR1 | P-CAD VH CDR2 | P-CAD VH CDR3 |
|---|---|---|---|
| 165 | SYGIS<br>SEQ ID NO: 25 | WISAYNGNTNYAQKLQG<br>SEQ ID NO: 26 | IDTANAFDI<br>SEQ ID NO: 31 |
| 177 | SYGIS<br>SEQ ID NO: 25 | WISAYNGNTNYAQKLQG<br>SEQ ID NO: 26 | IDTANAFDI<br>SEQ ID NO: 31 |
| 178 | SYGIS<br>SEQ ID NO: 25 | WISAYNGNTNYAQKLQG<br>SEQ ID NO: 26 | IDTANAFDI<br>SEQ ID NO: 31 |
| 179 | SYGIS<br>SEQ ID NO: 25 | WISAYNGNTNYAQKLQG<br>SEQ ID NO: 26 | IDTANAFDI<br>SEQ ID NO: 31 |
| 180 | SYGIS<br>SEQ ID NO: 25 | WISAYNGNTNYAQKLQG<br>SEQ ID NO: 26 | IDTANAFDI<br>SEQ ID NO: 31 |
| 281 | SYGIS<br>SEQ ID NO: 25 | WISAYNGNTNYAQKLQG<br>SEQ ID NO: 26 | INAPNNFDI<br>SEQ ID NO: 32 |

TABLE 7b

P-CAD VH CDR sequences using AbM numbering.

| P-CAD scFv Clone # | P-CAD VH CDR1 | P-CAD VH CDR2 | P-CAD VH CDR3 |
|---|---|---|---|
| 33 | GYTFTSYGIS<br>SEQ ID NO: 33 | WISAYNGNTN<br>SEQ ID NO: 34 | IGSGVAFDI<br>SEQ ID NO: 27 |
| 34 | GYTFTSYGIS<br>SEQ ID NO: 33 | WISAYNGNTN<br>SEQ ID NO: 34 | IDTASAFDI<br>SEQ ID NO: 28 |
| 35 | GYTFTSYGIS<br>SEQ ID NO: 33 | WISAYNGNTN<br>SEQ ID NO: 34 | IDTASAFDI<br>SEQ ID NO: 28 |
| 153 | GYTFTSYGIS<br>SEQ ID NO: 33 | WISAYNGNTN<br>SEQ ID NO: 34 | IDTANAFGI<br>SEQ ID NO: 29 |
| 154 | GYTFTSYGIS<br>SEQ ID NO: 33 | WISAYNGNTN<br>SEQ ID NO: 34 | IDTATAFDI<br>SEQ ID NO: 30 |
| 163 | GYTFTSYGIS<br>SEQ ID NO: 33 | WISAYNGNTN<br>SEQ ID NO: 34 | IDTASAFDI<br>SEQ ID NO: 28 |
| 165 | GYTFTSYGIS<br>SEQ ID NO: 33 | WISAYNGNTN<br>SEQ ID NO: 34 | IDTANAFDI<br>SEQ ID NO: 31 |
| 177 | GYTFTSYGIS<br>SEQ ID NO: 33 | WISAYNGNTN<br>SEQ ID NO: 34 | IDTANAFDI<br>SEQ ID NO: 31 |
| 178 | GYTFTSYGIS<br>SEQ ID NO: 33 | WISAYNGNTN<br>SEQ ID NO: 34 | IDTANAFDI<br>SEQ ID NO: 31 |
| 179 | GYTFTSYGIS<br>SEQ ID NO: 33 | WISAYNGNTN<br>SEQ ID NO: 34 | IDTANAFDI<br>SEQ ID NO: 31 |
| 180 | GYTFTSYGIS<br>SEQ ID NO: 33 | WISAYNGNTN<br>SEQ ID NO: 34 | IDTANAFDI<br>SEQ ID NO: 31 |
| 281 | GYTFTSYGIS<br>SEQ ID NO: 33 | WISAYNGNTN<br>SEQ ID NO: 34 | INAPNNFDI<br>SEQ ID NO: 32 |

Tables 7c provides the CDR sequences for the anti-P-cadherin VL scFv clones generated.

TABLE 7c

P-CAD VL CDR sequences using Kabat/AbM numbering.

| P-CAD scFv Clone # | P-CAD VL CDR1 | P-CAD VL CDR2 | P-CAD VL CDR3 |
|---|---|---|---|
| 33 | SGSSSNIGNNYVS<br>SEQ ID NO: 35 | DNNKRPS<br>SEQ ID NO: 37 | GTWDSSLSAYV<br>SEQ ID NO: 39 |
| 34 | SGSSSNIGNNYVS<br>SEQ ID NO: 35 | DNNKRPS<br>SEQ ID NO: 37 | GTWDSSLSAWV<br>SEQ ID NO: 40 |
| 35 | SGSSSNIGNNYVS<br>SEQ ID NO: 35 | DNNKRPS<br>SEQ ID NO: 37 | GTWDSSLSAVV<br>SEQ ID NO: 41 |
| 153 | SGSSSNIGNNYVS<br>SEQ ID NO: 35 | DNNKRPS<br>SEQ ID NO: 37 | GTWDSSLSGVV<br>SEQ ID NO: 42 |
| 154 | SGSSSNIGNNYVS<br>SEQ ID NO: 35 | DNNKRPS<br>SEQ ID NO: 37 | GTWDSSLSSYV<br>SEQ ID NO: 43 |
| 163 | SGSSSNIGNNYVS<br>SEQ ID NO: 35 | DNNKRPS<br>SEQ ID NO: 37 | GTWDSSLSAYV<br>SEQ ID NO: 39 |
| 165 | SGSSSNIGNNYVS<br>SEQ ID NO: 35 | DNNKRPS<br>SEQ ID NO: 37 | GTWDSSLSAYV<br>SEQ ID NO: 39 |
| 177 | SGSSSNIGNNYVS<br>SEQ ID NO: 35 | DNNKRPS<br>SEQ ID NO: 37 | GTWDSSLSAYV<br>SEQ ID NO: 39 |
| 178 | SGSSSNIGNNYVS<br>SEQ ID NO: 35 | DNNKRPS<br>SEQ ID NO: 37 | GTWDSSLSAVV<br>SEQ ID NO: 41 |
| 179 | SGSRSNIGNNYVS<br>SEQ ID NO: 36 | DSNKRPS<br>SEQ ID NO: 38 | GTWDSSLSSWV<br>SEQ ID NO: 44 |
| 180 | SGSSSNIGNNYVS<br>SEQ ID NO: 35 | DNNKRPS<br>SEQ ID NO: 37 | GTWDSSLSAYV<br>SEQ ID NO: 39 |
| 281 | SGSSSNIGNNYVS<br>SEQ ID NO: 35 | DNNKRPS<br>SEQ ID NO: 37 | GTWDSSLSAWV<br>SEQ ID NO: 40 |

Table 8 shows the amino acid mutations found in affinity-matured P-cadherin clones. The data suggests potential effects on VL/VH folding and ligand interaction based on the solved crystal structure. Mutations within the CDR binding pocket showed potential for improved ligand interaction. Mutations found outside the CDR binding pocket suggested a role for improved VL/VH folding.

TABLE 8

Amino acid mutations of affinity-matured P-cadherin clones.

| P-CAD Clone # | VL mutations P-CAD 35 | | | VH mutations P-CAD 35 | | |
|---|---|---|---|---|---|---|
| | Sequential | VL chain | VL Chothia | Sequential | VH chain | VH Chothia |
| 153 | A98G | A98G | A95BG | S103N, D106G | S221N, D224G | S99N, D101G |
| 154 | A98S (V99Y, G103T, L107V) | A98S V99Y G103T L107V | A95BS V96Y G100T L104V | S103T | S221T | S99T |
| 165 | T81A (V99Y, G103T, L107V) | T81A V99Y G103T L107V | T80A V96Y G100T L104V | S103N | S221N | S99N |
| 177 | (V99Y, G103T, L107V) | V99Y G103T L107V | V96Y G100T L104V | S103N | S221N | S99N |
| 178 | — | — | — | S103N | S221N | S99N |
| 179 | S26R, N52S, A98S, V99W | S26R N52S A98S V99W | S27R N51S A95BS V96W | S103N | S221N | S99N |
| 180 | L4V, (V99Y, G103T, L107V) | L4V V99Y G103T L107V | L4V V96Y G100T L104V | S103N | S221N | S99N |

Table 9 provides the VL and VH amino acid sequences for the anti-CD3 scFv clones generated by the techniques described herein.

TABLE 9

CD3 VL and VH amino acids sequences.

| SEQ ID NO. | SEQUENCE |
|---|---|
| SEQ ID NO: 45<br>Anti hu CD3 humanized CD3-1 VH | EVQLVESGGGLVQPGGSLRLSCAASGFTFSTYAMNWVRQAPGKGLEWV<br>GRIRSKYNNYATYYADSVKGRFTISRDDSKNSLYLQMNSLKTEDTAVYYCV<br>RHGNFGNSYVSWFAYWGQGTLVTVSS |
| SEQ ID NO: 46<br>Anti hu CD3 humanized CD3-2 VH | EVQLVESGGGLVQPGGSLRLSCAASGFTFNTYAMNWVRQAPGKGLEWV<br>ARIRSKYNNYATYYADSVKDRFTISRDDSKNSLYLQMNSLKTEDTAVYYCV<br>RHGNFGNSYVSWFAYWGQGTLVTVSS |
| SEQ ID NO: 47<br>Anti hu CD3 humanized CD3-1 VL and CD3-2 VL (CD3-1-2) | QAVVTQEPSLTVSPGGTVTLTCRSSTGAVTTSNYANWVQQKPGQAPRGLI<br>GGTNKRAPWTPARFSGSLLGGKAALTITGAQAEDEADYYCALWYSNLWVF<br>GGGTKLTVL |

Tables 10a and 10b provide the CDR sequences for the anti-CD3 VH scFv clones generated, using the Kabat and AbM numbering designations, respectively.

TABLE 10a

CD3 VH CDR sequences using Kabat numbering.

| CD3 Clone # | CD3 VH CDR1 | CD3 VH CDR2 | CD3 VH CDR3 |
|---|---|---|---|
| CD3-1 | TYAMN<br>SEQ ID NO: 48 | RIRSKYNNYATYYADSVKG<br>SEQ ID NO: 49 | HGNFGNSYVSWFAY<br>SEQ ID NO: 51 |
| CD3-2 | TYAMN<br>SEQ ID NO: 48 | RIRSKYNNYATYYADSVKD<br>SEQ ID NO: 50 | HGNFGNSYVSWFAY<br>SEQ ID NO: 51 |

TABLE 10b

CD3 VH CDR sequences using AbM numbering.

| CD3 Clone # | CD3 VH CDR1 | CD3 VH CDR2 | CD3 VH CDR3 |
|---|---|---|---|
| CD3-1 | GFTFSTYAMN<br>SEQ ID NO: 52 | RIRSKYNNYATY<br>SEQ ID NO: 54 | HGNFGNSYVSWFAY<br>SEQ ID NO: 51 |
| CD3-2 | GFTFNTYAMN<br>SEQ ID NO: 53 | RIRSKYNNYATY<br>SEQ ID NO: 54 | HGNFGNSYVSWFAY<br>SEQ ID NO: 51 |

Tables 10c provides the CDR sequences for the anti-CD3 VL scFv clones generated.

TABLE 10c

CD3-1 and CD3-2 VL CDR sequences using Kabat/AbM numbering.

| CD3 Clone # | CD3 VL CDR1 | CD3 VL CDR2 | CD3 VL CDR3 |
|---|---|---|---|
| CD3-1 and CD3-2 | RSSTGAVTTSNYAN<br>SEQ ID NO: 55 | GTNKRAP<br>SEQ ID NO: 56 | ALWYSNLWV<br>SEQ ID NO: 57 |

Example 2

Construction of an Anti-P-Cadherin/Anti-Human CD3 LP-DART

Anti-P-cadherin/anti-human CD3 DART proteins were amplified by PCR such that each DART protein contained a restriction enzyme cloning site at each end for cloning into the mammalian expression vector, see Table 11 and FIGS. 33A and 33B.

TABLE 11

Anti-P-cadherin/anti-human CD3 DART proteins.

| DART | SEQUENCES |
|---|---|
| 35 | P-CAD 35VL(SEQ ID NO: 5)-Linker 1 (SEQ ID NO: 68)-CD3-1 VH(SEQ ID NO: 45 or 46), and CD3-1-2VL(SEQ ID NO: 47)-Linker 1 (SEQ ID NO: 69)-P-CAD 35VH(SEQ ID NO: 6) |
| 153 | P-CAD 153 VL (SEQ ID NO: 7)-Linker 1 (SEQ ID NO: 68)-CD3 VH (SEQ ID NO: 45 or 46), and CD3 VL (SEQ ID NO: 47)-Linker 1 (SEQ ID NO: 69)-P-CAD 153 VH (SEQ ID NO: 8) |
| 154 | P-CAD 154 VL (SEQ ID NO: 9)-Linker 1 (SEQ ID NO: 68)-CD3 VH (SEQ ID NO: 45 or 46), and CD3 VL (SEQ ID NO: 47)-Linker 1 (SEQ ID NO: 69)-P-CAD 153 VH (SEQ ID NO: 10) |

Thereafter, nucleic acids encoding the DART protein sequences were fused to each nucleic acid encoding the modified Fc constructs e.g. the "knob" Fc chain (SEQ ID NO: 63) and the "hole" Fc chain (SEQ ID NO: 64), each connected to the C-terminus of the DART with a cysteine linker, such as GCPPCP (SEQ ID NO: 73), GGTGGCPPCP (SEQ ID NO 74), GEPKSSDKTHTCPPCP (SEQ ID NO 75) and GGTGGGEPKSSDKTHTCPPCP (SEQ ID NO 76).

After PCR amplification, both the DART and Fc chain nucleic acids were digested with BspEI and either HindIII (5' DART cloning site) or EcoRI (3' Fc cloning site). Digested DNAs were isolated by excision from agarose gels and subsequent purification prior to ligation into the HindIII-EcoRI digested expression vector for 30 minutes at room temperature. Ligations were then transformed into competent E. coli DH5α and grown overnight at 37° C. on agarose plates containing 100 µg/mL carbenicillin. Colonies were counted, picked and grown overnight in YT-broth+100 µg/mL Carbenicillin and DNA isolated using standard methods. All DNA constructs were then sequenced on both strands prior to mammalian cell expression. Complimentary construct pairs were then co-transfected into 1 L log phase cultures containing 1 million cells/ml HEK 293 cells. 24 hours post-transfection, tryptone was added to a final concentration of 0.75% and cells were allowed to grow an additional 5 days before harvesting. Spent cultures were then collected, centrifuged to remove cell debris then passed through a 20 µm filter. Protein purification was then performed utilizing techniques known in the art. Schematic examples of anti-P-cadherin/anti-human CD3 LP-DARTs are shown in FIGS. 1A and 1B.

Example 3

Binding Properties of P-Cadherin scFv-Fc and DART Proteins

The binding properties of P-cadherin scFv-Fc constructs (P-cadherin VH and VL fused to a human IgG Fc region) and DART proteins to P-cadherin protein constructs and to P-cadherin expressing cells were analyzed using standard ELISA techniques. The data in Table 12 demonstrates that the phage derived P-cadherin scFv-Fc constructs had strong binding to recombinant human P-cadherin and no detectable binding to murine P-cadherin.

TABLE 12

Binding properties of P-cadherin scFv-Fc to P-cadherin protein constructs.

| P-CAD Clone # | huP-cad-ECD EC50 (nM) | huP-cad-ECD biotinylated EC50(nM) | muP-cad-ECD EC50 (nM) |
|---|---|---|---|
| 33 scFv-Fc | 3.464 | 0.1012 | NB |
| 34 scFv-Fc | 11.16 | 0.1943 | NB |
| 35 scFv-Fc | 2.5 | 0.01762 | NB |
| PF03732010 | 1.936 | 0.0188 | 2.333 |
| Neg Control | NB | NB | NB |

NB = no detectable binding

The binding properties of P-cadherin scFv-Fc to various P-cadherin expressing cell types in cell-based ELISA is shown in Table 13. The phage derived P-cadherin scFv-Fc constructs demonstrated strong binding to H1650 cells and to the SW480-huPcad and CHO-huPcad cell types.

TABLE 13

Binding properties of P-cadherin scFv-Fc to P-cadherin expressing cells.

| P-CAD Clone # | SW480-huPcad EC50 (nM) | H1650 EC50 (nM) | CHO-huPcad EC50(nM) | CHO Parental EC50 (nM) |
|---|---|---|---|---|
| 33 scFv-Fc | 0.4243 | 0.5669 | 0.4931 | NB |
| 34 scFv-Fc | 0.4422 | 0.494 | 0.3938 | NB |
| 35 scFv-Fc | 0.1734 | 0.1631 | 0.2761 | NB |
| PF-03732010 | 0.1665 | 0.2092 | 0.3293 | NB |
| Neg Control | NB | NB | NB | NB |

NB = no detectable binding

As shown in Table 14, anti-P-cadherin EK-DART proteins of the present invention demonstrated strong binding in ELISA format to cell surface expressed P-cadherin on H1650 cells and to recombinant human P-cadherin-Fc but no binding to other cadherin family members, E-cadherin and VE-cadherin. The EK-DART is an E/K coil domain construct. The PF EK-DART is a positive control utilizing the VH and VL from anti-P-cadherin clinical mAb PF-03732010 as described in Example 1. All EK-DART proteins in Table 14 comprise CD3-2.

TABLE 14

Binding properties of P-cadherin EK-DART proteins.

| DART | Hu P-cadherin-Fc EC50 (nM) | E-cadherin-Fc EC50 (nM) | VE-cadherin-Fc EC50 (nM) | H1650 EC50 (nM) | CHO Parental EC50 (nM) |
|---|---|---|---|---|---|
| 33 EK-DART | 1.8 | NB | NB | 60.1 | NB |
| 34 EK-DART | 2.85 | NB | NB | 67.95 | NB |
| 35 EK-DART | 1.92 | NB | NB | 24.87 | NB |
| PF EK-DART | 2.1 | NB | NB | 19.69 | NB |
| 20 EK-DART | 12.3 | NB | NB | ~114.7 | NB |
| 30 EK-DART | 3.68 | NB | NB | 141.9 | NB |
| Neg Control EK-DART | NB | NB | NB | NB | NB |

NB = no detectable binding

Example 4

Surface Plasmon Resonance (SPR) Analysis of DART Proteins

Binding affinity of EK-DART proteins to P-cadherin and CD3 was analyzed by SPR using a BIACORE® 3000 biosensor (GE Healthcare). The antigens huCD3$_{\epsilon\delta}$ and either human P-cadherin-Fc or human/cynomolgus monkey/murine P-cadherin-ECD were immobilized on the CM-5 sensor chip by amine coupling kit as recommended by the manufacturer. Table 15 shows the binding affinity of phage derived EK-DART proteins against cynomolgus monkey ("cyno") P-cadherin ECD and Table 16 shows the binding affinity of phage derived EK-DART proteins against human soluble CD3 protein. All EK-DART proteins in Tables 15 and 16 comprise CD3-2.

TABLE 15

Binding affinity of EK-DART proteins against cyno P-cadherin ECD.

| DART | ka (1/Ms) | kd (1/s) | $K_D$ (nM) |
|---|---|---|---|
| 33 EK-DART | 1.15E+06 | 5.78E−02 | 46.4 |
| 34 EK-DART | 7.05E+05 | 8.33E−02 | 129.3 |
| 35 EK-DART | 3.18E+05 | 1.38E−02 | 43.4 |
| PF EK-DART | 2.11E+05 | 2.51E−03 | 11.90 |
| 20 EK-DART | 3.46E+06 | 7.04E−03 | 2.03 |
| 30 EK-DART | 4.72E+06 | 6.48E−03 | 1.37 |

TABLE 16

Binding affinity of EK-DART proteins against human soluble CD3.

| DART | ka (1/Ms) | kd (1/s) | $K_D$ (nM) |
|---|---|---|---|
| 33 EK-DART | 2.28E+05 | 4.03E−03 | 17.7 |
| 34 EK-DART | 1.95E+05 | 4.45E−03 | 22.8 |
| 35 EK-DART | 1.89E+05 | 4.47E−03 | 23.6 |
| PF EK-DART | 4.11E+05 | 3.95E−03 | 9.61 |
| 20 EK-DART | 9.79E+05 | 6.09E−03 | 5.19 |
| 30 EK-DART | 3.53E+05 | 4.57E−03 | 13.6 |

In Table 17, the Biacore data demonstrates the binding affinity of optimized EK-DART proteins, with CD3-2, to cyno P-cadherin ECD compared with the parental 35 EK-DART with CD3-2. All EK-DART proteins in Table 17 comprise CD3-2.

TABLE 17

Binding affinity of EK-DART proteins against cyno P-cadherin ECD.

| DART | ka (1/Ms) | kd(1/s) | KD (pM) |
|---|---|---|---|
| 35 EK-DART | 6.14E+05 | 2.15E−02 | 35050 ± 2950 |
| 153 EK-DART | 7.32E+05 | 1.72E−05 | 231.5 ± 17.5 |
| 154 EK-DART | 1.04E+06 | 3.90E−03 | 3930.0 ± 910 |
| 165 EK-DART | 8.34E+05 | 3.09E−04 | 370.0 ± 87 |
| 177 EK-DART | 8.02E+05 | 3.83E−04 | 483.0 ± 82 |
| 178 EK-DART | 1.67E+05 | 2.16E−04 | 1310.0 ± 140 |
| 179 EK-DART | 1.11E+06 | 4.58E−03 | 4165.0 ± 255 |
| 180 EK-DART | 7.71E+05 | 7.44E−04 | 965.5 ± 19.5 |

In Table 18, the Biacore data demonstrates the binding affinity of the parental 35 EK-DART and optimized EK-DART proteins to soluble CD3$_{\delta\epsilon}$. All EK-DART proteins in Table 18 comprise CD3-2.

TABLE 18

Binding affinity of EK-DART proteins against human soluble CD3.

| DART | ka (1/Ms) | kd(1/s) | KD (nM) |
|---|---|---|---|
| 35 EK-DART | 1.89E+05 | 4.47E−03 | 23.6 |
| 153 EK-DART | 4.03E+05 | 6.31E−03 | 15.65 ± 1.75 |
| 154 EK-DART | 4.56E+05 | 7.68E−03 | 17.10 ± 0.90 |
| 165 EK-DART | 2.78E+05 | 4.17E−03 | 14.90 ± 2.80 |
| 177 EK-DART | 2.53E+05 | 4.43E−03 | 19.95 ± 6.55 |
| 178 EK-DART | 2.30E+05 | 5.26E−03 | 23.10 ± 1.10 |
| 179 EK-DART | 3.06E+05 | 6.41E−03 | 25.75 ± 9.25 |
| 180 EK-DART | 7.06E+05 | 1.11E−02 | 15.9 ± 1.00 |

The binding affinity versus cyno P-cadherin at pH7.4 of various DART formats is shown in Table 19. DART proteins in the VF, EK, LP, MP3-C-terminal and MP3-N-terminal formats with P-cadherin clone 153 VH and VL binding domains were compared. 153 VF-DART demonstrated the highest binding affinity and fastest on rate. The KDs were similar to the 153 EK-DART and 153 LP-DART proteins. 153 MP3-DART proteins had slightly lower binding affinities to cyno P-cadherin as indicated by slower on rates. The % activity (Rmax) was low and similar for all 153 DART proteins. All DART proteins in Table 19 comprise CD3-1, except 153 EK-DART which comprises CD3-2.

TABLE 19

Binding affinity of various DART formats against cyno P-cadherin.

| DART | Ligand | ka (1/Ms) | kd (1/s) | t½ (min) | Rmax (RU) | *% Rmax | % Chi2/ Rmax | KD (nM) |
|---|---|---|---|---|---|---|---|---|
| 153 EK-DART CD3-2 | Cyno P-cadherin | 5.24E+05 | 2.11E−04 | 51.56 | 23.2 | 17.3 | 0.24 | 0.403 |
| 153 EK-DART | Cyno P-cadherin | 5.17E+05 | 2.22E−04 | 48.98 | 14.0 | 14.9 | 0.33 | 0.430 |
| | | | | | | 16.1 | AVG | 0.417 ± 0.014 |
| 153VF-DART CD3-1 | Cyno P-cadherin | 7.22E+05 | 2.40E−04 | 45.35 | 22.66 | 15.0 | 0.32 | 0.332 |
| 153VF-DART | Cyno P-cadherin | 7.52E+05 | 2.29E−04 | 47.59 | 21.68 | 14.4 | 0.43 | 0.304 |
| | | | | | | 14.7 | AVG | 0.318 ± 0.014 |
| 153 LP-DART | Cyno P-cadherin | 2.93E+05 | 2.00E−04 | 54.36 | 36.6 | 12.1 | 0.16 | 0.683 |
| 153 LP-DART | Cyno P-cadherin | 5.81E+05 | 2.09E−04 | 52.20 | 75.1 | 11.7 | 0.37 | 0.359 |
| | | | | | | 11.9 | AVG | 0.521 ± 0.162 |

TABLE 19-continued

Binding affinity of various DART formats against cyno P-cadherin.

| DART | Ligand | ka (1/Ms) | kd (1/s) | t½ (min) | Rmax (RU) | *% Rmax | % Chi2/ Rmax | KD (nM) |
|---|---|---|---|---|---|---|---|---|
| 153-MP3 C-terminal DART | Cyno P-cadherin | 6.80E+04 | 1.06E−04 | 102.38 | 129.1 | 19.5 | 0.15 | 1.56 |
| 153-MP3 C-terminal DART | Cyno P-cadherin | 8.46E+04 | 1.79E−04 | 60.90 | 73.9 | 16.3 | 0.19 | 2.11 |
|  |  |  |  |  |  | 17.9 | AVG | 1.84 ± 0.28 |
| 153-MP3 N-terminal DART | Cyno P-cadherin | 1.22E+05 | 2.96E−04 | 36.82 | 72.4 | 16.1 | 1.34 | 2.43 |
| 153-MP3 N-terminal DART | Cyno P-cadherin | 8.19E+04 | 2.28E−04 | 47.78 | 149.6 | 22.7 | 0.71 | 2.78 |
|  |  |  |  |  |  | 19.4 | AVG | 2.610.18 |

The binding affinity versus shCD3 (soluble human CD3) at pH7.4 of various DART formats is shown in Table 20. DART proteins in the VF, EK, LP, MP3 C-terminal and MP3 N-terminal formats with P-cadherin clone #153 VH and VL binding domains were compared. 153 VF-DART demonstrated the fastest on rate and highest binding affinity to shCD3. The 153 EK, LP and MP3 DART proteins had similar affinities to shCD3. The % activity (Rmax) for shCD3 was better than that observed for cyno P-cadherin. All DART proteins in Table 20 comprise CD3-1, except 153 EK-DART which comprises CD3-2.

TABLE 20

Binding affinity of various DART formats against human soluble CD3.

| DART | Ligand | ka (1/Ms) | kd (1/s) | t½ (min) | Rmax (RU) | *% Rmax | % Chi2/ Rmax | KD (nM) |
|---|---|---|---|---|---|---|---|---|
| 153 EK-DART CD3-2 | shCD3 | 2.77E+05 | 6.18E−03 | 1.76 | 80.94 | 55.5 | 0.09 | 22.3 |
| 153 EK-DART CD3-2 | shCD3 | 2.83E+05 | 6.80E−03 | 1.60 | 62.68 | 31.1 | 0.04 | 24.0 |
|  |  |  |  |  |  | 43.3 | AVG | 23.15 ± 0.85 |
| 153 VF-DART CD3-1 | shCD3 | 1.13E+06 | 5.25E−03 | 2.07 | 90.92 | 69.1 | 0.85 | 4.65 |
| 153 VF-DART | shCD3 | 1.16E+06 | 5.55E−03 | 1.96 | 89.81 | 68.2 | 0.94 | 4.77 |
|  |  |  |  |  |  | 68.7 | AVG | 4.71 ± 0.06 |
| 153 LP-DART | shCD3 | 4.18E+05 | 5.20E−03 | 2.09 | 170.3 | 64.7 | 1.07 | 12.4 |
| 153 LP-DART | shCD3 | 5.37E+05 | 5.72E−03 | 1.90 | 129.8 | 35.7 | 0.64 | 10.6 |
|  |  |  |  |  |  | 50.2 | AVG | 11.5 ± 0.9 |
| 153 MP3-C-terminal DART | shCD3 | 4.20E+05 | 7.14E−03 | 1.52 | 133 | 35.3 | 0.29 | 17.0 |
| 153 MP3-C-terminal DART | shCD3 | 5.65E+05 | 7.19E−03 | 1.51 | 113.9 | 30.2 | 0.40 | 12.7 |
|  |  |  |  |  |  | 32.8 | AVG | 14.9 ± 2.2 |
| 153 MP3-N-terminal DART | shCD3 | 4.74E+05 | 6.62E−03 | 1.65 | 120.7 | 32.3 | 0.65 | 14.0 |
| 153 MP3-N-terminal DART | shCD3 | 5.32E+05 | 5.82E−03 | 1.87 | 128.1 | 34.3 | 0.42 | 11.0 |
|  |  |  |  |  |  | 33.3 | AVG | 12.5 ± 1.5 |

Example 5

Characterization of P-Cadherin DART Proteins

Differential scanning calorimetry (DSC) analysis was used to characterize the thermal stability of phage derived EK-DART proteins was conducted. Table 21 demonstrates that the P-cadherin EK-DART proteins had favorable thermal profiles with Tm1 transitions above 65° C. Forced aggregation analysis demonstrates the resistance to thermal stress of P-cadherin EK-DART proteins at 40° C. All EK-DART proteins in Table 21 comprise CD3-2.

TABLE 21

DSC analysis of P-cadherin EK-DART proteins.

| DART | DSC $T_{onset}$ | DSC $T_m1$ | Forced Aggregation (% aggregate at 40 C. ON) | pH Reversibility (% reduction in monomer) |
|---|---|---|---|---|
| 35 EK-DART | NA | 67.15 ± 0.09 | NA | NA |
| 153 EK-DART | 59.8 | 67.82 ± 0.02 | 41 | 6 |
| 154 EK-DART | 63.06 | 68.40 ± 0.01 | 40 | 3 |
| 165 EK-DART | 63.28 | 68.53 ± 0.01 | 39 | <1 |
| 177 EK-DART | 63.31 | 68.54 ± 0.01 | 39 | 1 |
| 178 EK-DART | 61.96 | 66.92 ± 0.02 | 32 | <1 |
| 179 EK-DART | 61.56 | 67.15 ± 0.03 | 31 | 7 |
| 180 EK-DART | 63.36 | 68.52 ± 0.01 | 32 | 1.5 |

Additional biophysical properties of affinity-matured P-cadherin EK-DART proteins are shown in Table 22a. The theoretical pI of these molecules is around 8.5. All EK-DART proteins in Table 22a comprise CD3-2.

TABLE 22a

Biophysical properties of P-cadherin EK-DART proteins.

| DART | Calculated DART Biochemical Properties | | | | |
|---|---|---|---|---|---|
| | Residue Count | Molar Mass (g/mol) | pI | Charge at pH 7.00 | $\epsilon_{280}$ (M$^{-1}$ cm$^{-1}$) | $\epsilon_{280}$ (L·g$^{-1}$ cm$^{-1}$) |
| 35 EK-DART | 547 | 57223.56 | 8.5 | 6.67 | 116365 | 2.0335 |
| 153 EK-DART | 547 | 57179.54 | 8.62 | 7.67 | 116365 | 2.0351 |
| 154 EK-DART | 547 | 57347.65 | 8.5 | 6.67 | 117855 | 2.0551 |
| 165 EK-DART | 547 | 57314.63 | 8.5 | 6.67 | 117855 | 2.0563 |
| 177 EK-DART | 547 | 57344.66 | 8.5 | 6.67 | 117855 | 2.0552 |
| 178 EK-DART | 547 | 57250.59 | 8.5 | 6.67 | 116365 | 2.0326 |
| 179 EK-DART | 547 | 57396.76 | 8.62 | 7.67 | 121865 | 2.1232 |
| 180 EK-DART | 547 | 57330.63 | 8.5 | 6.67 | 117855 | 2.0557 |

Table 22b shows functional characterization of affinity-matured P-cadherin VF-DART proteins. Data from two types of cytotoxic T lymphocyte (CTL) assays showed retained cytotoxicity of a bispecific heterodimeric diabody without E-K coils. Higher affinity to ligands corresponded to higher potency in CTL, as was seen in the EK-DART. All VF-DART proteins in Table 22b comprise CD3-1.

TABLE 22b

Functional characterization of P-cadherin VF-DART proteins.

| DART | Biacore affinity P-CAD Cyno monomeric ECD (nM) | Biacore affinity soluble CD3 (nM) | DU145 CTL (LDH) EC50 (nM) | HCT116 CTL (Luc) EC50 (nM) |
|---|---|---|---|---|
| 153 VF-DART | 0.31 | 4.71 | 0.0004 | 0.0005 |
| 154 VF-DART | 2.85 | 3.69 | 0.0024 | 0.008 |
| 35 VF-DART | NT | NT | 0.012 | .041 |

Table 22c contains biophysical characterization data of affinity-matured P-cadherin VF-DART proteins. Analysis of VF-DART proteins indicated that no significant increase in aggregation was detected until 65° C. Data suggests that the VF-DART format improved forced aggregation profile at low temperatures while not impacting Tm1. LC/MS data indicated proper heterodimer formation following expression and purification. All VF-DART proteins in Table 22c comprise CD3-1.

TABLE 22c

Biophysical characterization data of P-cadherin VF-DART proteins.

| DART | DSC Tm1 | Forced Aggregation | pH Sensitivity - % Increase in Aggregation | Mass Spec Observations (final pool) | Capillary Electrophoresis pI and Observations |
|---|---|---|---|---|---|
| 153 VF-DART | 69.82 | Increase in HMW >55 C. O/N; similar profile to clinical mAb | 0 | >99% correct | 8.18 |
| 154 VF-DART | 70.08 | Increase in HMW >55 C. O/N; similar profile to clinical mAb | 0 | >99% correct | NT |
| 35 VF-DART | 68.68 | Increase in HMW >55 C. O/N; similar profile to clinical mAb | 0 | >99% correct | NT |

Example 6

Characterization of P-Cadherin LP-DART Proteins

Table 23 summarizes various functional and biophysical data for eight different P-cadherin LP-DART constructs (#1-#8) generated with the parental clone P-CAD 35 and CD3-2.

For example, the first polypeptide chain (1) of LP-DART #1 has the designation: CD3 VL×P-CAD 35 VH-knob, where the CD3 VL refers to the anti-CD3-2 antibody VL binding region of SEQ ID NO: 47, P-CAD 35 VH refers to the anti-P-cadherin antibody clone 35 VH binding region of SEQ ID NO: 6, and "knob" refers to the Fc knob chain of SEQ ID NO: 63. The second polypeptide chain (2) of LP-DART #1 has the designation: P-CAD 35VL×CD3VH-hole, where the P-CAD 35VL refers to the anti-P-cadherin antibody clone 35 VL binding region of SEQ ID NO: 5, CD3 VH refers to the anti-CD3-2 antibody VH binding region of SEQ ID NO: 46, and "hole" refers to the Fc hole chain of SEQ ID NO: 64. Various cysteine linkers (Linker 2) with a truncated IgG1 hinge having the sequence CPPCP (SEQ ID NO 60) and at least one glycine residue were analyzed. The LP-DART constructs #1-#8 were compared to parental 35 EK-DART.

The data demonstrated that a shorter linker (Linker 2) between the DART portion and the Fc domain correlated to higher affinity to each ligand and higher potency in the CTL assay. This suggested that a shorter linker (Linker 2) prevented the Fc domain from interfering with the ligand binding sites on the DART portion. The data also suggested that the orientation: CD3 VLxP-CAD 35 VH-hole and P-CAD 35 VLxCD3 VH-knob, as shown in LP-DART #5 through LP-DART #8, was optimal for LP-DART generation.

TABLE 23

Functional and biophysical data for P-cadherin LP-DART proteins.

|  | LP-DART #1 | LP-DART #2 | LP-DART #3 | LP-DART #4 | LP-DART #5 | LP-DART #6 | LP-DART #7 | LP-DART #8 | 35 EK-DART |
|---|---|---|---|---|---|---|---|---|---|
| First Chain | CD3VLx P-CAD 35VH-knob | CD3VLx P-CAD 35VH-knob | CD3VLx P-CAD 35VH-knob | CD3VLx P-CAD 35VH-knob | CD3VLx P-CAD 35VH-hole | CD3VLx P-CAD 35VH-hole | CD3VLx P-CAD 35VH-hole | CD3VLx P-CAD 35VH-hole |  |
| Second Chain | P-CAD 35VLx CD3VH-hole | P-CAD 35VLx CD3VH-hole | P-CAD 35VLx CD3VH-hole | P-CAD 35VLx CD3VH-hole | P-CAD 35VLx CD3VH-knob | P-CAD 35VLx CD3VH-knob | P-CAD 35VLx CD3VH-knob | P-CAD 35VLx CD3VH-knob |  |
| Linker (Linker 2) | GCPPCP SEQ ID NO: 73 | GGTGG CPPCP SEQ ID NO: 74 | GEPKSS DKTHTC PPCP SEQ ID NO: 75 | GGTGG GEPKSS DKTHTC PPCP SEQ ID NO: 76 | GCPPCP SEQ ID NO: 73 | GGTGG CPPCP SEQ ID NO: 74 | GEPKSS DKTHTC PPCP SEQ ID NO: 75 | GGTGG GEPKSS DKTHTC PPCP SEQ ID NO: 76 |  |
| Capture Yield (mg/L) | 24 | 23 | 35 | 28 | 20 | 24 | 27 | 34 | 5 |
| % Agg Post capture | 40% | 37% | 33% | 39% | 33% | 40% | 40% | 45% | 7% |
| Cyno-Pcad KD (nM) | 108.0 | 73.5 | 85.7 | 128.0 | 62.1 | 86.6 | 96.6 | 104.0 | 42.8 |
| shCD3 KD (nM) | 32.9 | 47.9 | 47.2 | 55.1 | 30.2 | 42.1 | 49.1 | 55.6 | 17.1 |
| T cell Cytoxicity (nM) | 0.79 | 0.92 | 1.60 | 2.45 | 0.74 | 1.29 | 2.85 | 2.27 | 0.33 |

Table 24 shows the in vitro functional characterization of several P-cadherin LP-DART proteins incorporating the high affinity P-cadherin VH and VL binding domains as well as the high affinity anti-CD3 VH and VL binding domains. The data demonstrate that an increased affinity correlates to increased CTL potency; similar to the correlation observed for the P-cadherin VF-DART and EK-DART formats. All LP-DART proteins in Table 24 comprise CD3-1. As with the 33, 34 and 35 parental clones, 153 LP-DART did not bind to murine P-cadherin.

TABLE 24

Functional characterization of P-cadherin LP-DART proteins.

| DART | Biacore affinity Cyno P-cadherin monomeric ECD (nM) | Biacore affinity murine P-cadherin ECD | Biacore affinity soluble CD3 (nM) | DU145 CTL (LDH) EC50 (nM) | HCT116 CTL (Luc) EC50 (nM) |
|---|---|---|---|---|---|
| 153 LP-DART | 0.521 | NB | 11.5 | 0.0006 | 0.0004 |
| 154 LP-DART | 5.5 | NT | 7.18 | 0.0017 | 0.0072 |
| 35 LP-DART | NT | NT | NT | 0.0073 | 0.107 |

NT = not tested;
NB = no binding

Table 25 shows the biophysical characterization of several P-cadherin LP-DART proteins. DSC of the P-cadherin LP-DART proteins showed a similar Tm1 value as was obtained with the P-cadherin EK-DART and VF-DART proteins. Forced aggregation analysis suggested an improved stability at lower temperatures over the P-cadherin EK-DART format and an overall profile similar to clinical mAbs. LC/MS data indicated proper heterodimer formation following expression and purification. All LP-DART proteins in Table 25 comprise CD3-1.

saturation FACS binding. $2.5 \times 10^5$ cells per sample were transferred to 96-well round bottom polypropylene plates. Cells were stained with 5 µg/ml and 10 µg/ml phycoerythrin (PE) labeled anti-human P-cadherin mAb (PF-03732010) conjugated at a ratio of 1:1 mAb to PE (eBioscience) or with PE conjugated to a control mouse IgG1 mAb (Biolegend) for 30 minutes at room temperature. Cells were washed and resuspended with FACS buffer plus 10 ng/ml propidium iodide prior to acquisition using LSRII with FACS Diva software. QuantiBRITE PE beads (BD Pharmingen) were

TABLE 25

Biophysical characterization of P-cadherin LP-DART proteins.

| Construct | DSC Tm1 | Forced Aggregation | pH Sensitivity - % Increase in Aggregation | Mass Spec Observations (final pool) | Capillary Electrophoresis pI and Observations |
|---|---|---|---|---|---|
| 153 LP-DART | 68.91 | Increase in HMW >55 C. O/N; similar profile to clinical mAb | 0 | >99% correct | 8.26, Shouldering |
| 154 LP-DART | 68.63 | Increase in HMW >55 C. O/N; similar profile to clinical mAb | 0 | >99% correct | NT |
| 35 LP-DART | 68.39 | Increase in HMW >55 C. O/N; similar profile to clinical mAb | 0 | >99% correct | NT |

NT = not tested

Table 26 provides the Biacore SPR data of P-cadherin LP-DART proteins, 153 LP-DART and 154 LP-DART, binding to cyno P-cadherin ECD and soluble $CD3_{\delta\epsilon}$. The data demonstrate that there was a minor decrease in affinity to each ligand compared to the affinity of the corresponding EK-DART. All LP-DART proteins in Table 26 comprise CD3-1.

reconstituted using 0.5 mL FACS buffer and acquired using the LSRII with the same voltage settings as the tumor cell samples. The PE geometric mean fluorescent intensity of both beads and tumor cells was used to calculate the number of PE labeled antibodies bound per cell (ABC) following the manufacturer prescribed protocol for the QuantiBRITE PE Bead Kit. A linear regression curve fit between receptor

TABLE 26

Binding properties of P-cadherin LP-DART proteins cyno P-cadherin and soluble CD3.

| DART | Ligand | ka (1/Ms) | kd (1/s) | t½ (min) | Rmax (RU) | *% Rmax | % Chi2/ Rmax | KD (nM) |
|---|---|---|---|---|---|---|---|---|
| 153 LP-DART | Cyno P-Cadherin | 2.93E+05 | 2.00E−04 | 54.36 | 36.6 | 12.1 | 0.16 | 0.683 |
|  |  | 5.81E+05 | 2.09E−04 | 52.20 | 75.1 | 11.7 | 0.37 | 0.359 |
|  |  |  |  |  |  | 11.9 | AVG | 0.521 ± 0.162 |
| 154 LP-DART | Cyno P-Cadherin | 6.07E+05 | 3.32E−03 | 3.27 | 46.29 | 32.3 | 0.49 | 5.47 |
|  |  | 6.20E+05 | 3.43E−03 | 3.18 | 46.38 | 32.4 | 0.56 | 5.53 |
|  |  |  |  |  |  | 32.35 | AVG | 5.50 ± 0.03 |
| 153 LP-DART | shCD3 | 4.18E+05 | 5.20E−03 | 2.09 | 170.3 | 64.7 | 1.07 | 12.4 |
|  |  | 5.37E+05 | 5.72E−03 | 1.90 | 129.8 | 35.7 | 0.64 | 10.6 |
|  |  |  |  |  |  | 50.2 | AVG | 11.5 ± 0.9 |
| 154 LP-DART | shCD3 | 6.13E+05 | 4.42E−03 | 2.47 | 476.7 | 42.5 | 5.73 | 7.20 |
|  |  | 6.37E+05 | 4.56E−03 | 2.39 | 475.0 | 42.3 | 5.41 | 7.16 |
|  |  |  |  |  |  | 42.4 | AVG | 7.18 ± 0.02 |

Example 7

Quantification of P-Cadherin Expression

A. Quantification of P-Cadherin Expression on Cancer Cell Lines Engineered to Express Luciferase for In Vitro Studies Flow cytometry experiments were conducted to evaluate anti-P-cadherin mAb (PF-03732010) binding to determine the relative level of endogenous cell surface P-cadherin expression across a panel of 10 cancer cell lines. All tumor cells lines for in vitro testing were engineered to express luciferase. Tumor cell lines demonstrating a range of P-cadherin receptor expression were collected as described for saturation FACS binding.

density and cytotoxicity EC50 was determined by plotting the $Log_{10}$ value of the average receptor density determined by Quantibrite assay at 5 µg/mL and 10 µg/mL PE labeled anti-P-cadherin mAb for each tumor cell line versus the $Log_{10}$ value of the average in vitro cytotoxicity EC50 for that same target tumor cell line using GraphPad Prism 5.0 software.

A broad range of cell surface P-cadherin expression was observed across the panel and the anti-P-cadherin mAb bound to cell lines that were derived from a variety of cancer types, including breast cancer, lung cancer and colorectal cancer, as shown in Table 27. In contrast, the control mAb did not show appreciable binding. MFI=Mean fluorescence intensity; ABC=Antibodies bound per cell.

TABLE 27

Endogenous cell surface P-cadherin expression level on luciferase expressing cancer cell lines

| Cell Line | Tumor Type | MFI, Control mAb | MFI, P-cadherin mAb | ABC, P-cadherin mAb |
|---|---|---|---|---|
| H1650_Luc | Lung Cancer | 254 | 7,958 | 37,582 |
| HCT116_Luc | Colorectal cancer | 229 | 5,661 | 26,421 |
| BT20_Luc | Breast Cancer | 225 | 5,235 | 24,349 |
| SUM149_Luc | Breast Cancer | 213 | 3,717 | 16,982 |
| H322_Luc | Lung Cancer | 242 | 3,233 | 16,576 |
| H1975_Luc | Lung Cancer | 373 | 3,155 | 15,429 |
| LoVo_Luc | Colorectal cancer | 175 | 1,389 | 5,805 |
| SW480_Luc | Colorectal cancer | 151 | 1,256 | 5,304 |
| HT29_Luc | Colorectal cancer | 282 | 787 | 2,421 |
| Ls174T_Luc | Colorectal cancer | 94 | 290 | 929 |
| Colo205_Luc | Colorectal cancer | 173 | 357 | 874 |
| SW620_Luc | Colorectal cancer | 125 | 276 | 715 |

B. Quantification of P-Cadherin Expression on Cancer Cell Lines for in vivo Studies Flow cytometry experiments were conducted to evaluate anti-P-cadherin mAb (Pfizer PF-03732010) binding to determine the relative level of endogenous cell surface P-cadherin expression across a panel of cancer cell lines for in vivo studies. Tumor cell lines demonstrating a range of P-cadherin receptor expression were collected as described for saturation FACS binding. $2.5 \times 10^5$ cells per sample were transferred to 96 well round bottom polypropylene plates. Cells were stained with 5 μg/ml and 10 μg/ml phycoerythrin (PE) labeled anti-human P-cadherin mAb conjugated at a ratio of 1:1 mAb to PE (eBioscience) or with 7.5 μg/mL PE conjugated to a control mouse IgG1 mAb (Biolegend) for 30 minutes at room temperature. Cells were washed and resuspended with FACS buffer plus 10 ng/mL propidium iodide prior to acquisition using LSRII with FACS Diva software. QuantiBRITE PE beads (BD Pharmingen) were reconstituted using 0.5 ml FACS buffer and acquired using the LSRII with the same voltage settings as the tumor cell samples. The average PE geometric mean fluorescent intensity of both beads and tumor cells was used to calculate the number of PE labeled antibodies bound per cell (ABC) following the manufacturer prescribed protocol for the QuantiBRITE PE Bead Kit.

A broad range of cell surface P-cadherin expression was observed on cell lines derived from colorectal and breast cancer and ranked accordingly; HCT116>SUM149>SW480>Ls174T>SW620, as shown in Table 28. In contrast, the isotype control mAb did not show appreciable binding to any of the cell lines.

TABLE 28

Endogenous cell surface P-cadherin expression level on cancer cell lines.

| Cell Line | Tumor Type | MFI, Control mAb | MFI, P-cadherin mAb | ABC, P-cadherin mAb |
|---|---|---|---|---|
| HCT116 | Colorectal cancer | 239 | 8,033 | 43,801 |
| SW480 | Colorectal cancer | 171 | 2,468 | 12,665 |
| Ls174T | Colorectal cancer | 222 | 986 | 4,160 |
| SW620 | Colorectal cancer | 88 | 297 | 1,117 |
| SUM149 | Breast Cancer | 68 | 2,872 | 15,426 |

Example 8

In Vitro Cytotoxicity Assays

A. EK-DART Cytotoxic T-Lymphocyte (CTL) Assays

EK-DART proteins showing strong recombinant P-cadherin/CD3 protein binding as well as a strong cell binding signal (>3× background or EC50≈PF03732010-DART) were screened in T cell directed cell killing assays as previously described (Moore et al., Blood, 117(17): 4542-4551, 2011). Table 29 demonstrates effective T cell directed cytotoxicity for P-cadherin EK-DART proteins of the present invention. In the presence of human PBMC at an E:T ratio of 30:1, CHO cells engineered to over express human P-cadherin and a cancer cell line that expresses endogenously high levels of P-cadherin (H1650) were both effectively lysed by the EK-DART proteins following 24 hour incubation as measured using an LDH release assay. Extending incubation time to 40 hours further increased the potency of cell killing as anticipated by the mechanism of action of redirected T cell killing with the P-cadherin EK-DART molecules. In contrast, no killing was observed on the parental CHO cell line as anticipated based on lack of P-cadherin expression. All EK-DART proteins in Table 29 comprise CD3-2.

TABLE 29

T cell directed cytotoxicity for P-cadherin EK-DART proteins.

| DART | CHO-CDh3 (24 h) EC50 (nM) | H1650 (24 h) EC50 (nM) | H1650 (40 h) EC50 (nM) |
|---|---|---|---|
| 33 EK-DART | 0.309 | 4.104 | 1.124 |
| 34 EK-DART | 0.7365 | 5.604 | 1.6 |
| 35 EK-DART | 0.0398 | 0.5014 | 0.0532 |
| PF EK-DART | 0.0284 | 0.4038 | 0.505 |
| 20 EK-DART | 168.64 | 36.44 | NT |
| 30 EK-DART | NR | NR | NT |

T cell directed cytotoxicity of optimized P-cadherin EK-DART proteins against tumor cell expressing human P-cadherin and a constitutively-expressed luciferase reporter construct is shown in Table 30. All EK-DART proteins in Table 30 comprise CD3-2.

TABLE 30

T cell directed cytotoxicity for P-cadherin EK-DART proteins.

| DART | HCT116 Luc 48 hr 10:1 D43905 EC50 nM | H1650 LDH 24 hr 30:1 D41183 EC50 nM |
|---|---|---|
| 153 EK-DART | 0.0005 | 0.0008 |
| 154 EK-DART | 0.0166 | 0.0107 |
| 165 EK-DART | 0.0015 | 0.0011 |
| 177 EK-DART | 0.0007 | 0.0011 |
| 178 EK-DART | 0.0018 | 0.0008 |
| 179 EK-DART | 0.0432 | 0.0178 |
| 180 EK-DART | 0.0018 | 0.0016 |
| 35 EK-DART | 0.2051 | 0.1016 |

B. LP-DART Cytotoxic T-Lymphocyte (CTL) Assays

Mediated cell killing of 153 LP-DART was assessed by cytotoxic T-lymphocyte (CTL) assay. CHO parental and CHO P-cadherin cells at a 10:1 effector (T cell) to target (CHO cell) ratio were incubated with CD3+ T cells in the presence of increasing concentrations of 153 LP-DART. Cell viability was measured after 48 hours and a half maximal effective concentration (EC50) was calculated to be 0.41 pM. The results showed that 153 LP-DART demonstrated potent killing on CHO P-cadherin cells, however no activity was detectable above the negative control on the CHO parental cells. Therefore, CTL activity was dependent on P-cadherin expression.

Mediated tumor killing of 153 LP-DART was assessed by cytotoxic T-lymphocyte (CTL) assay. T cell directed cytotoxicity of optimized 153 LP-DART proteins against tumor cell expressing human P-cadherin and a constitutively-expressed luciferase reporter construct was analyzed. CD3+ T cells were incubated with a panel of cancer cell lines at a 3:1 effector (T cell) to target (cancer cell) ratio in the presence of increasing concentrations of 153 LP-DART. Cell viability was measured after 72 hours and a half maximal effective concentration (EC50) for each cancer cell line was calculated, as shown in Table 31. The data demonstrates that 153 LP-DART mediates potent anti-tumor activity in the cancer models. EC50=half maximal effective concentration; S.D.=standard deviation; pM=picomolar; NA=no activity.

TABLE 31

Cytotoxic T-lymphocyte activity of 153 LP-DART in luciferase expressing cancer cell lines.

| Cell Line | Tumor Type | EC50 ± S.D. (pM) |
|---|---|---|
| H1650_Luc | Lung Cancer | 4.24 ± 0.66 |
| HCT116_Luc | Colorectal cancer | 5.6 ± 3.61 |
| BT20v_Luc | Breast Cancer | 4.72 ± 2.43 |
| SUM149_Luc | Breast Cancer | 0.35 ± 0.10 |
| H1975_Luc | Lung Cancer | 0.96 ± 0.31 |
| H322_Luc | Lung Cancer | 5.78 ± 3.09 |
| LoVo_Luc | Colorectal cancer | 1.65 ± 0.91 |
| SW480_Luc | Colorectal cancer | 53.37 ± 30.73 |
| HT29_Luc | Colorectal cancer | 41.19 ± 22.17 |
| Ls174T_Luc | Colorectal cancer | 1439.07 ± 2462.25 |
| Colo205_Luc | Colorectal cancer | 191.28 ± 203.58 |
| SW620_Luc | Colorectal cancer | NA |

C. Comparison of CTL Activity to Cell Surface P-Cadherin Expression Levels

Tumor cell lines from section A demonstrating a range of P-cadherin receptor expression were collected and $2.5 \times 10^5$ cells per sample were transferred to 96-well round bottom polypropylene plates. Cells were stained with 5 µg/ml and 10 µg/ml phycoerythrin (PE) labeled anti-human P-cadherin mAb (Pfizer PF-03732010) conjugated at a ratio of 1:1 mAb to PE (eBioscience) or with PE conjugated to a control mouse IgG1 mAb (Biolegend) for 30 minutes at room temperature. Cells were washed and resuspended with FACS buffer plus 10 ng/ml propidium iodide prior to acquisition using LSRII with FACS Diva software. QuantiBRITE PE beads (BD Pharmingen) were reconstituted using 0.5 mL FACS buffer and acquired using the LSRII with the same voltage settings as the tumor cell samples. The PE geometric mean fluorescent intensity of both beads and tumor cells was used to calculate the number of PE labeled antibodies bound per cell (ABC) following the manufacturer prescribed protocol for the QuantiBRITE PE Bead Kit.

Figure 8:
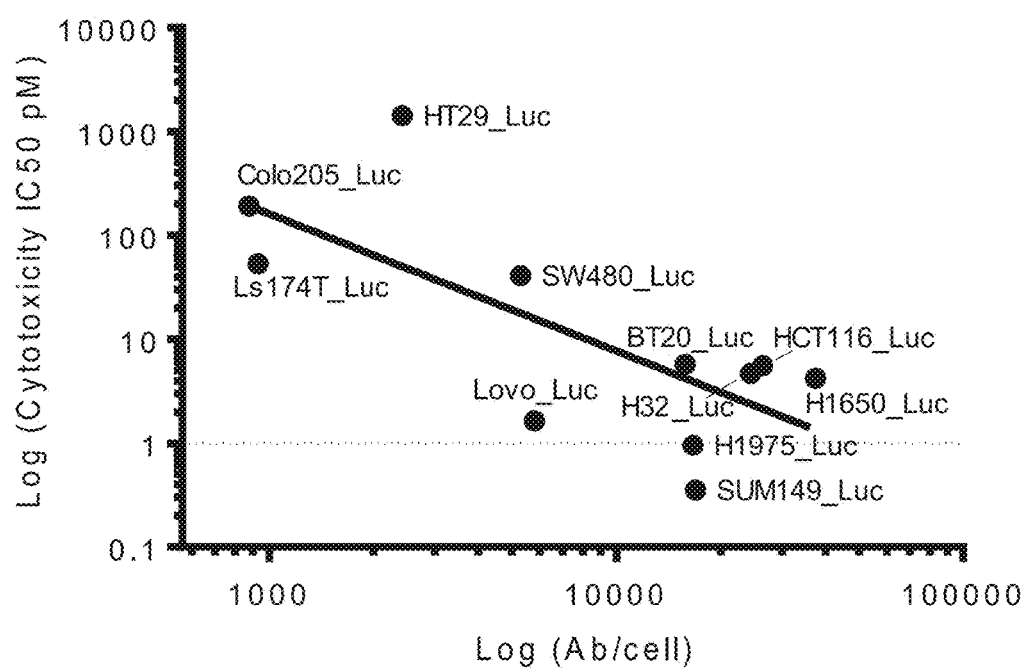
FIG. 8 provides a linear regression analysis comparing cytotoxic T lymphocyte (CTL) activity to relative cell surface P-cadherin expression.
Figure 9:
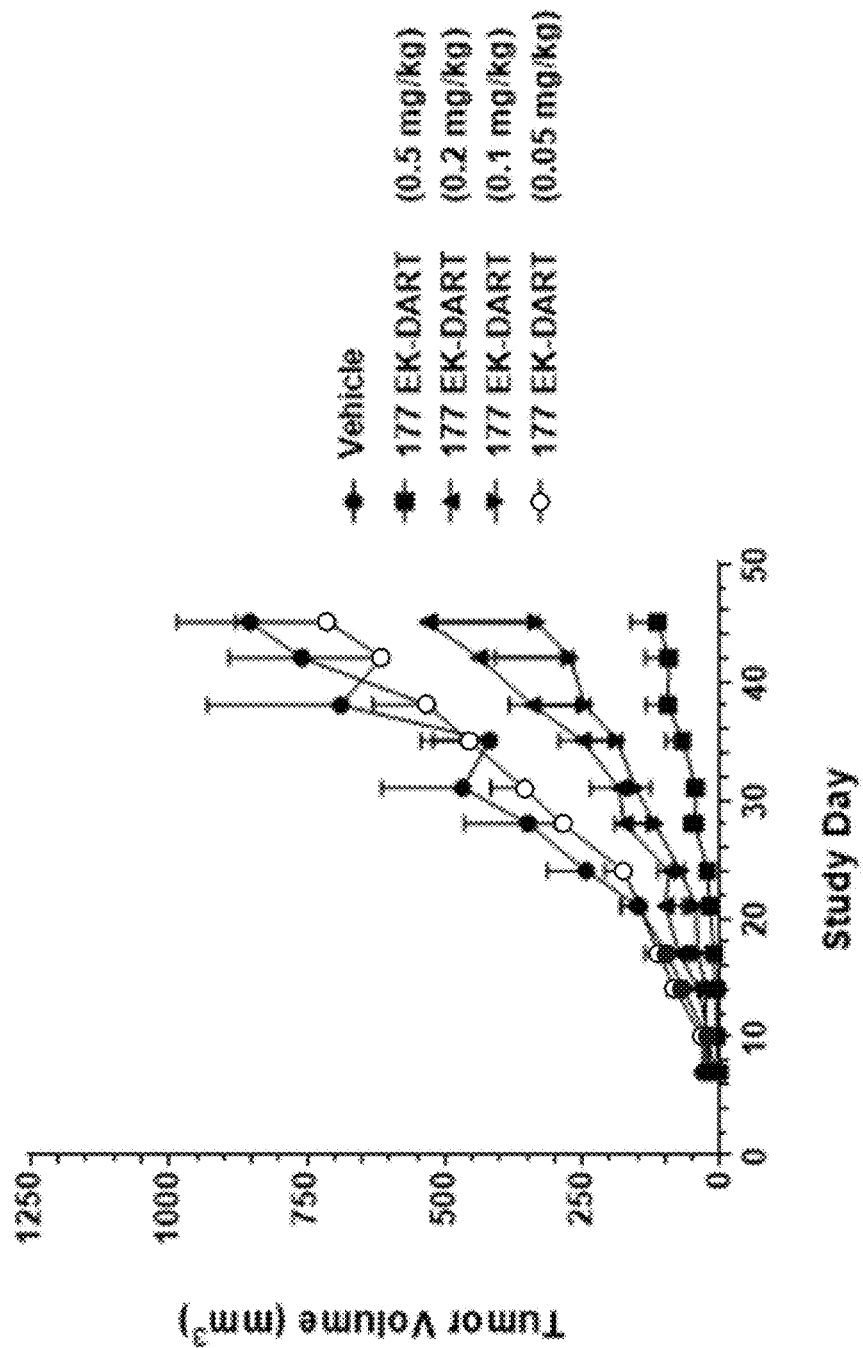
FIG. 9 demonstrates the in vivo ability of 177 EK-DART to decrease tumor volume in murine HCT116 colorectal cancer model.
Figure 10:
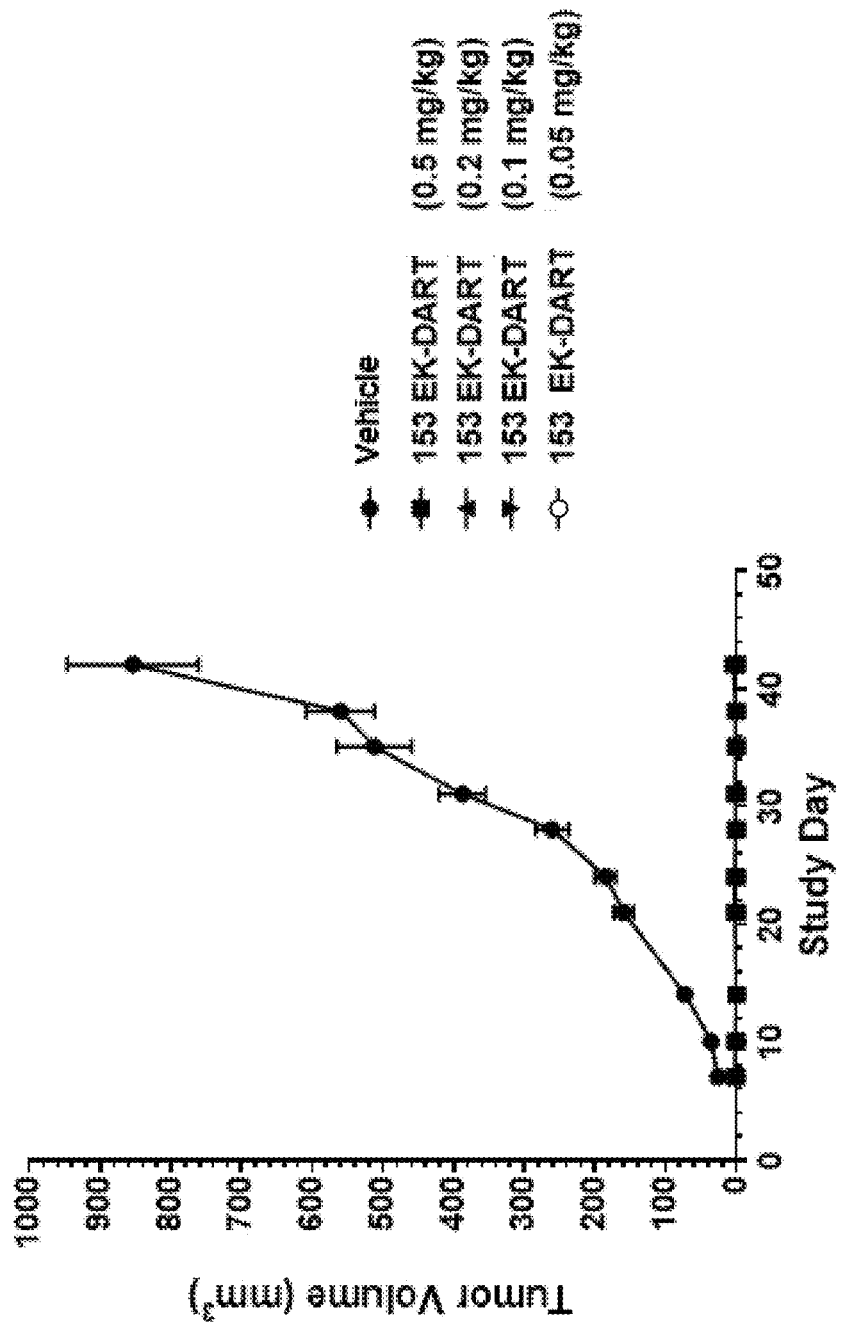
FIG. 10 demonstrates the in vivo ability of 153 EK-DART to decrease tumor volume in murine HCT116 colorectal cancer model.
Figure 11:
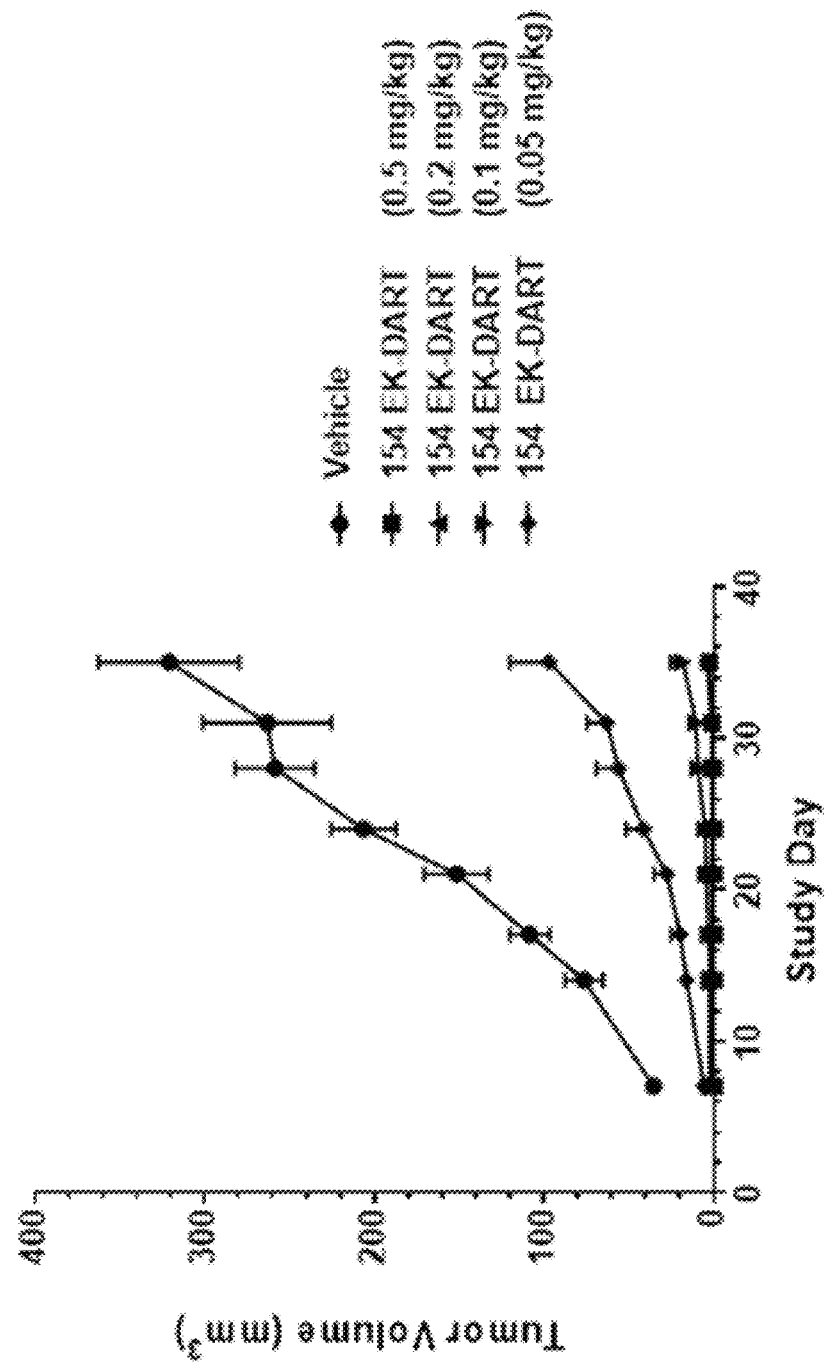
FIG. 11 demonstrates the in vivo ability of 154 EK-DART to decrease tumor volume in murine HCT116 colorectal cancer model.
Figure 12:
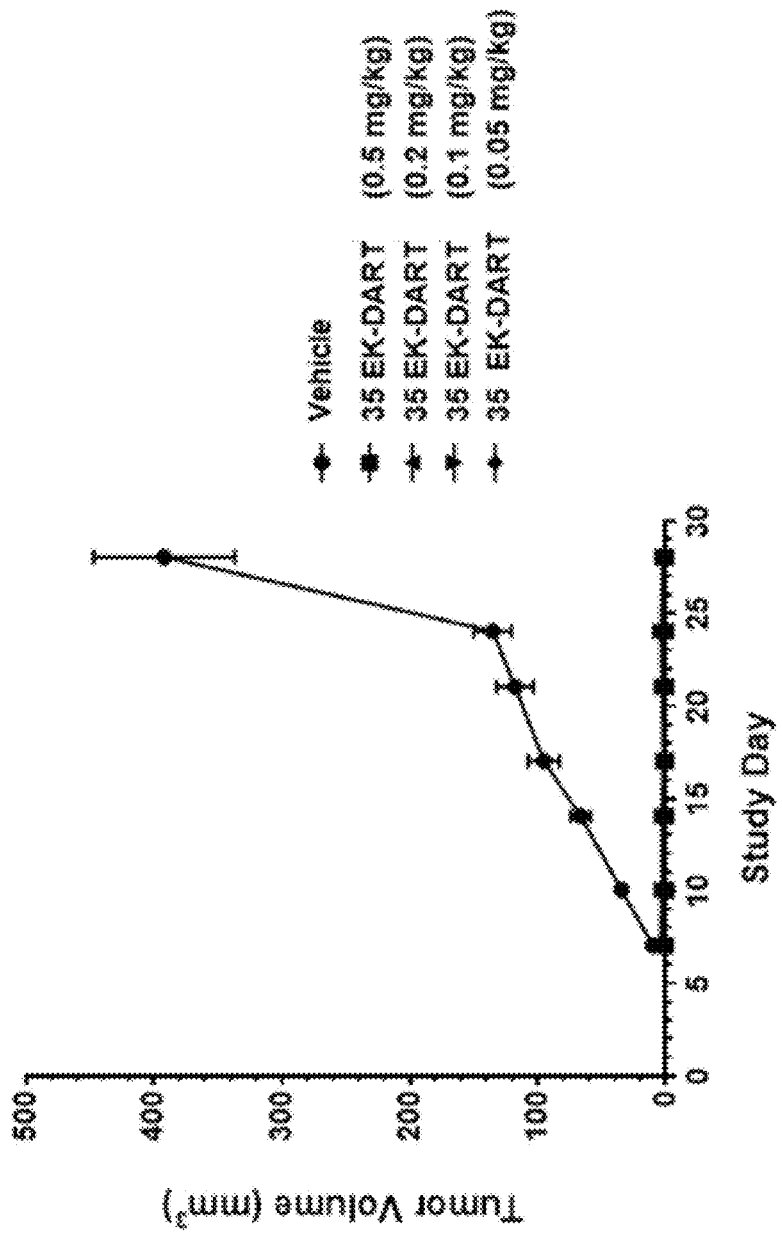
FIG. 12 demonstrates the in vivo ability of 35 EK-DART to decrease tumor volume in murine HCT116 colorectal cancer model.
Figure 13:
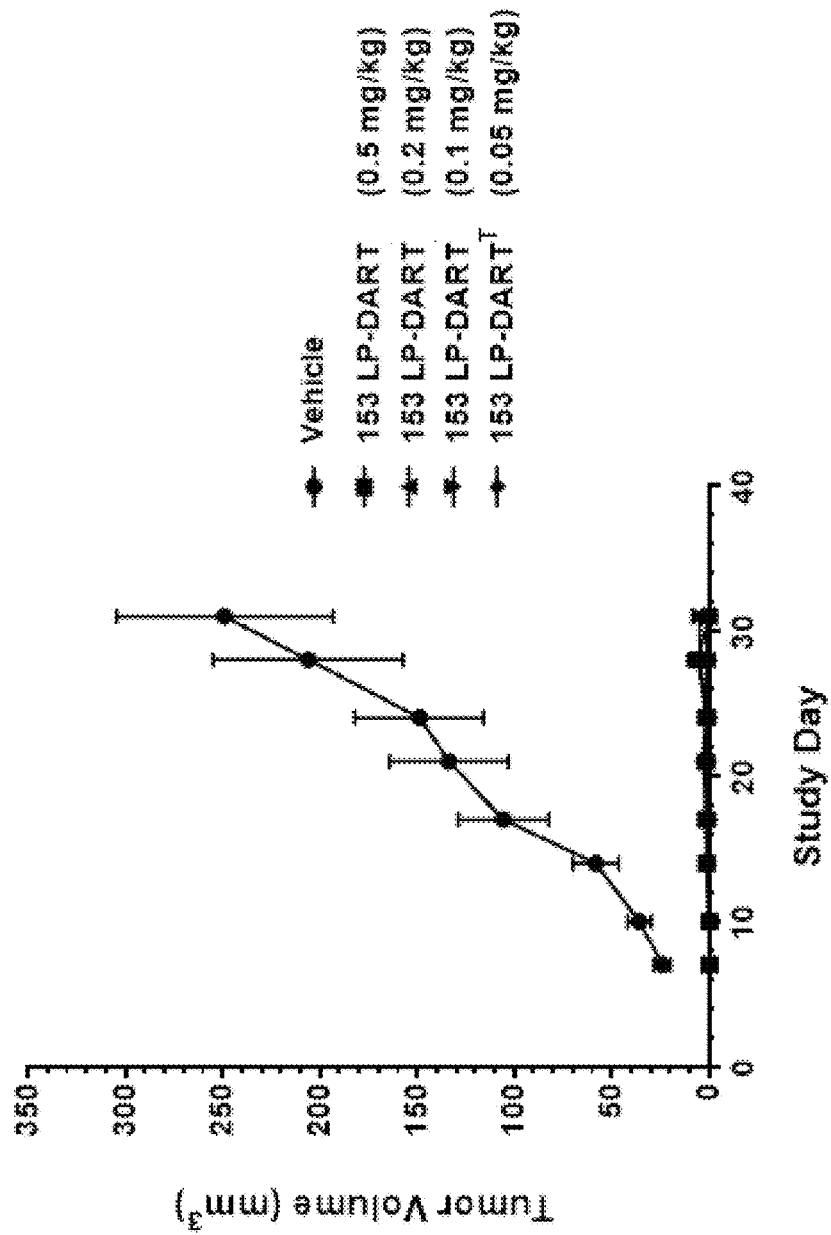
FIG. 13 demonstrates the in vivo ability of 153 LP-DART to decrease tumor volume in murine HCT116 colorectal cancer model.
Figure 14:
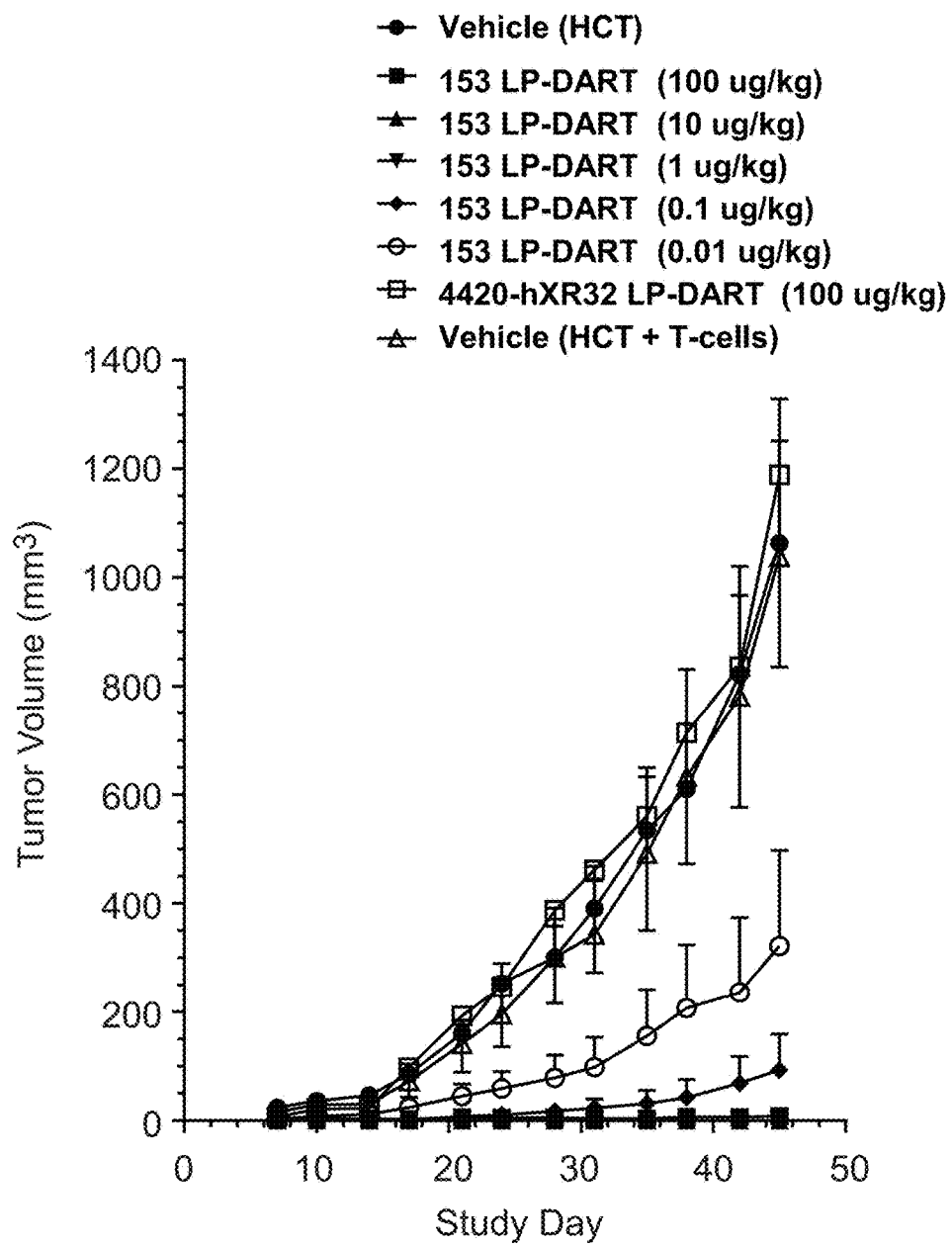
FIG. 14 demonstrates the in vivo ability of 153 LP-DART to decrease tumor volume in murine HCT116 colorectal cancer model.

A linear regression curve fit between receptor density and cytotoxicity EC50 was determined by plotting the $Log_{10}$ value of the average receptor density determined by Quantibrite assay at 5 µg/mL and 10 µg/mL PE labeled anti-P-cadherin mAb for each tumor cell line versus the $Log_{10}$ value of the average in vitro cytotoxicity EC50 for that same target tumor cell line using GraphPad Prism 5.0 software. As shown in FIG. 8, there was a significant relationship between lower EC50s and increased binding of anti-P-cadherin mAb to the cell surface, P value=0.0127. This indicates that CTL activity was correlated with P-cadherin expression levels.

Example 9

Human PBMC Reconstitution Xenograft Studies

Various DART proteins demonstrating potent T cell directed cytotoxicity (<10 ng/mL EC50) were tested in vivo in xenograft reconstitution experiments as described below.

A. Isolation of PBMCs and T Cells from Human Whole Blood

PBMCs from healthy human donors were isolated from whole blood by using Ficoll gradient centrifugation. In brief, whole blood was diluted 1:1 with sterile PBS. Thirty-five mL of the diluted blood was layered onto 15 mL FICOLL-PAQUE™ Plus in 50-mL tubes and the tubes were centrifuged at 1400 rpm for 20 min with the brake off. The buffy coat layer between the two phases was collected into a 50 mL tube and washed with 45 mL PBS by centrifuging the tubes at 600×g (1620 rpm) for 5 min. The supernatant was discarded and the cell pellet was washed once with PBS and viable cell count was determined by Trypan Blue dye exclusion. The PBMCs were resuspended to a final concentration of $2.5 \times 10^6$ cells/mL in complete medium (RPMI 1640, 10% FBS, 2 mM Glutamine, 10 mM HEPES, 100µ/100µ/mL penicillin/Streptomycin (P/S).

B. T Cell Isolation and Activation

Human T cells were isolated from heparinized whole blood according to the manufacturer's protocol provided in the RosettaSep T cell isolation kit. The purified T cells were subsequently activated by exposing the cells to anti-CD3 (OKT-3; 1 µg/mL) and anti-CD28 (66 µg/mL) antibodies for a period of 48 hours. Following stimulation, the cells were grown in RPMI 1640 medium with 10% FBS and 1% penicillin/streptomycin in the presence of IL-2 (7.6 ng/mL) for up to 3 weeks.

C. Tumor Model

Human T cells and tumor cells (HCT116, Du145 or H1650) were combined at a ratio of 1:5 ($1 \times 10^6$ and $5 \times 10^6$, respectively) and suspended in 200 µL of sterile saline and injected subcutaneously (SC) on Study Day 0 (SD0). Various P-cadherin EK-DART (CD3-2), LP-DART (CD3-1) or a control DART (CD3-2) proteins, along with a control, were administered intravenously (IV) via tail vein injections in 100 µL at SD0, 1, 2, and 3. Each treatment group contained eight animals.

P-CAD 177 EK-DART in a HCT116 Tumor Model: P-CAD 177 EK-DART was administered at a dose of 0.5, 0.2, 0.1 or 0.05 mg/kg to four treatment groups and a vehicle control (HCT116 cells alone implanted or +T cells) was administered to one treatment group (0 mg/kg).

P-CAD 153 EK-DART in a HCT116 Tumor Model: P-CAD 153 EK-DART was administered at a dose of 0.5, 0.2, 0.1 or 0.05 mg/kg to four treatment groups and a vehicle control (HCT116 cells alone implanted or +T cells) was administered to one treatment group (0 mg/kg).

P-CAD 154 EK-DART in a HCT116 Tumor Model: P-CAD 154 EK-DART was administered at a dose of 0.5, 0.2, 0.1 or 0.05 mg/kg to four treatment groups and a vehicle control (HCT116 cells alone implanted or +T cells) was administered to one treatment group (0 mg/kg).

P-CAD 35 EK-DART in a HCT116 Tumor Model: P-CAD 35 EK-DART was administered at a dose of 0.5, 0.2, 0.1 or 0.05 mg/kg to four treatment groups and a vehicle control (HCT116 cells alone implanted or +T cells) was administered to one treatment group (0 mg/kg).

P-CAD 153 LP-DART in a HCT116 Tumor Model: Treatment groups were administered P-CAD 153 LP-DART at a dose of 0.5, 0.2, 0.1 or 0.05 mg/kg, or a vehicle control (HCT116 cells alone implanted or +T cells).

P-CAD 153 LP-DART in a HCT116 Tumor Model: Treatment groups were administered P-CAD 153 LP-DART at a dose of 100, 10, 1, 0.1, or 0.01 µg/kg, or a vehicle control (HCT116 cells implanted alone), a vehicle control (HCT116 cells implanted +T cells) or a 4420-hXR32 LP-DART (100 µg/kg) control.

P-CAD 153 LP-DART in a Du145 Tumor Model: Treatment groups were administered P-CAD 153 LP-DART at a dose of 100, 10, 1, 0.1, or 0.01 µg/kg or a vehicle control (Du145 cells implanted alone), a vehicle control (HCT116 cells implanted +T cells) or a 4420-hXR32 LP-DART (100 µg/kg) control.

P-CAD 153 LP-DART in an H1650 Tumor Model: Treatment groups were administered P-CAD 153 LP-DART at a dose of 100, 10, 1, 0.1, or 0.01 µg/kg, or a vehicle control (H1650 cells implanted alone), a vehicle control (H1650 cells implanted +T cells) or a 4420-hXR32 LP-DART (100 µg/kg) control.

C. Data Collection and Statistical Analysis

Animal weights: Individual animal weights were recorded twice weekly until study completion beginning at the time of tumor cell injection.

Moribundity/Mortality: Animals were observed twice weekly for general moribundity and daily for mortality. Animal deaths were assessed as drug-related or technical based on factors including gross observation and weight loss; animal deaths were recorded daily.

Tumor volume: Individual tumor volumes were recorded twice weekly beginning within one week of tumor implantation and continuing until study completion.

$$\text{Tumor Volume (mm}^3) = \frac{\text{Length (mm)} \times \text{width}^2}{2}$$

Animals experiencing technical or drug-related deaths were censored from the data calculations.

Tumor growth inhibition: Tumor growth inhibition (TGI) values were calculated for each group containing treated animals using the formula:

$$1 - \frac{\text{Mean Final Tumor Volume (Treated)} - \text{Mean Initial Tumor Volume (Treated)}}{\text{Mean Final Tumor Volume (Control)} - \text{Mean Initial Tumor Volume (Control)}} \times 100$$

Animals experiencing a partial or complete response, or animals experiencing technical or drug-related deaths were censored from the TGI calculations. The National Cancer Institute criteria for compound activity is TGI>58% (Corbett et al. (2004) *Anticancer Drug Development Guide*; Totowa, N.J.: Humana 99-123).

Partial/Complete Tumor Response: Individual mice possessing tumors measuring less than 1 mm³ on Day 1 were classified as having partial response (PR) and a percent tumor regression (% TR) value was determined using the formula:

$$1 - \frac{\text{Final Tumor Volume (mm}^3)}{\text{Initial Tumor Volume (mm}^3)} \times 100\%$$

Individual mice lacking palpable tumors were classified as undergoing a complete response (CR).

Tumor Volume Statistics: Statistical analyses were carried out between treated and control groups comparing tumor volumes. For these analyses, a two-way analysis of variance followed by a Bonferroni post-test were employed. All analyses were performed using GraphPad PRISM® software (version 5.02). Weight and tumor data from individual animals experiencing technical or drug-related deaths were censored from analysis. However, tumor data from animals reporting partial or complete responses were included in these calculations.

D. HCT116 Tumor Model Results

The cell line HCT116 was pre-mixed with activated T cells and implanted subcutaneous (SC) in NOD/SCID gamma knockout mice (N=8/group) on study day 0 (SD0) as detailed above. Treatment with the various P-cadherin EK-DART, LP-DART or a control DART proteins was initiated on the same day the tumor cell/T cell mixture was implanted [(SD0)] and proceeded subsequently with daily injections for an additional 3 days for a total of 4 daily injections. The animals were treated with P-cadherin EK-DART, LP-DART or a control DART proteins at 4 dose levels (0.5, 0.2, 0.1, and 0.05 mg/kg). Results are shown in FIGS. 9-14.

The HCT116 tumors in the vehicle-treated group (HCT116 cells alone or plus T cells) demonstrated a relatively aggressive growth profile in vivo. At study day 20 (SD20), the average volume of the tumors in the vehicle-treated group was approximately 125 mm³ and by study day 35 (SD35) the tumors had reached an average volume of approximately 450 mm³. By the end of the experiment on study day 45 (SD45), the tumors had reached an average volume of approximately 750 mm³. The growth of the HCT116 tumors was significantly inhibited at all dose levels for most of the P-cadherin DART proteins tested. By the end of the experiment on SD45, the average volume of the tumors ranged from around 100 to 0 mm³ for all treatments except the 177 EK-DART which ranged from around 500 to 100 mm³.

E. Du145 Results

Figure 15:
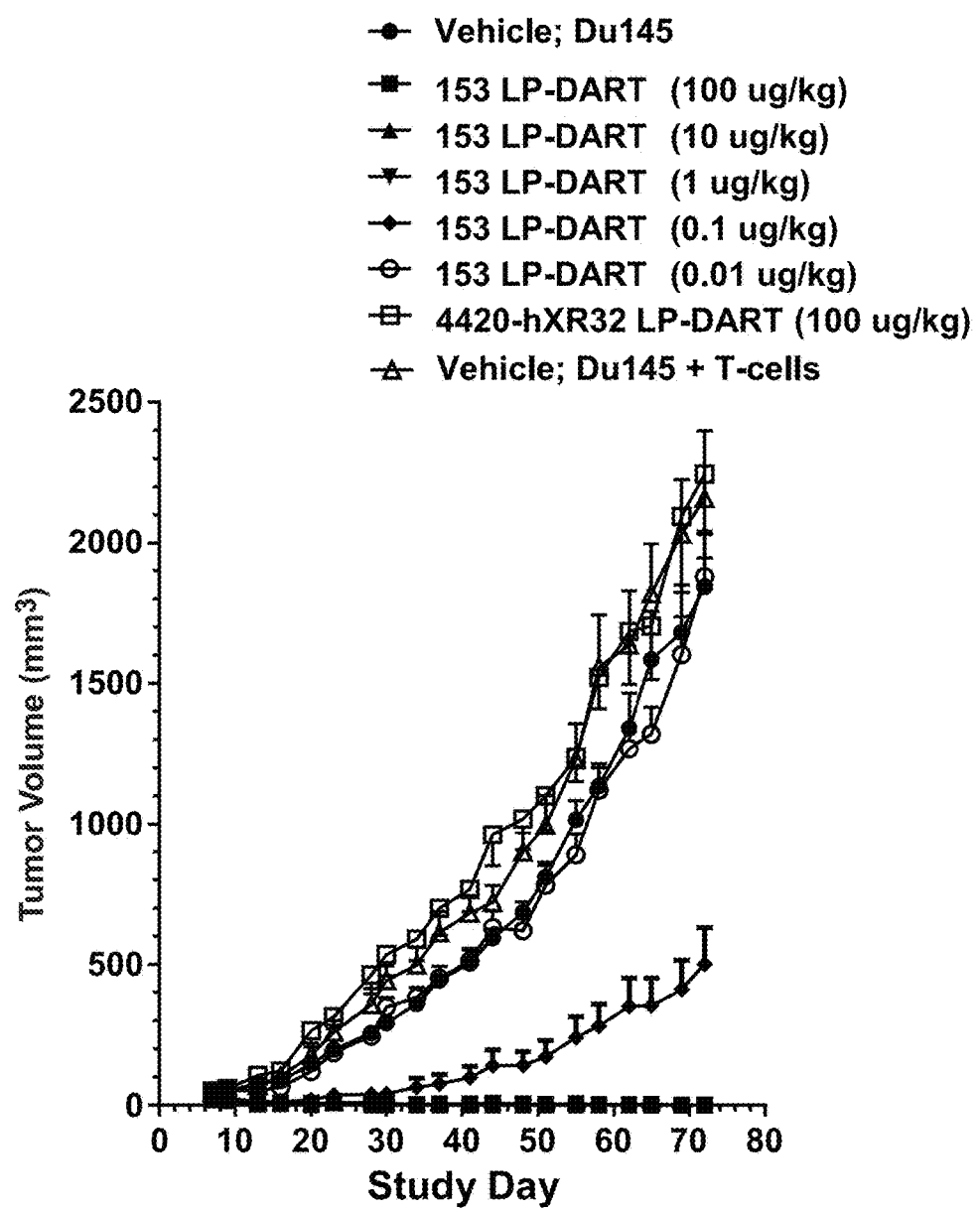
FIG. 15 demonstrates the in vivo ability of 153 LP-DART to decrease tumor volume in murine Du145 prostate cancer model.

The cell line Du145 was pre-mixed with activated T cells and implanted SC in NOD/SCID gamma knockout mice (N=8/group) on SD0 as detailed above. Treatment with 153 LP-DART was initiated on the same day the tumor cell/T cell mixture was implanted [(SD0)] and proceeded subsequently with daily injections for an additional 3 days for a total of 4 daily injections. The animals were treated with 153 LP-DART at 5 dose levels (100, 10, 1, 0.1, and 0.01 µg/kg). Results are shown in FIG. 15.

The Du145 tumors in the vehicle-treated group (Du145 cells alone or plus T cells) demonstrated a relatively aggressive growth profile in vivo. The growth of the Du145 tumors was significantly inhibited at 100, 10 and 1 µg/kg dose level of 153 LP-DART and by the end of the experiment (SD74) the average volume of the tumors was 0 mm³. At the 0.1 µg/kg dose level of 153 LP-DART the growth of the Du145 tumors was significantly inhibited and by the end of the experiment (SD74) the average volume of the tumors was approximately 500 mm³.

F. H1650 Results

The cell line H1650 was pre-mixed with activated T cells and implanted SC in NOD/SCID gamma knockout mice (N=8/group) on SD0 as detailed above. Treatment with 153 LP-DART was initiated on the same day the tumor cell/T cell mixture was implanted [(SD0)] and proceeded subsequently with daily injections for an additional 3 days for a total of 4 daily injections. The animals were treated with 153

LP-DART at 5 dose levels (100, 10, 1, 0.1, and 0.01 µg/kg). Results are shown in FIG. 16.

The H1650 tumors in the vehicle-treated group (H1650 cells alone or plus T cells) demonstrated a relatively aggressive growth profile in vivo. The growth of the H1650 tumors was significantly inhibited at 100, 10 and 1 µg/kg dose level of 153 LP-DART and by the end of the experiment (SD49) the average volume of the tumors was 50 mm$^3$. At the 0.1 µg/kg dose level of 153 LP-DART the growth of the H1650 tumors was significantly inhibited and by the end of the experiment (SD49) the average volume of the tumors was approximately 400 mm$^3$.

The various EK-DART, LP-DART and control DART proteins effectively inhibited the growth of HCT116, Du145 and H1650 tumors implanted SC in NOD/SCID mice in the context of the Winn model when dosing was initiated on the day of implantation and continued for 3 or more consecutive days. Based on the criteria established by the National Cancer Institute, the various DART proteins at the 0.1 mg/kg dose level and higher (TGI>58) is considered active in the three models.

Example 10

Established Tumor Human PBMC Engrafted Model

Four separate xenograft tumor models of human colorectal cancer classified with P-cadherin high (HCT116), medium (SW480), low (Ls174T) and negative (SW620) expression based upon quantitative flow cytometry analysis were established. HCT116 demonstrates the highest relative level of cell surface P-cadherin expression (43,801 ABC, Table 28), SW480 demonstrates a relatively moderate level of cell surface P-cadherin expression (12,665 ABC, Table 28) and Ls174T demonstrates a relatively low level of cell surface P-cadherin expression (4,160 ABC, Table 28).

NOD scid gamma (NSG) animals were subcutaneously implanted into the right flank with 5×10$^6$ HCT116, 5×10$^6$ SW480, 2×10$^6$ Ls174T or 5×10$^6$ SW620 tumor cells on day 0. Seven days prior to randomization (day 5) based upon anticipated tumor growth, animals were inoculated with 5×10$^6$ freshly isolated human peripheral blood mononuclear cells (PBMC) via intraperitoneal injection of 0.2 mL cell suspension in PBS. One week following PBMC implant (day 12) the tumor volume was measured for all study animals and blood samples collected for flow cytometry. The red blood cells from each sample were lysed with BD Pharmlyse solution (BD Pharmingen) and resulting cell pellets stained for human CD3, human CD4, and human CD8 and analyzed by flow cytometry using a BD Pharmingen LSRII with FACS Diva software. The human CD3+ cells as a percent of total lymphocytes determined by forward scatter versus side scatter gating was established for each animal. Tumor measurements were collected using a digital Vernier caliper (Mitutoyo America, Aurora, Ill.), and volumes were calculated by use of the modified ellipsoid formula ½(width$^2$×length).

Two parameter randomization was used to establish treatment groups of n=10 animals per group providing equal weighting between tumor volume and human CD3+ cell engraftment values. Animals were dosed intravenously with 0.05 mg/kg or 0.5 mg/kg 153 LP-DART (CD3-1), 0.5 mg/kg negative control bispecific (heterodimeric diabody Fc fusion protein against FITC and CD3 epsilon) or DPBS as vehicle to the lateral tail vein of each animal. Biweekly tumor measurements were collected to assess tumor growth inhibition versus controls, along with continuous monitoring for signs of graft versus host disease (e.g. decreased body weight, hair loss, hunched posture).

Figure 17A:
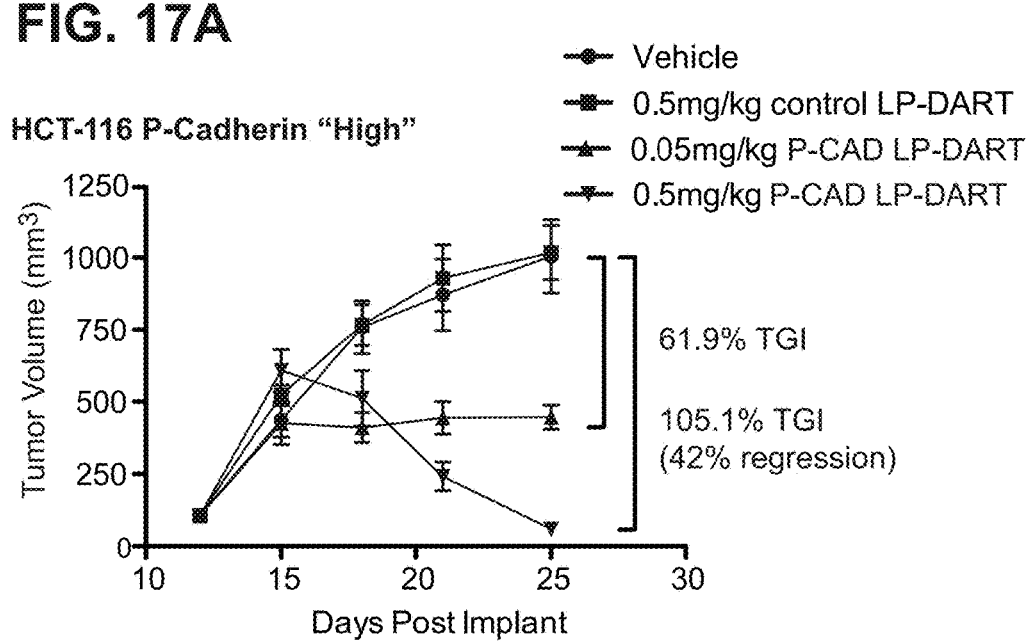
FIGS. 17A-17D demonstrate the in vivo ability of 153 LP-DART to decrease tumor volume in an established tumor+engrafted human T cell model, 17E demonstrates a one way ANOVA analysis of the tumor volume.
Figure 17B:
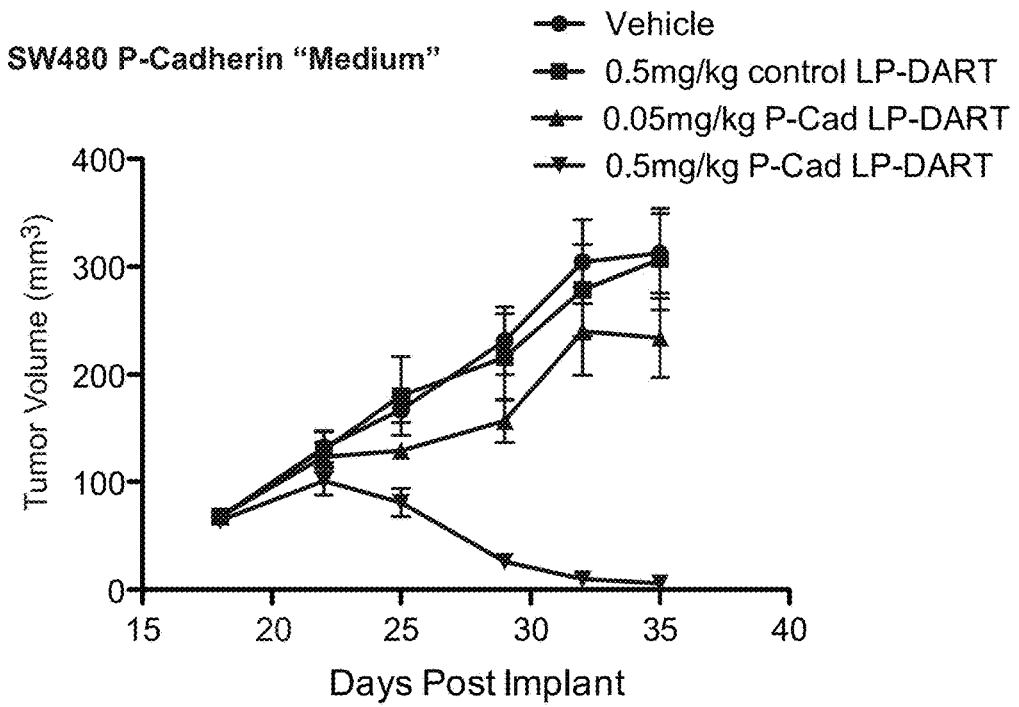
Figure 17C:
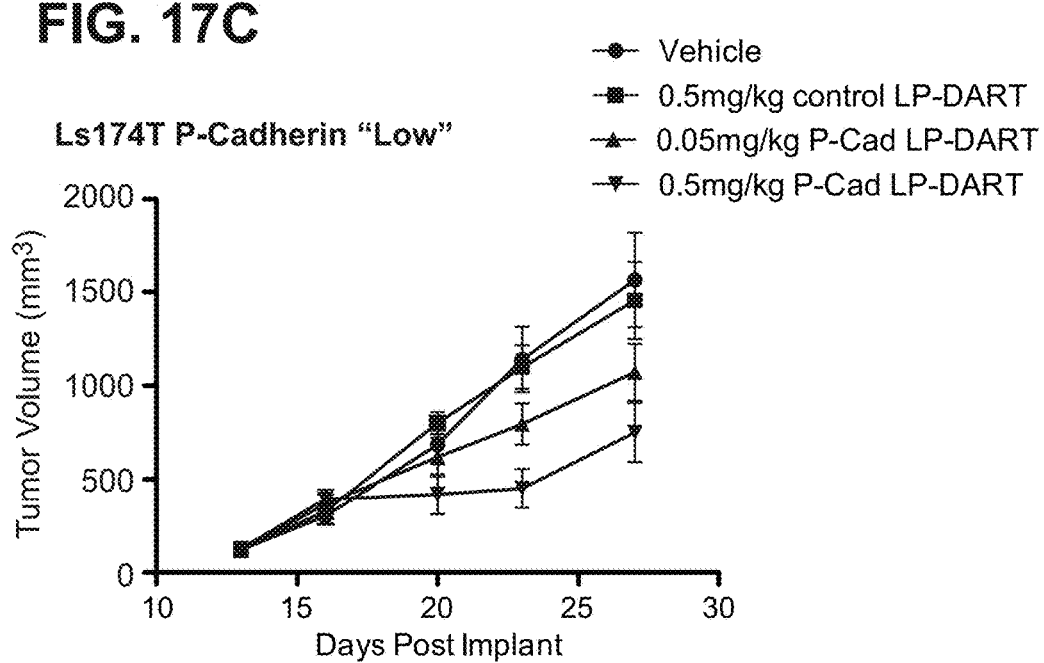
Figure 17D:
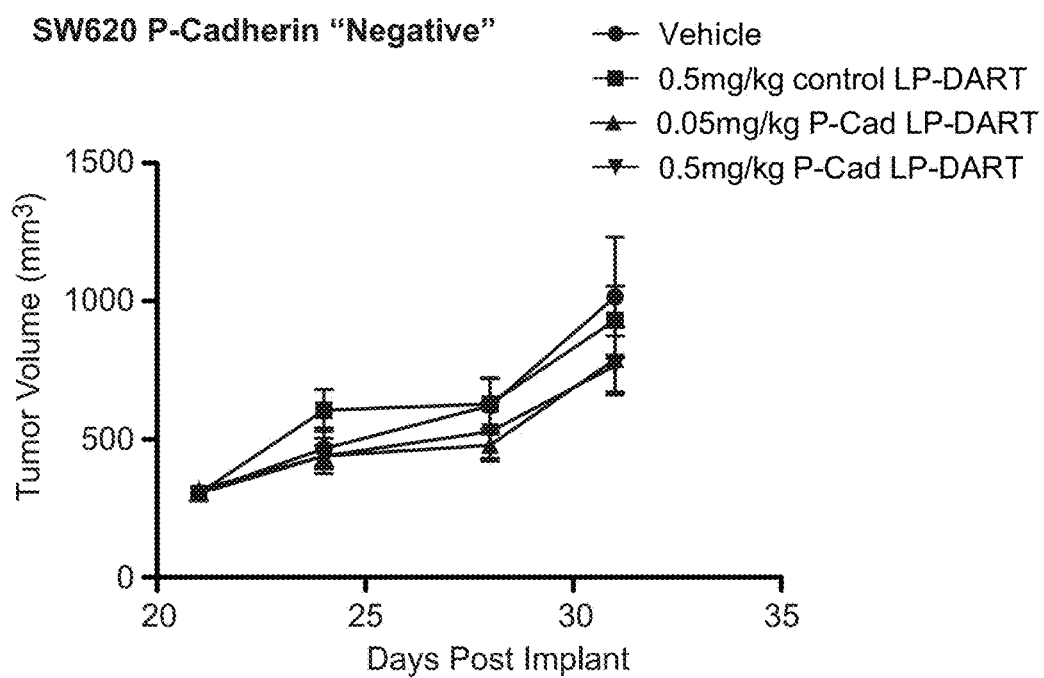

Tumor growth plots demonstrating the tumor volume (mm$^3$) plotted versus time are shown in FIGS. 17A-17D and corresponding data tables are shown below in Tables 32-35. The data demonstrates that weekly 153 LP-DART administrations resulted in tumor regression at the highest dose (0.5 mg/kg) for the HCT116 (high), SW480 (medium) tumor models and moderate efficacy at the highest dose (0.5 mg/kg) for the Ls174T (low) tumor model. Administration of the negative control bispecific showed no increase in tumor inhibition compared to vehicle treated mice. In the HCT116 tumor model, FIG. 17A shows a 61.9% and 105.1% tumor growth inhibition (TGI) at 0.05 and 0.5 mg/kg doses of 153 LP-DART, respectively. FIGS. 17A-17D further demonstrate that tumor growth inhibition of the established xenograft tumors was dependent on P-cadherin level expression.

TABLE 32

Tumor growth inhibition in HCT116 tumor models.

| Days from Study Start | Vehicle | | 0.5 mg/kg Control LP-DART | | 0.05 mg/kg P-cadherin LP-DART | | 0.5 mg/kg P-cadherin LP-DART | |
|---|---|---|---|---|---|---|---|---|
| | Mean tumor volume (mm$^3$) | SEM | Mean tumor volume (mm$^3$) | SEM | Mean tumor volume (mm$^3$) | SEM | Mean tumor volume (mm$^3$) | SEM |
| 0 | 107 | 13 | 106 | 13 | 105 | 12 | 106 | 12 |
| 3 | 436 | 58 | 522 | 35 | 426 | 74 | 608 | 73 |
| 6 | 759 | 92 | 766 | 71 | 410 | 52 | 511 | 95 |
| 9 | 871 | 124 | 929 | 115 | 444 | 56 | 241 | 49 |
| 13 | 1005 | 127 | 1017 | 93 | 446 | 42 | 60 | 10 |

TABLE 33

Tumor growth inhibition in SW480 tumor models.

| Days from Study Start | Vehicle Mean tumor volume (mm³) | SEM | 0.5 mg/kg Control LP-DART Mean tumor volume (mm³) | SEM | 0.05 mg/kg P-cadherin LP-DART Mean tumor volume (mm³) | SEM | 0.5 mg/kg P-cadherin LP-DART Mean tumor volume (mm³) | SEM |
|---|---|---|---|---|---|---|---|---|
| 0 | 67 | 6 | 68 | 7 | 68 | 6 | 64 | 7 |
| 4 | 132 | 14 | 130 | 18 | 123 | 13 | 101 | 13 |
| 7 | 167 | 12 | 180 | 37 | 129 | 8 | 81 | 13 |
| 11 | 232 | 31 | 216 | 40 | 157 | 20 | 26 | 3 |
| 14 | 305 | 39 | 278 | 42 | 240 | 41 | 10 | 3 |

TABLE 34

Tumor growth inhibition in Ls174T tumor models.

| Days from Study Start | Vehicle Mean tumor volume (mm³) | SEM | 0.5 mg/kg Control LP-DART Mean tumor volume (mm³) | SEM | 0.05 mg/kg P-cadherin LP-DART Mean tumor volume (mm³) | SEM | 0.5 mg/kg P-cadherin LP-DART Mean tumor volume (mm³) | SEM |
|---|---|---|---|---|---|---|---|---|
| 0 | 121 | 12 | 121 | 14 | 118 | 13 | 126 | 18 |
| 3 | 301 | 43 | 328 | 40 | 366 | 51 | 393 | 51 |
| 7 | 686 | 103 | 801 | 59 | 619 | 104 | 420 | 107 |
| 10 | 1142 | 175 | 1099 | 116 | 796 | 110 | 451 | 106 |
| 14 | 1565 | 253 | 1456 | 206 | 1072 | 152 | 751 | 158 |

TABLE 35

Tumor growth inhibition with engrafted human T cells of SW620

| Days from Study Start | Vehicle Mean tumor volume (mm³) | SEM | 0.5 mg/kg Control LP-DART Mean tumor volume (mm³) | SEM | 0.05 mg/kg P-cadherin LP-DART Mean tumor volume (mm³) | SEM | 0.5 mg/kg P-cadherin LP-DART Mean tumor volume (mm³) | SEM |
|---|---|---|---|---|---|---|---|---|
| 0 | 308 | 29 | 305 | 29 | 319 | 28 | 304 | 28 |
| 3 | 467 | 74 | 605 | 76 | 440 | 37 | 441 | 64 |
| 7 | 622 | 102 | 628 | 91 | 480 | 47 | 528 | 106 |
| 10 | 1014 | 219 | 930 | 125 | 790 | 117 | 767 | 106 |

Figure 17E:
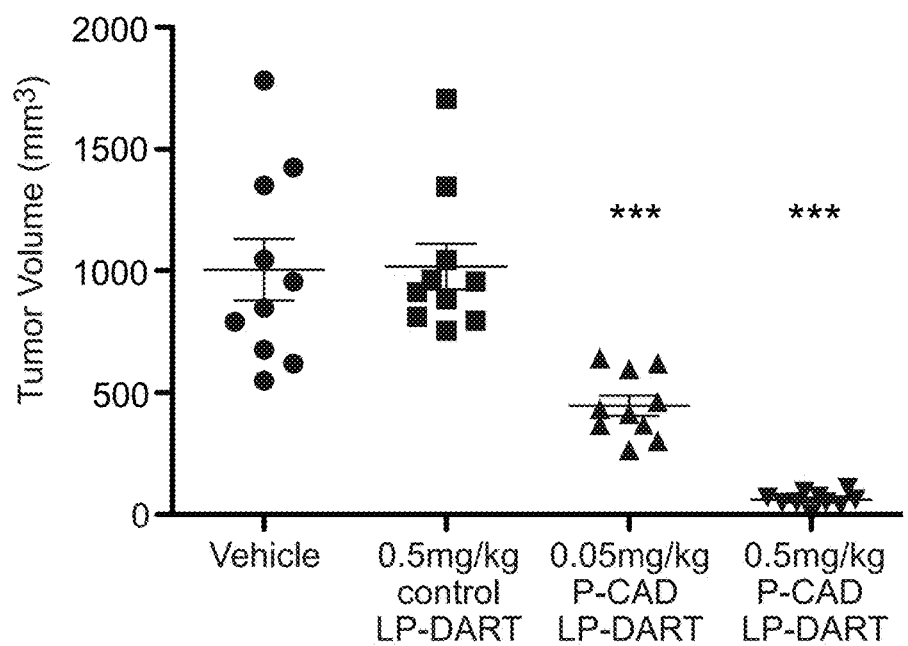

FIG. 17E shows one way ANOVA analysis of the tumor volume (mm³) collected at day 25 post implant of the HCT116 tumor model with Dunnet's multiple comparison test to the vehicle control group. The data demonstrates significant tumor growth inhibition (*p<0.05) in both the 0.05 mg/kg and 0.5 mg/kg dosed groups with 153 LP-DART.

The results of pharmacokinetic analysis of P-cadherin 153 LP-DART treated HCT116 tumor bearing NSG animals is shown in Table 36. Animals were administered a single IV dose of 0.05 or 0.5 mg/kg 153 LP-DART and euthanized in n=3 groups at the indicated time-points following dosing to collect serum and tumor. Assay of the LP-DART was performed by sandwich ELISA against a standard curve. The 153 LP-DART demonstrated extended serum and tumor half-life.

TABLE 36

Pharmacokinetic analysis of 153 LP- DART treated animals.

| IV Dose (mg/kg) | Tissue | Co (μg/mL) | Cmax (μg/mL) | Tmax (hours) | AUC(0-Tlast) (μg*hours/mL) | AUC(0, inf) (μg*hours/mL) | CL (0-t) (mL/kg/hours) | Vdss (L/kg) | T½ (hours) | T½ (days) |
|---|---|---|---|---|---|---|---|---|---|---|
| 0.05 | Serum | 0.675 | 0.648 | 0.25 | 43.7 | 61 | 1.14 | 150 | 144 | 6 |
| 0.5 | Serum | 11.5 | 11 | 0.25 | 647 | 827 | 0.773 | 89.9 | 115 | 4.79 |
| 0.05 | Tumor | nd | 0.0561 | 48 | 7.48 | 10.8 | nd | nd | 130 | 5.42 |
| 0.5 | Tumor | nd | 1.04 | 48 | 167 | 199 | nd | nd | 88.4 | 3.68 |

Example 11

Established Tumor Human T Cell Adoptive Transfer Model

Tumor growth inhibition with adoptive transfer of human T cells of HCT116 (colon) and SUM149 (breast) was analyzed. HCT116 demonstrates the highest relative level of cell surface P-cadherin expression (43,801 ABC, Table 28) and SUM149 demonstrates a relatively moderate level of cell surface P-cadherin expression (15,426 ABC, Table 28). T cells were resuspended to $0.5 \times 10^6$ cells/ml with OpTmizer CTS T Cell Expansion Serum-Free Media supplemented with 2× GlutaMax-1, 1% PenStrep, and 20 ng/ml recombinant human IL-2 (Life Technologies, Carlsbad, Calif.). Dynabeads Human T-Expander CD3/CD28 magnetic beads (Life Technologies) were then added to T cells at 1×10e6 beads/ml (2 beads/cell), and the cells were cultured for one week according to the manufacturer's protocol. At the time of harvest, beads were removed with a magnet, and cells were resuspended in DPBS at $1 \times 10^7$ cells/ml for in vivo inoculation.

For xenograft studies, NSG mice were inoculated with either $5 \times 10^6$ HCT116 cells in the flank or $5 \times 10^6$ SUM149 cells in the mammary fat pad in a total injection volume of 0.2 mL. HCT116 cells were suspended in DPBS, while SUM149 cells were suspended in growth media and mixed 1:1 with Matrigel Basement Membrane Matrix (BD Biosciences, San Jose, Calif.).

Tumor measurements were collected using a digital Vernier caliper (Mitutoyo America, Aurora, Ill.), and volumes were calculated by use of the modified ellipsoid formula ½(width²×length). Mice were randomized and received the initial dose once tumors had reached growth phase, and $2 \times 10^6$ cultured T cells/mouse were inoculated the following day. Mice were dosed in 0.2 mL bolus injection weekly up to 5 times, and all compound and T cell administrations were intravenous via the lateral tail vein of each animal. Biweekly tumor measurements were collected along with continuous monitoring for signs of graft versus host disease (e.g. decreased body weight, hair loss, hunched posture).

Figure 18A:
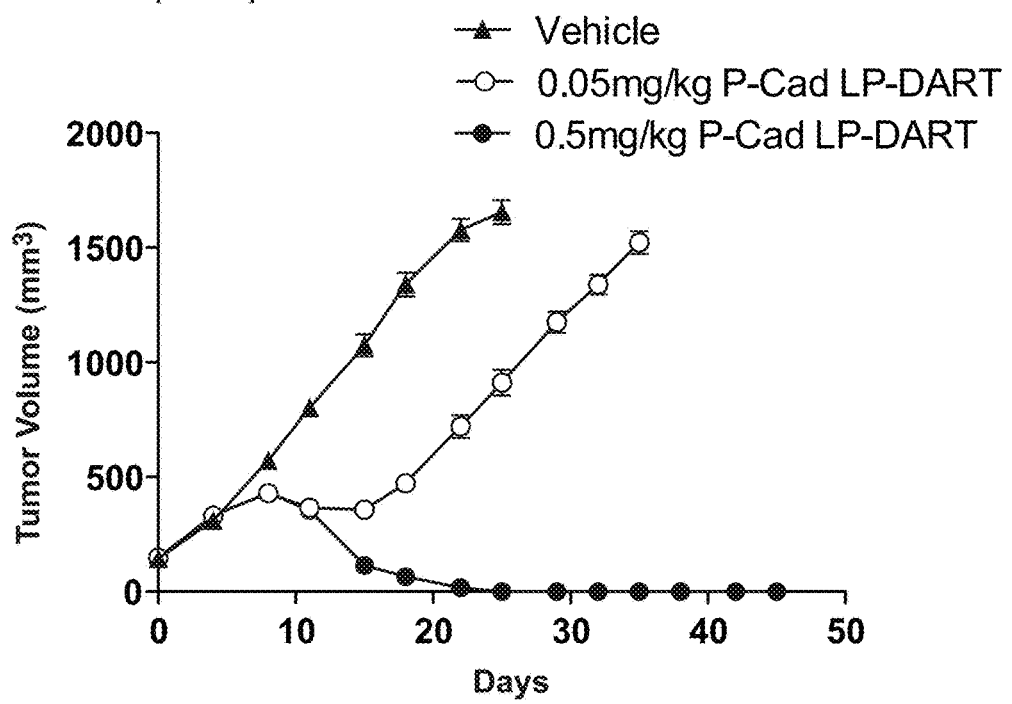
FIGS. 18A and 18B demonstrate the in vivo ability of 153 LP-DART to decrease tumor volume in an established tumor human T cell adoptive transfer model.
Figure 18B:
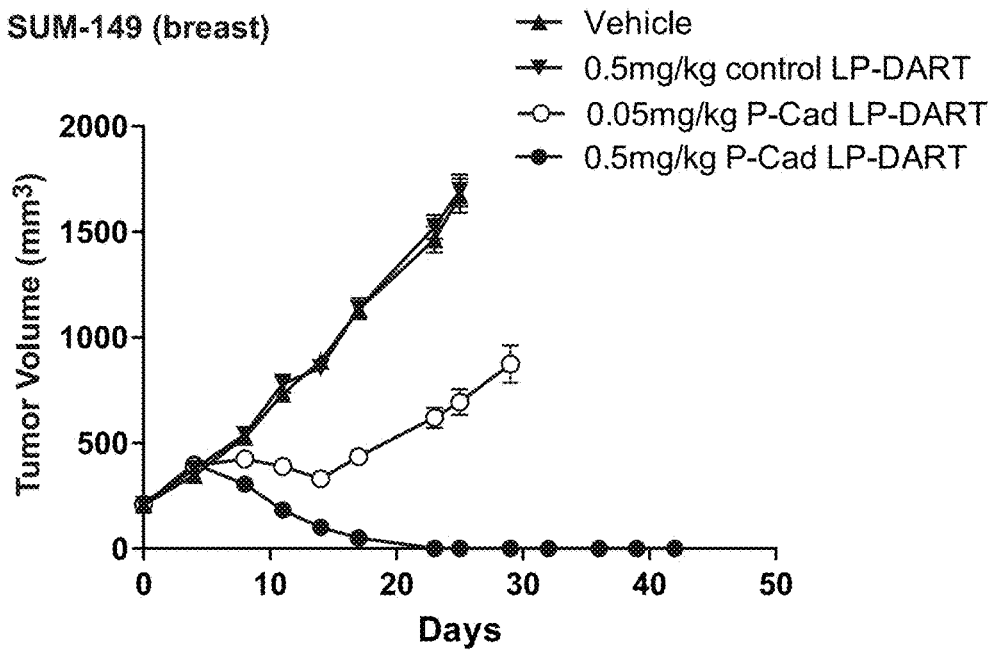

Tumor growth inhibition with adoptive transfer of human T cells of HCT116 (colon) is shown in FIG. 18A (Table 37) and SUM149 (breast) is shown in FIG. 18B (Table 38). Weekly administration of 153 LP-DART (CD3-1) resulted in a dose response with tumor regressions at the highest dose (0.5 mg/kg) and tumor stasis with eventual relapse at the lower dose (0.05 mg/kg). Administration of the negative control LP-DART showed no increase in tumor inhibition compared to vehicle treated mice. Compared to the above engrafted T cell model of Example 10, the adoptive T cell transfer model allows for prolonged 153 LP-DART dosing before the mice succumb to GVHD (2 weeks and 6 weeks, respectively).

TABLE 37

Tumor growth inhibition with adoptive transfer of human T cells of HCT116.

| Days from Randomization | Vehicle Mean tumor Volume (mm³) | SEM | 0.05 mg/kg P-cadherin 153 LP-DART Mean tumor Volume (mm³) | SEM | 0.5 mg/kg P-cadherin 153 LP-DART Mean tumor Volume (mm³) | SEM |
|---|---|---|---|---|---|---|
| 0 | 144 | 11 | 147 | 10 | 147 | 12 |
| 4 | 310 | 22 | 333 | 19 | 333 | 34 |
| 8 | 573 | 37 | 429 | 31 | 430 | 34 |
| 11 | 803 | 38 | 365 | 35 | 354 | 35 |
| 15 | 1074 | 48 | 357 | 29 | 114 | 22 |
| 18 | 1340 | 53 | 473 | 30 | 65 | 22 |
| 22 | 1577 | 48 | 720 | 49 | 18 | 13 |
| 25 | 1655 | 53 | 911 | 56 | 0 | 0 |
| 29 | — | — | 1175 | 46 | 0 | 0 |
| 32 | — | — | 1339 | 44 | 0 | 0 |
| 35 | — | — | 1523 | 50 | 0 | 0 |
| 38 | — | — | — | — | 0 | 0 |
| 42 | — | — | — | — | 0 | 0 |
| 45 | — | — | — | — | 0 | 0 |

TABLE 38

Tumor growth inhibition with adoptive transfer of human T cells of SUM149.

| Days from Randomization | Vehicle Mean tumor volume (mm³) | SEM | 0.5 mg/kg Control LP-DART Mean tumor Volume (mm³) | SEM | 0.05 mg/kg P-cadherin 153 LP-DART Mean tumor Volume (mm³) | SEM | 0.5 mg/kg P-cadherin 153 LP-DART Mean tumor Volume (mm³) | SEM |
|---|---|---|---|---|---|---|---|---|
| 0 | 208 | 5 | 207 | 5 | 209 | 6 | 207 | 13 |
| 4 | 348 | 13 | 342 | 41 | 393 | 18 | 400 | 22 |
| 8 | 528 | 18 | 541 | 30 | 424 | 17 | 306 | 27 |
| 11 | 733 | 36 | 782 | 42 | 389 | 24 | 183 | 15 |
| 14 | 889 | 39 | 856 | 36 | 330 | 18 | 101 | 7 |
| 17 | 1132 | 42 | 1137 | 49 | 435 | 26 | 50 | 10 |
| 23 | 1464 | 61 | 1524 | 57 | 620 | 47 | 0 | 0 |

TABLE 38-continued

Tumor growth inhibition with adoptive transfer of human T cells of SUM149.

| | Vehicle | | 0.5 mg/kg Control LP-DART | | 0.05 mg/kg P-cadherin 153 LP-DART | | 0.5 mg/kg P-cadherin 153 LP-DART | |
|---|---|---|---|---|---|---|---|---|
| Days from Randomization | Mean tumor volume (mm$^3$) | SEM | Mean tumor Volume (mm$^3$) | SEM | Mean tumor Volume (mm$^3$) | SEM | Mean tumor Volume (mm$^3$) | SEM |
| 25 | 1671 | 81 | 1696 | 75 | 694 | 60 | 0 | 0 |
| 29 | — | — | — | — | 874 | 89 | 0 | 0 |
| 32 | — | — | — | — | — | — | 0 | 0 |
| 36 | — | — | — | — | — | — | 0 | 0 |
| 39 | — | — | — | — | — | — | 0 | 0 |
| 42 | — | — | — | — | — | — | 0 | 0 |

Example 12

P-Cadherin Positive Patient Derived Xenograft (PDX)

In vivo tumor growth inhibition of a P-cadherin positive PDX was analyzed. P-cadherin positive patient derived colorectal tumor xenograft, PDX-CRX-11260, was identified by positive staining of FFPE tumor samples with anti-P-cadherin antibody. PDX-CRX-11260 tumor tissue was implanted to NSG animals and grown to roughly 100 mm$^3$. The animals were randomized into dose groups of n=7 and dosed with vehicle, 0.05 mg/kg 153 LP-DART (CD3-1), or 0.5 mg/kg 153 LP-DART (CD3-1) weekly. One day following the initial dose all animals received 2×10$^6$ in vitro expanded human T cells.

Figure 19:
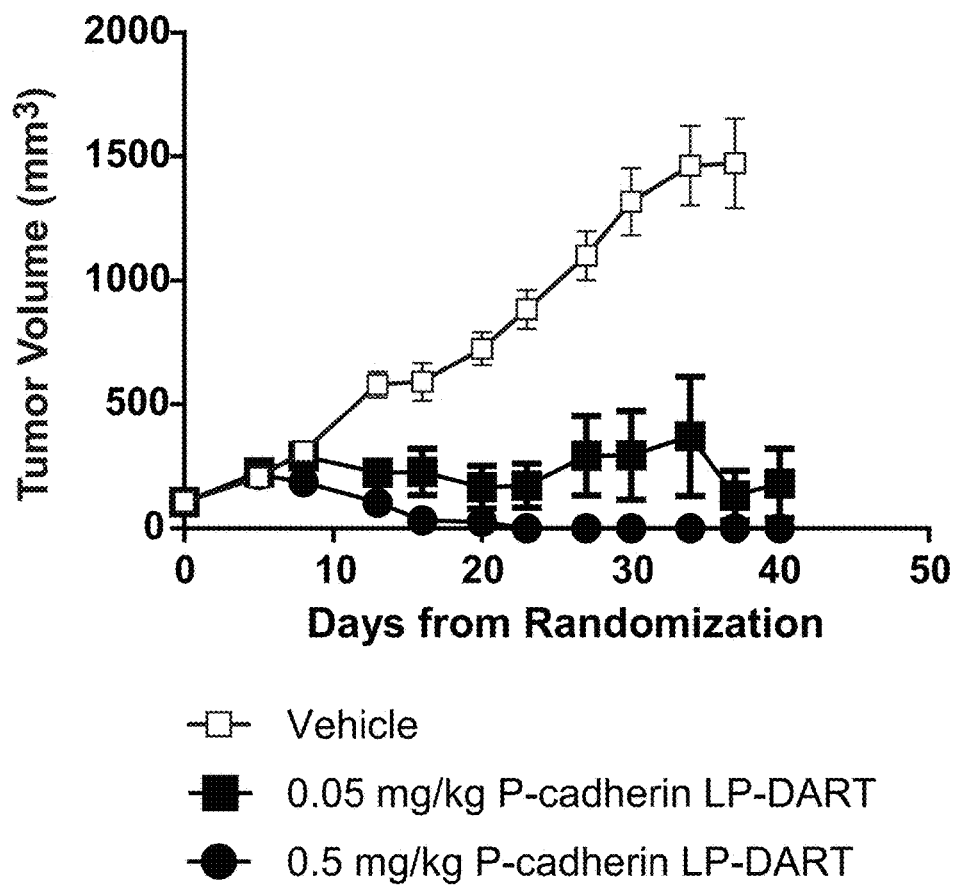
FIG. 19 demonstrates the in vivo ability of 153 LP-DART to decrease tumor volume in a P-cadherin positive patient derived colorectal tumor xenograft.

Tumor growth inhibition of PDX-CRX-11260 is shown in FIG. 19A (Table 39). The 0.05 mg/kg 153 LP-DART dose group demonstrated 3 of 7 animals having complete responses and the 0.5 mg/kg 153 LP-DART dose group demonstrated 7 of 7 animals having complete responses. The data demonstrates that 153 LP-DART exhibits potent tumor growth inhibition of a P-cadherin positive colon tumor PDX.

nized six days following dosing to assess tumor infiltrating human CD3+ lymphocytes. Tumor samples were collected into gentleMACS C tubes containing human tumor cell dissociation buffer (Miltenyi Biotech) and processed to single cell suspension using the manufacturer suggested protocol for soft human tumors using the gentleMACS tissue dissociator (Miltenyi Biotech). The cell suspensions were then washed with DPBS containing 2 mM EDTA and viable cell counts determined by trypan blue exclusion and hemocytometer. 1×10$^6$ live cells from each sample were collected into PBS containing 2% FBS and 0.02% sodium azide and stained with CD3 FITC (BD Pharmingen) for 30 min on ice. Following washing, propidium iodide was added to each sample immediately prior to analysis using LSRII with FACS Diva software (BD Pharmingen).

The data was analyzed by FlowJo software (Treestar) and the percent CD3+ cells of total live cell events was plotted in a grouped plot with significance determined via 1 way ANOVA with Dunnett's Multiple Comparison test versus

TABLE 39

Tumor growth inhibition P-cadherin positive PDX-CRX-11260.

| | Vehicle | | 0.05 mg/kg P-cadherin 153 LP-DART | | 0.5 mg/kg P-cadherin 153 LP-DART | |
|---|---|---|---|---|---|---|
| Days from Randomization | Mean tumor Volume (mm$^3$) | SEM | Mean tumor Volume (mm$^3$) | SEM | Mean tumor Volume (mm$^3$) | SEM |
| 0 | 107 | 6 | 106 | 5 | 106 | 6 |
| 5 | 206 | 22 | 226 | 23 | 215 | 22 |
| 8 | 311 | 20 | 290 | 37 | 186 | 16 |
| 13 | 579 | 52 | 224 | 52 | 104 | 28 |
| 16 | 591 | 77 | 227 | 93 | 33 | 17 |
| 20 | 725 | 67 | 165 | 87 | 25 | 17 |
| 23 | 884 | 79 | 172 | 89 | 0 | 0 |
| 27 | 1101 | 99 | 292 | 161 | 0 | 0 |
| 30 | 1318 | 136 | 294 | 179 | 0 | 0 |
| 34 | 1463 | 161 | 370 | 240 | 0 | 0 |
| 37 | 1473 | 181 | 132 | 101 | 0 | 0 |
| 40 | — | — | 181 | 141 | 0 | 0 |

Example 13

Dose Dependent Accumulation of Tumor Infiltrating Lymphocytes (TILs)

Figure 20:
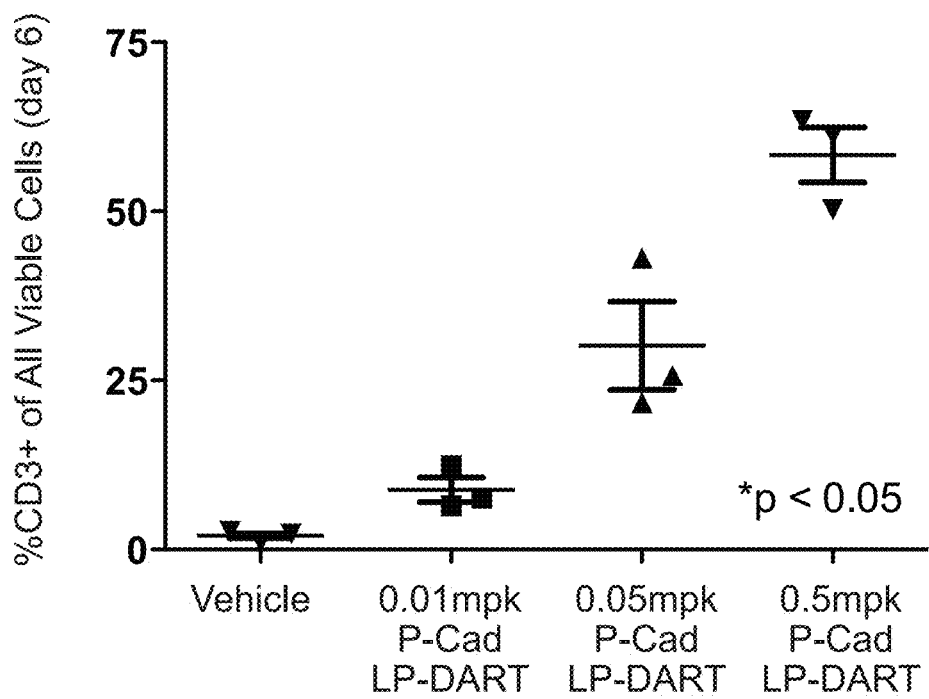
FIG. 20 shows a 153 LP-DART mediated dose dependent increase in tumor infiltrating lymphocytes (TILS).

HCT116 tumor bearing mice engrafted with human peripheral blood mononuclear cells (PBMC) and dosed with varying levels of 153 LP-DART (CD3-1) (n=3) were euthauntreated control samples using GraphPad Prism 5.0 software. The results shown in FIG. 20 and Table 40 demonstrate a dose dependent increase in tumor infiltrating lymphocytes (TILS). Further, immunohistochemistry (IHC) staining of human CD3 of the tumor tissue (not shown) demonstrated that 153 LP-DART treatment of animals having P-cadherin positive tumors and human T cells resulted in intra-tumoral accumulation of CD3+ lymphocytes.

TABLE 40

Dose dependent accumulation of tumor infiltrating lymphocytes (TILs).

| Dose of 153 LP-DART | Mouse | % CD3+ of all viable cells |
| --- | --- | --- |
| 0.01 mg/kg | 1 | 7.60 |
| | 2 | 6.48 |
| | 3 | 12.40 |
| 0.05 mg/kg | 1 | 43.00 |
| | 2 | 21.70 |
| | 3 | 25.70 |
| 0.5 mg/kg | 1 | 61.30 |
| | 2 | 63.40 |
| | 3 | 50.30 |

Example 14

Biodistribution and Tumor Targeting of P-Cadherin LP-DART Using FMT Imaging

NSG or athymic nude mice with established subcutaneous HCT116 xenografts were used. Studies that included engraftment of T cells received T cells isolated from healthy human volunteers. The bio-distribution studies were initiated when the tumors reached 300-500 mm$^3$. P-cadherin 153 LP-DART (CD3-1) or a negative control-DART (non-targeted domain×CD3 binding domain) was conjugated with a near-infrared fluorophore VivoTag680XL (VT680), with ratios of fluorphore to bispecific labeling between 1 to 2.75, resulting in: P-Cadherin 153 LP-DART-VivoTag680XL and Control-LP-DART-VivoTag680XL.

The labeling efficiency was determined by spectrophotometer. T cells used in trafficking studies were labeled with CellVue815 (CV815). Cell surface P-cadherin expression and P-cadherin 153 LP-DART binding was determined by flow cytometry. T cell activity was measured with cytotoxic T-lymphocyte (CTL) assays. FMT imaging was performed longitudinally post injection of labeled bispecifics. Data was analyzed using TrueQuant software. Plasma and tissues were collected at various time points for PK analysis by ELISA.

A. In vitro Characterization of Labeled Biologic Molecule

To determine whether the VT680 labeling affected the molecule properties, quality control studies were performed: in vitro binding to cells by FACS analysis and cytotoxicity assays for molecule activity. The properties were compared for VT680 labeled and unlabeled control LP-DART and P-cadherin 153 LP-DART. For T cells labeled with CV815, T cell expansion and also cytotoxicity on effector cells were evaluated. Table 41 shows the molecules used for the biodistribution study. DOL=degree of labeling.

TABLE 41

VivoTag680XL labeled molecules.

| Molecules | DOL | ~Ab/Dose |
| --- | --- | --- |
| P-Cadherin 153 LP-DART-VivoTag680X | 2.62 | 0.925 mg/kg |
| Control-LP-DART-VivoTag680XL | 2.75 | 0.9 mg/kg |

Direct soluble P-cadherin ELISA to evaluate the binding capability: FIG. 21A demonstrates that VT680 labeling to P-cadherin 153 LP-DART had minimal effect on P-cadherin binding. The minimal decrease was DOL dependent. Control-LP-DART (labeled or unlabeled) did not bind to P-cadherin.

Direct soluble CD3 ELISA to evaluate the binding capability: FIG. 21B demonstrates that VT680 labeling to P-cadherin 153 LP-DART significantly reduced binding to CD3 epsilon/delta protein. The decrease in binding was DOL dependent. Control LP-DART had lower binding than P-cadherin 153 LP-DART. VT680 labeling significantly reduced the binding to CD3 epsilon/delta.

Figure 21C:
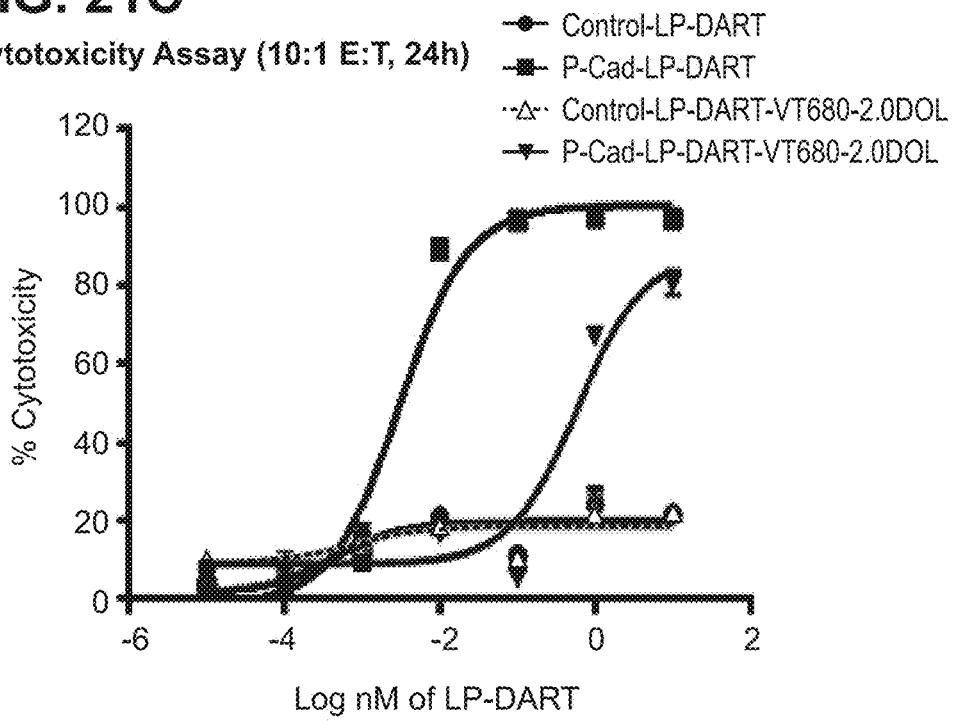

HCT116 cells expressing luciferase were utilized as "target" cells for in vitro cytotoxicity with purified human T lymphocyte "effector" cells in a 24 hour assay at a 10:1 effector to target ratio against a titration of P-cadherin 153 LP-DART. The cytotoxicity plot shown in FIG. 21C illustrates that the cytotoxicity was reduced when P-Cadherin 153 LP-DART was labeled with VT680 at 2.0 DOL.

Figure 21D:
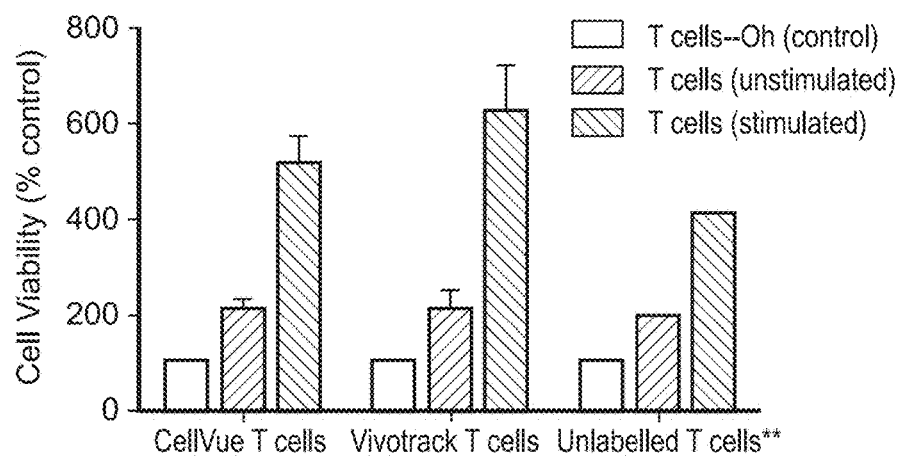

Comparison of cell viability and expansion of T cells after labeling with cell labeling dyes: Human T cells isolated from donors were labeled with fluorescent cell tracking dyes—VivoTrack680 and CellVue815 (CV815). FIG. 21D demonstrates that neither VivoTrack680 or CV815 affected the cell viability or expansion of T cells.

B. In vivo FMT Imaging and PK Analysis Data

Biodistribution and targeting of P-cadherin 153 LP-DART in HCT116 xenograft model was analyzed using longitudinal FMT imaging. One million HCT116 cells in 50% matrigel were injected into the SQ flanks of the female nu/nu mice (8 weeks old). The tumors were allowed to grow up to ~300-500 mm$^3$ in size. The animals were injected with probes (VT680 labeled biologic molecules) equivalent to 1 nmoles of VT680 (Table 41). In vivo FMT Imaging (whole body) was performed longitudinally at 5 min, 24 hr, 48 hr, 96 hr and 240 hr post injection. Blood (plasma) samples were collected at each time point. At intermittent time point and end of the study, the animals were euthanized and perfused with PBS/Saline to remove the blood from vascular compartment. The tissues (tumor, liver, spleen, kidney, lungs and brain) were imaged ex vivo. The FMT data was analyzed using TrueQuant software. After ex vivo imaging, the tissues were flash frozen for future PK analysis. PK analysis of plasma and tissue samples was performed by ELISA. T cell engraftment was not performed in the biodistribution study.

Figure 22A:
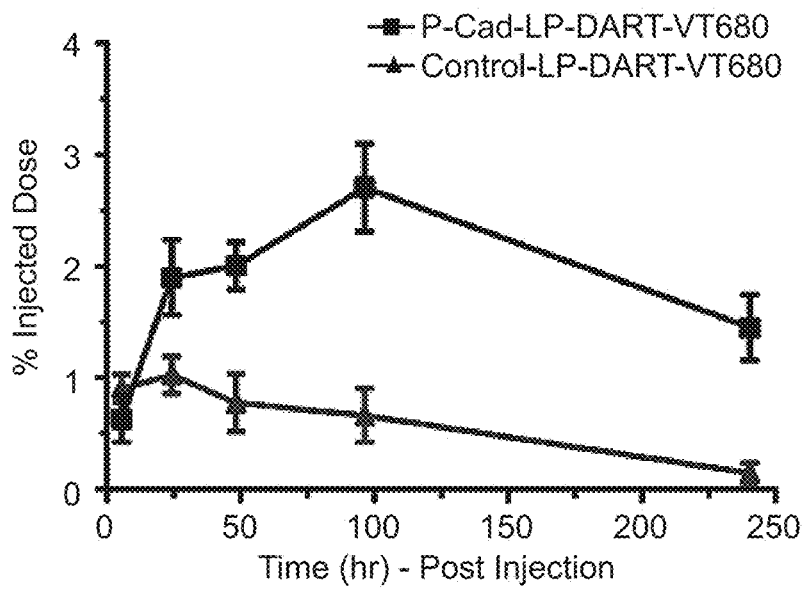
FIGS. 22A-22D provide biodistribution and targeting of 153 LP-DART in a HCT116 xenograft model using longitudinal FMT imaging.
Figure 22B:
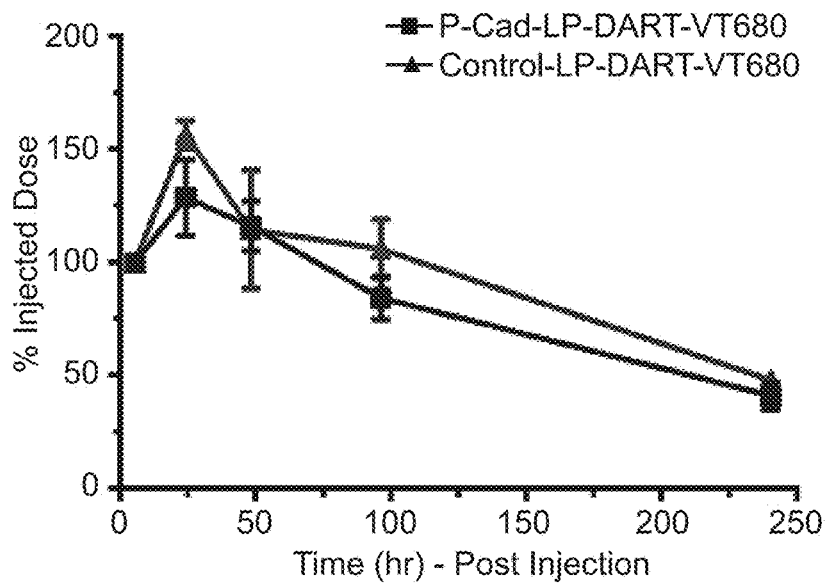

FMT imaging showed that P-cadherin 153 LP-DART specifically targeted HCT116 tumors. Non-invasive in vivo FMT imaging revealed high levels of P-cadherin 153 LP-DART accumulation in the tumors (images not shown) compared to control LP-DART. The in vivo kinetics revealed that the peak accumulation in tumors was about 96 hours post injection, as shown in FIG. 22A. Whole body distribution and clearance data demonstrating the composite of accumulation and clearance from various tissues, tumor and vascular compartments showed no overall significant difference between P-cadherin 153 LP-DART and control-LP-DART, as shown in FIG. 22B.

Figure 22C:
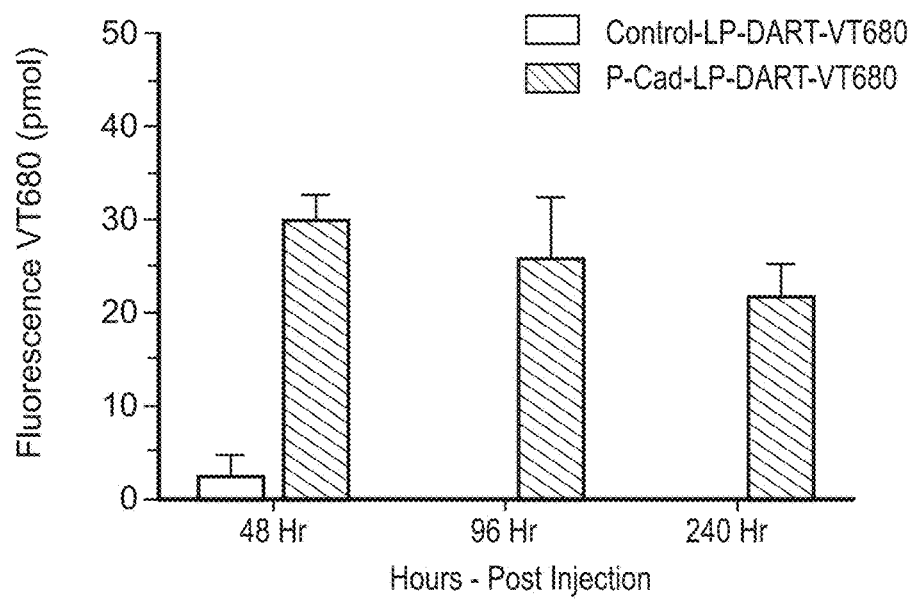
Figure 22D:
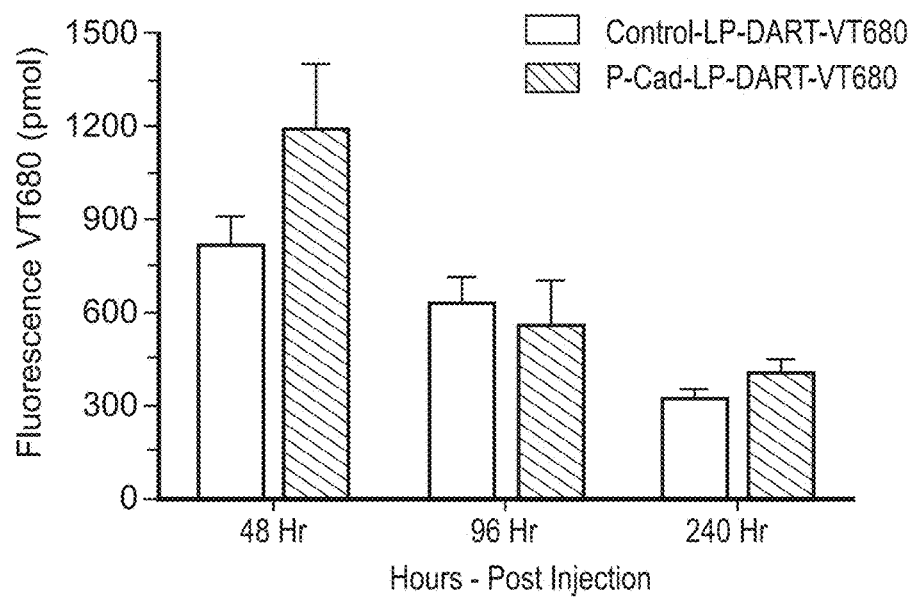
Figure 23A:
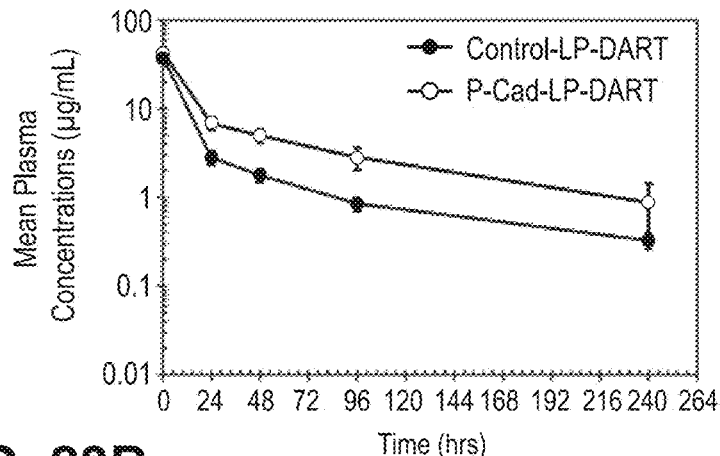
FIGS. 23A-23C show the pharmacokinetic data (ELISA) from the FMT imaging study.
Figure 23B:
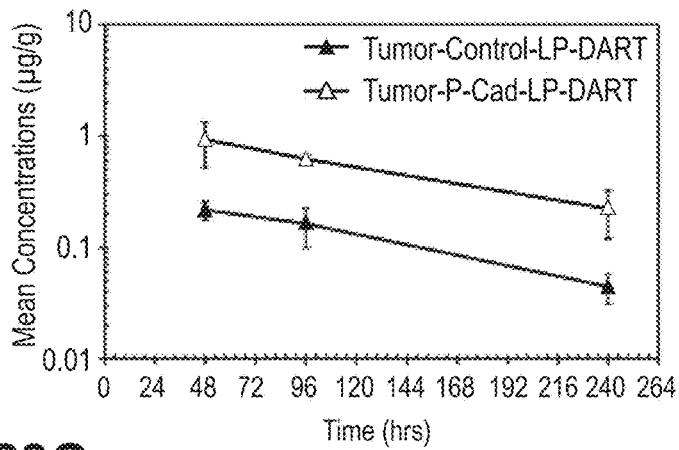
Figure 23C:
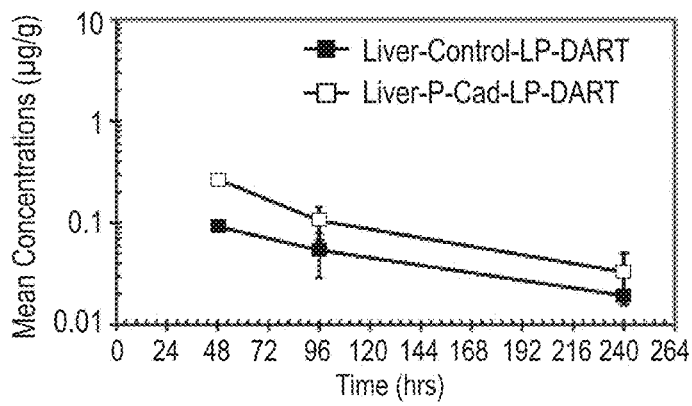

As shown in FIGS. 22C and 22D, ex vivo analysis of tumor and selected tissues at 48, 96 and 240 hours demonstrated that the P-cadherin 153 LP-DART penetrated into the tissue. Tumors showed 20-30 fold higher accumulation of P-cadherin 153 LP-DART compared to control-LP-DART at all time points. At 240 hours post-injection, there was still measurable P-cadherin 153 LP-DART detected in tumors. Ex vivo comparison of accumulation in various organs (liver (FIG. 22D), kidney, spleen, lungs and brain (data not shown) showed no difference between P-cadherin 153 LP-DART or negative control DART A comparison of FMT data with pharmacokinetic methods was conducted to confirm the profiles of FMT imaging. Samples from the FMT study were evaluated by routine pharmacokinetic method, ELISA. The PK data from tumor and liver showed similar trends as FMT imaging data described above. As shown in FIG. 23A, the plasma profile showed ~2-3 fold longer plasma exposure of P-Cad-LP-DART compared to Control-LP-DART. As shown in FIG. 23B, the evaluation of Ex vivo tumor sample showed ~7 fold increase in accumulation of P-Cad-LP-DART. As shown in FIG. 23C, the evaluation of ex vivo liver samples showed increased accumulation at 48 hours, however there was no significant difference at 96 and 240 hours.

C. Cellular Tracking of Engrafted T Cells

Cellular tracking of engrafted T cells in a HCT116 model using FMT imaging was conducted. One million HCT116 cells in 50% matrigel were injected into the SQ flanks of the female NSG mice (8 weeks old). When the tumors were ~300-500 mm$^3$ in size, P-cadherin 153 LP-DART (labeled or unlabeled with VT680) was injected via SQ route. After 24 hours of injecting the drugs, five million T cells labeled with CV815 were injected via IV route. FMT imaging was performed longitudinally after cell engraftment. Sequential imaging was performed using 680 nm and 800 nm laser for P-cadherin 153 LP-DART-VT680 and T Cell-CV815 groups.

Figure 24A:
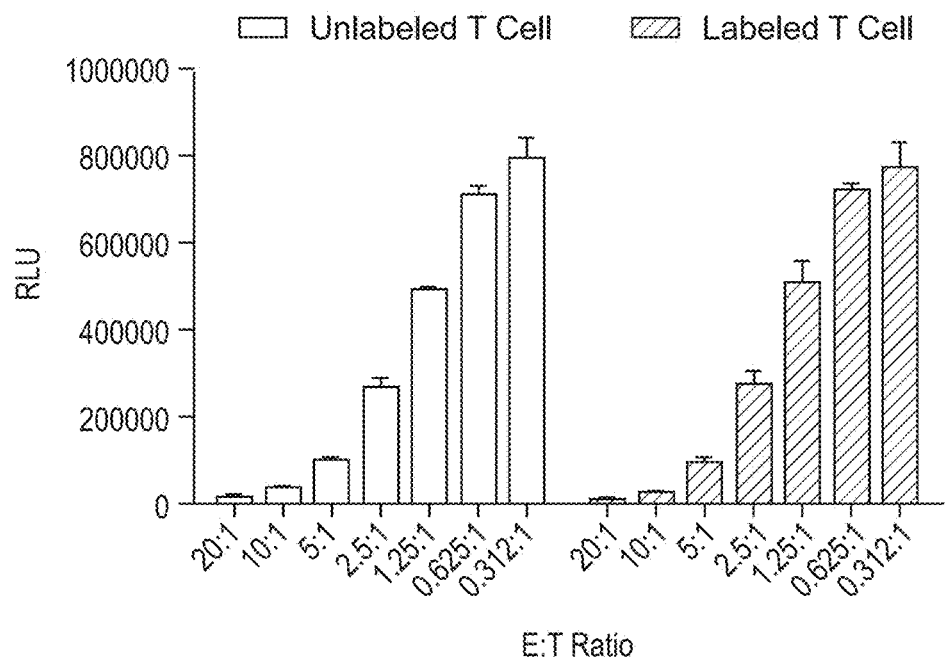
FIG. 24A shows the evaluation of T cell activity of fluorphore labeled and unlabeled T cells and 24B shows the cellular tracking kinetics of fluorophore labeled T cells in a HCT116 tumor model using FMT imaging (in vivo).
Figure 24B:
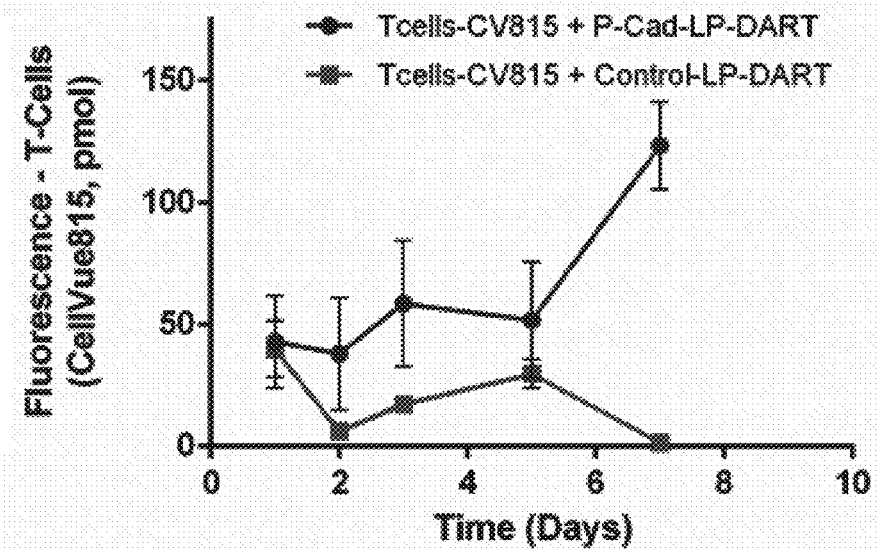

The cell trafficking studies with CellVue labeled T cells showed the co-localization of T cells and P-cadherin 153 LP-DART in tumors. As shown in FIG. 24A, the evaluation of T cell activity of CV815 labeled and unlabeled T cells demonstrates that the labeling of T cells with fluorophore did not have an effect on the cytotoxic ability of T cells (in vitro). As shown in FIG. 24B, the in vivo trafficking kinetics of fluorophore labeled T cells in tumor by FMT imaging demonstrates significantly increased T cell trafficking and accumulation on day 7 post cell engraftment in the P-cadherin 153 LP-DART injected group.

FMT images (not shown) demonstrated targeting of VivoTag680 labeled P-cadherin 153 LP-DART and trafficking of CV815 labeled T cells to tumor on day 5 and day 7 post cell engraftment. This group received CV815 labeled T cells+P-Cadherin 153 LP-DART labeled with VivoTag680. P-Cadherin 153 LP-DART-VT680 with a DOL of 1.0 was used. DOL of 1.0 has shown to minimally affect the binding to P-Cadherin and CD3 proteins.

Example 15

Crystallization and Structure Determination

Figure 25:
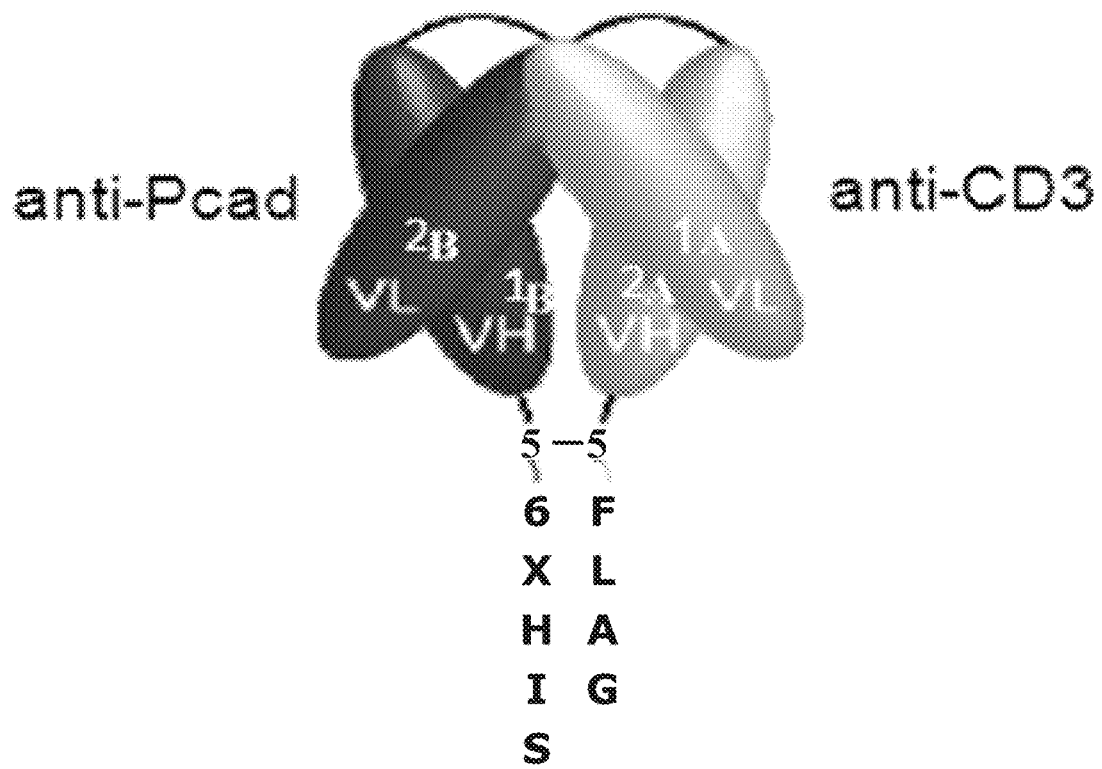
FIG. 25 provides a schematic representation of a DART construct designed for crystallography, having a C-terminal His tag designated "6×HIS" covalently linked to the P-CAD VH domain and a C-terminal FLAG designated "FLAG" covalently linked to the CD3 VH domain.

For crystallization trials a purified DART protein shown in FIG. 25 was utilized. In particular, the DART protein (having a clone 35 P-CAD VL/VH binding domain and a clone CD3 binding domain) was designed for crystallography without heterodimer promoting domains and having a C-terminal His tag HHHHHH (SEQ ID NO: 78) designated "6xHIS" covalently linked to the P-CAD 35 VH domain and a C-terminal FLAG sequence GGCGGDYKDDDDK (SEQ ID NO: 79) designated "FLAG" covalently linked to a CD3 VH domain (herein after designated "crystallography 35 DART").

The purified crystallography 35 DART was concentrated to 9.6 mg/ml in a protein solution containing TBS. The crystals were obtained by hanging-drop vapor-diffusion method from a condition containing 15% PEG 8K and 0.5 M lithium sulfate. The hexagonal plate-like crystals had symmetry consistent with trigonal space group P321 with cell parameters a=b=142.81 Å; c=62.69 Å and with one crystallography 35 DART molecule in the crystallographic asymmetric unit. The crystals were cryo-protected using reservoir solution containing 25% ethylene glycol and were flash frozen in liquid nitrogen. A data set to a 2.0 Å resolution was collected from a single frozen crystal at IMCA beamline 17-ID at the Argonne National Laboratory (APS). The data were processed and scaled using autoPROC and SCALA. The final data set was 96.8% complete with average redundancy of 9.9 and with $R_{sym}$ of 14.2%.

The structure was determined by molecular replacement with PHASER starting with the single chain Fv fragment models prepared from the Brookhaven PDB entry code, 1 moe. The solution was obtained by searching for each of the four subunits of the crystallography 35 DART molecule separately. Several iterative rounds of manual adjustment and model rebuilding using COOT and crystallographic refinement using autoBUSTER yielded the final crystallography 35 DART model with a crystallographic $R_{work}$ of 17.6% and $R_{free}$ of 20.5%, where $R_{work}=||F_{obs}|-|F_{calc}||/|F_{obs}|$ and $R_{free}$ is equivalent to $R_{work}$, but calculated for a randomly chosen 5% of reflections omitted from the refinement process.

The final crystallography 35 DART model comprised two chains, heavy (H) and light (L), with residues 1-110, 117-239 of chain H and residues 2-110, 116-246 of chain L. Non-protein atoms present in the model included 574 water molecules and 5 sulfate ions. Missing amino acids in the linker regions (11 residues) were not modeled into the structure because of the lack of electron density, very likely due to disorder.

Figure 26:
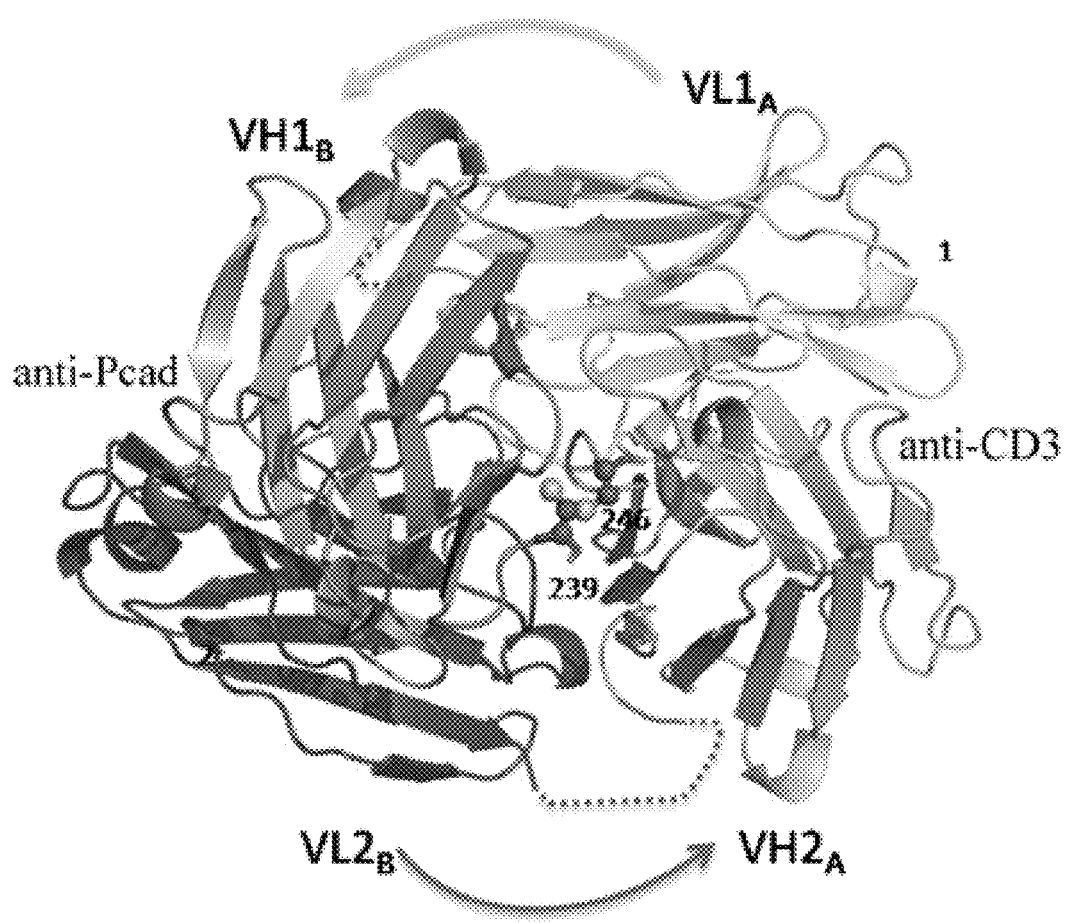
FIG. 26 provides a graphical depiction of the crystal structure of the crystallography 35 DART protein.

FIG. 26 shows a graphical depiction of the crystal structure of the crystallography 35 DART protein. In the crystal, crystallography 35 DART assembled into a very compact spherical structure that differed considerably from the previously published diabody structures (FIG. 27) (see Carmichael et al., J. Mol. Biol. 326: 341-351 (2003); Perisic, et al., Structure, 2(12): 1217-1226, (1994)). It has an unexpectedly extensive interface between subunits and clear evidence for stabilization of the structure by a disulfide linkage between the two polypeptide chains, Cys$^{239}$ (VH1B)-Cys$^{246}$ (VL2A). The four subunits, VL1A VH1B, VL2B and VH2A, all contributed to the binding interface, with the most contribution coming from the framework amino acid residues of both chains. The latter observation suggested that other DART proteins, constructed with other CDR sequences, with binding to diverse tumor-associated antigens, may share a similar architecture and a similar domain interface with the crystallography 35 DART.

Figure 28:
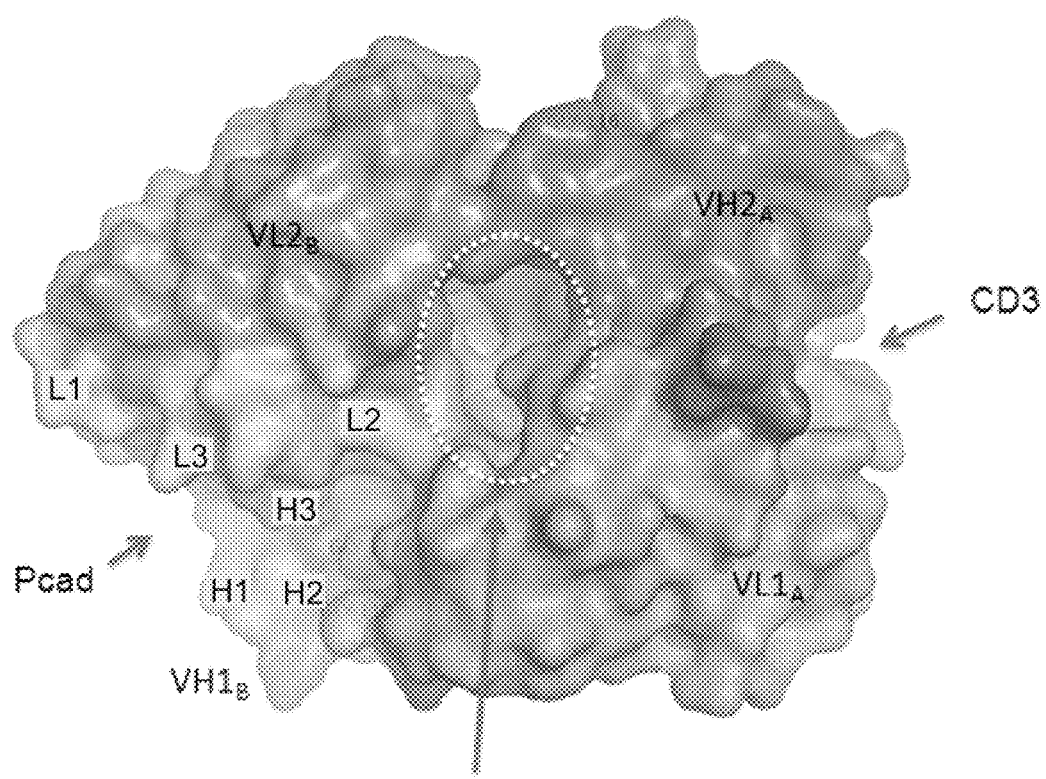
FIG. 28 provides a schematic of a crystallography 35 DART protein variant with a more stable interdomain association through site-directed mutagenesis in the interdomain interface containing large interior voids/holes that may be filled up with increasing side chain volumes with various amino acids.

Despite the relatively tight packing, the crystallography 35 DART interface was not as highly enriched and as shaped complementary as naturally occurring interfaces in Fab molecules, characterized by a high degree of interchain association between the heavy and light chain domains. In crystallography 35 DART, a few depressions in one chain or domain that were not complemented by protrusions in the other resulted in small interior packing defects and large voids, filled with bound water in the crystal structure (FIG. 28).

The two antigen binding sites on the crystallography 35 DART were separated from each other by about 40 Å and were located on the orthogonally opposite sides of the molecule. In this context, "orthogonally opposite sides" means the two binding sites on the crystallography 35 DART were opposing each other at an angle of ~90°.

Figure 27:
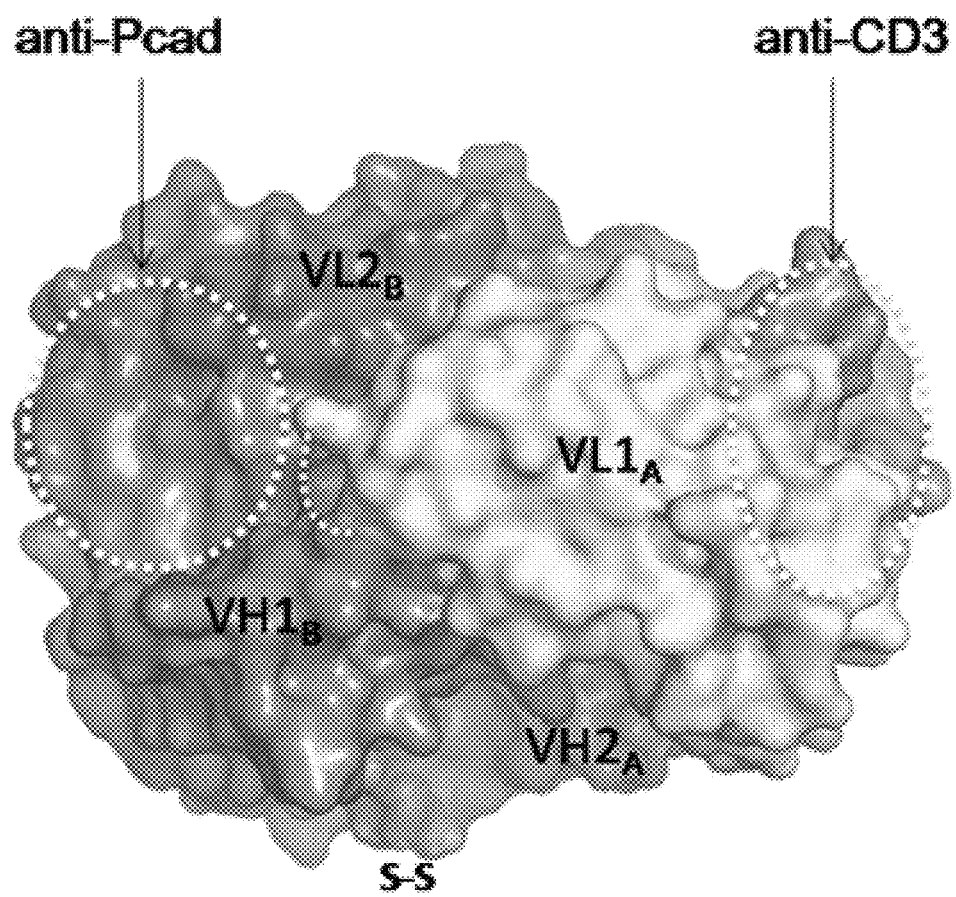
FIG. 27 provides a graphical depiction of the crystallography 35 DART protein showing the antigen binding sites for the anti-CD3 CDR regions and the anti-P-CAD CDR regions.

The anti-CD3 CDR regions were positioned remotely from the subunit interface whereas the anti-P-CAD CDR regions were within a more adjacent area (see FIG. 27).

In addition, novel single chain DART (scDART) variants were generated to address the problem of two chain diabody mispairing (various VH and VL chain directionalities may be used based on the crystal structure). Additional cysteine residues were engineered to induce the covalent linkage within scDART proteins to further improve the stability of the single chain diabody. The method was a variation of Dani et al. (Prot. Eng. 16(3): 187-193 (2003)) utilizing further analysis to rank the quality of each site. Various disulfide bond locations were also engineered using this method to reduce solvent accessibility of the disulfide bond as well as to reduce the length of linkers. For example, modeling positions for the introduction of stereochemically optimal disulfides suggested the following amino acid residue-pairs for cysteine mutagenesis (see FIG. 29): $Gln^{121}$ (VH1B)$Gly^{160}$(VL1A), $Val^{129}$(VH1B)$Gly^{244}$(VL1A), $Val^{123}$(VH1B)$Gly^{160}$(VL1A), $Gly^{126}$(VH1B)$Ser^{242}$ (VL1A), and $Ala^{127}$(VH1B)$Ser^{242}$(VL1A).

Further, using the Discovery Studio (Accelrys Software Inc) stability prediction protocols and the Rosetta v2.3 stability protocol, DART variants (including scDART variants) were engineered through site-directed mutagenesis in the interdomain interface to fill up large interior voids/holes (FIG. 26) in an attempt to further improve the stability of interdomain association. For example, increasing side chain volumes at positions $Ala^{44}$(VL1A), $Val^{213}$(VH2A), $Leu^{238}$ (VH2A), or $Met^{231}$(VL2B) by replacing the relatively small amino acids for amino acids with bulky aromatic side-chains like phenylalanine, tyrosine, or tryptophan. Further engineered were single surface cysteine mutants probing various positions based on the crystal structure for a site specific bio-conjugation approach.

Example 16

Epitope Mapping of P-Cadherin 153 LP-DART

Figure 34:
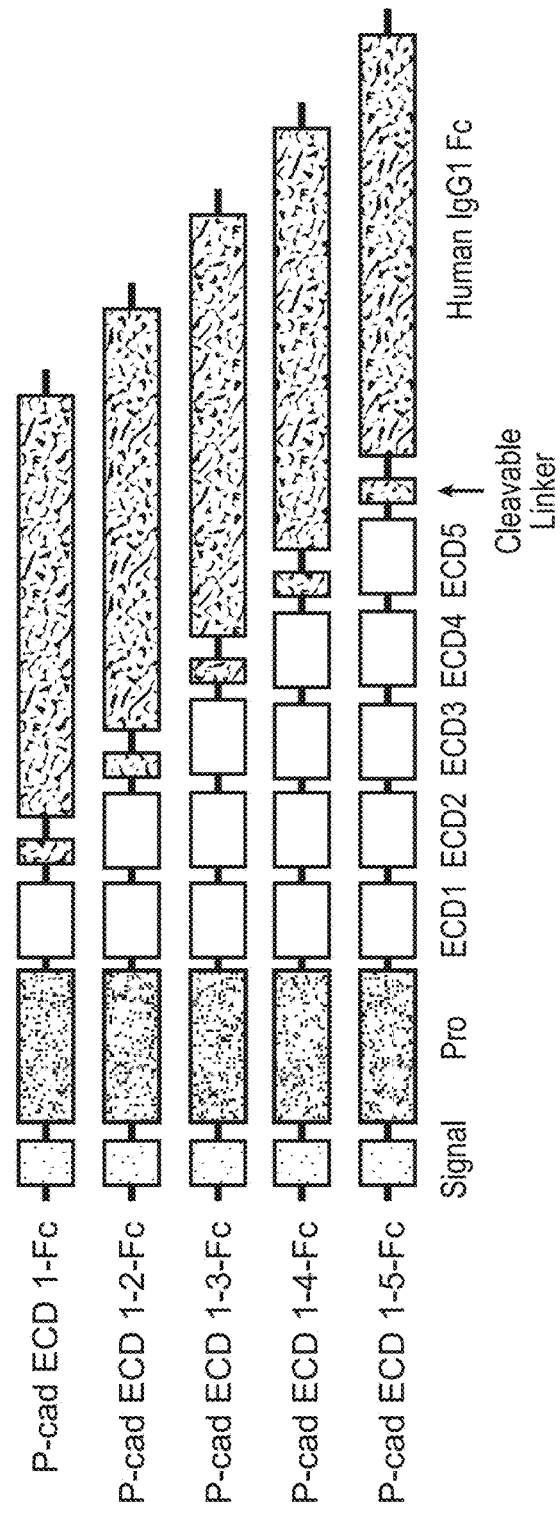
FIG. 34 provides P-cadherin-extra cellular domain (ECD)-Fc fusion protein constructs for eptitope mapping of P-cadherin 153 LP-DART.

To identify the binding epitope of the P-cadherin 153 LP-DART, soluble P-cadherin-extra cellular domain (ECD)-Fc fusion protein constructs were generated. Each P-cadherin-Fc construct comprised a signal peptide, pro-peptide and a P-cadherin ECD subdomain region (either ECD1, ECD1-2, ECD1-3, ECD1-4, or ECD1-5) genetically fused to the hinge and CH2 and CH3 domains of human IgG1 via cleavable linker, as shown in FIG. 34. The ECD1, ECD2, ECD3, ECD4, and ECD5 P-cadherin subdomain fragments used to generate the ECD-Fc constructs correspond with the sequences identified in the full length p-cadherin epitope (UniProt P22223, CADH3, Human Cadherin-3), shown in FIG. 35 and further characterized in Table 42.

TABLE 42

P-cadherin domains and subdomains generated.

| Domain | Residues | SEQ ID NO: |
|---|---|---|
| Full length P-cadherin (UniProt P22223) | 1-829 | 159 |
| P-cadherin Signal Peptide | 1-24 | 160 |
| P-cadherin Propetide | 25-107 | 161 |
| P-cadherin Extra Cellular Domain 1 | 108-215 | 162 |
| P-cadherin Extra Cellular Domain 2 | 216-328 | 163 |
| P-cadherin Extra Cellular Domain 3 | 329-440 | 164 |
| P-cadherin Extra Cellular Domain 4 | 441-546 | 165 |
| P-cadherin Extra Cellular Domain 5 | 547-650 | 166 |
| P-cadherin Transmembrane and Cytoplasmic | 651-829 | 167 |
| P-cadherin Extra Cellular Domain 1-2 | 108-328 | 168 |
| P-cadherin Extra Cellular Domain 1-3 | 108-440 | 169 |
| P-cadherin Extra Cellular Domain 1-4 | 108-546 | 170 |
| P-cadherin Extra Cellular Domain 1-5 | 108-650 | 171 |

All constructs were confirmed by DNA sequencing and transiently transfected into FreeStyle™ 293 HEK cells (Life Technologies, Grand Island, N.Y.) according to the manufacturer's method and expressed over 5-7 days. For enhanced processing of the propeptide, an expression vector containing the PACE cleavage enzyme was co-transfected along with the P-cadherin-containing vector. Soluble protein of interest was purified using standard Protein A chromatographic techniques (Protein A FF, GE Healthcare, Piscataway, N.J.) followed by gel filtration size exclusion chromatography (Superdex200, GE Healthcare, Piscataway, N.J.). Purified protein was characterized for purity and activity by binding ELISA using commercially-available anti-human P-cadherin monoclonal and polyclonal antibodies. Purified P-cadherin ECD-Fc constructs were used in a protein ELISA to determine which ECD subdomain(s) of P-cadherin the 153 LP-DART bound to.

Table 43 shows the binding results of the 153 LP-DART, and various other anti-P-cadherin DART molecules to the P-cadherin ECD-Fc constructs generated, along with a polyclonal Ab (R&D Systems, Minneapolis, Minn.) used to confirm proper expression and folding the ECD-Fc constructs. The results show that 153 LP-DART did not bind to ECD1-Fc or ECD1-2-Fc, but did bind to all constructs that contain ECD3 (ECD1-3-Fc, ECD1-4-Fc and ECD1-5-Fc). This data demonstrates that 153 LP-DART binds to human P-cadherin within ECD3.

TABLE 43

Binding of P-cadherin DARTs to P-cadherin ECD-Fc constructs

| P-cad ECD -Fc Construct | 35 EK-DART | 153 EK-DART | 153 LP-DART | PF EK-DART | 20 EK-DART | 30 EK-DART | Polyclonal Ab (AF-761) |
|---|---|---|---|---|---|---|---|
| ECD 1-Fc | No | No | No | No | No | Yes | Yes |
| ECD 1-2-Fc | No | No | No | Yes | Yes | Yes | Yes |
| ECD 1-3-Fc | Yes | Yes | Yes | Yes | Yes | Yes | Yes |
| ECD 1-4-Fc | Yes | Yes | Yes | Yes | Yes | Yes | Yes |
| ECD 1-5-Fc | Yes | Yes | Yes | Yes | Yes | Yes | Yes |

As shown in Table 24 (above), 153 LP-DART does not bind to murine P-cadherin, therefore 153 LP-DART recognizes an epitope on ECD3 of human P-cadherin (SEQ ID NO: 164) where it differs in sequence from murine P-cadherin ECD3 (SEQ ID NO: 172). Table 44 shows an alignment of human and murine P-cadherin ECD-3 illustrates the differences between these orthologs. (;) represents similar, (.) represents different and (—) represents very different residues.

TABLE 44

Alignment of human and mouse P-cadherin extracellular domain 3 (ECD3).

| ECD3 | Sequence |
|---|---|
| huPcadECD3 | DPQKYEAHVPENAVGHEVQRLTVTDLDAPNSPAWRATYLIMGGDDGDHFTITTHPESNQGILTTRK |
| muPcadECD3 | EPQKYEAWVPENEVGHEVQRLTVTDLDVPNSPAWRATYHIVGGDDGDHFTITTHPETNQGVLTTKK |
|  | :****__**********.********_*:*************:*:***:* |
| huPcadECD3 | GLDFEAKNQHTLYVEVTNEAPFVLKLPTSTATIVVHVEDVNEAPVF (SEQ ID NO: 164) |
| muPcadECD3 | GLDFEAQDQHTLYVEVTNEAPFAVKLPTATATVVVHVKDVNEAPVF (SEQ ID NO: 172) |
|  | ****::**********.::*:**:***** |

To determine whether binding epitope and binding affinity had an effect on potency in T-cell retargeting cytotoxicity assays, the results of the cytotoxic T-lymphocyte (CTL) assays for various anti-P-cadherin EK-DARTs was analyzed. The cytotoxicity values (see Table 29) were compared to the binding affinity to soluble and cell surface-expressed P-cadherin by Biacore and ELISA (see Tables 14-16, 24). The PF-DART binds to P-cadherin in ECD2 with single digit nM binding affinity and has sub-nM CTL cytotoxic activity. The 35 EK-DART (parental clone of 153 EK-DART) binds to P-cadherin in ECD3 with a binding affinity of approximately 35 nM, almost 35 times less than that of the PF-DART but still kills with similar potency (sub-nM). This data suggests that binding in ECD3, which is closer to the cell membrane, results in higher CTL potency. The 153 LP-DART also binds to P-cadherin in ECD3 with much stronger binding affinity than 35 EK-DART (0.5 nM), and shows the highest CTL activity (sub-pM).

Example 17

Paratope Mapping of Anti-P-Cadherin CDRs

To further understand which amino acid (AA) residues in the complementarity determining regions (CDRs) are involved in scFv 153 binding to human P-cadherin, all non-alanine CDR AAs were individually mutated to alanine by parallel site-directed mutagenesis.

Site-Directed Mutagenesis

Sixty three oligos (33-45 bases in length) were designed (Table 45). Oligo length was adjusted for each oligo to have comparable predicted melting temperature (Tm) values. Each oligo was designed to be the reverse complement of the sense strand of clone 153 scFv and to be flanked by 15-21 bases on either side of the "AGC" (reverse complement of alanine codon, GCT).

TABLE 45

Designed oligos.

| Sequence Name | Sequence | Tm | SEQ ID NO. |
|---|---|---|---|
| pcdAlaH1-1 | GCT GGT AAA GGT GTA AGC AGA AGC CTT GCA GGA | 66 | 173 |
| pcdAlaH1-2 | ACC GTA GCT GGT AAA GGT AGC ACC AGA AGC CTT GCA GGA | 69 | 174 |
| pcdAlaH1-3 | GAT ACC GTA GCT GGT AAA AGC GTA ACC AGA AGC CTT GCA | 66 | 175 |
| pcdAlaH1-4 | GAT ACC GTA GCT GGT AGC GGT GTA ACC AGA AGC | 65 | 176 |
| pcdAlaH1-5 | CCA GCT GAT ACC GTA GCT AGC AAA GGT GTA ACC AGA AGC | 66 | 177 |
| pcdAlaH1-6 | CAC CCA GCT GAT ACC GTA AGC GGT AAA GGT GTA ACC AGA | 67 | 178 |
| pcdAlaH1-7 | TCG CAC CCA GCT GAT ACC AGC GCT GGT AAA GGT GTA ACC | 70 | 179 |
| pcdAlaH1-8 | TCG CAC CCA GCT GAT AGC GTA GCT GGT AAA GGT | 67 | 180 |
| pcdAlaH1-9 | CTG TCG CAC CCA GCT AGC ACC GTA GCT GGT AAA | 68 | 181 |
| pcdAlaH1-10 | GGC CTG TCG CAC CCA AGC GAT ACC GTA GCT GGT | 71 | 182 |
| pcdAlaH2-1 | ACC ATT GTA AGC GCT GAT AGC TCC CAT CCA CTC AAG CCC | 69 | 183 |
| pcdAlaH2-2 | GTT ACC ATT GTA AGC GCT AGC CCA TCC CAT CCA CTC AAG | 67 | 184 |
| pcdAlaH2-3 | TGT GTT ACC ATT GTA AGC AGC GAT CCA TCC CAT CCA CTC | 66 | 185 |
| pcdAlaH2-5 | TGC ATA GTT TGT GTT ACC ATT AGC AGC GCT GAT CCA TCC CAT CCA | 68 | 186 |
| pcdAlaH2-6 | TGC ATA GTT TGT GTT ACC AGC GTA AGC GCT GAT CCA TCC | 67 | 187 |
| pcdAlaH2-7 | CTG TGC ATA GTT TGT GTT AGC ATT GTA AGC GCT GAT CCA | 65 | 188 |
| pcdAlaH2-8 | GAG CTT CTG TGC ATA GTT TGT AGC ACC ATT GTA AGC GCT GAT CCA | 67 | 189 |
| pcdAlaH2-9 | GAG CTT CTG TGC ATA GTT AGC GTT ACC ATT GTA AGC GCT | 65 | 190 |

TABLE 45-continued

Designed oligos.

| Sequence Name | Sequence | Tm | SEQ ID NO. |
|---|---|---|---|
| pcdAlaH2-10 | CTG GAG CTT CTG TGC ATA AGC TGT GTT ACC ATT GTA AGC | 65 | 191 |
| pcdAlaH2-11 | GCC CTG GAG CTT CTG TGC AGC GTT TGT GTT ACC ATT GTA | 68 | 192 |
| pcdAlaH2-13 | GAC TCT GCC CTG GAG CTT AGC TGC ATA GTT TGT GTT ACC | 66 | 193 |
| pcdAlaH2-14 | GGT GAC TCT GCC CTG GAG AGC CTG TGC ATA GTT TGT GTT | 69 | 194 |
| pcdAlaH2-15 | CAT GGT GAC TCT GCC CTG AGC CTT CTG TGC ATA GTT TGT | 68 | 195 |
| pcdAlaH2-16 | GGT CAT GGT GAC TCT GCC AGC GAG CTT CTG TGC ATA GTT | 69 | 196 |
| pcdAlaH2-17 | GGT CAT GGT GAC TCT AGC CTG GAG CTT CTG TGC | 67 | 197 |
| pcdAlaH3-1 | ACC AAA AGC ATT AGC TGT ATC AGC AGT CGC ACA GTA ATA CAC GGC | 67 | 198 |
| pcdAlaH3-2 | AAA AGC ATT AGC TGT AGC GAT AGT CGC ACA GTA | 62 | 199 |
| pcdAlaH3-3 | GAT ACC AAA AGC ATT AGC AGC ATC GAT AGT CGC ACA GTA | 64 | 200 |
| pcdAlaH3-5 | GCC CCA GAT ACC AAA AGC AGC AGC TGT ATC GAT AGT CGC | 68 | 201 |
| pcdAlaH3-7 | TTG GCC CCA GAT ACC AGC AGC ATT AGC TGT ATC | 65 | 202 |
| pcdAlaH3-8 | CCC TTG GCC CCA GAT AGC AAA AGC ATT AGC TGT | 66 | 203 |
| pcdAlaH3-9 | CAT TGT CCC TTG GCC CCA AGC ACC AAA AGC ATT AGC TGT | 69 | 204 |
| pcdAlaL1-1 | GTT GGA GCT GCT TCC AGC GCA GGA GAT GGT GAC | 69 | 205 |
| pcdAlaL1-2 | AAT GTT GGA GCT GCT AGC AGA GCA GGA GAT GGT | 66 | 206 |
| pcdAlaL1-3 | ATT CCC AAT GTT GGA GCT AGC TCC AGA GCA GGA GAT GGT | 68 | 207 |
| pcdAlaL1-4 | ATT ATT CCC AAT GTT GGA AGC GCT TCC AGA GCA GGA GAT | 66 | 208 |
| pcdAlaL1-5 | ATA ATT ATT CCC AAT GTT AGC GCT GCT TCC AGA GCA GGA | 65 | 209 |
| pcdAlaL1-6 | GGA TAC ATA ATT ATT CCC AAT AGC GGA GCT GCT TCC AGA GCA GGA | 67 | 210 |
| pcdAlaL1-7 | GGA TAC ATA ATT ATT CCC AGC GTT GGA GCT GCT TCC AGA | 65 | 211 |
| pcdAlaL1-8 | CCA GGA TAC ATA ATT ATT AGC AAT GTT GGA GCT GCT TCC | 62 | 212 |
| pcdAlaL1-9 | GTA CCA GGA TAC ATA ATT AGC CCC AAT GTT GGA GCT GCT | 65 | 213 |
| pcdAlaL1-10 | CTG GTA CCA GGA TAC ATA AGC ATT CCC AAT GTT GGA GCT | 65 | 214 |
| pcdAlaL1-11 | CTG CTG GTA CCA GGA TAC AGC ATT ATT CCC AAT GTT GGA | 65 | 215 |
| pcdAlaL1-12 | GAG CTG CTG GTA CCA GGA AGC ATA ATT ATT CCC AAT GTT | 64 | 216 |
| pcdAlaL1-13 | TGG GAG CTG CTG GTA CCA AGC TAC ATA ATT ATT CCC AAT | 65 | 217 |
| pcdAlaL2-1 | TGA GGG TCG CTT ATT ATT AGC ATA AAT GAG GAG TTT GGG | 63 | 218 |
| pcdAlaL2-2 | CCC TGA GGG TCG CTT ATT AGC GTC ATA AAT GAG GAG TTT | 65 | 219 |
| pcdAlaL2-3 | AAT CCC TGA GGG TCG CTT AGC ATT GTC ATA AAT GAG GAG | 65 | 220 |
| pcdAlaL2-4 | GTC AGG AAT CCC TGA GGG TCG AGC ATT ATT GTC ATA AAT GAG GAG | 66 | 221 |
| pcdAlaL2-5 | TCG GTC AGG AAT CCC TGA GGG AGC CTT ATT ATT GTC ATA AAT GAG | 66 | 222 |
| pcdAlaL2-6 | TCG GTC AGG AAT CCC TGA AGC TCG CTT ATT ATT GTC ATA | 64 | 223 |
| pcdAlaL2-7 | TCG GTC AGG AAT CCC AGC GGG TCG CTT ATT ATT | 66 | 224 |
| pcdAlaL3-1 | GCT GCT ATC CCA TGT AGC GCA GTA ATA ATC GGC | 64 | 225 |
| pcdAlaL3-2 | CAG GCT GCT ATC CCA AGC TCC GCA GTA ATA ATC | 64 | 226 |
| pcdAlaL3-3 | ACC ACT CAG GCT GCT ATC AGC TGT TCC GCA GTA ATA ATC | 66 | 227 |

TABLE 45-continued

Designed oligos.

| Sequence Name | Sequence | Tm | SEQ ID NO. |
|---|---|---|---|
| pcdAlaL3-4 | ACC ACT CAG GCT GCT AGC CCA TGT TCC GCA GTA | 69 | 228 |
| pcdAlaL3-5 | CAC ACC ACT CAG GCT AGC ATC CCA TGT TCC GCA | 68 | 229 |
| pcdAlaL3-6 | GAA TAC CAC ACC ACT CAG AGC GCT ATC CCA TGT TCC GCA | 68 | 230 |
| pcdAlaL3-7 | GCC GAA TAC CAC ACC ACT AGC GCT GCT ATC CCA TGT TCC | 69 | 231 |
| pcdAlaL3-8 | GCC GAA TAC CAC ACC AGC CAG GCT GCT ATC CCA | 70 | 232 |
| pcdAlaL3-9 | TCC GCC GAA TAC CAC AGC ACT CAG GCT GCT ATC | 68 | 233 |
| pcdAlaL3-10 | CCC TCC GCC GAA TAC AGC ACC ACT CAG GCT GCT | 71 | 234 |
| pcdAlaL3-11 | GGT CCC TCC GCC GAA AGC CAC ACC ACT CAG GCT | 72 | 235 |

Single-stranded DNA was produced using a published protocol (Tonikian R et al, Nat. Protoc. 2007; 2(6):1368-86). Briefly, phage expression vector was transformed into CJ236 electro-competent cells according to the manufacturer's protocol (Lucigen, Middleton, Wis.) and 0.05% of cells were plated on LB/Amp plates. After overnight growth, six 1-mL cultures, grown in 2× TY/2% glucose supplemented with 100 μg/mL ampicillin, 10 ug/mL chloramphenicol, and 1e+10 M13KO7 helper phage particles, were inoculated with independent colonies and grown at 37° C. for 2 hours before kanamycin was added to 25 μg/mL. After 4 more hours of shaking at 37° C., cultures showing turbidity were pooled and expanded into a 120 mL culture (2× TY/2% glucose supplemented with 100 μg/mL ampicillin, 25 μg/mL kanamycin, 0.25 μg/mL uridine) in a 2-L baffled flask. Following overnight growth, culture supernatant was rescued via centrifugation (6000 rpm, 10 minutes) and 20 mL PEG/NaCl was added to 100 mL supernatant and phage was purified by PEG-precipitation. Purified phage (resuspended in 1 mL PBS) was lysed and single-stranded uracil DNA was purified (Qiaprep spin M13 kit, Cat. #: 27704) according to manufacturer's protocol. DNA was quantified by Nanodrop (Thermo).

Oligos were ordered in normalized form in tris-EDTA buffer (50 μM in 200 μL). Next, 200 pmoles of each oligo (4 μL) were phosphorylated in 96-well format at 37° C. for 90 minutes and heat inactivated 65° C. for 20 minutes. The reaction mixture contained the following: 4 μL oligo, 2 μL 10×PNK buffer, 2 μL 10 mM ATP, 1 μL 100 mM DTT, 11 μL water, 2 μL T4 PNK (T4 Polynucleotide Kinase). Site-directed mutagenesis reactions were set up in 96-well format as follows: 2.2 μL single-stranded uracil template DNA (200 ng), 2 μL Pfu Turbo Cx buffer, 2 μL 100 mM DTT, 0.4 μL NAD+, 0.16 μL dNTPs, 10 μL water, 0.2 μL (0.5 units of Pfu turbo Cx), 1 μL Taq DNA Ligase, 2 μL of 20-fold diluted phosphorylation reaction (0.9 pmoles). The reaction was incubated as follows: 95° C. for 3 min, 55° C. for 90 sec, 68° C. for 15 min, 45° C. for 15 min. Next, 1 μL (1 pmole) 5' phosphorylated OmpA oligo was added and the reaction was incubated further as follows: 95° C. for 30 sec, 55° C. for 45 sec, 68° C. for 10 min, 45° C. for 15 min. Following these incubations, 2 μL or 2 units UDG: Uracil DNA glycosylase and 5 units ExonucleaseIII enzyme mix were added to digest the template, first at 37° C. for 60 min then at 65° C. for 20 min. Finally, 2 μL from each reaction (63 total reactions) were pooled and 0.3 μL was electroporated into ER2738 electro-competent cells for sequencing.

Preparation of Phage Expressing scFv for Use in ELISAs

ScFvs may be expressed on the surface of a phage particle. To prepare phage expressing scFv on their surface, 96-deep well plates containing 1 mL 2× TY media with 2% glucose/100 μg/mL ampicillin were inoculated with 0.5-1 μL from thawed glycerol stocks (one clone per well) using the QPix™2 Colony picker (Molecular Devices, Sunnyvale Calif.) and grown at 37° C. (900 rpm) for ~4 hours. Next, 5 μL of a 1:29 dilution of helper phage (8.3×10$^{13}$ pfu) was added and the plates and incubated for a further 30 minutes at 37° C. with no shaking then 1 hour at 300 rpm. Plates were centrifuged and the media was replaced with a kanamycin/non-glucose containing media (2× TY with 50 μg/mL kanamycin and 100 μg/mL ampicillin). Plates were grown overnight at 25° C. (900 rpm), and phage were harvested in the supernatant following centrifugation.

ELISA to Measure Binding of scFv Proteins to Human P-Cadherin-Fc.

P-cadherin-ECD1-3-Fc protein or negative control protein was coated overnight at 4° C. on 96-well Nunc Maxisorp® plates (Thermo Fisher Scientific, Madison, Conn.) at a concentration of 2 μg/mL in PBS+$Ca^{2+}$ and $Mg^{2+}$. Plates were washed three times using PBS+$Ca^{2+}$ and $Mg^{2+}$ and blocked for 1 hour at room temperature in 3% milk/PBS+$Ca^{2+}$ and $Mg^{2+}$. Phage samples prepared as described above were added to the blocked plates for 1 hour at room temperature. Plates were washed three times with PBS+$Ca^{2+}$ and $Mg^{2+}$ prior to the addition of secondary antibody (anti M13-HRP 1:2000, GE Healthcare, Piscataway, N.J.). Plates were incubated for a further 1 hour at room temperature and washed six times with PBS+$Ca^{2+}$ and $Mg^{2+}$. Signal was developed using TMB (SurModics, Eden Prairie, Minn.), the reaction stopped with $H_2SO_4$ and the absorbance read at 450 nm on an EnVision® plate reader (Perkin Elmer, Waltham, Mass.).

Assessment of Binding to Human P-Cadherin

Binding of phage preparations of anti-P-cadherin scFv 153 alanine-mutants to human P-cadherin-Fc protein were tested by ELISA. Data was plotted as total binding signal (OD450) and as a percent of binding compared to the parental clone 153. A Z-score was then calculated based on the standard deviation of the percent binding of clone 153. Data for this assay is presented in Table 46 and Table 47.

Results indicate good expression of scFv on phage and demonstrate expected binding activity of clone 153. Certain CDR residues are deemed important because mutation to Ala negatively impacts human P-cadherin binding and has a Z-score of lower than −1. Certain CDR residues are deemed moderately important because mutation to Ala results in a Z-score between −0.2 and −1.0. These results suggest that $H_{1.8}$, $H_{2.5}$, $H_{3.1}$, $H_{3.7}$ and $L_{3.3}$ are important AAs for human P-cadherin binding, while $H_{2.6}$, $H_{2.16}$, $F_{3.5}$, $F_{3.9}$, $L_{1.8}$, $L_{2.2}$, $L_{2.3}$, $L_{3.2}$ and $L_{3.2}$ are moderately important for binding.

TABLE 46

Binding of anti-P-cadherin clone 153 alanine-mutants.

| CDR-VH | Parental sequence | Human P-cadherin-Fc binding (OD450) | % of binding of Clone #153 to human P-cadherin-Fc | Z Score |
|---|---|---|---|---|
| H1.1-Ala | G | 1.79 | 135 | 0.7 |
| H1.2-Ala | Y | 2.36 | 179 | 1.7 |
| H1.3-Ala | T | 2.30 | 174 | 1.6 |
| H1.4-Ala | F | 2.33 | 177 | 1.6 |
| H1.5-Ala | T | 2.05 | 155 | 1.2 |
| H1.6-Ala | S | 1.97 | 149 | 1.0 |
| H1.7-Ala | Y | 1.71 | 129 | 0.6 |
| H1.8-Ala | G | 0.36 | 27 | −1.5 |
| H1.9-Ala | I | 2.21 | 167 | 1.4 |
| H1.10-Ala | S | 2.13 | 161 | 1.3 |
| H2.1-Ala | W | 1.37 | 103 | 0.1 |
| H2.2-Ala | I | 2.20 | 166 | 1.4 |
| H2.3-Ala | S | 1.83 | 138 | 0.8 |
| H2.4-Ala | A | | | |
| H2.5-Ala | Y | 0.45 | 34 | −1.4 |
| H2.6-Ala | N | 1.06 | 80 | −0.4 |
| H2.7-Ala | G | 1.50 | 114 | 0.3 |
| H2.8-Ala | N | 2.14 | 162 | 1.3 |
| H2.9-Ala | T | 2.03 | 154 | 1.1 |
| H2.10-Ala | N | 2.27 | 172 | 1.5 |
| H2.11-Ala | Y | 2.15 | 163 | 1.3 |
| H2.12-Ala | A | | | |
| H2.13-Ala | Q | 2.01 | 152 | 1.1 |
| H2.14-Ala | K | 1.54 | 117 | 0.4 |
| H2.15-Ala | L | 1.34 | 101 | 0.0 |
| H2.16-Ala | Q | 0.90 | 68 | −0.7 |
| H2.17-Ala | G | 2.14 | 162 | 1.3 |
| H3.1-Ala | I | 0.17 | 13 | −1.8 |
| H3.2-Ala | D | 2.22 | 168 | 1.4 |
| H3.3-Ala | T | 2.26 | 171 | 1.5 |
| H3.4-Ala | A | | | |
| H3.5-Ala | N | 0.77 | 58 | −0.9 |
| H3.6-Ala | A | | | |
| H3.7-Ala | F | 0.31 | 23 | −1.6 |
| H3.8-Ala | G | 1.36 | 103 | 0.1 |
| H3.9-Ala | I | 0.80 | 61 | −0.8 |
| P-cad 153 | — | 1.32 | 100 | 0.0 |

TABLE 47

Binding of anti-P-cadherin clone 153 alanine-mutants.

| CDR-VL | Parental sequence | Human P-cadherin-Fc binding (OD450) | % of binding of Clone #153 to human P-cadherin-Fc | Z Score |
|---|---|---|---|---|
| L1.1-Ala | S | 2.19 | 166 | 1.4 |
| L1.2-Ala | G | 1.28 | 97 | −0.1 |
| L1.3-Ala | S | 2.19 | 165 | 1.4 |
| L1.4-Ala | S | 2.31 | 175 | 1.6 |
| L1.5-Ala | S | 1.70 | 129 | 0.6 |
| L1.6-Ala | N | 1.16 | 88 | −0.3 |
| L1.7-Ala | I | 1.42 | 108 | 0.2 |
| L1.8-Ala | G | 1.00 | 75 | −0.5 |
| L1.9-Ala | N | 1.71 | 129 | 0.6 |
| L1.10-Ala | N | 1.81 | 137 | 0.8 |
| L1.11-Ala | Y | 1.84 | 139 | 0.8 |
| L1.12-Ala | V | 2.29 | 173 | 1.6 |

TABLE 47-continued

Binding of anti-P-cadherin clone 153 alanine-mutants.

| CDR-VL | Parental sequence | Human P-cadherin-Fc binding (OD450) | % of binding of Clone #153 to human P-cadherin-Fc | Z Score |
|---|---|---|---|---|
| L1.13-Ala | S | 2.26 | 171 | 1.5 |
| L2.1-Ala | D | 1.45 | 110 | 0.2 |
| L2.2-Ala | N | 1.35 | 102 | 0.0 |
| L2.3-Ala | N | 0.98 | 74 | −0.5 |
| L2.4-Ala | K | 2.13 | 161 | 1.3 |
| L2.5-Ala | R | 2.25 | 170 | 1.5 |
| L2.6-Ala | P | 2.28 | 172 | 1.5 |
| L2.7-Ala | S | 2.16 | 163 | 1.3 |
| L3.1-Ala | G | 2.02 | 153 | 1.1 |
| L3.2-Ala | T | 0.81 | 61 | −0.8 |
| L3.3-Ala | W | 0.18 | 14 | −1.8 |
| L3.4-Ala | D | 0.92 | 70 | −0.6 |
| L3.5-Ala | S | 2.16 | 163 | 1.3 |
| L3.6-Ala | S | 2.29 | 173 | 1.5 |
| L3.7-Ala | L | 2.29 | 173 | 1.6 |
| L3.8-Ala | S | 2.28 | 173 | 1.5 |
| L3.9-Ala | G | 2.19 | 166 | 1.4 |
| L3.10-Ala | V | 1.86 | 141 | 0.9 |
| L3.11-Ala | V | 1.38 | 104 | 0.1 |
| P-cad 153 | — | 1.32 | 100 | 0.0 |

The Alanine scan data and structural information (Example 15) provided herein suggest that a significant number of CDR residues in anti-P-cadherin scFv 153 could be substituted without significantly impact antigen binding. Thus further analyses were conducted to determine which CDR residues may be substituted without significant impact on P-cadherin binding. Tables 48-65 show the predicted Delta Delta G (DDG) stability for each position using the Discovery Studio 4.0 Stability prediction algorithm. Stability score (DDG) indicate the predicted effect of the mutation on protein stability.

TABLES 48

Alternative VH CDR1 residues (DDG <=1.0 kcal/mol)

| CDR position (column 1) | Residue from P-cad 153 (column 2) | Alternative residues (column 3) |
|---|---|---|
| H1.1 | G | R, Q, I, L, C, F, T, G, V, W, M, Y, N, E, P, K, H, D, S, or A |
| H1.2 | Y | H, R, C, Q, Y, I, F, K, M, V, L, N, or T |
| H1.3 | T | N, C, R, V, L, T, I, S, K, Q, M, W, A, F, Y, H, or D |
| H1.4 | F | F or Y |
| H1.5 | T | W, R, I, C, K, Y, M, V, F, T, S, L, Q, E, A, N, H, D, or G |
| H1.6 | S | R, I, M, N, Y, C, H, Q, L, K, F, V, T, E, A, S, D, W, or G |
| H1.7 | Y | K, R, L, H, F, Q, N, C, Y, M, I, T, V, or A |
| H1.8 | G | P, R, F, W, H, C, Y, I, M, K, G, S, Q, A, L, N, T, or D |
| H1.9 | I | Y, F, K, I, W, or L |
| H1.10 | S | R, C, L, N, S, V, T, or A |

TABLES 49

Alternative VH CDR1 residues (DDG <= 0.5 kcal/mol)

| CDR position (column 1) | Residue from P-cad 153 (column 2) | Alternative residues (column 3) |
|---|---|---|
| H1.1 | G | R, Q, I, L, C, F, T, G, V, W, M, Y, N, or E |

TABLES 49-continued

Alternative VH CDR1 residues (DDG <= 0.5 kcal/mol)

| CDR position (column 1) | Residue from P-cad 153 (column 2) | Alternative residues (column 3) |
|---|---|---|
| H1.2 | Y | H, R, C, Q, Y, I, F, K, M, V, or L |
| H1.3 | T | N, C, R, V, L, T, I, S, K, Q, or M |
| H1.4 | F | F or Y |
| H1.5 | T | W, R, I, C, K, Y, M, V, F, T, S, L, Q, E, A, N, or H |
| H1.6 | S | R, I, M, N, Y, C, H, Q, L, K, F, V, T, E, A, S, D, or W |
| H1.7 | Y | K, R, L, H, F, Q, N, C, Y, M, I, or T |
| H1.8 | G | P, R, F, W, H, C, Y, I, M, K, G, S, Q, A, L or N |
| H1.9 | I | Y, F, K, I, W, or L |
| H1.10 | S | R, C, L, N, S, V, or T |

TABLES 50

Alternative VH CDR1 residues (DDG <= 0 kcal/mol)

| CDR position (column 1) | Residue from P-cad 153 (column 2) | Alternative residues (column 3) |
|---|---|---|
| H1.1 | G | R, Q, I, L, C, F, T, or G |
| H1.2 | Y | H, R, C, a or Y |
| H1.3 | T | N, C, R, V, L, or T |
| H1.4 | F | F |
| H1.5 | T | W, R, , I, C, K, Y, M, V, F, or T |
| H1.6 | S | R, I, M, N, Y, C, H, Q, L, K, F, V, T, E, A, or S |
| H1.7 | Y | K, R, L, H, F, Q, N, C, or Y |
| H1.8 | G | P, R, F, W, H, C, Y, I, M, K, or G |
| H1.9 | I | Y, F, K, or I |
| H1.10 | S | R, C, L, N, or S |

TABLES 51

Alternative VH CDR2 residues (DDG <= 1.0 kcal/mol)

| CDR position (column 1) | Residue from P-cad 153 (column 2) | Alternative residues (column 3) |
|---|---|---|
| H2.1 | W | W |
| H2.2 | I | W, F, Y, I, V, H, L, or Q |
| H2.3 | S | W, F, L, R, C, H, T, N, Y, Q, K, A, I, V, S, M, E, or D |
| H2.4 | A | I, Y, V, Q, F, H, K, C, N, T, E, L, M, D, P, S, A, or W |
| H2.5 | Y | C, P, T, S, L, V, M, F, W, Q, K, G, I, A, N, H, E, D, Y, R |
| H2.6 | N | I, Q, W, V, C, L, K, E , T, M, F, Y, R, S, A, N, H, D, or G |
| H2.7 | G | G, C, L, N, W, F, S, Y, T, D, I, or M |
| H2.8 | N | Q, C, I, Y, W, L, T, V, K, M, H, F, S, R, A, E, N, D, or G |
| H2.9 | T | F, L, V, W, H, C, Y, K, I, Q, R, T, M, N, A, S, or D |
| H2.10 | N | R, W, K, F, C, T, L, Y, N, Q, V, H, M, A, S, or D |
| H2.11 | Y | L, F, W, N, Y, H, K, R, I, M, V, C, Q, or E |
| H2.12 | A | W, F, I, Y, L, R, V, M, H, N, C, Q K, T, D, E, A, or S |
| H2.13 | Q | P, R, Q, C, T, I, W, F, K, L, Y, S, V, M, D, or H |
| H2.14 | K | W, C, I, F, T, R, Y, L, Q, S, V, D, N, M, K, A, H, E, or G |
| H2.15 | L | W, I, L, V, F, K, R, H, Y, or M |

TABLES 51-continued

Alternative VH CDR2 residues (DDG <= 1.0 kcal/mol)

| CDR position (column 1) | Residue from P-cad 153 (column 2) | Alternative residues (column 3) |
|---|---|---|
| H2.16 | Q | W, F, C, T, L, R, N, Q, A, S, M, K, E, H, Y, or G |
| H2.17 | G | P, G, T, M, C, E, or V |

TABLES 52

Alternative VH CDR2 residues (DDG <= 0.5 kcal/mol)

| CDR position (column 1) | Residue from P-cad 153 (column 2) | Alternative residues (column 3) |
|---|---|---|
| H2.1 | W | W |
| H2.2 | I | W, F, Y, I, or V |
| H2.3 | S | W, F, L, R, C, H, T, N, Y, Q, K, A, I, V, S, M, or E |
| H2.4 | A | I, Y, V, Q, F, H, K, C, N, T, E, L, M, D, P, S, A, or W |
| H2.5 | Y | C, P, T, S, L, V, M, F, W, Q, K, G, I, A, N, H, E, D, or Y |
| H2.6 | N | I, Q, W, V, C, L, K, E, T, M, F, Y, R, S, A, N, H, D, or G |
| H2.7 | G | G, C, L, or N |
| H2.8 | N | Q, C, I, Y, W, L, T, V, K, M, H, F, S, R, A, E, N, or D |
| H2.9 | T | F, L, V, W, H, C, Y, K, I, Q, R, T, M, N, A, or S |
| H2.10 | N | R, W, K, F, C, T, L, Y, N, Q, V, H, M, A, or S |
| H2.11 | Y | L, F, W, N, Y, H, K, R, I, M, or V |
| H2.12 | A | W, F, I, Y, L, R, V, M, H, N, C, Q, K, T, D, E, A, or S |
| H2.13 | Q | P, R, Q, C, T, I, W, F, K, L, Y, or S |
| H2.14 | K | W, C, I, F, T, R, Y, L, Q, S, V, D, N, M, K, A, H, or E |
| H2.15 | L | W, I, L, V, F, K, R, or H |
| H2.16 | Q | W, F, C, T, L, R, N, Q, A, S, M, or K |
| H2.17 | G | P or G |

TABLES 53

Alternative VH CDR2 residues (DDG <= 0 kcal/mol)

| CDR position (column 1) | Residue from P-cad 153 (column 2) | Alternative residues (column 3) |
|---|---|---|
| H2.1 | W | W |
| H2.2 | I | W, F, Y, or I |
| H2.3 | S | W, F, L, R, C, H, T, N, Y, Q, K, A, I, V, or S |
| H2.4 | A | I, Y, V, Q, F, H, K, C, N, T, E, L, M, D, P, S, or A |
| H2.5 | Y | C, P, T, S, L, V, M, F, W, Q, K, G, I, A, N, H, E, D, or Y |
| H2.6 | N | I, Q, W, V, C, L, K, E, T, M, F, Y, R, S, A, N, or H |
| H2.7 | G | G |
| H2.8 | N | Q, C, I, Y, W, L, T, V, K, M, H, F, S, R, A, E, or N |
| H2.9 | T | F, L, V, W, H, C, Y, K, I, Q, R, or T |
| H2.10 | N | R, W, K, F, C, T, L, Y, or N |
| H2.11 | Y | L, F, W, N, or Y |
| H2.12 | A | W, F, I, Y, L, R, V, M, H, N, C, Q, K, T, D, E, or A |
| H2.13 | Q | P, R, or Q |
| H2.14 | K | W, C, I, F, T, R, Y, L, Q, S, V, D, N, M, or K |
| H2.15 | L | W, I, or L |

TABLES 53-continued

Alternative VH CDR2 residues (DDG <= 0 kcal/mol)

| CDR position (column 1) | Residue from P-cad 153 (column 2) | Alternative residues (column 3) |
|---|---|---|
| H2.16 | Q | W, F, C, T, L, R, N, or Q |
| H2.17 | G | P or G |

TABLES 54

Alternative VH CDR3 residues (DDG <= 1.0 kcal/mol)

| CDR position (column 1) | Residue from P-cad 153 (column 2) | Alternative residues (column 3) |
|---|---|---|
| H3.1 | I | F, Y, I, R, W, or L |
| H3.2 | D | F, I, C, M, W, Q, L, H, V, N, R, T, D, S, E, A, Y, or K |
| H3.3 | T | H, W, C, I, S, L, T, F, Q, Y, V, A, M, K, N, G, D, or E |
| H3.4 | A | Y, I, M, W, R, H, V, F, C, K, N, Q, L, D, T, S, A, or E |
| H3.5 | N | W, L, V, I, P, C, Y, M, H, T, N, F, D, A, or S |
| H3.6 | A | F, W, C, H, N, R, Y, L, A, Q, E, M, T, I, S, K, or D |
| H3.7 | F | Y, F, or W |
| H3.8 | G | W, F, Y, I, L, Q, R, H, M, N, V, C, T, K, E, D, S, A, P, or G |
| H3.9 | I | W, Y, F, R, I, L, C, V, H, N, K, T, Q, M, or D |

TABLES 55

Alternative VH CDR3 residues (DDG <= 0.5 kcal/mol)

| CDR position (column 1) | Residue from P-cad 153 (column 2) | Alternative residues (column 3) |
|---|---|---|
| H3.1 | I | F, Y, I, or R |
| H3.2 | D | F, I, C, M, W, Q, L, H, V, N, R, T, D, S, E, A, Y, or K |
| H3.3 | T | H, W, C, I, S, L, T, F, Q, Y, V, A, or M |
| H3.4 | A | Y, I, M, W, R, H, V, F, C, K, N, Q, L, D, T, S, A, or E |
| H3.5 | N | W, L, V, I, P, C, Y, M, H, T, N, F, or D |
| H3.6 | A | F, W, C, H, N, R, Y, L, A, Q, E, M, T, I, or S |
| H3.7 | F | Y, F, or W |
| H3.8 | G | W, F, Y, I, L, Q, R, H, M, N, V, C, T, K, E, D, S, A, P, or G |
| H3.9 | I | W, Y, F, R, I, L, C, V, H, N, or K |

TABLES 56

Alternative VH CDR3 residues (DDG <= 0 kcal/mol)

| CDR position (column 1) | Residue from P-cad 153 (column 2) | Alternative residues (column 3) |
|---|---|---|
| H3.1 | I | F, Y, I, or R |
| H3.2 | D | F, I, C, M, W, Q, L, H, V, N, R, T, or D |
| H3.3 | T | H, W, C, I, S, L, or T |
| H3.4 | A | Y, I, M, W, R, H, V, F, C, K, N, Q, L, D, T, S, or A |
| H3.5 | N | W, L, V, I, P, C, Y, M, H, T, or N |
| H3.6 | A | F, W, C, H, N, R, Y, L, or A |
| H3.7 | F | Y or F |
| H3.8 | G | W, F, Y, I, L, Q, R, H, M, N, V, C, T, K, E, D, S, A, P, or G |
| H3.9 | I | W, Y, F, R, or I |

TABLE 57

Alternative VL CDR1 residues (DDG <= 1.0 kcal/mol)

| CDR position (column 1) | Residue from P-cad 153 (column 2) | Alternative residues (column 3) |
|---|---|---|
| L1.1 | S | W, C, I, F, Y, T, H, N, M, Q, K, L, S, A, V, D, R, E, or G |
| L1.2 | G | G |
| L1.3 | S | R, Q, Y, L, K, F, M, N, W, C, I, T, V, S, E, A, H, D, or G |
| L1.4 | S | C, L, F, S, I, T, W, N, Y, V, D, A, K, Q, M, H, or R |
| L1.5 | S | F, C, I, T, V, N, H, L, Y, S, R, Q, W, A, M, E, K, or D |
| L1.6 | N | L, Q, F, M, N, C, K, H, or T |
| L1.7 | I | I, Q, H, F, L, or V |
| L1.8 | G | R, Q, L, T, G, C, E, D, M, Y, or S |
| L1.9 | N | C, W, I, L, F, R, V, T, K, N, S, M, Q, Y, E, A, H, or D |
| L1.10 | N | Q, F, N, L, C, Y, H, R, W, or M |
| L1.11 | Y | M, H, K, V, Q, L, Y, C, I, N, F, T, S, E, or W |
| L1.12 | V | I, N, V, L, C, or T |
| L1.13 | S | W, R, F, K, I, H, V, C, T, L, N, M, Q, Y, S, A, D, or E |

TABLE 58

Alternative VL CDR1 residues (DDG <= 0.5 kcal/mol)

| CDR position (column 1) | Residue from P-cad 153 (column 2) | Alternative residues (column 3) |
|---|---|---|
| L1.1 | S | W, C, I, F, Y, T, H, N, M, Q, K, L, S, A, V, D, R, or E |
| L1.2 | G | G |
| L1.3 | S | R, Q, Y, L, K, F, M, N, W, C, I, T, V, S, E, A, H, or D |
| L1.4 | S | C, L, F, S, I, T, W, N, Y, or V |
| L1.5 | S | F, C, I, T, V, N, H, L, Y, S, R, Q, W, A, M, or E |
| L1.6 | N | L, Q, F, M, N, or C |
| L1.7 | I | I, Q, or H |
| L1.8 | G | R, Q, L, T, G, or C |
| L1.9 | N | C, W, I, L, F, R, V, T, K, N, S, M, Q, Y, E, A, H, or D |
| L1.10 | N | Q, F, N, L, or C |
| L1.11 | Y | M, H, K, V, Q, L, Y, C, or I |
| L1.12 | V | I, N, or V |
| L1.13 | S | W, R, F, K, I, H, V, C, T, L, N, M, Q, Y, S, or A |

TABLE 59

Alternative VL CDR1 residues (DDG <= 0 kcal/mol)

| CDR position (column 1) | Residue from P-cad 153 (column 2) | Alternative residues (column 3) |
|---|---|---|
| L1.1 | S | W, C, I, F, Y, T, H, N, M, Q, K, L, or S |
| L1.2 | G | G |
| L1.3 | S | R, Q, Y, L, K, F, M, N, W, C, I, T, V, or S |
| L1.4 | S | C, L, F, or S |
| L1.5 | S | F, C, I, T, V, N, H, L, Y, or S |
| L1.6 | N | L, Q, F, M, or N |
| L1.7 | I | I |
| L1.8 | G | R, Q, L, T, or G |
| L1.9 | N | C, W, I, L, F, R, V, T, K, or N |
| L1.10 | N | Q, F, or N |
| L1.11 | Y | M, H, K, V, Q, L, or Y |
| L1.12 | V | I, N, or V |
| L1.13 | S | W, R, F, K, I, H, V, C, T, L, N, M, Q, Y, or S |

TABLE 60

Alternative VL CDR2 residues (DDG <= 1.0 kcal/mol)

| CDR position (column 1) | Residue from P-cad 153 (column 2) | Alternative residues (column 3) |
|---|---|---|
| L2.1 | D | I, L, V, F, Y, W, C, R, Q, N, M, H, E, T, P, K, D, S, A, or G |
| L2.2 | N | W, L, F, I, C, N, R, V, Q, Y, E, D, H, or M |
| L2.3 | N | C, Q, L, F, Y, W, E, R, M, H, A, N, T, K, D, S, I, V, or G |
| L2.4 | K | R, K, I, L, C, Q, V, W, Y, M, F, or H |
| L2.5 | R | R, Q, L, W, K, or H |
| L2.6 | P | R, K, I, W, F, L, Q, C, M, Y, H, V, N, T, A, E, S, P, or D |
| L2.7 | S | C, L, I, T, S, K, M, R, V, F, P, A, W, Q, D, N, G, or Y |

TABLE 61

Alternative VL CDR2 residues (DDG <= 0.5 kcal/mol)

| CDR position (column 1) | Residue from P-cad 153 (column 2) | Alternative residues (column 3) |
|---|---|---|
| L2.1 | D | I, L, V, F, Y, W, C, R, Q, N, M, H, E, T, P, K, D, S, or A |
| L2.2 | N | W, L, F, I, C, N, R, V, or Q |
| L2.3 | N | C, Q, L, F, Y, W, E, R, M, H, A, N, T, K, D, S, or I |
| L2.4 | K | R, K, I, L, C, Q, or V |
| L2.5 | R | R or Q |
| L2.6 | P | R, K, I, W, F, L, Q, C, M, Y, H, V, N, T, A, E, S, or P |
| L2.7 | S | C, L, I, T, S, K, M, R, V, F, P, or A |

TABLE 62

Alternative VL CDR2 residues (DDG <= 0 kcal/mol)

| CDR position (column 1) | Residue from P-cad 153 (column 2) | Alternative residues (column 3) |
|---|---|---|
| L2.1 | D | I, L, V, F, Y, W, C, R, Q, N, M, H, E, T, P, K, or D |

TABLE 62-continued

Alternative VL CDR2 residues (DDG <= 0 kcal/mol)

| CDR position (column 1) | Residue from P-cad 153 (column 2) | Alternative residues (column 3) |
|---|---|---|
| L2.2 | N | W, L, F, I, C, or N |
| L2.3 | N | C, Q, L, F, Y, W, E, R, M, H, A, or N |
| L2.4 | K | R or K |
| L2.5 | R | R |
| L2.6 | P | R, K, I, W, F, L, Q, C, M, Y, H, V, N, T, A, E, S, or P |
| L2.7 | S | C, L, I, T, or S |

TABLE 63

Alternative VL CDR3 residues (DDG <= 1.0 kcal/mol)

| CDR position (column 1) | Residue from P-cad 153 (column 2) | Alternative residues (column 3) |
|---|---|---|
| L3.1 | G | W, R, Y, F, L, N, Q, C, M, I, H, T, A, D, E, S, K, V, or G |
| L3.2 | T | N, C, V, T, S, or A |
| L3.3 | W | W |
| L3.4 | D | F, N, D, E, H, Q, Y, R, or W |
| L3.5 | S | T, I, R, L, C, F, Y, W, Q, M, H, E, N, V, S, D, K, or A |
| L3.6 | S | I, H, C, M, N, L, V, Q, E, S, T, A, K, D, F, Y, G, R, or W |
| L3.7 | L | L, C, R, I, H, Q, E, T, V, M, K, F, or Y |
| L3.8 | S | W, L, C, F, T, N, V, Y, I, M, H, Q S, K, E, D, A, R, or G |
| L3.9 | G | L, Y, Q, F, H, I, C, R, M, N, D, W, E, K, T, V, A, S, or G |
| L3.10 | V | I, F, K, L, H, Y, M, V, Q, W, T, N, or C |
| L3.11 | V | Q, W, R, F, T, C, Y, V, E, L, N, I, K, or M |

TABLE 64

Alternative VL CDR3 residues (DDG <= 0.5 kcal/mol)

| CDR position (column 1) | Residue from P-cad 153 (column 2) | Alternative residues (column 3) |
|---|---|---|
| L3.1 | G | W, R, Y, F, L, N, Q, C, M, I, H, T, A, D, E, S, K, V, or G |
| L3.2 | T | N, C, V, or T |
| L3.3 | W | W |
| L3.4 | D | F, N, D, or E |
| L3.5 | S | T, I, R, L, C, F, Y, W, Q, M, H, E, N, V, S, D, K, or A |
| L3.6 | S | I, H, C, M, N, L, V, Q, E, S, T, A, or K |
| L3.7 | L | L, C, R, I, H, Q, E, T, or V |
| L3.8 | S | W, L, C, F, T, N, V, Y, I, M, H, Q, S, K, E, D, A, or R |
| L3.9 | G | L, Y, Q, F, H, I, C, R, M, N, D, W, E, K, T, V, A, S, or G |
| L3.10 | V | I, F, K, L, H, Y, M, V, Q, W, or T |
| L3.11 | V | Q, W, R, F, T, C, Y, V, E, L, or N |

TABLE 65

Alternative VL CDR3 residues (DDG <= 0 kcal/mol)

| CDR position (column 1) | Residue from P-cad 153 (column 2) | Alternative residues (column 3) |
|---|---|---|
| L3.1 | G | W, R, Y, F, L, N, Q, C, M, I, H, T, A, D, E, S, K, V, or G |

TABLE 65-continued

Alternative VL CDR3 residues (DDG <= 0 kcal/mol)

| CDR position (column 1) | Residue from P-cad 153 (column 2) | Alternative residues (column 3) |
|---|---|---|
| L3.2 | T | N, C, V, or T |
| L3.3 | W | W |
| L3.4 | D | F, N, D, or E |
| L3.5 | S | T, I, R, L, C, F, Y, W, Q, M, H, E, N, V, or S |
| L3.6 | S | I, H, C, M, N, L, V, Q, E, or S |
| L3.7 | L | L |
| L3.8 | S | W, L, C, F, T, N, V, Y, I, M, H, Q, or S |
| L3.9 | G | L, Y, Q, F, H, I, C, R, M, N, D, W, E, K, T, V, A, S, or G |
| L3.10 | V | I, F, K, L, H, Y, M, or V |
| L3.11 | V | Q, W, R, F, T, C, Y, or V |

Tables 66-71 show the results of Abysis analysis of human sequences at each CDR position. Each CDR from anti-P-cadherin 153 was compared with the corresponding CDR from human antibody sequences from a database. This database combined all human sequence from several databases including: the PDB, Kabat database, IMGT database, VBASE, and Pfizer's internal database. Human antibody sequences in this database were Kabat numbered with Abysis, and the frequencies of CDR residues were calculated only using CDRs with the same length as those found in the anti-P-cadherin clone 153. Tables 66-71 show alternative amino acids at each position wherein the listed residues are present in at least 5% or 10% of the human sequences. Original P-cadherin 153 residues are also included in column 3 and column 4 even if they do not fall in above 5% or 10% category.

TABLES 66

Alternative VH CDR1 residues (Abysis)

| CDR position (column 1) | Residue from P-cad 153 (column 2) | Alternative residues (>5% of human sequences) (column 3) | Alternative residues (>10% of human sequences) (column 4) |
|---|---|---|---|
| H1.1 | G | G | G |
| H1.2 | Y | Y, F, or G | Y, F, or G |
| H1.3 | T | T or S | T or S |
| H1.4 | F | F | F |
| H1.5 | T | S or T | S or T |
| H1.6 | S | S, G, N, or D | S, G, or N |
| H1.7 | Y | Y | Y |
| H1.8 | G | A, Y, W, or G | A, Y, W, or G |
| H1.9 | I | M, I, or W | M or I |
| H1.10 | S | S, H, N, or G | S, H, N, or G |

TABLES 67

Alternative VH CDR2 residues (Abysis)

| CDR position (column 1) | Residue from P-cad 153 (column 2) | Alternative residues (>5% of human sequences) (column 3) | Alternative residues (>10% of human sequences) (column 4) |
|---|---|---|---|
| H2.1 | W | W, I, G, A, V, R, or S | W, I, G, or A |
| H2.2 | I | I | I |
| H2.3 | S | S, N, Y, or I | S, N, Y, or I |
| H2.4 | A | P, G, Y, A, or S | P, G, or A |
| H2.5 | Y | S, N, D, G, I, or Y | S, N, D, G, I, or Y |
| H2.6 | N | G, S, D, N, or F | G, S, D, or N |
| H2.7 | G | G or S | G or S |
| H2.8 | N | N, S, T, D, G, or Y | N, S, T, D, or G |
| H2.9 | T | T, K, A, or I | T, K, or A |
| H2.10 | N | Y, N, R, S, or G | Y, N, or R |
| H2.11 | Y | Y | Y |
| H2.12 | A | A or S | A or S |
| H2.13 | Q | Q, D, or P | Q, D, or P |
| H2.14 | K | S or K | S or K |
| H2.15 | L | F, V, or L | F, V, or L |
| H2.16 | Q | Q or K | Q or K |
| H2.17 | G | G | G |

TABLES 68

Alternative VH CDR3 residues (Abysis)

| CDR position (column 1) | Residue from P-cad 153 (column 2) | Alternative residues (>5% of human sequences) (column 3) | Alternative residues (>10% of human sequences) (column 4) |
|---|---|---|---|
| H3.1 | I | G, D, P, V, F, S, or I | G, D, or I |
| H3.2 | D | G, R, I, L, V, S, Q, or D | G, R, or D |
| H3.3 | T | G, R, V, S, L, K, Y, or T | G or T |
| H3.4 | A | G, I, Y, R, F, L, S, or A | G, I, Y, R, or A |
| H3.5 | N | G, S, Y, D, V, E, R, or N | G, S, Y, or N |
| H3.6 | A | G, A, R, Y, or P | G, A, or R |
| H3.7 | F | F, M, P, or L | F, M, or P |
| H3.8 | G | D, E, or G | D, E, or G |
| H3.9 | I | Y, V, or I | Y, V, or I |

TABLES 69

Alternative VL CDR1 residues (Abysis)

| CDR position (column 1) | Residue from P-cad 153 (column 2) | Alternative residues (>5% of human sequences) (column 3) | Alternative residues (>10% of human sequences) (column 4) |
|---|---|---|---|
| L1.1 | S | S or T | S |
| L1.2 | G | G or R | G |
| L1.3 | S | S | S |
| L1.4 | S | S, R, or T | S |
| L1.5 | S | S or G | S |
| L1.6 | N | N or S | N |
| L1.7 | I | I or V | I |
| L1.8 | G | G or A | G |
| L1.9 | N | S, N, or G | S or N |
| L1.10 | N | N or Y | N |
| L1.11 | Y | Y, T, or S | Y or T |
| L1.12 | V | V | V |
| L1.13 | S | S, N, Y, or Q | S, N, or Y |

TABLES 70

Alternative VL CDR2 residues (Abysis)

| CDR position (column 1) | Residue from P-cad 153 (column 2) | Alternative residues (>5% of human sequences) (column 3) | Alternative residues (>10% of human sequences) (column 4) |
|---|---|---|---|
| L2.1 | D | D, G, E, A, S, or R | D, G, E, A, or S |
| L2.2 | N | A, N, V, D, or T | A, N, or V |
| L2.3 | N | S, N, or T | S or N |
| L2.4 | K | N, S, Q, K, or T | N, S, Q, or K |
| L2.5 | R | R or L | R or L |
| L2.6 | P | P, A, Q, or E | P, A, or Q |
| L2.7 | S | S or T | S or T |

TABLES 71

Alternative VL CDR3 residues (Abysis)

| CDR position (column 1) | Residue from P-cad 153 (column 2) | Alternative residues (>5% of human sequences) (column 3) | Alternative residues (>10% of human sequences) (column 4) |
|---|---|---|---|
| L3.1 | G | A, Q, G, or S | A, Q, G, or S |
| L3.2 | T | S, A, T, or V | S, A, or T |
| L3.3 | W | W, Y, or R | W or Y |
| L3.4 | D | D, A, or T | D |
| L3.5 | S | S, D, or G | S or D |
| L3.6 | S | S | S |
| L3.7 | L | L, S, or G | L or S |
| L3.8 | S | S, N, T, R, or D | S, N, or T |
| L3.9 | G | G, A, H, or L | G or A |
| L3.10 | V | V, W, Y, G, or P | V, W, or Y |
| L3.11 | V | V, L, or I | V |

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A bispecific heterodimeric diabody that specifically binds to an epitope of human P-cadherin and to an epitope of CD3 comprising a first polypeptide chain and a second polypeptide chain, wherein:
   a. the first polypeptide comprises, in the N-terminal to C-terminal direction:
      i. a Domain 1, comprising a sub-Domain 1A and a sub-Domain 1B, and
      ii. a first heterodimer-promoting domain; and
   b. the second polypeptide chain comprises, in the N-terminal to C-terminal direction:
      i. a Domain 2, comprising a sub-Domain 2B and a sub-Domain 2A and
      ii. a second heterodimer-promoting domain, and
   wherein sub-Domain 1A and sub-Domain 2A form a P-cadherin VL/VH binding domain comprising a variable heavy (VH) domain of an anti-P-cadherin antibody (P-CAD VH) and a variable light (VL) domain of an anti-P-cadherin antibody (P-CAD VL), and sub-Domain 1B and sub-Domain 2B form a CD3 VL/VH binding domain comprising a VL domain of an anti-CD3 antibody (CD3 VL) and a VH binding domain of an anti-CD3 antibody (CD3 VH); or
   wherein sub-Domain 1A and sub-Domain 2A form a CD3 VL/VH binding domain comprising a CD3 VL and a CD3 VH, and sub-Domain 1B and sub-Domain 2B form a P-cadherin VL/VH binding domain comprising a P-CAD VH and a P-CAD VL; and wherein the first and second polypeptide chains comprise:
      i. a P-CAD VL CDR1, a P-CAD VL CDR2, and a P-CAD VL CDR3 of a P-CAD VL comprising a sequence of SEQ ID NO: 1, 3, 5, 7, 9, 11, 13, 15, 17, 19, 21 or 23;
      ii. a CD3 VH CDR1, a CD3 VH CDR2, and a CD3 VH CDR3 of a CD3 VH comprising a sequence of SEQ ID NO: 45 or 46;
      iii. a CD3 VL CDR1, a CD3 VL CDR2, and a CD3 VL CDR3 of a CD3 VL comprising a sequence of SEQ ID NO: 47; and/or
      iv. a P-CAD VH CDR1, a P-CAD VH CDR2, and a P-CAD VH CDR3 of a P-CAD VH comprising a sequence of SEQ ID NO: 2, 4, 6, 8, 10, 12, 14, 16, 18, 20, 22 or 24;
   c. the sub-Domain 1A and the sub-Domain 1B are linked by a glycine-serine linker (Linker 1), and the sub-Domain 2B and the sub-Domain 2A are linked by a glycine-serine linker (Linker 1);
   d. the first heterodimer-promoting domain comprises a cysteine linker (Linker 2) on sub-Domain 1B and/or the second heterodimer-promoting domain comprises a cysteine linker (Linker 2) on sub-Domain 2A; and
   e. the first and second polypeptide chains are covalently bonded to one another by at least one disulfide bond.

2. The bispecific heterodimeric diabody of claim 1, wherein the sub-Domain 1A comprises a P-CAD VL or a CD3 VL, and the sub-Domain 1B comprises a P-CAD VH if the sub-Domain 1A comprises CD3 VL or the sub-Domain 1B comprises a CD3 VH if the sub-Domain 1A comprises P-CAD VL; and wherein the sub-Domain 2B comprises a P-CAD VL or a CD3 VL depending on the VL domain selected for sub-Domain 1A, and the sub-Domain 2A comprises P-CAD VH if the sub-Domain 2B comprises CD3 VL or the sub-Domain 2A comprises a CD3 VH if the sub-Domain 2B comprises P-CAD VL.

3. The bispecific heterodimeric diabody of claim 1, wherein the sub-Domain 1A comprises a P-CAD VL and the sub-Domain 1B comprises a CD3 VH, and the sub-Domain 2B comprises a CD3 VL and the sub-Domain 2A comprises a P-CAD VH.

4. The bispecific heterodimeric diabody of claim 1, wherein the sub-Domain 1A comprises a CD3 VL and the sub-Domain 1B comprises a P-CAD VH, and the sub-Domain 2B comprises a P-CAD VL and the sub-Domain 2A a CD3 VH.

5. The bispecific heterodimeric diabody of claim 1, wherein the sub-Domain 1A comprises a P-CAD VH or a CD3 VH, and the sub-Domain 1B comprises a P-CAD VL if the sub-Domain 1A comprises CD3 VH or the sub-Domain 1B comprises a CD3 VL if the sub-Domain 1A comprises a P-CAD VH; and wherein the sub-Domain 2B comprises a P-CAD VH or a CD3 VH depending on the VH domain selected for sub-Domain 1A, and the sub-Domain 2A comprises P-CAD VL if the sub-Domain 2B comprises a CD3 VH or the sub-Domain 2A comprises a CD3 VL if the sub-Domain 2B comprises a P-CAD VH.

6. The bispecific heterodimeric diabody of claim 1 or 5, wherein the sub-Domain 1A comprises a P-CAD VH and the sub-Domain 1B comprises a CD3 VL, and the sub-Domain 2B comprises a CD3 VH and the sub-Domain 2A comprises a P-CAD VL.

7. The bispecific heterodimeric diabody of claim 1 or 5, wherein the sub-Domain 1A comprises a CD3 VH and the sub-Domain 1B comprises a P-CAD VL, and the sub-Domain 2B comprises a P-CAD VH and the sub-Domain 2A comprises a CD3 VL.

8. The bispecific heterodimeric diabody of claim 1, wherein the first heterodimer-promoting domain and the second heterodimer-promoting domain comprise an IgG Fc region comprising a CH2 and a CH3 domain, wherein the amino acid sequence of the CH2 domain and/or the CH3 domain comprises at least one amino acid modification, as compared to a wild-type IgG Fc region, to form a knob or a hole.

9. The bispecific heterodimeric diabody of claim 8, wherein the first heterodimer-promoting domain and the second heterodimer-promoting domain are not both knobs or both holes; and/or wherein the first heterodimer-promoting domain and the second heterodimer-promoting domain form an IgG immunoglobulin Fc region.

10. The bispecific heterodimeric diabody of claim 9, wherein the IgG Fc region forming the knob comprises a sequence of SEQ ID NO: 63, and the IgG Fc region forming the hole comprises a sequence of SEQ ID NO: 64.

11. The bispecific heterodimeric diabody of claim 1, wherein the glycine-serine linker (Linker 1) comprises a sequence of SEQ ID NO: 68 or SEQ ID NO: 69.

12. The bispecific heterodimeric diabody of claim 1, wherein the sub-Domain 1A and the sub-Domain 1B do not associate to form a VL/VH epitope binding domain, and the sub-Domain 2B and the sub-Domain 2A do not associate to form a VL/VH epitope binding domain.

13. The bispecific heterodimeric diabody of claim 1, wherein the Linker 2 of the first heterodimer-promoting domain and/or the second heterodimer-promoting domain further comprises at least one glycine residue.

14. The bispecific heterodimeric diabody of claim 13, wherein the Linker 2 of the first heterodimer-promoting domain and/or the second heterodimer-promoting domain comprises a sequence of GFNRGEC (SEQ ID NO: 70), GVEPKSC (SEQ ID NO: 71), GGCGGG (SEQ ID NO: 72), GCPPCP (SEQ ID NO: 73), GGTGGCPPCP (SEQ ID NO: 74), GEPKSSDKTHTCPPCP (SEQ ID NO: 75) or GGTGGGEPKSSDKTHTCPPCP (SEQ ID NO: 76).

15. The bispecific heterodimer diabody of claim 14, wherein the Linker 2 of the first heterodimer-promoting domain comprises the sequence of GCPPCP (SEQ ID NO: 73), GGTGGCPPCP (SEQ ID NO: 74), GEPKSSDKTHTCPPCP (SEQ ID NO: 75) or GGTGGGEPKSSDKTHTCPPCP (SEQ ID NO: 76), and the Linker 2 of the second heterodimer-promoting domain comprises the sequence of GCPPCP (SEQ ID NO: 73), GGTGGCPPCP (SEQ ID NO: 74), GEPKSSDKTHTCPPCP (SEQ ID NO: 75) or GGTGGGEPKSSDKTHTCPPCP (SEQ ID NO: 76).

16. The bispecific heterodimer diabody of claim 14, wherein the Linker 2 of the first heterodimer-promoting domain comprises the sequence of GGCGGG (SEQ ID NO: 72), and the Linker 2 of the second heterodimer-promoting domain comprises the sequence of GGCGGG (SEQ ID NO: 72).

17. The bispecific heterodimeric diabody of claim 14, wherein the Linker 2 of the first heterodimer-promoting domain comprises the sequence of GFNRGEC (SEQ ID NO: 70) and the Linker 2 of the second heterodimer-promoting domain comprises the sequence of GVEPKSC (SEQ ID NO: 71), or the Linker 2 of the first heterodimer-promoting domain comprises the sequence of GVEPKSC (SEQ ID NO: 71) and the Linker 2 of the second heterodimer-promoting domain comprises the sequence of GFNRGEC (SEQ ID NO: 70).

18. The bispecific heterodimeric diabody of claim 1, wherein the bispecific heterodimeric diabody:
a. binds to extracellular domain 3 (ECD3) of human P-cadherin,
b. binds to an epitope on human P-cadherin but does not bind to an epitope on E-cadherin or VE-cadherin, or
c. demonstrates a lower EC50 in the presence of increased human P-cadherin expression levels or increased human P-cadherin receptor density levels.

19. A bispecific heterodimer diabody that specifically binds to an epitope of P-cadherin and to an epitope of CD3 comprising a first polypeptide chain and a second polypeptide chain, wherein:
a. the first polypeptide chain comprises, in the N-terminal to C-terminal direction:
i. a Domain 1, comprising a sub-Domain 1A and a sub-Domain 1B, and
ii. a first heterodimer-promoting domain; and
b. the second polypeptide chain comprises, in the N-terminal to C-terminal direction:
i. a Domain 2, comprising a sub-Domain 2B and a sub-Domain 2A and
ii. a second heterodimer-promoting domain, and
wherein sub-Domain 1A and sub-Domain 2A form a P-cadherin VL/VH binding domain comprising a variable heavy (VH) domain of an anti-P-cadherin antibody (P-CAD VH) and a variable light (VL) domain of an anti-P-cadherin antibody (P-CAD VL), and sub-Domain 1B and sub-Domain 2B form a CD3 VL/VH binding domain comprising a VL domain of an anti-CD3 antibody (CD3VL) and a VH binding domain of an anti-CD3 antibody (CD3 VH); or
wherein sub-Domain 1A and sub-Domain 2A form a CD3 VL/VH binding domain comprising a CD3 VL and a CD3 VH, and sub-Domain 1B and sub-Domain 2B form a P-cadherin VL/VH binding domain comprising a P-CAD VH and a P-CAD VL; and
wherein the polypeptide chain comprises:
  i. a P-CAD VL CDR1 sequence comprising $X_{L1.1}$-$X_{L1.2}$-$X_{L1.3}$-$X_{L1.4}$-$X_{L1.6}$-$X_{L1.7}$-$X_{L1.8}$-$X_{L1.9}$-$X_{L1.10}$-$X_{L1.11}$-$X_{L1.12}$-$X_{L1.13}$, wherein
$X_{L1.1}$ is W, C, I, F, Y, T, H, N, M, Q, K, L, S, A, V, D, R, E, or G,
$X_{L1.2}$ is G,
$X_{L1.3}$ is R, Q, Y, L, K, F, M, N, W, C, I, T, V, S, E, A, H, D, or G,
$X_{L1.4}$ is C, L, F, S, I, T, W, N, Y, V, D, A, K, Q, M, H, or R,
$X_{L1.5}$ is F, C, I, T, V, N, H, L, Y, S, R, Q, W, A, M, E, K, or D,
$X_{L1.6}$ is L, Q, F, M, N, C, K, H, or T,
$X_{L1.7}$ is I, Q, H, F, L, or V,
$X_{L1.8}$ is R, Q, L, T, G, C, E, D, M, Y, or S,
$X_{L1.9}$ is C, W, I, L, F, R, V, T, K, N, S, M, Q, Y, E, A, H, or D,
$X_{L1.10}$ is Q, F, N, L, C, Y, H, R, W, or M,
$X_{L1.11}$ is M, H, K, V, Q, L, Y, C, I, N, F, T, S, E, or W,
$X_{L1.12}$ is I, N, V, L, C, or T,
$X_{L1.13}$ is W, R, F, K, I, H, V, C, T, L, N, M, Q, Y, S, A, D, or E,
  ii. a P-CAD VL CDR2 sequence comprising $X_{L2.1}$-$X_{L2.2}$-$X_{L2.3}$-$X_{L2.4}$-$X_{L2.5}$-$X_{L2.6}$-$X_{L2.7}$, wherein
$X_{L2.1}$ is I, L, V, F, Y, W, C, R, Q, N, M, H, E, T, P, K, D, S, A, or G,
$X_{L2.2}$ is W, L, F, I, C, N, R, V, Q, Y, E, D, H, or M,
$N_{L2.3}$ is C, Q, L, F, Y, W, E, R, M, H, A, N, T, K, D, S, I, V, or G,
$X_{L2.4}$ is R, K, L, C, Q, V, W, Y, M, F, or H,
$X_{L2.5}$ is R, Q, L, W, K, or H,
$X_{L2.6}$ is R, K, I, W, F, L, Q, C, M, Y, H, V, N, T, A, E, S, P, or D,
$X_{L2.7}$ is C, L, T, S, K, M, R, V, F, P, A, W, Q, D, N, G, or Y,
  iii. a P-CAD VL CDR3 $X_{L3.1}$-$X_{L3.2}$-$X_{L3.3}$-$X_{L3.4}$-$X_{L3.5}$-$X_{L3.6}$-$X_{L3.7}$-$X_{L3.8}$-$X_{L3.9}$-$X_{L3.10}$-$X_{L3.11}$, wherein
$X_{L3.1}$ is W, R, Y, F, L, N, Q, C, M, I, H, T, A, D, E, S, K, V, or G,
$X_{L3.2}$ is N, C, V, T, S, or A,
$X_{L3.3}$ is W,
$X_{L3.4}$ is F, N, D, E, H, Q, Y, R, or W,
$X_{L3.5}$ is T, R, L, C, F, Y, W, Q, M, H, E, N, V, S, D, K, or A,
$X_{L3.6}$ is I, H, C, M, N, L, V, Q, E, S, T, A, K, D, F, Y, G, R, or W,
$X_{L3.7}$ is L, C, R, I, H, Q, E, T, V, M, K, F, or Y,
$X_{L3.8}$ is W, L, C, F, T, N, V, Y, M, H, Q, S, K, E, D, A, R, or G,
$X_{L3.9}$ is L, Y, Q, F, H, C, R, M, N, D, W, E, K, T, V, A, S, or G,
$X_{L3.10}$ is I, F, K, L, H, Y, M, V, Q, W, T, N, or C,
$X_{L3.11}$ is Q, W, R, F, T, C, Y, V, E, L, N, I, K, or M,
  iv. a P-CAD VH CDR1 sequence comprising $X_{H1.1}$-$X_{H1.2}$-$X_{H1.3}$-$X_{H1.4}$, $X_{H1.5}$-$X_{H1.6}$-$X_{H1.7}$-$X_{H1.8}$-$X_{H1.9}$-$X_{H1.10}$ or $X_{H1.5}$-$X_{H1.6}$-$X_{H1.7}$-$X_{H1.8}$-$X_{H1.9}$-$X_{H1.10}$, wherein
$X_{H1.1}$ is R, Q, I, LC, F, T, G, V, W, M, Y, N, E, P, K, H, D, S, or A,
$X_{H1.2}$ is H, R, C, Q, Y, I, F, K, M, V, L, N, or T,
$X_{H1.3}$ is N, C, R, V, L, T, I, S, K, Q, M, W, A, F, Y, H, or D,
$X_{H1.4}$ is F or Y,
$X_{H1.5}$ is W, R, I, C, K, Y, M, V, F, T, S, L, Q, E, A, N, H, D, or G,
$X_{H1.6}$ is R, I, M, N, Y, C, H, Q, L, K, F, V, T, E, A, 5, D, W, or G,
$X_{H1.7}$ is K, R, L, H, F, Q, N, C, Y, M, I, T, V, or A,
$X_{H1.8}$ is P, R, F, W, H, C, Y, 1, M, K, G, S, Q, A, L, N, T, or D,
$X_{H1.9}$ is Y, F, K, I, W, or L,
$X_{H1.10}$ is R, C, L, N, 5, V, T, or A,
  v. P-CAD VH CDR2 sequence comprising $X_{H2.1}$-$X_{H2.2}$-$X_{H2.3}$-$X_{H2.4}$-$X_{H2.5}$-$X_{H2.6}$-$X_{H2.7}$-$X_{H2.8}$-$X_{H2.9}$-$X_{H2.10}$ or $X_{H2.1}$-$X_{H2.2}$-$X_{H2.3}$-$X_{H2.4}$-$X_{H2.5}$-$X_{H2.6}$-$X_{H2.7}$-$X_{H2.8}$-$X_{H2.9}$-$X_{H2.10}$-$X_{H2.11}$-$X_{H2.12}$-$X_{H2.13}$-$X_{H2.14}$-$X_{H2.15}$-$X_{H2.16}$-$X_{H2.17}$ wherein
$X_{H2.1}$ is W,
$X_{H2.2}$ is W, F, Y, I, V, H, L, or Q,
$X_{H2.3}$ is W, F, L, R, C, H, T, N, Y, Q, K, A, I, V, S, M, E, or D,
$X_{H2.4}$ is I, Y, V, Q, F, H, K, C, N, T, E, L, M, D, P, S, A, or W,
$X_{H2.5}$ is C, P, T, S, L, V, M, F, W, Q, K, G, I, A, N, H, E, D, Y, R,
$X_{H2.6}$ is I, Q, W, V, C, L, K, E, T, M, F, Y, R, S, A, N, H, D, or G,
$X_{H2.7}$ is G, C, L, N, W, F, S, Y, T, D, I, or M,
$X_{H2.8}$ is Q, C, I, Y, W, L, T, V, K, M, H, F, S, R, A, E, N, D, or G,
$X_{H2.9}$ is F, L, V, W, H, C, Y, K, I, Q, R, T, M, N, A, S, or D,
$X_{H2.10}$ is R, W, K, F, C, T, L, Y, N, Q, V, H, M, A, S, or D,
$X_{H2.11}$ is L, F, W, N, Y, H, K, R, I, M, V, C, Q, or E,
$X_{H2.12}$ is W, F, I, Y, L, R, V, M, H, N, C, Q, K, T, D, E, A, or S,
$X_{H2.13}$ is P, R, Q, C, T, I, W, F, K, L, Y, S, V, M, D, or H,
$X_{H2.14}$ is W, C, I, F, T, R, Y, L, Q, S, V, D, N, M, K, A, H, E, or G,
$X_{H2.15}$ is W, L, V, F, K, R, H, Y, or M,
$X_{H2.16}$ is W, F, C, T, L, R, N, A, S, M, K, E, H, Y, or G,
$X_{H2.17}$ is P, G, T, M, C, E, or V,
and
  vi. a P-CAD VH CDR3 sequence comprising $X_{H3.1}$-$X_{H3.2}$-$X_{H3.3}$-$X_{H3.4}$-$X_{H3.5}$-$X_{H3.6}$-$X_{H3.7}$-$X_{H3.8}$-$X_{H3.9}$, wherein
$X_{H3.1}$ is F, Y, I, R, W, or L,
$N_{H3.2}$ is F, I, C, M, W, Q, L, H, V, N, R, T, D, S, E, A, Y, or K,
$X_{H3.3}$ is H, W, C, I, S, L, T, F, Q, Y, V, A, M, K, N, G, D, or E,
$X_{H3.4}$ is Y, I, M, W, R, H, V, F, C, K, N, Q, L, D, T, S, A, or E,
$X_{H3.5}$ is W, L, V, I, P, C, Y, M, H, T, N, F, D, A, or S,
$X_{H3.6}$ is F, W, C, H, N, R, Y, L, A, Q, E, M, T, I, S, K, or D,
$X_{H3.7}$ is Y, F, or W,
$X_{H3.8}$ is W, F, Y, I, L, Q, R, H, M, N, V, C, T, K, E, D, S, A, P, or G,
$X_{H3.9}$ is W, Y, F, R, I, L, C, V, H, N, K, T, Q, M, or D;
c. the sub-Domain 1A and the sub-Domain 1B are linked by a glycine-serine linker (Linker 1), and the sub-Domain 2B and the sub-Domain 2A are linked by a glycine-serine linker (Linker 1);
d. the first heterodimer-promoting domain comprises a cysteine linker (Linker 2) on sub-Domain 1B and/or the second heterodimer-promoting domain comprises a cysteine linker (Linker 2) on sub-Domain 2A; and e. the first and second polypeptide chains are covalently bonded to one another by at least one disulfide bond.

20. The bispecific heterodimer diabody of claim 19, wherein $X_{L3.3}$ is W, $X_{H2.5}$ is Y, $X_{H3.1}$ is I, $X_{H3.7}$ is F, $X_{L1.8}$ is G, $X_{L2.2}$ is N, $X_{L2.3}$ is N, $X_{L3.2}$ is T, $X_{H2.6}$ is N, $X_{H2.16}$ is Q, $X_{H3.5}$ is N and $X_{H3.9}$ is I.

21. The bispecific heterodimer diabody of claim 19, wherein $X_{L3.3}$ is W, $X_{H1.8}$ is G, $X_{H2.5}$ is Y, $X_{H3.1}$ is I, and $X_{H3.7}$ is F.

22. The bispecific heterodimeric diabody of claim 19, comprising:
   a. a P-CAD VL CDR1, a P-CAD VL CDR2, and a P-CAD VL CDR3 of a P-CAD VL comprising a sequence of SEQ ID NO: 1, 3, 5, 7, 9, 11, 13, 15, 17, 19, 21 or 23;
   b. a CD3 VH CDR1, a CD3 VH CDR2, and a CD3 VH CDR3 of a CD3 VH comprising a sequence of SEQ ID NO: 45 or 46;
   c. a CD3 VL CDR1, a CD3 VL CDR2, and a CD3 VL CDR3 of a CD3 VL comprising a sequence of SEQ ID NO: 47; and/or
   d. a P-CAD VH CDR1, a P-CAD VH CDR2, and a P-CAD VH CDR3 of a P-CAD VH comprising a sequence of SEQ ID NO: 2, 4, 6, 8, 10, 12, 14, 16, 18, 20, 22 or 24.

23. The bispecific heterodimeric diabody of claim 1 or 22, wherein:
   a. the P-CAD VL CDR1 comprises a sequence of SEQ ID NO: 35 or 36, the P-CAD VL CDR2 comprises a sequence of SEQ ID NO: 37 or 38, and the P-CAD VL CDR3 comprises a sequence of SEQ ID NO: 39, 40, 41, 42, 43 or 44;
   b. the CD3 VH CDR1 comprises a sequence of SEQ ID NO: 48, 52 or 53, the CD3 VH CDR2 comprises a sequence of SEQ ID NO: 49, 50 or 54, and the CD3 VH CDR3 comprises a sequence of SEQ ID NO: 51;
   c. the CD3 VL CDR1 comprises a sequence of SEQ ID NO: 55, the CD3 VL CDR2 comprises a sequence of SEQ ID NO: 56, and the CD3 VL CDR3 comprises a sequence of SEQ ID NO: 57; and/or
   d. the P-CAD VH CDR1 comprises a sequence of SEQ ID NO: 25 or 33, the P-CAD VH CDR2 comprises a sequence of SEQ ID NO: 26 or 34, and a P-CAD VH CDR3 comprising a sequence of SEQ ID NO: 27, 28, 29, 30, 31 or 32.

24. The bispecific heterodimeric diabody of claim 23, wherein the P-CAD VL CDR1 comprises the sequence of SEQ ID NO: 35, the P-CAD VL CDR2 comprises the sequence of SEQ ID NO: 37, the P-CAD VL CDR3 comprises the sequence of SEQ ID NO: 41, the P-CAD VH CDR1 comprises the sequence of SEQ ID NO: 25, the P-CAD VH CDR2 comprises the sequence of SEQ ID NO: 26, and the P-CAD VH CDR3 comprises the sequence of SEQ ID NO: 28.

25. The bispecific heterodimeric diabody of claim 23, wherein the P-CAD VL CDR1 comprises the sequence of SEQ ID NO: 35; the P-CAD VL CDR2 comprises the sequence of SEQ ID NO: 37; and the P-CAD VL CDR3 comprises the sequence of SEQ ID NO: 42, the P-CAD VH CDR1 comprises the sequence of SEQ ID NO: 25, the P-CAD VH CDR2 comprises the sequence of SEQ ID NO: 26, and the P-CAD VH CDR3 comprises the sequence of SEQ ID NO: 29.

26. The bispecific heterodimeric diabody of claim 23, wherein the P-CAD VL CDR1 comprises the sequence of SEQ ID NO: 35; the P-CAD VL CDR2 comprises the sequence of SEQ ID NO: 37, the P-CAD VL CDR3 comprises the sequence of SEQ ID NO: 43, the P-CAD VH CDR1 comprises the sequence of SEQ ID NO: 25, the P-CAD VH CDR2 comprises the sequence of SEQ ID NO: 26, and the P-CAD VH CDR3 comprises the sequence of SEQ ID NO: 30.

27. The bispecific heterodimeric diabody of claim 23, wherein the P-CAD VL CDR1 comprises the sequence of SEQ ID NO: 35; the P-CAD VL CDR2 comprises the sequence of SEQ ID NO: 37, the P-CAD VL CDR3 comprises the sequence of SEQ ID NO: 39, the P-CAD VH CDR1 comprises the sequence of SEQ ID NO: 25, the P-CAD VH CDR2 comprises the sequence of SEQ ID NO: 26, and the P-CAD VH CDR3 comprises the sequence of SEQ ID NO: 31.

28. The bispecific heterodimeric diabody of claim 23, wherein:
   a. the P-CAD VL comprises a sequence of SEQ ID NO: 1, 3, 5, 7, 9, 11, 13, 15, 17, 19, 21 or 23;
   b. the CD3 VH comprises a sequence of SEQ ID NO: 45 or 46;
   c. the CD3 VL comprises the sequence of SEQ ID NO: 47; and
   d. the P-CAD VH comprises a sequence of SEQ ID NO: 2, 4, 6, 8, 10, 12, 14, 16, 18, 20, 22 or 24.

29. The bispecific heterodimeric diabody of claim 28, wherein the P-CAD VL comprises the sequence of SEQ ID NO: 5, and the P-CAD VH comprises the sequence of SEQ ID NO: 6.

30. The bispecific heterodimeric diabody of claim 28, wherein the P-CAD VL comprises the sequence of SEQ ID NO: 7, and the P-CAD VH comprises the sequence of SEQ ID NO: 8.

31. The bispecific heterodimeric diabody of claim 28, wherein the P-CAD VL comprises the sequence of SEQ ID NO: 9 and the P-CAD VH comprises the sequence of SEQ ID NO: 10.

32. The bispecific heterodimeric diabody of claim 28, wherein the P-CAD VL comprises the sequence of SEQ ID NO: 15 and the P-CAD VH comprises the sequence of SEQ ID NO: 16.

33. A bispecific heterodimeric diabody that specifically binds to an epitope of human P-cadherin and to an epitope of CD3 comprising a first polypeptide chain and a second polypeptide chain, wherein the first polypeptide chain comprises a sequence of SEQ ID NO: 90 and the second polypeptide chain comprises a sequence of SEQ ID NO: 91.

34. A pharmaceutical composition comprising: a therapeutically effective amount of the bispecific heterodimeric diabody of claim 1, 23, or 33, and a pharmaceutically acceptable carrier.

* * * * *

UNITED STATES PATENT AND TRADEMARK OFFICE
CERTIFICATE OF CORRECTION

PATENT NO. : 9,884,921 B2
APPLICATION NO. : 14/751704
DATED : February 6, 2018
INVENTOR(S) : Chad Michael May et al.

Page 1 of 1

It is certified that error appears in the above-identified patent and that said Letters Patent is hereby corrected as shown below:

In the Claims

Column 301, Claim 19
Line 5, insert --$X_{L1.5}$-- between "$X_{L1.4}$" and "$X_{L1.6}$"
Line 31, replace "$N_{L2.3}$" with $X_{L2.3}$
Line 33, insert --I-- between "K" and "L"
Line 37, insert --I-- between "L" and "T"
Line 46, insert --I-- between "T" and "R"
Line 51, insert --I-- between "Y" and "M"
Line 53, insert --I-- between "H" and "C"
Line 58, replace "$X_{H1.4}$," with $X_{H1.4}$-

Column 302, Claim 19
Line 38, insert --I-- between "W" and "L"
Line 39, insert --Q-- between "N" and "A"
Line 46, replace "$N_{H3.2}$" with $X_{H3.2}$ Signed and Sealed this
Seventh Day of August, 2018

Andrei Iancu
*Director of the United States Patent and Trademark Office*

SEQUENCE LISTING

```
<160> NUMBER OF SEQ ID NOS: 239

<210> SEQ ID NO 1
<211> LENGTH: 110
<212> TYPE: PRT
<213> ORGANISM: Artificial Sequence
<220> FEATURE:
<223> OTHER INFORMATION: Synthetic peptide sequence

<400> SEQUENCE: 1

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Tyr Val Phe Gly Thr Gly Thr Lys Val Thr Val Leu
            100                 105                 110

<210> SEQ ID NO 2
<211> LENGTH: 118
<212> TYPE: PRT
<213> ORGANISM: Artificial Sequence
<220> FEATURE:
<223> OTHER INFORMATION: Synthetic peptide sequence

<400> SEQUENCE: 2

Gln Met Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Leu Ile Gly Ser Gly Val Ala Phe Asp Ile Trp Gly Gln Gly Thr
            100                 105                 110

Met Val Thr Val Ser Ser
            115

<210> SEQ ID NO 3
<211> LENGTH: 110
<212> TYPE: PRT
<213> ORGANISM: Artificial Sequence
<220> FEATURE:
<223> OTHER INFORMATION: Synthetic peptide sequence

<400> SEQUENCE: 3

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 4
<211> LENGTH: 118
<212> TYPE: PRT
<213> ORGANISM: Artificial Sequence
<220> FEATURE:
<223> OTHER INFORMATION: Synthetic peptide sequence

<400> SEQUENCE: 4

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

```
Ala Thr Ile Asp Thr Ala Ser Ala Phe Asp Ile Trp Gly Gln Gly Thr
                100                 105                 110

Met Val Thr Val Ser Ser
        115

<210> SEQ ID NO 5
<211> LENGTH: 110
<212> TYPE: PRT
<213> ORGANISM: Artificial Sequence
<220> FEATURE:
<223> OTHER INFORMATION: Synthetic peptide sequence

<400> SEQUENCE: 5

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu
                100                 105                 110

<210> SEQ ID NO 6
<211> LENGTH: 118
<212> TYPE: PRT
<213> ORGANISM: Artificial Sequence
<220> FEATURE:
<223> OTHER INFORMATION: Synthetic peptide sequence

<400> SEQUENCE: 6

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Ile Asp Thr Ala Ser Ala Phe Asp Ile Trp Gly Gln Gly Thr
                100                 105                 110

Met Val Thr Val Ser Ser
        115

<210> SEQ ID NO 7
<211> LENGTH: 110
<212> TYPE: PRT
<213> ORGANISM: Artificial Sequence
<220> FEATURE:
<223> OTHER INFORMATION: Synthetic peptide sequence
```

<400> SEQUENCE: 7

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Val Val Phe Gly Gly Gly Thr Lys Leu Thr Val Leu
            100                 105                 110

<210> SEQ ID NO 8
<211> LENGTH: 118
<212> TYPE: PRT
<213> ORGANISM: Artificial Sequence
<220> FEATURE:
<223> OTHER INFORMATION: Synthetic peptide sequence

<400> SEQUENCE: 8

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Ile Asp Thr Ala Asn Ala Phe Gly Ile Trp Gly Gln Gly Thr
            100                 105                 110

Met Val Thr Val Ser Ser
        115

<210> SEQ ID NO 9
<211> LENGTH: 110
<212> TYPE: PRT
<213> ORGANISM: Artificial Sequence
<220> FEATURE:
<223> OTHER INFORMATION: Synthetic peptide sequence

<400> SEQUENCE: 9

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
50                  55                  60

-continued

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ser Tyr Val Phe Gly Thr Gly Thr Lys Val Thr Val Leu
            100                 105                 110

<210> SEQ ID NO 10
<211> LENGTH: 118
<212> TYPE: PRT
<213> ORGANISM: Artificial Sequence
<220> FEATURE:
<223> OTHER INFORMATION: Synthetic peptide sequence

<400> SEQUENCE: 10

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Ile Asp Thr Ala Thr Ala Phe Asp Ile Trp Gly Gln Gly Thr
            100                 105                 110

Met Val Thr Val Ser Ser
        115

<210> SEQ ID NO 11
<211> LENGTH: 110
<212> TYPE: PRT
<213> ORGANISM: Artificial Sequence
<220> FEATURE:
<223> OTHER INFORMATION: Synthetic peptide sequence

<400> SEQUENCE: 11

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Tyr Val Phe Gly Thr Gly Thr Lys Val Thr Val Leu
            100                 105                 110

<210> SEQ ID NO 12
<211> LENGTH: 118
<212> TYPE: PRT

<213> ORGANISM: Artificial Sequence
<220> FEATURE:
<223> OTHER INFORMATION: Synthetic peptide sequence

<400> SEQUENCE: 12

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Phe Ser Trp Met Arg Gln Ala Pro Gly Gln Gly Leu Glu Trp Met
        35                  40                  45

Gly Trp Ile Ser Ala Tyr Asn Gly Asn Thr Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Ile Asp Thr Ala Ser Ala Phe Asp Ile Trp Gly Gln Gly Thr
                100                 105                 110

Met Val Thr Val Ser Ser
            115
```

<210> SEQ ID NO 13
<211> LENGTH: 110
<212> TYPE: PRT
<213> ORGANISM: Artificial Sequence
<220> FEATURE:
<223> OTHER INFORMATION: Synthetic peptide sequence

<400> SEQUENCE: 13

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Ala Gly Asp Glu Ala Asp Tyr Tyr Cys Gly Thr Trp Asp Ser Ser Leu
                85                  90                  95

Ser Ala Tyr Val Phe Gly Thr Gly Thr Lys Val Thr Val Leu
                100                 105                 110
```

<210> SEQ ID NO 14
<211> LENGTH: 118
<212> TYPE: PRT
<213> ORGANISM: Artificial Sequence
<220> FEATURE:
<223> OTHER INFORMATION: Synthetic peptide sequence

<400> SEQUENCE: 14

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45
```

Gly Trp Ile Ser Ala Tyr Asn Gly Asn Thr Asn Tyr Ala Gln Lys Leu
            50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Thr Ile Asp Thr Ala Asn Ala Phe Asp Ile Trp Gly Gln Gly Thr
            100                 105                 110

Met Val Thr Val Ser Ser
            115

<210> SEQ ID NO 15
<211> LENGTH: 110
<212> TYPE: PRT
<213> ORGANISM: Artificial Sequence
<220> FEATURE:
<223> OTHER INFORMATION: Synthetic peptide sequence

<400> SEQUENCE: 15

Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
            50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Tyr Val Phe Gly Thr Gly Thr Lys Val Thr Val Leu
            100                 105                 110

<210> SEQ ID NO 16
<211> LENGTH: 118
<212> TYPE: PRT
<213> ORGANISM: Artificial Sequence
<220> FEATURE:
<223> OTHER INFORMATION: Synthetic peptide sequence

<400> SEQUENCE: 16

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
            50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Thr Ile Asp Thr Ala Asn Ala Phe Asp Ile Trp Gly Gln Gly Thr
            100                 105                 110

Met Val Thr Val Ser Ser

-continued

```
<210> SEQ ID NO 17
<211> LENGTH: 110
<212> TYPE: PRT
<213> ORGANISM: Artificial Sequence
<220> FEATURE:
<223> OTHER INFORMATION: Synthetic peptide sequence

<400> SEQUENCE: 17

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu
            100                 105                 110

<210> SEQ ID NO 18
<211> LENGTH: 118
<212> TYPE: PRT
<213> ORGANISM: Artificial Sequence
<220> FEATURE:
<223> OTHER INFORMATION: Synthetic peptide sequence

<400> SEQUENCE: 18

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Ile Asp Thr Ala Asn Ala Phe Asp Ile Trp Gly Gln Gly Thr
            100                 105                 110

Met Val Thr Val Ser Ser
        115

<210> SEQ ID NO 19
<211> LENGTH: 110
<212> TYPE: PRT
<213> ORGANISM: Artificial Sequence
<220> FEATURE:
<223> OTHER INFORMATION: Synthetic peptide sequence

<400> SEQUENCE: 19

Gln Ser Val Leu Thr Gln Pro Pro Ser Val Ser Ala Ala Pro Gly Gln
1               5                   10                  15
```

```
Lys Val Thr Ile Ser Cys Ser Gly Ser Arg Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Ser Asn Lys Arg Pro Ser Gly Ile Pro Asp Arg Phe Ser
50                      55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ser Trp Val Phe Gly Gly Gly Thr Lys Leu Thr Val Leu
            100                 105                 110

<210> SEQ ID NO 20
<211> LENGTH: 118
<212> TYPE: PRT
<213> ORGANISM: Artificial Sequence
<220> FEATURE:
<223> OTHER INFORMATION: Synthetic peptide sequence

<400> SEQUENCE: 20

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Ile Asp Thr Ala Asn Ala Phe Asp Ile Trp Gly Gln Gly Thr
            100                 105                 110

Met Val Thr Val Ser Ser
            115

<210> SEQ ID NO 21
<211> LENGTH: 110
<212> TYPE: PRT
<213> ORGANISM: Artificial Sequence
<220> FEATURE:
<223> OTHER INFORMATION: Synthetic peptide sequence

<400> SEQUENCE: 21

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                      55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
```

```
                    85                  90                  95

Ser Ala Tyr Val Phe Gly Thr Gly Thr Lys Val Thr Val Leu
                100                 105                 110

<210> SEQ ID NO 22
<211> LENGTH: 118
<212> TYPE: PRT
<213> ORGANISM: Artificial Sequence
<220> FEATURE:
<223> OTHER INFORMATION: Synthetic peptide sequence

<400> SEQUENCE: 22

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Thr Ile Asp Thr Ala Asn Ala Phe Asp Ile Trp Gly Gln Gly Thr
                100                 105                 110

Met Val Thr Val Ser Ser
        115

<210> SEQ ID NO 23
<211> LENGTH: 110
<212> TYPE: PRT
<213> ORGANISM: Artificial Sequence
<220> FEATURE:
<223> OTHER INFORMATION: Synthetic peptide sequence

<400> SEQUENCE: 23

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
                100                 105                 110

<210> SEQ ID NO 24
<211> LENGTH: 118
<212> TYPE: PRT
<213> ORGANISM: Artificial Sequence
<220> FEATURE:
<223> OTHER INFORMATION: Synthetic peptide sequence

<400> SEQUENCE: 24
```

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Ile Asn Ala Pro Asn Asn Phe Asp Ile Trp Gly Gln Gly Thr
            100                 105                 110

Met Val Thr Val Ser Ser
            115
```

<210> SEQ ID NO 25
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 25

```
Ser Tyr Gly Ile Ser
1               5
```

<210> SEQ ID NO 26
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 26

```
Trp Ile Ser Ala Tyr Asn Gly Asn Thr Asn Tyr Ala Gln Lys Leu Gln
1               5                   10                  15

Gly
```

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 27

```
Ile Gly Ser Gly Val Ala Phe Asp Ile
1               5
```

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 28

```
Ile Asp Thr Ala Ser Ala Phe Asp Ile
1               5
```

```
<210> SEQ ID NO 29
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 29

Ile Asp Thr Ala Asn Ala Phe Gly Ile
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 30

Ile Asp Thr Ala Thr Ala Phe Asp Ile
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 31

Ile Asp Thr Ala Asn Ala Phe Asp Ile
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 32

Ile Asn Ala Pro Asn Asn Phe Asp Ile
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 33

Gly Tyr Thr Phe Thr Ser Tyr Gly Ile Ser
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 34

Trp Ile Ser Ala Tyr Asn Gly Asn Thr Asn
1               5                   10
```

```
<210> SEQ ID NO 35
<211> LENGTH: 13
<212> TYPE: PRT
<213> ORGANISM: Artificial Sequence
<220> FEATURE:
<223> OTHER INFORMATION: Synthetic peptide sequence

<400> SEQUENCE: 35

Ser Gly Ser Ser Ser Asn Ile Gly Asn Asn Tyr Val Ser
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Synthetic peptide sequence

<400> SEQUENCE: 36

Ser Gly Ser Arg Ser Asn Ile Gly Asn Asn Tyr Val Ser
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 37

Asp Asn Asn Lys Arg Pro Ser
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 38

Asp Ser Asn Lys Arg Pro Ser
1               5

<210> SEQ ID NO 39
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 39

Gly Thr Trp Asp Ser Ser Leu Ser Ala Tyr Val
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 40

Gly Thr Trp Asp Ser Ser Leu Ser Ala Trp Val
1               5                   10

<210> SEQ ID NO 41
```

```
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 41

Gly Thr Trp Asp Ser Ser Leu Ser Ala Val Val
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 42

Gly Thr Trp Asp Ser Ser Leu Ser Gly Val Val
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 43

Gly Thr Trp Asp Ser Ser Leu Ser Ser Tyr Val
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 44

Gly Thr Trp Asp Ser Ser Leu Ser Ser Trp Val
1               5                   10

<210> SEQ ID NO 45
<211> LENGTH: 125
<212> TYPE: PRT
<213> ORGANISM: Artificial Sequence
<220> FEATURE:
<223> OTHER INFORMATION: Synthetic peptide sequence

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
```

```
                100                 105                 110
Ala Tyr Trp Gly Gln Gly Thr Leu Val Thr Val Ser Ser
        115                 120                 125

<210> SEQ ID NO 46
<211> LENGTH: 125
<212> TYPE: PRT
<213> ORGANISM: Artificial Sequence
<220> FEATURE:
<223> OTHER INFORMATION: Synthetic peptide sequence

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 47
<211> LENGTH: 109
<212> TYPE: PRT
<213> ORGANISM: Artificial Sequence
<220> FEATURE:
<223> OTHER INFORMATION: Synthetic peptide sequence

<400> SEQUENCE: 47

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 48
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 48
```

```
Thr Tyr Ala Met Asn
1               5

<210> SEQ ID NO 49
<211> LENGTH: 19
<212> TYPE: PRT
<213> ORGANISM: Artificial Sequence
<220> FEATURE:
<223> OTHER INFORMATION: Synthetic peptide sequence

<400> SEQUENCE: 49

Arg Ile Arg Ser Lys Tyr Asn Asn Tyr Ala Thr Tyr Tyr Ala Asp Ser
1               5                   10                  15

Val Lys Gly

<210> SEQ ID NO 50
<211> LENGTH: 19
<212> TYPE: PRT
<213> ORGANISM: Artificial Sequence
<220> FEATURE:
<223> OTHER INFORMATION: Synthetic peptide sequence

<400> SEQUENCE: 50

Arg Ile Arg Ser Lys Tyr Asn Asn Tyr Ala Thr Tyr Tyr Ala Asp Ser
1               5                   10                  15

Val Lys Asp

<210> SEQ ID NO 51
<211> LENGTH: 14
<212> TYPE: PRT
<213> ORGANISM: Artificial Sequence
<220> FEATURE:
<223> OTHER INFORMATION: Synthetic peptide sequence

<400> SEQUENCE: 51

His Gly Asn Phe Gly Asn Ser Tyr Val Ser Trp Phe Ala Tyr
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 52

Gly Phe Thr Phe Ser Thr Tyr Ala Met Asn
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 53

Gly Phe Thr Phe Asn Thr Tyr Ala Met Asn
1               5                   10

<210> SEQ ID NO 54
<211> LENGTH: 12
<212> TYPE: PRT
<213> ORGANISM: Artificial Sequence
<220> FEATURE:
```

<223> OTHER INFORMATION: Synthetic peptide sequence

<400> SEQUENCE: 54

Arg Ile Arg Ser Lys Tyr Asn Asn Tyr Ala Thr Tyr
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Synthetic peptide sequence

<400> SEQUENCE: 55

Arg Ser Ser Thr Gly Ala Val Thr Thr Ser Asn Tyr Ala Asn
1               5                   10

<210> SEQ ID NO 56
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 56

Gly Thr Asn Lys Arg Ala Pro
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 57

Ala Leu Trp Tyr Ser Asn Leu Trp Val
1               5

<210> SEQ ID NO 58
<211> LENGTH: 18
<212> TYPE: DNA
<213> ORGANISM: Artificial Sequence
<220> FEATURE:
<223> OTHER INFORMATION: Synthetic nucleotide sequence

<400> SEQUENCE: 58
ggagattttc aacgtgaa                                              18

<210> SEQ ID NO 59
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 59
ctcttctgag atgagttttt g                                          21

<210> SEQ ID NO 60
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 60

```
Cys Pro Pro Cys Pro
1               5
```

<210> SEQ ID NO 61
<211> LENGTH: 28
<212> TYPE: PRT
<213> ORGANISM: Artificial Sequence
<220> FEATURE:
<223> OTHER INFORMATION: Synthetic peptide sequence

<400> SEQUENCE: 61

```
Glu Val Ala Ala Leu Glu Lys Glu Val Ala Ala Leu Glu Lys Glu Val
1               5                   10                  15
Ala Ala Leu Glu Lys Glu Val Ala Ala Leu Glu Lys
            20                  25
```

<210> SEQ ID NO 62
<211> LENGTH: 28
<212> TYPE: PRT
<213> ORGANISM: Artificial Sequence
<220> FEATURE:
<223> OTHER INFORMATION: Synthetic peptide sequence

<400> SEQUENCE: 62

```
Lys Val Ala Ala Leu Lys Glu Lys Val Ala Ala Leu Lys Glu Lys Val
1               5                   10                  15
Ala Ala Leu Lys Glu Lys Val Ala Ala Leu Lys Glu
            20                  25
```

<210> SEQ ID NO 63
<211> LENGTH: 216
<212> TYPE: PRT
<213> ORGANISM: Artificial Sequence
<220> FEATURE:
<223> OTHER INFORMATION: Synthetic peptide sequence

<400> SEQUENCE: 63

```
Ala Pro Glu Ala Ala Gly Ala Pro Ser Val Phe Leu Phe Pro Pro Lys
1               5                   10                  15
Pro Lys Asp Thr Leu Met Ile Ser Arg Thr Pro Glu Val Thr Cys Val
            20                  25                  30
Val Val Asp Val Ser His Glu Asp Pro Glu Val Lys Phe Asn Trp Tyr
        35                  40                  45
Val Asp Gly Val Glu Val His Asn Ala Lys Thr Lys Pro Arg Glu Glu
    50                  55                  60
Gln Tyr Asn Ser Thr Tyr Arg Val Val Ser Val Leu Thr Val Leu His
65                  70                  75                  80
Gln Asp Trp Leu Asn Gly Lys Glu Tyr Lys Cys Lys Val Ser Asn Lys
                85                  90                  95
Ala Leu Pro Ala Pro Ile Glu Lys Thr Ile Ser Lys Ala Lys Gly Gln
            100                 105                 110
Pro Arg Glu Pro Gln Val Cys Thr Leu Pro Pro Ser Arg Glu Glu Met
        115                 120                 125
Thr Lys Asn Gln Val Ser Leu Trp Cys Leu Val Lys Gly Phe Tyr Pro
    130                 135                 140
Ser Asp Ile Ala Val Glu Trp Glu Ser Asn Gly Gln Pro Glu Asn Asn
145                 150                 155                 160
Tyr Lys Thr Thr Pro Pro Val Leu Asp Ser Asp Gly Ser Phe Phe Leu
                165                 170                 175
```

```
Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 64
<211> LENGTH: 216
<212> TYPE: PRT
<213> ORGANISM: Artificial Sequence
<220> FEATURE:
<223> OTHER INFORMATION: Synthetic peptide sequence

<400> SEQUENCE: 64

Ala Pro Glu Ala Ala Gly Ala Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Cys Arg Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 65
<211> LENGTH: 217
<212> TYPE: PRT
<213> ORGANISM: Artificial Sequence
<220> FEATURE:
<223> OTHER INFORMATION: Synthetic peptide sequence

<400> SEQUENCE: 65

Ala Pro Glu Ala Ala Gly Ala Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45
```

```
Val Asp Gly Val Glu Val His Asn Ala Lys Thr Lys Pro Arg Glu Glu
     50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Pro Gly Lys
    210                 215

<210> SEQ ID NO 66
<211> LENGTH: 217
<212> TYPE: PRT
<213> ORGANISM: Artificial Sequence
<220> FEATURE:
<223> OTHER INFORMATION: Synthetic peptide sequence

<400> SEQUENCE: 66

Ala Pro Glu Ala Ala Gly Ala Pro Ser Val Phe Leu Phe Pro Pro Lys
  1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
     50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190
```

Phe Ser Cys Ser Val Met His Glu Ala Leu His Asn His Tyr Thr Gln
        195                 200                 205
Lys Ser Leu Ser Leu Ser Pro Gly Lys
    210                 215

<210> SEQ ID NO 67
<211> LENGTH: 6
<212> TYPE: DNA
<213> ORGANISM: Artificial Sequence
<220> FEATURE:
<223> OTHER INFORMATION: Synthetic nucleotide sequence

<400> SEQUENCE: 67 tccgga                                                                6

<210> SEQ ID NO 68
<211> LENGTH: 8
<212> TYPE: PRT
<213> ORGANISM: Artificial Sequence
<220> FEATURE:
<223> OTHER INFORMATION: Synthetic peptide sequence

<400> SEQUENCE: 68

Gly Gly Gly Ser Gly Gly Gly Gly
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 69

Gly Gly Gly Gly Ser Gly Gly Gly Gly
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 70

Gly Phe Asn Arg Gly Glu Cys
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 71

Gly Val Glu Pro Lys Ser Cys
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic peptide sequence

```
<400> SEQUENCE: 72

Gly Gly Cys Gly Gly Gly
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 73

Gly Cys Pro Pro Cys Pro
1               5

<210> SEQ ID NO 74
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 74

Gly Gly Thr Gly Gly Cys Pro Pro Cys Pro
1               5                   10

<210> SEQ ID NO 75
<211> LENGTH: 16
<212> TYPE: PRT
<213> ORGANISM: Artificial Sequence
<220> FEATURE:
<223> OTHER INFORMATION: Synthetic peptide sequence

<400> SEQUENCE: 75

Gly Glu Pro Lys Ser Ser Asp Lys Thr His Thr Cys Pro Pro Cys Pro
1               5                   10                  15

<210> SEQ ID NO 76
<211> LENGTH: 21
<212> TYPE: PRT
<213> ORGANISM: Artificial Sequence
<220> FEATURE:
<223> OTHER INFORMATION: Synthetic peptide sequence

<400> SEQUENCE: 76

Gly Gly Thr Gly Gly Gly Glu Pro Lys Ser Ser Asp Lys Thr His Thr
1               5                   10                  15

Cys Pro Pro Cys Pro
            20

<210> SEQ ID NO 77
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 77

Lys Ala Pro Ser Ser Ser Pro Met Glu
1               5

<210> SEQ ID NO 78
<211> LENGTH: 6
<212> TYPE: PRT
<213> ORGANISM: Artificial Sequence
<220> FEATURE:
```

<223> OTHER INFORMATION: Synthetic peptide sequence

<400> SEQUENCE: 78

His His His His His His
1               5

<210> SEQ ID NO 79
<211> LENGTH: 13
<212> TYPE: PRT
<213> ORGANISM: Artificial Sequence
<220> FEATURE:
<223> OTHER INFORMATION: Synthetic peptide sequence

<400> SEQUENCE: 79

Gly Gly Cys Gly Gly Asp Tyr Lys Asp Asp Asp Asp Lys
1               5                   10

<210> SEQ ID NO 80
<211> LENGTH: 277
<212> TYPE: PRT
<213> ORGANISM: Artificial Sequence
<220> FEATURE:
<223> OTHER INFORMATION: Synthetic peptide sequence

<400> SEQUENCE: 80

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu Gly Gly
            100                 105                 110

Gly Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Thr Tyr Ala Met Asn Trp Val Arg Gln Ala Pro Gly
145                 150                 155                 160

Lys Gly Leu Glu Trp Val Gly Arg Ile Arg Ser Lys Tyr Asn Asn Tyr
                165                 170                 175

Ala Thr Tyr Tyr Ala Asp Ser Val Lys Gly Arg Phe Thr Ile Ser Arg
            180                 185                 190

Asp Asp Ser Lys Asn Ser Leu Tyr Leu Gln Met Asn Ser Leu Lys Thr
        195                 200                 205

Glu Asp Thr Ala Val Tyr Tyr Cys Val Arg His Gly Asn Phe Gly Asn
    210                 215                 220

Ser Tyr Val Ser Trp Phe Ala Tyr Trp Gly Gln Gly Thr Leu Val Thr
225                 230                 235                 240

Val Ser Ser Gly Gly Cys Gly Gly Lys Val Ala Ala Leu Lys Glu
                245                 250                 255

Lys Val Ala Ala Leu Lys Glu Lys Val Ala Ala Leu Lys Glu Lys Val

Ala Ala Leu Lys Glu
         275

<210> SEQ ID NO 81
<211> LENGTH: 270
<212> TYPE: PRT
<213> ORGANISM: Artificial Sequence
<220> FEATURE:
<223> OTHER INFORMATION: Synthetic peptide sequence

<400> SEQUENCE: 81

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Gln Ser Gly Ala Glu
        115                 120                 125

Val Lys Lys Pro Gly Ala Ser Val Lys Val Ser Cys Lys Ala Ser Gly
    130                 135                 140

Tyr Thr Phe Thr Ser Tyr Gly Ile Ser Trp Val Arg Gln Ala Pro Gly
145                 150                 155                 160

Gln Gly Leu Glu Trp Met Gly Trp Ile Ser Ala Tyr Asn Gly Asn Thr
                165                 170                 175

Asn Tyr Ala Gln Lys Leu Gln Gly Arg Val Thr Met Thr Thr Asp Thr
            180                 185                 190

Ser Thr Ser Thr Ala Tyr Met Glu Leu Arg Ser Leu Arg Ser Asp Asp
        195                 200                 205

Thr Ala Val Tyr Tyr Cys Ala Thr Ile Asp Thr Ala Ser Ala Phe Asp
    210                 215                 220

Ile Trp Gly Gln Gly Thr Met Val Thr Val Ser Ser Gly Gly Cys Gly
225                 230                 235                 240

Gly Gly Glu Val Ala Ala Leu Glu Lys Glu Val Ala Ala Leu Glu Lys
                245                 250                 255

Glu Val Ala Ala Leu Glu Lys Glu Val Ala Ala Leu Glu Lys
            260                 265                 270

<210> SEQ ID NO 82
<211> LENGTH: 277
<212> TYPE: PRT
<213> ORGANISM: Artificial Sequence
<220> FEATURE:
<223> OTHER INFORMATION: Synthetic peptide sequence

<400> SEQUENCE: 82

Gln Ser Val Leu Thr Gln Pro Pro Ser Val Ser Ala Ala Pro Gly Gln
1               5                   10                  15

```
Lys Val Thr Ile Ser Cys Ser Gly Ser Ser Asn Ile Gly Asn Asn
                20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                85                  90                  95

Ser Gly Val Val Phe Gly Gly Gly Thr Lys Leu Thr Val Leu Gly Gly
            100                 105                 110

Gly Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
        130                 135                 140

Phe Thr Phe Asn Thr Tyr Ala Met Asn Trp Val Arg Gln Ala Pro Gly
145                 150                 155                 160

Lys Gly Leu Glu Trp Val Ala Arg Ile Arg Ser Lys Tyr Asn Asn Tyr
                165                 170                 175

Ala Thr Tyr Tyr Ala Asp Ser Val Lys Asp Arg Phe Thr Ile Ser Arg
            180                 185                 190

Asp Asp Ser Lys Asn Ser Leu Tyr Leu Gln Met Asn Ser Leu Lys Thr
        195                 200                 205

Glu Asp Thr Ala Val Tyr Tyr Cys Val Arg His Gly Asn Phe Gly Asn
210                 215                 220

Ser Tyr Val Ser Trp Phe Ala Tyr Trp Gly Gln Gly Thr Leu Val Thr
225                 230                 235                 240

Val Ser Ser Gly Gly Cys Gly Gly Gly Lys Val Ala Ala Leu Lys Glu
                245                 250                 255

Lys Val Ala Ala Leu Lys Glu Lys Val Ala Ala Leu Lys Glu Lys Val
            260                 265                 270

Ala Ala Leu Lys Glu
        275

<210> SEQ ID NO 83
<211> LENGTH: 270
<212> TYPE: PRT
<213> ORGANISM: Artificial Sequence
<220> FEATURE:
<223> OTHER INFORMATION: Synthetic peptide sequence

<400> SEQUENCE: 83

Gln Ala Val Val Thr Gln Glu Pro Ser Leu Thr Val Ser Pro Gly Gly
 1               5                  10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
 50                  55                  60

Ser Gly Ser Leu Leu Gly Gly Lys Ala Ala Leu Thr Ile Thr Gly Ala
 65                  70                  75                  80

Gln Ala Glu Asp Glu Ala Asp Tyr Tyr Cys Ala Leu Trp Tyr Ser Asn
                85                  90                  95
```

-continued

Leu Trp Val Phe Gly Gly Gly Thr Lys Leu Thr Val Leu Gly Gly Gly
            100                 105                 110

Gly Ser Gly Gly Gly Gly Glu Val Gln Leu Val Gln Ser Gly Ala Glu
        115                 120                 125

Val Lys Lys Pro Gly Ala Ser Val Lys Val Ser Cys Lys Ala Ser Gly
130                 135                 140

Tyr Thr Phe Thr Ser Tyr Gly Ile Ser Trp Val Arg Gln Ala Pro Gly
145                 150                 155                 160

Gln Gly Leu Glu Trp Met Gly Trp Ile Ser Ala Tyr Asn Gly Asn Thr
                165                 170                 175

Asn Tyr Ala Gln Lys Leu Gln Gly Arg Val Thr Met Thr Thr Asp Thr
            180                 185                 190

Ser Thr Ser Thr Ala Tyr Met Glu Leu Arg Ser Leu Arg Ser Asp Asp
        195                 200                 205

Thr Ala Val Tyr Tyr Cys Ala Thr Ile Asp Thr Ala Asn Ala Phe Gly
210                 215                 220

Ile Trp Gly Gln Gly Thr Met Val Thr Val Ser Ser Gly Gly Cys Gly
225                 230                 235                 240

Gly Gly Glu Val Ala Ala Leu Glu Lys Glu Val Ala Ala Leu Glu Lys
                245                 250                 255

Glu Val Ala Ala Leu Glu Lys Glu Val Ala Ala Leu Glu Lys
            260                 265                 270

<210> SEQ ID NO 84
<211> LENGTH: 277
<212> TYPE: PRT
<213> ORGANISM: Artificial Sequence
<220> FEATURE:
<223> OTHER INFORMATION: Synthetic peptide sequence

<400> SEQUENCE: 84

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ser Tyr Val Phe Gly Thr Gly Thr Lys Val Thr Val Leu Gly Gly
            100                 105                 110

Gly Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
130                 135                 140

Phe Thr Phe Asn Thr Tyr Ala Met Asn Trp Val Arg Gln Ala Pro Gly
145                 150                 155                 160

Lys Gly Leu Glu Trp Val Ala Arg Ile Arg Ser Lys Tyr Asn Asn Tyr
                165                 170                 175

Ala Thr Tyr Tyr Ala Asp Ser Val Lys Asp Arg Phe Thr Ile Ser Arg
            180                 185                 190

Asp Asp Ser Lys Asn Ser Leu Tyr Leu Gln Met Asn Ser Leu Lys Thr
            195                 200                 205

Glu Asp Thr Ala Val Tyr Tyr Cys Val Arg His Gly Asn Phe Gly Asn
    210                 215                 220

Ser Tyr Val Ser Trp Phe Ala Tyr Trp Gly Gln Gly Thr Leu Val Thr
225                 230                 235                 240

Val Ser Ser Gly Gly Cys Gly Gly Lys Val Ala Ala Leu Lys Glu
                245                 250                 255

Lys Val Ala Ala Leu Lys Glu Lys Val Ala Ala Leu Lys Glu Lys Val
            260                 265                 270

Ala Ala Leu Lys Glu
        275

<210> SEQ ID NO 85
<211> LENGTH: 270
<212> TYPE: PRT
<213> ORGANISM: Artificial Sequence
<220> FEATURE:
<223> OTHER INFORMATION: Synthetic peptide sequence

<400> SEQUENCE: 85

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Gln Ser Gly Ala Glu
        115                 120                 125

Val Lys Lys Pro Gly Ala Ser Val Lys Val Ser Cys Lys Ala Ser Gly
    130                 135                 140

Tyr Thr Phe Thr Ser Tyr Gly Ile Ser Trp Val Arg Gln Ala Pro Gly
145                 150                 155                 160

Gln Gly Leu Glu Trp Met Gly Trp Ile Ser Ala Tyr Asn Gly Asn Thr
                165                 170                 175

Asn Tyr Ala Gln Lys Leu Gln Gly Arg Val Thr Met Thr Thr Asp Thr
            180                 185                 190

Ser Thr Ser Thr Ala Tyr Met Glu Leu Arg Ser Leu Arg Ser Asp Asp
        195                 200                 205

Thr Ala Val Tyr Tyr Cys Ala Thr Ile Asp Thr Ala Thr Ala Phe Asp
    210                 215                 220

Ile Trp Gly Gln Gly Thr Met Val Thr Val Ser Ser Gly Gly Cys Gly
225                 230                 235                 240

Gly Gly Glu Val Ala Ala Leu Glu Lys Glu Val Ala Ala Leu Glu Lys
                245                 250                 255

Glu Val Ala Ala Leu Glu Lys Glu Val Ala Ala Leu Glu Lys
            260                 265                 270

```
<210> SEQ ID NO 86
<211> LENGTH: 277
<212> TYPE: PRT
<213> ORGANISM: Artificial Sequence
<220> FEATURE:
<223> OTHER INFORMATION: Synthetic peptide sequence

<400> SEQUENCE: 86

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Tyr Val Phe Gly Thr Gly Thr Lys Val Thr Val Leu Gly Gly
            100                 105                 110

Gly Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Thr Tyr Ala Met Asn Trp Val Arg Gln Ala Pro Gly
145                 150                 155                 160

Lys Gly Leu Glu Trp Val Gly Arg Ile Arg Ser Lys Tyr Asn Asn Tyr
                165                 170                 175

Ala Thr Tyr Tyr Ala Asp Ser Val Lys Gly Arg Phe Thr Ile Ser Arg
            180                 185                 190

Asp Asp Ser Lys Asn Ser Leu Tyr Leu Gln Met Asn Ser Leu Lys Thr
        195                 200                 205

Glu Asp Thr Ala Val Tyr Tyr Cys Val Arg His Gly Asn Phe Gly Asn
    210                 215                 220

Ser Tyr Val Ser Trp Phe Ala Tyr Trp Gly Gln Gly Thr Leu Val Thr
225                 230                 235                 240

Val Ser Ser Gly Gly Cys Gly Gly Lys Val Ala Ala Leu Lys Glu
                245                 250                 255

Lys Val Ala Ala Leu Lys Glu Lys Val Ala Ala Leu Lys Glu Lys Val
            260                 265                 270

Ala Ala Leu Lys Glu
        275

<210> SEQ ID NO 87
<211> LENGTH: 270
<212> TYPE: PRT
<213> ORGANISM: Artificial Sequence
<220> FEATURE:
<223> OTHER INFORMATION: Synthetic peptide sequence

<400> SEQUENCE: 87

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30
```

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
     50                  55                  60

Ser Gly Ser Leu Leu Gly Gly Lys Ala Ala Leu Thr Ile Thr Gly Ala
 65                  70                  75                  80

Gln Ala Glu Asp Glu Ala Asp Tyr Tyr Cys Ala Leu Trp Tyr Ser Asn
                 85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Gln Ser Gly Ala Glu
            115                 120                 125

Val Lys Lys Pro Gly Ala Ser Val Lys Val Ser Cys Lys Ala Ser Gly
130                 135                 140

Tyr Thr Phe Thr Ser Tyr Gly Ile Ser Trp Val Arg Gln Ala Pro Gly
145                 150                 155                 160

Gln Gly Leu Glu Trp Met Gly Trp Ile Ser Ala Tyr Asn Gly Asn Thr
                165                 170                 175

Asn Tyr Ala Gln Lys Leu Gln Gly Arg Val Thr Met Thr Thr Asp Thr
            180                 185                 190

Ser Thr Ser Thr Ala Tyr Met Glu Leu Arg Ser Leu Arg Ser Asp Asp
        195                 200                 205

Thr Ala Val Tyr Tyr Cys Ala Thr Ile Asp Thr Ala Asn Ala Phe Asp
210                 215                 220

Ile Trp Gly Gln Gly Thr Met Val Thr Val Ser Ser Gly Gly Cys Gly
225                 230                 235                 240

Gly Gly Glu Val Ala Ala Leu Glu Lys Glu Val Ala Ala Leu Glu Lys
            245                 250                 255

Glu Val Ala Ala Leu Glu Lys Glu Val Ala Ala Leu Glu Lys
                260                 265                 270

<210> SEQ ID NO 88
<211> LENGTH: 465
<212> TYPE: PRT
<213> ORGANISM: Artificial Sequence
<220> FEATURE:
<223> OTHER INFORMATION: Synthetic peptide sequence

<400> SEQUENCE: 88

Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
     50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Val Val Phe Gly Gly Gly Thr Lys Leu Thr Val Leu Gly Gly
            100                 105                 110

Gly Ser Gly Gly Gly Gly Glu Val Gln Leu Val Glu Ser Gly Gly Gly
            115                 120                 125

Leu Val Gln Pro Gly Gly Ser Leu Arg Leu Ser Cys Ala Ala Ser Gly
130                 135                 140

Phe Thr Phe Ser Thr Tyr Ala Met Asn Trp Val Arg Gln Ala Pro Gly
145                 150                 155                 160

Lys Gly Leu Glu Trp Val Gly Arg Ile Arg Ser Lys Tyr Asn Asn Tyr
                165                 170                 175

Ala Thr Tyr Tyr Ala Asp Ser Val Lys Gly Arg Phe Thr Ile Ser Arg
            180                 185                 190

Asp Asp Ser Lys Asn Ser Leu Tyr Leu Gln Met Asn Ser Leu Lys Thr
        195                 200                 205

Glu Asp Thr Ala Val Tyr Tyr Cys Val Arg His Gly Asn Phe Gly Asn
    210                 215                 220

Ser Tyr Val Ser Trp Phe Ala Tyr Trp Gly Gln Gly Thr Leu Val Thr
225                 230                 235                 240

Val Ser Ser Gly Cys Pro Cys Pro Ala Pro Glu Ala Ala Gly Ala
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Asp Val Ser His Glu
                275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Cys
        355                 360                 365

Thr Leu Pro Pro Ser Arg Glu Glu Met Thr Lys Asn Gln Val Ser Leu
    370                 375                 380

Trp Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly
465

<210> SEQ ID NO 89
<211> LENGTH: 458
<212> TYPE: PRT
<213> ORGANISM: Artificial Sequence
<220> FEATURE:
<223> OTHER INFORMATION: Synthetic peptide sequence

<400> SEQUENCE: 89

Gln Ala Val Val Thr Gln Glu Pro Ser Leu Thr Val Ser Pro Gly Gly
1               5                   10                  15

```
Thr Val Thr Leu Thr Cys Arg Ser Ser Thr Gly Ala Val Thr Thr Ser
             20                  25                  30

Asn Tyr Ala Asn Trp Val Gln Gln Lys Pro Gly Gln Ala Pro Arg Gly
         35                  40                  45

Leu Ile Gly Gly Thr Asn Lys Arg Ala Pro Trp Thr Pro Ala Arg Phe
 50                  55                  60

Ser Gly Ser Leu Leu Gly Gly Lys Ala Ala Leu Thr Ile Thr Gly Ala
 65                  70                  75                  80

Gln Ala Glu Asp Glu Ala Asp Tyr Tyr Cys Ala Leu Trp Tyr Ser Asn
                 85                  90                  95

Leu Trp Val Phe Gly Gly Gly Thr Lys Leu Thr Val Leu Gly Gly Gly
                100                 105                 110

Gly Ser Gly Gly Gly Gly Glu Val Gln Leu Val Gln Ser Gly Ala Glu
            115                 120                 125

Val Lys Lys Pro Gly Ala Ser Val Lys Val Ser Cys Lys Ala Ser Gly
        130                 135                 140

Tyr Thr Phe Thr Ser Tyr Gly Ile Ser Trp Val Arg Gln Ala Pro Gly
145                 150                 155                 160

Gln Gly Leu Glu Trp Met Gly Trp Ile Ser Ala Tyr Asn Gly Asn Thr
                165                 170                 175

Asn Tyr Ala Gln Lys Leu Gln Gly Arg Val Thr Met Thr Thr Asp Thr
            180                 185                 190

Ser Thr Ser Thr Ala Tyr Met Glu Leu Arg Ser Leu Arg Ser Asp Asp
        195                 200                 205

Thr Ala Val Tyr Tyr Cys Ala Thr Ile Asp Thr Ala Ser Ala Phe Asp
        210                 215                 220

Ile Trp Gly Gln Gly Thr Met Val Thr Val Ser Ser Gly Cys Pro Pro
225                 230                 235                 240

Cys Pro Ala Pro Glu Ala Ala Gly Ala Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
        290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Cys Arg Glu
        355                 360                 365

Glu Met Thr Lys Asn Gln Val Ser Leu Ser Cys Ala Val Lys Gly Phe
        370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
            405                 410                 415

Phe Leu Val Ser Lys Leu Thr Val Asp Lys Ser Arg Trp Gln Gln Gly
        420                 425                 430
```

-continued

Asn Val Phe Ser Cys Ser Val Met His Glu Ala Leu His Asn His Tyr
            435                 440                 445

Thr Gln Lys Ser Leu Ser Leu Ser Pro Gly
    450                 455

<210> SEQ ID NO 90
<211> LENGTH: 465
<212> TYPE: PRT
<213> ORGANISM: Artificial Sequence
<220> FEATURE:
<223> OTHER INFORMATION: Synthetic peptide sequence

<400> SEQUENCE: 90

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Val Val Phe Gly Gly Gly Thr Lys Leu Thr Val Leu Gly Gly
            100                 105                 110

Gly Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Thr Tyr Ala Met Asn Trp Val Arg Gln Ala Pro Gly
145                 150                 155                 160

Lys Gly Leu Glu Trp Val Gly Arg Ile Arg Ser Lys Tyr Asn Asn Tyr
                165                 170                 175

Ala Thr Tyr Tyr Ala Asp Ser Val Lys Gly Arg Phe Thr Ile Ser Arg
            180                 185                 190

Asp Asp Ser Lys Asn Ser Leu Tyr Leu Gln Met Asn Ser Leu Lys Thr
        195                 200                 205

Glu Asp Thr Ala Val Tyr Tyr Cys Val Arg His Gly Asn Phe Gly Asn
    210                 215                 220

Ser Tyr Val Ser Trp Phe Ala Tyr Trp Gly Gln Gly Thr Leu Val Thr
225                 230                 235                 240

Val Ser Ser Gly Cys Pro Pro Cys Pro Ala Pro Glu Ala Ala Gly Ala
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

```
Glu Tyr Lys Cys Lys Val Ser Asn Lys Ala Leu Pro Ala Pro Ile Glu
                340                 345                 350

Lys Thr Ile Ser Lys Ala Lys Gly Gln Pro Arg Glu Pro Gln Val Cys
            355                 360                 365

Thr Leu Pro Pro Ser Arg Glu Glu Met Thr Lys Asn Gln Val Ser Leu
        370                 375                 380

Trp Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly
465

<210> SEQ ID NO 91
<211> LENGTH: 458
<212> TYPE: PRT
<213> ORGANISM: Artificial Sequence
<220> FEATURE:
<223> OTHER INFORMATION: Synthetic peptide sequence

<400> SEQUENCE: 91

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Gln Ser Gly Ala Glu
        115                 120                 125

Val Lys Lys Pro Gly Ala Ser Val Lys Val Ser Cys Lys Ala Ser Gly
    130                 135                 140

Tyr Thr Phe Thr Ser Tyr Gly Ile Ser Trp Val Arg Gln Ala Pro Gly
145                 150                 155                 160

Gln Gly Leu Glu Trp Met Gly Trp Ile Ser Ala Tyr Asn Gly Asn Thr
                165                 170                 175

Asn Tyr Ala Gln Lys Leu Gln Gly Arg Val Thr Met Thr Thr Asp Thr
            180                 185                 190

Ser Thr Ser Thr Ala Tyr Met Glu Leu Arg Ser Leu Arg Ser Asp Asp
        195                 200                 205

Thr Ala Val Tyr Tyr Cys Ala Thr Ile Asp Thr Ala Asn Ala Phe Gly
    210                 215                 220
```

Ile Trp Gly Gln Gly Thr Met Val Thr Val Ser Ser Gly Cys Pro Pro
225                 230                 235                 240

Cys Pro Ala Pro Glu Ala Ala Gly Ala Pro Ser Val Phe Leu Phe Pro
            245                 250                 255

Pro Lys Pro Lys Asp Thr Leu Met Ile Ser Arg Thr Pro Glu Val Thr
        260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
                340                 345                 350

Gly Gln Pro Arg Glu Pro Gln Val Tyr Thr Leu Pro Pro Cys Arg Glu
                355                 360                 365

Glu Met Thr Lys Asn Gln Val Ser Leu Ser Cys Ala Val Lys Gly Phe
370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Val Ser Lys Leu Thr Val Asp Lys Ser Arg Trp Gln Gln Gly
                420                 425                 430

Asn Val Phe Ser Cys Ser Val Met His Glu Ala Leu His Asn His Tyr
                435                 440                 445

Thr Gln Lys Ser Leu Ser Leu Ser Pro Gly
                450                 455

<210> SEQ ID NO 92
<211> LENGTH: 465
<212> TYPE: PRT
<213> ORGANISM: Artificial Sequence
<220> FEATURE:
<223> OTHER INFORMATION: Synthetic peptide sequence

<400> SEQUENCE: 92

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ser Tyr Val Phe Gly Thr Gly Thr Lys Val Thr Val Leu Gly Gly
                100                 105                 110

Gly Ser Gly Gly Gly Gly Glu Val Gln Leu Val Glu Ser Gly Gly Gly
            115                 120                 125

Leu Val Gln Pro Gly Gly Ser Leu Arg Leu Ser Cys Ala Ala Ser Gly
    130                 135                 140

Phe Thr Phe Ser Thr Tyr Ala Met Asn Trp Val Arg Gln Ala Pro Gly
145                 150                 155                 160

Lys Gly Leu Glu Trp Val Gly Arg Ile Arg Ser Lys Tyr Asn Asn Tyr
                165                 170                 175

Ala Thr Tyr Tyr Ala Asp Ser Val Lys Gly Arg Phe Thr Ile Ser Arg
            180                 185                 190

Asp Asp Ser Lys Asn Ser Leu Tyr Leu Gln Met Asn Ser Leu Lys Thr
        195                 200                 205

Glu Asp Thr Ala Val Tyr Tyr Cys Val Arg His Gly Asn Phe Gly Asn
    210                 215                 220

Ser Tyr Val Ser Trp Phe Ala Tyr Trp Gly Gln Gly Thr Leu Val Thr
225                 230                 235                 240

Val Ser Ser Gly Cys Pro Cys Pro Ala Pro Glu Ala Ala Gly Ala
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Asp Val Ser His Glu
                275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Cys
        355                 360                 365

Thr Leu Pro Pro Ser Arg Glu Glu Met Thr Lys Asn Gln Val Ser Leu
    370                 375                 380

Trp Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly
465

<210> SEQ ID NO 93
<211> LENGTH: 458
<212> TYPE: PRT
<213> ORGANISM: Artificial Sequence
<220> FEATURE:
<223> OTHER INFORMATION: Synthetic peptide sequence

<400> SEQUENCE: 93

Gln Ala Val Val Thr Gln Glu Pro Ser Leu Thr Val Ser Pro Gly Gly
1               5                   10                  15

```
Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
            50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Gln Ser Gly Ala Glu
            115                 120                 125

Val Lys Lys Pro Gly Ala Ser Val Lys Val Ser Cys Lys Ala Ser Gly
            130                 135                 140

Tyr Thr Phe Thr Ser Tyr Gly Ile Ser Trp Val Arg Gln Ala Pro Gly
145                 150                 155                 160

Gln Gly Leu Glu Trp Met Gly Trp Ile Ser Ala Tyr Asn Gly Asn Thr
                165                 170                 175

Asn Tyr Ala Gln Lys Leu Gln Gly Arg Val Thr Met Thr Thr Asp Thr
            180                 185                 190

Ser Thr Ser Thr Ala Tyr Met Glu Leu Arg Ser Leu Arg Ser Asp Asp
            195                 200                 205

Thr Ala Val Tyr Tyr Cys Ala Thr Ile Asp Thr Ala Thr Ala Phe Asp
210                 215                 220

Ile Trp Gly Gln Gly Thr Met Val Thr Val Ser Ser Gly Cys Pro Pro
225                 230                 235                 240

Cys Pro Ala Pro Glu Ala Ala Gly Ala Pro Ser Val Phe Leu Phe Pro
            245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
            275                 280                 285

Trp Tyr Val Asp Gly Val Glu Val His Asn Ala Lys Thr Lys Pro Arg
            290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Cys Arg Glu
            355                 360                 365

Glu Met Thr Lys Asn Gln Val Ser Leu Ser Cys Ala Val Lys Gly Phe
            370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Val Ser Lys Leu Thr Val Asp Lys Ser Arg Trp Gln Gln Gly
            420                 425                 430

Asn Val Phe Ser Cys Ser Val Met His Glu Ala Leu His Asn His Tyr
```

```
                    435                 440                 445
Thr Gln Lys Ser Leu Ser Leu Ser Pro Gly
    450                 455

<210> SEQ ID NO 94
<211> LENGTH: 465
<212> TYPE: PRT
<213> ORGANISM: Artificial Sequence
<220> FEATURE:
<223> OTHER INFORMATION: Synthetic peptide sequence

<400> SEQUENCE: 94

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Tyr Val Phe Gly Thr Gly Thr Lys Val Thr Val Leu Gly Gly
            100                 105                 110

Gly Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
130                 135                 140

Phe Thr Phe Ser Thr Tyr Ala Met Asn Trp Val Arg Gln Ala Pro Gly
145                 150                 155                 160

Lys Gly Leu Glu Trp Val Gly Arg Ile Arg Ser Lys Tyr Asn Asn Tyr
                165                 170                 175

Ala Thr Tyr Tyr Ala Asp Ser Val Lys Gly Arg Phe Thr Ile Ser Arg
            180                 185                 190

Asp Asp Ser Lys Asn Ser Leu Tyr Leu Gln Met Asn Ser Leu Lys Thr
        195                 200                 205

Glu Asp Thr Ala Val Tyr Tyr Cys Val Arg His Gly Asn Phe Gly Asn
    210                 215                 220

Ser Tyr Val Ser Trp Phe Ala Tyr Trp Gly Gln Gly Thr Leu Val Thr
225                 230                 235                 240

Val Ser Ser Gly Cys Pro Pro Cys Pro Ala Pro Glu Ala Ala Gly Ala
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
```

```
                    340                 345                 350
Lys Thr Ile Ser Lys Ala Lys Gly Gln Pro Arg Glu Pro Gln Val Cys
                355                 360                 365

Thr Leu Pro Pro Ser Arg Glu Glu Met Thr Lys Asn Gln Val Ser Leu
    370                 375                 380

Trp Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
        450                 455                 460

Gly
465

<210> SEQ ID NO 95
<211> LENGTH: 458
<212> TYPE: PRT
<213> ORGANISM: Artificial Sequence
<220> FEATURE:
<223> OTHER INFORMATION: Synthetic peptide sequence

<400> SEQUENCE: 95

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Gln Ser Gly Ala Glu
        115                 120                 125

Val Lys Lys Pro Gly Ala Ser Val Lys Val Ser Cys Lys Ala Ser Gly
    130                 135                 140

Tyr Thr Phe Thr Ser Tyr Gly Ile Ser Trp Val Arg Gln Ala Pro Gly
145                 150                 155                 160

Gln Gly Leu Glu Trp Met Gly Trp Ile Ser Ala Tyr Asn Gly Asn Thr
                165                 170                 175

Asn Tyr Ala Gln Lys Leu Gln Gly Arg Val Thr Met Thr Thr Asp Thr
            180                 185                 190

Ser Thr Ser Thr Ala Tyr Met Glu Leu Arg Ser Leu Arg Ser Asp Asp
        195                 200                 205

Thr Ala Val Tyr Tyr Cys Ala Thr Ile Asp Thr Ala Asn Ala Phe Asp
    210                 215                 220

Ile Trp Gly Gln Gly Thr Met Val Thr Val Ser Ser Gly Cys Pro Pro
```

```
            225                 230                 235                 240
    Cys Pro Ala Pro Glu Ala Ala Gly Ala Pro Ser Val Phe Leu Phe Pro
                    245                 250                 255
    Pro Lys Pro Lys Asp Thr Leu Met Ile Ser Arg Thr Pro Glu Val Thr
                260                 265                 270
    Cys Val Val Asp Val Ser His Glu Asp Pro Glu Val Lys Phe Asn
            275                 280                 285
    Trp Tyr Val Asp Gly Val Glu Val His Asn Ala Lys Thr Lys Pro Arg
            290                 295                 300
    Glu Glu Gln Tyr Asn Ser Thr Tyr Arg Val Val Ser Val Leu Thr Val
    305                 310                 315                 320
    Leu His Gln Asp Trp Leu Asn Gly Lys Glu Tyr Lys Cys Lys Val Ser
                    325                 330                 335
    Asn Lys Ala Leu Pro Ala Pro Ile Glu Lys Thr Ile Ser Lys Ala Lys
                340                 345                 350
    Gly Gln Pro Arg Glu Pro Gln Val Tyr Thr Leu Pro Pro Cys Arg Glu
                355                 360                 365
    Glu Met Thr Lys Asn Gln Val Ser Leu Ser Cys Ala Val Lys Gly Phe
            370                 375                 380
    Tyr Pro Ser Asp Ile Ala Val Glu Trp Glu Ser Asn Gly Gln Pro Glu
    385                 390                 395                 400
    Asn Asn Tyr Lys Thr Thr Pro Pro Val Leu Asp Ser Asp Gly Ser Phe
                    405                 410                 415
    Phe Leu Val Ser Lys Leu Thr Val Asp Lys Ser Arg Trp Gln Gln Gly
                420                 425                 430
    Asn Val Phe Ser Cys Ser Val Met His Glu Ala Leu His Asn His Tyr
                435                 440                 445
    Thr Gln Lys Ser Leu Ser Leu Ser Pro Gly
                450                 455

<210> SEQ ID NO 96
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 96

Asp Lys Thr His Thr Cys Pro Pro Cys Pro
1               5                   10

<210> SEQ ID NO 97
<211> LENGTH: 330
<212> TYPE: DNA
<213> ORGANISM: Artificial Sequence
<220> FEATURE:
<223> OTHER INFORMATION: Synthetic nucleotide sequence

<400> SEQUENCE: 97
cagtctgtgc tgacgcagcc gccctcagtg tctgcggccc caggacagaa ggtcaccatc      60
tcctgctctg gaagcagctc caacattggg aataattatg tatcctggta ccagcagctc     120
ccaggaacag cccccaaact cctcatttat gacaataata gcgaccctca gggattcct      180 gaccgattct ctggctccaa gtctggcacg tcagccaccc tgggcatcac cggactccag     240
actggggacg aggccgatta ttactgcgga acatgggata gcagcctgag tgctgtggta     300
ttcggcggag ggaccaagct gaccgtccta                                       330
```

<210> SEQ ID NO 98
<211> LENGTH: 354
<212> TYPE: DNA
<213> ORGANISM: Artificial Sequence
<220> FEATURE:
<223> OTHER INFORMATION: Synthetic nucleotide sequence

<400> SEQUENCE: 98

```
gaggtccagc tggtgcagtc tggagctgag gtgaagaagc ctggggcctc agtgaaggtc    60
tcctgcaagg cttctggtta cacctttacc agctacggta tcagctgggt gcgacaggcc   120
cctggacaag ggcttgagtg gatgggatgg atcagcgctt acaatggtaa cacaaactat   180
gcacagaagc tccagggcag agtcaccatg accacagaca catccacgag cacagcctac   240
atggagctga ggagcctgag atctgacgac acggccgtgt attactgtgc gactatcgat   300
acagctagtg cttttgatat ctgggggccaa gggacaatgg tcaccgtctc ttcc         354
```

<210> SEQ ID NO 99
<211> LENGTH: 330
<212> TYPE: DNA
<213> ORGANISM: Artificial Sequence
<220> FEATURE:
<223> OTHER INFORMATION: Synthetic nucleotide sequence

<400> SEQUENCE: 99

```
cagtctgtgc tgacgcagcc gccctcagtg tctgcggccc caggacagaa ggtcaccatc    60
tcctgctctg gaagcagctc caacattggg aataattatg tatcctggta ccagcagctc   120
ccaggaacag cccccaaact cctcatttat gacaataata gcgaccctc agggattcct    180 gaccgattct ctggctccaa gtctggcacg tcagccaccc tgggcatcac cggactccag   240
actggggacg aggccgatta ttactgcgga acatgggata gcagcctgag tggtgtggta   300
ttcggcggag ggaccaagct gaccgtccta                                    330
```

<210> SEQ ID NO 100
<211> LENGTH: 354
<212> TYPE: DNA
<213> ORGANISM: Artificial Sequence
<220> FEATURE:
<223> OTHER INFORMATION: Synthetic nucleotide sequence

<400> SEQUENCE: 100

```
gaggtccagc tggtgcagtc tggagctgag gtgaagaagc ctggggcctc agtgaaggtc    60
tcctgcaagg cttctggtta cacctttacc agctacggta tcagctgggt gcgacaggcc   120
cctggacaag ggcttgagtg gatgggatgg atcagcgctt acaatggtaa cacaaactat   180
gcacagaagc tccagggcag agtcaccatg accacagaca catccacgag cacagcctac   240
atggagctga ggagcctgag atctgacgac acggccgtgt attactgtgc gactatcgat   300
acagctaatg cttttggtat ctgggggccaa gggacaatgg tcaccgtctc gtcc         354
```

<210> SEQ ID NO 101
<211> LENGTH: 330
<212> TYPE: DNA
<213> ORGANISM: Artificial Sequence
<220> FEATURE:
<223> OTHER INFORMATION: Synthetic nucleotide sequence

<400> SEQUENCE: 101

```
cagtctgtgc tgacgcagcc gccctcagtg tctgcggccc caggacagaa ggtcaccatc    60
tcctgctctg gaagcagctc caacattggg aataattatg tatcctggta ccagcagctc   120
```

```
ccaggaacag cccccaaact cctcatttat gacaataata agcgaccctc agggattcct    180
gaccgattct ctggctccaa gtctggcacg tcagccaccc tgggcatcac cggactccag    240
actggggacg aggccgatta ttactgcgga acatgggata gcagcctgag ttcttatgtc    300
ttcggaactg ggaccaaggt caccgtccta                                    330

<210> SEQ ID NO 102
<211> LENGTH: 354
<212> TYPE: DNA
<213> ORGANISM: Artificial Sequence
<220> FEATURE:
<223> OTHER INFORMATION: Synthetic nucleotide sequence

<400> SEQUENCE: 102
gaggtccagc tggtgcagtc tggagctgag gtgaagaagc ctggggcctc agtgaaggtc     60
tcctgcaagg cttctggtta cacctttacc agctacggta tcagctgggt gcgacaggcc    120
cctggacaag gcttgagtg gatgggatgg atcagcgctt acaatggtaa cacaaactat     180
gcacagaagc tccagggcag agtcaccatg accacagaca catccacgag cactgcctac    240
atggagctga ggagcctgag atctgacgac acggccgtgt attactgtgc gactatcgat    300
acagctactg cttttgatat ctggggccaa gggacaatgg tcaccgtctc gtcc          354

<210> SEQ ID NO 103
<211> LENGTH: 330
<212> TYPE: DNA
<213> ORGANISM: Artificial Sequence
<220> FEATURE:
<223> OTHER INFORMATION: Synthetic nucleotide sequence

<400> SEQUENCE: 103
cagtctgtct tgacgcagcc gccctcagtg tctgcggccc caggacagaa ggtcaccatc     60
tcctgctctg gaagcagctc caacattggg aataattatg tatcctggta ccagcagctc    120
ccaggaacag cccccaaact cctcatttat gacaataata agcgaccctc agggattcct    180
gaccgattct ctggctccaa gtctggcacg tcagccaccc tgggcatcac cggactccag    240
actggggacg aggccgatta ttactgcgga acatgggata gcagcctgag tgcatatgtc    300
ttcggaactg ggaccaaggt caccgtccta                                    330

<210> SEQ ID NO 104
<211> LENGTH: 354
<212> TYPE: DNA
<213> ORGANISM: Artificial Sequence
<220> FEATURE:
<223> OTHER INFORMATION: Synthetic nucleotide sequence

<400> SEQUENCE: 104
gaggtccagc tggtgcagtc tggagctgag gtgaagaagc ctggggcctc agtgaaggtc     60
tcctgcaagg cttctggtta cacctttacc agctacggtt tcagctggat gcgacaggcc    120
cctggacaag gcttgagtg gatgggatgg atcagcgctt acaatggtaa cacaaactat     180
gcacagaagc tccagggcag agtcaccatg accacagaca catccacgag cacagcctac    240
atggagctga ggagcctgag atctgacgac acggccgtgt attactgtgc gactatcgat    300
acagctagtg cttttgatat ctggggccaa gggacaatgg tcaccgtctc gagc          354

<210> SEQ ID NO 105
<211> LENGTH: 330
<212> TYPE: DNA
```

```
<213> ORGANISM: Artificial Sequence
<220> FEATURE:
<223> OTHER INFORMATION: Synthetic nucleotide sequence

<400> SEQUENCE: 105
cagtctgtct tgacgcagcc gccctcagtg tctgcggccc caggacagaa ggtcaccatc      60
tcctgctctg gaagcagctc caacattggg aataattatg tatcctggta ccagcaactc     120
ccaggtacag cccccaaact cctcatttat gacaataata agcgaccctc agggattcct     180
gaccgattct ctggctccaa gtctggcacg tcagccaccc tgggcatcac cggactccag     240
gctggggacg aggccgatta ttactgcgga acatgggata gcagcctgag tgcttatgtc     300
ttcggaactg ggaccaaggt caccgtccta                                      330

<210> SEQ ID NO 106
<211> LENGTH: 354
<212> TYPE: DNA
<213> ORGANISM: Artificial Sequence
<220> FEATURE:
<223> OTHER INFORMATION: Synthetic nucleotide sequence

<400> SEQUENCE: 106
gaggtccagc tggtgcagtc tggagctgag gtgaagaagc ctggggcctc agtgaaggtc      60
tcctgcaagg cttctggtta cacctttacc agctacggta tcagctgggt gcgacaggcc     120
cctggacaag gcttgagtg gatgggatgg atcagcgctt acaatggtaa cacaaactat      180
gcacagaagc tccagggcag agtcaccatg accacagaca catccacgag cacagcctac     240
atggagctga ggagcctgag atctgacgac acggccgtgt attactgtgc gactatcgat     300
acagctaatg cttttgatat ctggggccaa gggacaatgg tcaccgtctc gagc            354

<210> SEQ ID NO 107
<211> LENGTH: 330
<212> TYPE: DNA
<213> ORGANISM: Artificial Sequence
<220> FEATURE:
<223> OTHER INFORMATION: Synthetic nucleotide sequence

<400> SEQUENCE: 107
cagtctgtct tgacgcagcc gccctcagtg tctgcggccc caggacagaa ggtcaccatc      60
tcctgctctg gaagcagctc caacattggg aataattatg tatcctggta ccagcagctc     120
ccaggaacag cccccaaact cctcatttat gacaataata agcgaccctc agggattcct     180
gaccgattct ctggctccaa gtctggcacg tcagccaccc tgggcatcac cggactccag     240
actggggacg aggccgatta ttactgcgga acatgggata gcagcctgag tgcttatgtc     300
ttcggaactg ggaccaaggt caccgtccta                                      330

<210> SEQ ID NO 108
<211> LENGTH: 354
<212> TYPE: DNA
<213> ORGANISM: Artificial Sequence
<220> FEATURE:
<223> OTHER INFORMATION: Synthetic nucleotide sequence

<400> SEQUENCE: 108
gaggtccagc tggtgcagtc tggagctgag gtgaagaagc ctggggcctc agtgaaggtc      60
tcctgcaagg cttctggtta cacctttacc agctacggta tcagctgggt gcgacaggcc     120
cctggacaag gcttgagtg gatgggatgg atcagcgctt acaatggtaa cacaaactat      180
gcacagaagc tccagggcag agtcaccatg accacagaca catccacgag cacagcctac     240
```

```
atggagctga ggagcctgag atctgacgac acggccgtgt attactgtgc gactatcgat    300
acagctaatg cttttgatat ctggggccaa gggacaatgg tcaccgtctc gagc          354
```

<210> SEQ ID NO 109
<211> LENGTH: 330
<212> TYPE: DNA
<213> ORGANISM: Artificial Sequence
<220> FEATURE:
<223> OTHER INFORMATION: Synthetic nucleotide sequence

<400> SEQUENCE: 109

```
cagtctgtgt tgacgcagcc gccctcagtg tctgcggccc caggacagaa ggtcaccatc    60
tcctgctctg gaagcagctc caacattggg aataattatg tatcctggta ccagcagctc   120
ccaggaacag cccccaaact cctcatttat gacaataata gcgaccctc agggattcct    180 gaccgattct ctggctccaa gtctggcacg tcagccaccc tgggcatcac cggactccag   240
actggggacg aggccgatta ttactgcgga acatgggata gcagcctgag tgctgtggta   300
ttcggcggag ggaccaagct gaccgtccta                                     330
```

<210> SEQ ID NO 110
<211> LENGTH: 354
<212> TYPE: DNA
<213> ORGANISM: Artificial Sequence
<220> FEATURE:
<223> OTHER INFORMATION: Synthetic nucleotide sequence

<400> SEQUENCE: 110

```
gaggtccagc tggtgcagtc tggagctgag gtgaagaagc ctggggcctc agtgaaggtc    60
tcctgcaagg cttctggtta cacctttacc agctacggta tcagctgggt gcgacaggcc   120
cctggacaag gcttgagtg gatgggatgg atcagcgctt acaatggtaa cacaaactat    180
gcacagaagc tccagggcag agtcaccatg accacagaca catccacgag cacagcctac   240
atggagctga ggagcctgag atctgacgac acggccgtgt attactgtgc gactatcgat    300
acagctaatg cttttgatat ctggggccaa gggacaatgg tcaccgtctc gagc          354
```

<210> SEQ ID NO 111
<211> LENGTH: 330
<212> TYPE: DNA
<213> ORGANISM: Artificial Sequence
<220> FEATURE:
<223> OTHER INFORMATION: Synthetic nucleotide sequence

<400> SEQUENCE: 111

```
cagtctgtcc tgacgcagcc gccctcagtg tctgcggccc caggacagaa ggtcaccatc    60
tcctgctctg gaagcaggtc caacattgga aataattatg tatcctggta ccagcaactc   120
ccaggaacag cccccaaact cctcatttat gacagtaata gcgaccctc agggattcct    180 gaccgattct ctggctccaa gtctggcacg tcagccaccc tgggcatcac cggactccag   240
actggggacg aggccgatta ttactgcgga acatgggata gcagcctgag ttcttgggtg    300
ttcggcggag ggaccaagct gaccgtccta                                     330
```

<210> SEQ ID NO 112
<211> LENGTH: 354
<212> TYPE: DNA
<213> ORGANISM: Artificial Sequence
<220> FEATURE:
<223> OTHER INFORMATION: Synthetic nucleotide sequence

<400> SEQUENCE: 112

```
gaggtccagc tggtgcagtc tggagctgag gtgaagaagc ctggggcctc agtgaaggtc    60
tcctgcaagg cttctggtta ccctttacc agctacggta tcagctgggt gcgacaggcc   120
cctggacaag ggcttgagtg gatgggatgg atcagcgctt acaatggtaa cacaaactat   180
gcacagaagc tccagggcag agtcaccatg accacagaca catccacgag cacagcctac   240
atggagctga ggagcctgag atctgacgac acggccgtgt attactgtgc gactatcgat   300
acagctaatg cttttgatat ctggggccaa gggacaatgg tcaccgtctc gagc          354
```

<210> SEQ ID NO 113
<211> LENGTH: 330
<212> TYPE: DNA
<213> ORGANISM: Artificial Sequence
<220> FEATURE:
<223> OTHER INFORMATION: Synthetic nucleotide sequence

<400> SEQUENCE: 113

```
cagtctgtgg tgacgcagcc gccctcagtg tctgcggccc caggacagaa ggtcaccatc    60
tcctgctctg gaagcagctc caacattggg aataattatg tatcctggta ccagcagctc   120
ccaggaacag cccccaaact cctcatttat gacaataata gcgaccctc agggattcct   180
gaccgattct ctggctccaa gtctggcacg tcagccaccc tgggcatcac cggactccag   240
actggggacg aggccgatta ttactgcgga acatgggata gcagcctgag tgcttatgtc   300
ttcggaactg ggaccaaggt caccgtccta                                    330
```

<210> SEQ ID NO 114
<211> LENGTH: 354
<212> TYPE: DNA
<213> ORGANISM: Artificial Sequence
<220> FEATURE:
<223> OTHER INFORMATION: Synthetic nucleotide sequence

<400> SEQUENCE: 114

```
gaggtccagc tggtgcagtc tggagctgag gtgaagaagc ctggggcctc agtgaaggtc    60
tcctgcaagg cttctggtta ccctttacc agctacggta tcagctgggt gcgacaggcc   120
cctggacaag ggcttgagtg gatgggatgg atcagcgctt acaatggtaa cacaaactat   180
gcacagaagc tccagggcag agtcaccatg accacagaca catccacgag cacagcctac   240
atggagctga ggagcctgag atctgacgac acggccgtgt attactgtgc gactatcgat   300
acagctaatg cttttgatat ctggggccaa gggacaatgg tcaccgtctc gagc          354
```

<210> SEQ ID NO 115
<211> LENGTH: 330
<212> TYPE: DNA
<213> ORGANISM: Artificial Sequence
<220> FEATURE:
<223> OTHER INFORMATION: Synthetic nucleotide sequence

<400> SEQUENCE: 115

```
cagtctgtgg tgacgcagcc gccctcagtg tctgcggccc caggacagaa ggtcaccatc    60
tcctgctctg gaagcagctc caacattggg aataattatg tatcctggta ccagcagctc   120
ccaggaacag cccccaaact cctcatttat gacaataata gcgaccctc agggattcct   180
gaccgattct ctggctccaa gtctggcacg tcagccaccc tgggcatcac cggactccag   240
actggggacg aggccgatta ttactgcgga acatgggata gcagcctgag tgcttgggtg   300
ttcggcggag ggaccaagct gaccgtccta                                    330
```

<210> SEQ ID NO 116
<211> LENGTH: 354
<212> TYPE: DNA
<213> ORGANISM: Artificial Sequence
<220> FEATURE:
<223> OTHER INFORMATION: Synthetic nucleotide sequence

<400> SEQUENCE: 116

| | |
|---|---|
| gaggtccagc tggtgcagtc tggagctgag gtgaagaagc ctggggcctc agtgaaggtc | 60 |
| tcctgcaagg cttctggtta cacctttacc agctacggta tcagctgggt gcgacaggcc | 120 |
| cctggacaag gcttgagtg gatgggatgg atcagcgctt acaatggtaa cacaaactat | 180 |
| gcacagaagc tccagggcag agtcaccatg accacagaca catccacgag cacagcctac | 240 |
| atggagctga ggagcctgag atctgacgac acggccgtgt attactgtgc gactattaat | 300 |
| gcgcctaata attttgatat ctggggccaa gggacaatgg tcaccgtctc gtcc | 354 |

<210> SEQ ID NO 117
<211> LENGTH: 1395
<212> TYPE: DNA
<213> ORGANISM: Artificial Sequence
<220> FEATURE:
<223> OTHER INFORMATION: Synthetic nucleotide sequence

<400> SEQUENCE: 117

| | |
|---|---|
| cagtctgtgc tgacgcagcc gccctcagtg tctgcggccc caggacagaa ggtcaccatc | 60 |
| tcctgctctg gaagcagctc aacattggg aataattatg tatcctgta ccagcagctc | 120 |
| ccaggaacag cccccaaact cctcatttat gacaataata gcgaccctc agggattcct | 180 |
| gaccgattct ctggctccaa gtctggcacg tcagccaccc tgggcatcac cggactccag | 240 |
| actggggacg aggccgatta ttactgcgga acatgggata gcagcctgag tgctgtggta | 300 |
| ttcggcggag ggaccaagct gaccgtccta ggtggcggat ccggcggcgg aggcgaggtg | 360 |
| cagctggtgg agtctggggg aggcttggtc cagcctggag ggtccctgag actctcctgt | 420 |
| gcagcctctg gattcacctt cagcacatac gctatgaatt gggtccgcca ggctccaggg | 480 |
| aaggggctgg agtgggttgg caggatcagg tccaagtaca caattatgc aacctactat | 540 |
| gccgactctg tgaagggcag attcaccatc tcaagagatg attcaaagaa ctcactgtat | 600 |
| ctgcaaatga acagcctgaa aaccgaggac acggccgtgt attactgtgt gagacacggt | 660 |
| aacttcggca attcttacgt gtcttggttt gcttattggg acaggggac actggtgact | 720 |
| gtgtcttccg gatgcccacc gtgcccagca cctgaagccg ctggggcacc gtcagtcttc | 780 |
| ctcttccccc caaaacccaa ggacaccctc atgatctccc ggacccctga ggtcacatgc | 840 |
| gtggtggtgg acgtgagcca cgaagaccct gaggtcaagt tcaactggta cgtggacggc | 900 |
| gtggaggtgc ataatgccaa gacaaagccg cggaggagc agtacaacag cacgtaccgt | 960 |
| gtggtcagcg tcctcaccgt cctgcaccag gactggctga atggcaagga gtacaagtgc | 1020 |
| aaggtctcca acaaagccct cccagccccc atcgagaaaa ccatctccaa agccaaaggg | 1080 |
| cagccccgag aaccacaggt gtgcaccctg cccccatccc gggaggagat gaccaagaac | 1140 |
| caggtcagcc tgtggtgcct ggtcaaaggc ttctatccca gcgacatcgc cgtggagtgg | 1200 |
| gagagcaatg ggcagccgga gaacaactac aagaccacgc ctcccgtgct ggactccgac | 1260 |
| ggctccttct tcctctatag caagctcacc gtggacaaga gcaggtggca gcaggggaac | 1320 |
| gtcttctcat gctccgtgat gcatgaggct ctgcacaacc actacacgca gaagagcctc | 1380 | tccctgtccc cgggt                                                      1395

<210> SEQ ID NO 118
<211> LENGTH: 1374
<212> TYPE: DNA
<213> ORGANISM: Artificial Sequence
<220> FEATURE:
<223> OTHER INFORMATION: Synthetic nucleotide sequence

<400> SEQUENCE: 118
caggctgtgg tgactcagga gccttcactg accgtgtccc caggcggaac tgtgaccctg      60
acatgcagat ccagcacagg cgcagtgacc acatctaact acgccaattg ggtgcagcag     120
aagccaggac aggcaccaag gggcctgatc ggggtacaa acaaagggc tccctggacc      180
cctgcacggt tttctggaag tctgctgggc ggaaaggccg ctctgactat taccggggca     240
caggccgagg acgaagccga ttactattgt gctctgtggt atagcaatct gtgggtgttc     300
gggggtggca caaaactgac tgtgctggga ggggtggat ccggtggagg tggcgaggtc     360
cagctggtgc agtctggagc tgaggtgaag aagcctgggg cctcagtgaa ggtctcctgc     420
aaggcttctg gttacacctt taccagctac ggtatcagct gggtgcgaca ggcccctgga     480
caagggcttg agtggatggg atggatcagc gcttacaatg gtaacacaaa ctatgcacag     540
aagctccagg gcagagtcac catgaccaca gacacatcca cgagcacagc ctacatggag     600
ctgaggagcc tgagatctga cgacacggcc gtgtattact gtgcgactat cgatacagct     660
agtgcttttg atatctgggg ccaagggaca atggtcaccg tctcttccgg atgtccaccg     720
tgcccagcac ctgaagccgc tggggcaccg tcagtcttcc tcttccccc aaaacccaag     780
gacaccctca tgatctcccg gacccctgag gtcacatgcg tggtggtgga cgtgagccac     840
gaagaccctg aggtcaagtt caactggtac gtggacggcg tggaggtgca taatgccaag     900
acaaagccgc gggaggagca gtacaacagc acgtaccgtg tggtcagcgt cctcaccgtc     960
ctgcaccagg actggctgaa tggcaaggag tacaagtgca aggtctccaa caaagccctc    1020
ccagccccca tcgagaaaac catctccaaa gccaagggc agccccgaga accacaggtg    1080
tacaccctgc cccatgccg ggaggagatg accaagaacc aggtcagcct gtcctgcgcg    1140
gtcaaaggct tctatcccag cgacatcgcc gtggagtggg agagcaatgg gcagccggag    1200
aacaactaca agaccacgcc tcccgtgctg gactccgacg gctccttctt cctcgttagc    1260
aagctcaccg tggacaagag caggtggcag caggggaacg tcttctcatg ctccgtgatg    1320
catgaggctc tgcacaacca ctacacgcag aagagcctct ccctgtcccc gggt         1374

<210> SEQ ID NO 119
<211> LENGTH: 1395
<212> TYPE: DNA
<213> ORGANISM: Artificial Sequence
<220> FEATURE:
<223> OTHER INFORMATION: Synthetic nucleotide sequence

<400> SEQUENCE: 119
cagtctgtgc tgacgcagcc gccctcagtg tctgcggccc caggacagaa ggtcaccatc      60
tcctgctctg gaagcagctc caacattggg aataattatg tatcctggta ccagcagctc     120
ccaggaacag cccccaaact cctcatttat gacaataata gcgaccctc agggattcct     180
gaccgattct ctggctccaa gtctggcacg tcagccaccc tgggcatcac cggactccag     240
actgggacg aggccgatta ttactgcgga acatggata gcagcctgag tggtgtggta     300
ttcggcggag ggaccaagct gaccgtccta ggtggcggat ccggcggcgg aggcgaggtg     360

```
cagctggtgg agtctggggg aggcttggtc cagcctggag ggtccctgag actctcctgt      420
gcagcctctg gattcacctt cagcacatac gctatgaatt gggtccgcca ggctccaggg      480
aaggggctgg agtgggttgg caggatcagg tccaagtaca acaattatgc aacctactat      540
gccgactctg tgaagggcag attcaccatc tcaagagatg attcaaagaa ctcactgtat      600
ctgcaaatga acagcctgaa aaccgaggac acggccgtgt attactgtgt gagacacggt      660
aacttcggca attcttacgt gtcttggttt gcttattggg acaggggac actggtgact       720 gtgtcttccg atgcccacc gtgcccagca cctgaagccg ctgggcacc gtcagtcttc        780 ctcttccccc caaaacccaa ggacaccctc atgatctccc ggacccctga ggtcacatgc      840
gtggtggtgg acgtgagcca cgaagaccct gaggtcaagt tcaactggta cgtggacggc      900
gtggaggtgc ataatgccaa gacaaagccg cgggaggagc agtacaacag cacgtaccgt     960
gtggtcagcg tcctcaccgt cctgcaccag gactggctga atggcaagga gtacaagtgc     1020
aaggtctcca acaaagccct cccagccccc atcgagaaaa ccatctccaa agccaaaggg     1080
cagccccgag aaccacaggt gtgcaccctg cccccatccc gggaggagat gaccaagaac     1140
caggtcagcc tgtggtgcct ggtcaaaggc ttctatccca gcgacatcgc cgtggagtgg     1200
gagagcaatg ggcagccgga gaacaactac aagaccacgc ctcccgtgct ggactccgac     1260
ggctccttct cctctatag caagctcacc gtggacaaga gcaggtggca gcaggggaac     1320
gtcttctcat gctccgtgat gcatgaggct ctgcacaacc actacacgca gaagagcctc     1380
tccctgtccc cgggt                                                       1395

<210> SEQ ID NO 120
<211> LENGTH: 1374
<212> TYPE: DNA
<213> ORGANISM: Artificial Sequence
<220> FEATURE:
<223> OTHER INFORMATION: Synthetic nucleotide sequence

<400> SEQUENCE: 120
caggctgtgg tgactcagga gccttcactg accgtgtccc caggcggaac tgtgaccctg       60
acatgcagat ccagcacagg cgcagtgacc acatctaact acgccaattg ggtgcagcag      120
aagccaggac aggcaccaag gggcctgatc gggggtacaa acaaaagggc tccctggacc      180
cctgcacggt tttctggaag tctgctgggc ggaaaggccg ctctgactat taccggggca      240
caggccgagg acgaagccga ttactattgt gctctgtggt atagcaatct gtgggtgttc      300
gggggtggca caaaactgac tgtgctggga ggggtggat ccggtggagg tggcgaggtc      360
cagctggtgc agtctggagc tgaggtgaag aagcctgggg cctcagtgaa ggtctcctgc      420
aaggcttctg gttacacctt taccagctac ggtatcagct gggtgcgaca ggcccctgga     480
caagggcttg agtggatggg atggatcagc gcttacaatg gtaacacaaa ctatgcacag     540
aagctccagg gcagagtcac catgaccaca gacacatcca cgagcacagc ctacatggag    600
ctgaggagcc tgagatctga cgacacggcc gtgtattact gtgcgactat cgatacagct      660
aatgcttttg gtatctgggg ccaagggaca atggtcaccg tctcgtccgg atgtccaccg      720
tgcccagcac ctgaagccgc tgggcaccg tcagtcttcc tcttcccccc aaaacccaag     780
gacaccctca tgatctcccg gacccctgag gtcacatgcg tggtggtgga cgtgagccac     840
gaagaccctg aggtcaagtt caactggtac gtggacggcg tggaggtgca taatgccaag     900
acaaagccgc gggaggagca gtacaacagc acgtaccgtg tggtcagcgt cctcaccgtc     960
```

```
ctgcaccagg actggctgaa tggcaaggag tacaagtgca aggtctccaa caaagccctc      1020
ccagccccca tcgagaaaac catctccaaa gccaaagggc agccccgaga accacaggtg      1080
tacaccctgc ccccatgccg ggaggagatg accaagaacc aggtcagcct gtcctgcgcg      1140
gtcaaaggct tctatcccag cgacatcgcc gtggagtggg agagcaatgg gcagccggag      1200
aacaactaca agaccacgcc tcccgtgctg gactccgacg gctccttctt cctcgttagc      1260
aagctcaccg tggacaagag caggtggcag caggggaacg tcttctcatg ctccgtgatg      1320
catgaggctc tgcacaacca ctacacgcag aagagcctct ccctgtcccc gggt           1374

<210> SEQ ID NO 121
<211> LENGTH: 1395
<212> TYPE: DNA
<213> ORGANISM: Artificial Sequence
<220> FEATURE:
<223> OTHER INFORMATION: Synthetic nucleotide sequence

<400> SEQUENCE: 121
cagtctgtgc tgacgcagcc gccctcagtg tctgcggccc caggacagaa ggtcaccatc        60
tcctgctctg gaagcagctc caacattggg aataattatg tatcctggta ccagcagctc       120
ccaggaacag ccccccaaact cctcatttat gacaataata gcgaccctc agggattcct        180 gaccgattct ctggctccaa gtctggcacg tcagccaccc tgggcatcac cggactccag       240
actggggacg aggccgatta ttactgcgga acatgggata gcagcctgag ttcttatgtc       300
ttcggaactg ggaccaaggt caccgtccta ggtggcggat ccggcggcgg aggcgaggtg       360
cagctggtgg agtctggggg aggcttggtc cagcctggag gtccctgag actctcctgt        420 gcagcctctg gattcacctt cagcacatac gctatgaatt gggtccgcca ggctccaggg       480
aaggggctgg agtgggttgg caggatcagg tccaagtaca caattatgc aacctactat        540 gccgactctg tgaagggcag attcaccatc tcaagagatg attcaaagaa ctcactgtat       600
ctgcaaatga acagcctgaa aaccgaggac acggccgtgt attactgtgt gagacacggt       660
aacttcggca attcttacgt gtcttggttt gcttattggg acaggggac actggtgact        720 gtgtcttccg gatgcccacc gtgcccagca cctgaagccg ctggggcacc gtcagtcttc       780
ctcttccccc caaaacccaa ggacaccctc atgatctccc ggacccctga ggtcacatgc       840
gtggtggtgg acgtgagcca cgaagaccct gaggtcaagt tcaactggta cgtggacggc       900
gtggaggtgc ataatgccaa gacaaagccg cgggaggagc agtacaacag cacgtaccgt       960
gtggtcagcg tcctcaccgt cctgcaccag gactggctga atggcaagga gtacaagtgc      1020
aaggtctcca caaagccct cccagccccc atcgagaaaa ccatctccaa agccaaaggg       1080
cagccccgag aaccacaggt gtgcaccctg ccccatccc gggaggagat gaccaagaac       1140
caggtcagcc tgtggtgcct ggtcaaaggc ttctatccca gcgacatcgc cgtggagtgg      1200
gagagcaatg ggcagccgga gaacaactac aagaccacgc ctcccgtgct ggactccgac      1260
ggctccttct tcctctatag caagctcacc gtggacaaga gcaggtggca gcaggggaac      1320
gtcttctcat gctccgtgat gcatgaggct ctgcacaacc actacacgca gaagagcctc      1380
tccctgtccc cgggt                                                      1395

<210> SEQ ID NO 122
<211> LENGTH: 1374
<212> TYPE: DNA
<213> ORGANISM: Artificial Sequence
<220> FEATURE:
<223> OTHER INFORMATION: Synthetic nucleotide sequence
```

<400> SEQUENCE: 122

```
caggctgtgg tgactcagga gccttcactg accgtgtccc caggcggaac tgtgaccctg      60
acatgcagat ccagcacagg cgcagtgacc acatctaact acgccaattg ggtgcagcag     120
aagccaggac aggcaccaag gggcctgatc gggggtacaa acaaaagggc tccctggacc     180
cctgcacggt tttctggaag tctgctgggc ggaaaggccg ctctgactat taccggggca     240
caggccgagg acgaagccga ttactattgt gctctgtggt atagcaatct gtgggtgttc     300
ggggtggca caaaactgac tgtgctggga ggggtggat ccggtggagg tggcgaggtc       360
cagctggtgc agtctggagc tgaggtgaag aagcctgggg cctcagtgaa ggtctcctgc     420
aaggcttctg gttacacctt taccagctac ggtatcagct gggtgcgaca ggcccctgga     480
caagggcttg agtggatggg atggatcagc gcttacaatg gtaacacaaa ctatgcacag     540
aagctccagg gcagagtcac catgaccaca gacacatcca cgagcactgc ctacatggag     600
ctgaggagcc tgagatctga cgacacggcc gtgtattact gtgcgactat cgatacagct     660
actgctttg atatctgggg ccaagggaca atggtcaccg tctcgtccgg atgtccaccg      720
tgcccagcac ctgaagccgc tggggcaccg tcagtcttcc tcttcccccc aaaacccaag     780
gacaccctca tgatctcccg gaccccctgag gtcacatgcg tggtggtgga cgtgagccac    840
gaagaccctg aggtcaagtt caactggtac gtggacggcg tggaggtgca taatgccaag    900
acaaagccgc gggaggagca gtacaacagc acgtaccgtg tggtcagcgt cctcaccgtc    960
ctgcaccagg actggctgaa tggcaaggag tacaagtgca aggtctccaa caaagccctc   1020
ccagccccca tcgagaaaac catctccaaa gccaagggc agccccgaga ccacaggtg    1080
tacaccctgc cccatgccg ggaggagatg accaagaacc aggtcagcct gtcctgcgcg    1140
gtcaaaggct tctatcccag cgacatcgcc gtggagtggg agagcaatgg gcagccggag   1200
aacaactaca agaccacgcc tcccgtgctg gactccgacg gctccttctt cctcgttagc   1260
aagctcaccg tggacaagag caggtggcag caggggaacg tcttctcatg ctccgtgatg   1320
catgaggctc tgcacaacca ctacacgcag aagagcctct ccctgtcccc gggt         1374
```

<210> SEQ ID NO 123
<211> LENGTH: 1395
<212> TYPE: DNA
<213> ORGANISM: Artificial Sequence
<220> FEATURE:
<223> OTHER INFORMATION: Synthetic nucleotide sequence

<400> SEQUENCE: 123

```
cagtctgtct tgacgcagcc gccctcagtg tctgcggccc caggacagaa ggtcaccatc      60
tcctgctctg gaagcagctc caacattggg aataattatg tatcctggta ccagcagctc     120
ccaggaacag cccccaaact cctcatttat gacaataata gcgaccctc agggattcct      180
gaccgattct ctggctccaa gtctggcacg tcagccaccc tgggcatcac cggactccag     240
actggggacg aggccgatta ttactgcgga acatgggata gcagcctgag tgcttatgtc     300
ttcggaactg ggaccaaggt caccgtccta ggtggcggat ccggcggcgg aggcgaggtg     360
cagctggtgg agtctggggg aggcttggtc agcctggag gtccctgag actctcctgt      420
gcagcctctg gattcacctt cagcacatac gctatgaatt gggtccgcca ggctccaggg    480
aaggggctgg agtgggttgg caggatcagg tccaagtaca caattatgc aacctactat     540
gccgactctg tgaagggcag attcaccatc tcaagagatg attcaaagaa ctcactgtat    600
```

```
ctgcaaatga acagcctgaa aaccgaggac acggccgtgt attactgtgt gagacacggt      660
aacttcggca attcttacgt gtcttggttt gcttattggg gacagggac actggtgact       720
gtgtcttccg gatgcccacc gtgcccagca cctgaagccg ctggggcacc gtcagtcttc      780
ctcttccccc caaaacccaa ggacaccctc atgatctccc ggacccctga ggtcacatgc      840
gtggtggtgg acgtgagcca cgaagaccct gaggtcaagt tcaactggta cgtggacggc      900
gtggaggtgc ataatgccaa gacaaagccg cgggaggagc agtacaacag cacgtaccgt      960
gtggtcagcg tcctcaccgt cctgcaccag gactggctga atggcaagga gtacaagtgc     1020
aaggtctcca acaaagccct cccagccccc atcgagaaaa ccatctccaa agccaaaggg     1080
cagccccgag aaccacaggt gtgcaccctg cccccatccc gggaggagat gaccaagaac     1140
caggtcagcc tgtggtgcct ggtcaaaggc ttctatccca gcgacatcgc cgtggagtgg     1200
gagagcaatg ggcagccgga gaacaactac aagaccacgc ctcccgtgct ggactccgac     1260
ggctccttct cctctatag caagctcacc gtggacaaga gcaggtggca gcagggaac       1320
gtcttctcat gctccgtgat gcatgaggct ctgcacaacc actacacgca gaagagcctc     1380
tccctgtccc cgggt                                                      1395
```

<210> SEQ ID NO 124
<211> LENGTH: 1374
<212> TYPE: DNA
<213> ORGANISM: Artificial Sequence
<220> FEATURE:
<223> OTHER INFORMATION: Synthetic nucleotide sequence

<400> SEQUENCE: 124

```
caggctgtgg tgactcagga gccttcactg accgtgtccc caggcggaac tgtgaccctg       60
acatgcagat ccagcacagg cgcagtgacc acatctaact acgccaattg ggtgcagcag      120
aagccaggac aggcaccaag gggcctgatc gggggtacaa acaaaagggc tccctggacc      180
cctgcacggt tttctggaag tctgctgggc ggaaaggccg ctctgactat taccggggca      240
caggccgagg acgaagccga ttactattgt gctctgtggt atagcaatct gtgggtgttc      300
gggggtggca caaaactgac tgtgctggga ggggtggat ccggtggagg tggcgaggtc       360
cagctggtgc agtctggagc tgaggtgaag aagcctgggg cctcagtgaa ggtctcctgc      420
aaggcttctg gttacacctt taccagctac ggtatcagct gggtgcgaca ggcccctgga      480
caagggcttg agtggatggg atggatcagc gcttacaatg gtaacacaaa ctatgcacag      540
aagctccagg gcagagtcac catgaccaca gacacatcca cgagcacagc ctacatggag      600
ctgaggagcc tgagatctga cgacacggcc gtgtattact gtgcgactat cgatacagct      660
aatgcttttg atatctgggg ccaagggaca atggtcaccg tctcgtccgg atgtccaccg      720
tgcccagcac ctgaagccgc tggggcaccg tcagtcttcc tcttccccc aaaacccaag       780
gacaccctca tgatctcccg gacccctgag gtcacatgcg tggtggtgga cgtgagccac      840
gaagaccctg aggtcaagtt caactggtac gtggacggcg tggaggtgca taatgccaag      900
acaaagccgc gggaggagca gtacaacagc acgtaccgtg tggtcagcgt cctcaccgtc      960
ctgcaccagg actggctgaa tggcaaggag tacaagtgca aggtctccaa caaagccctc     1020
ccagccccca tcgagaaaac catctccaaa gccaaaggc agccccgaga accacaggtg      1080
tacaccctgc ccccatgccg ggaggagatg accaagaacc aggtcagcct gtcctgcgcg     1140
gtcaaaggct tctatcccag cgacatcgcc gtggagtggg agagcaatgg gcagccggag     1200
aacaactaca agaccacgcc tcccgtgctg gactccgacg gctccttctt cctcgttagc     1260
```

```
aagctcaccg tggacaagag caggtggcag caggggaacg tcttctcatg ctccgtgatg    1320
catgaggctc tgcacaacca ctacacgcag aagagcctct ccctgtcccc gggt          1374
```

<210> SEQ ID NO 125
<211> LENGTH: 227
<212> TYPE: PRT
<213> ORGANISM: Artificial Sequence
<220> FEATURE:
<223> OTHER INFORMATION: Synthetic peptide sequence

<400> SEQUENCE: 125

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Gly Lys
225
```

<210> SEQ ID NO 126
<211> LENGTH: 681
<212> TYPE: DNA
<213> ORGANISM: Artificial Sequence
<220> FEATURE:
<223> OTHER INFORMATION: Synthetic nucleotide sequence

<400> SEQUENCE: 126

```
gacaaaactc acacatgccc accgtgccca gcacctgaag ccgcggggggc accgtcagtc    60 ttcctcttcc ccccaaaacc caaggacacc ctcatgatct cccggacccc tgaggtcaca   120
tgcgtggtgg tggacgtgag ccacgaagac cctgaggtca agttcaactg gtacgtggac   180
ggcgtggagg tgcataatgc caagacaaag ccgcgggagg agcagtacaa cagcacgtac   240
cgtgtggtca gcgtcctcac cgtcctgcac caggactggc tgaatggcaa ggagtacaag   300
```

-continued

```
tgcaaggtct ccaacaaagc cctcccagcc cccatcgaga aaaccatctc caaagccaaa    360
gggcagcccc gagaaccaca ggtgtacacc ctgcccccat cccggagga gatgaccaag     420 aaccaggtca gcctgagttg cgcagtcaaa ggcttctatc ccagcgacat cgccgtggag    480
tgggagagca atgggcagcc ggagaacaac tacaagacca cgcctcccgt gctggactcc    540
gacggctcct tcttcctcgt cagcaagctc accgtggaca agagcaggtg gcagcagggg    600
aacgtcttct catgctccgt gatgcatgag gctctgcaca accgctacac gcagaagagc    660
ctctccctgt ctccgggtaa a                                              681
```

<210> SEQ ID NO 127
<211> LENGTH: 486
<212> TYPE: PRT
<213> ORGANISM: Artificial Sequence
<220> FEATURE:
<223> OTHER INFORMATION: Synthetic peptide sequence

<400> SEQUENCE: 127

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Ala Pro Ser Ser Pro Met Glu Gln Ser Val Leu Thr
225                 230                 235                 240

Gln Pro Pro Ser Val Ser Ala Ala Pro Gly Gln Lys Val Thr Ile Ser
            245                 250                 255

Cys Ser Gly Ser Ser Ser Asn Ile Gly Asn Asn Tyr Val Ser Trp Tyr
        260                 265                 270

Gln Gln Leu Pro Gly Thr Ala Pro Lys Leu Leu Ile Tyr Asp Asn Asn
    275                 280                 285
```

```
Lys Arg Pro Ser Gly Ile Pro Asp Arg Phe Ser Gly Ser Lys Ser Gly
    290                 295                 300

Thr Ser Ala Thr Leu Gly Ile Thr Gly Leu Gln Thr Gly Asp Glu Ala
305                 310                 315                 320

Asp Tyr Tyr Cys Gly Thr Trp Asp Ser Ser Leu Ser Ala Val Val Phe
                325                 330                 335

Gly Gly Gly Thr Lys Leu Thr Val Leu Gly Gly Gly Ser Gly Gly
            340                 345                 350

Gly Gly Glu Val Gln Leu Val Glu Ser Gly Gly Gly Leu Val Gln Pro
            355                 360                 365

Gly Gly Ser Leu Arg Leu Ser Cys Ala Ala Ser Gly Phe Thr Phe Ser
    370                 375                 380

Thr Tyr Ala Met Asn Trp Val Arg Gln Ala Pro Gly Lys Gly Leu Glu
385                 390                 395                 400

Trp Val Gly Arg Ile Arg Ser Lys Tyr Asn Asn Tyr Ala Thr Tyr Tyr
                405                 410                 415

Ala Asp Ser Val Lys Gly Arg Phe Thr Ile Ser Arg Asp Asp Ser Lys
                420                 425                 430

Asn Ser Leu Tyr Leu Gln Met Asn Ser Leu Lys Thr Glu Asp Thr Ala
    435                 440                 445

Val Tyr Tyr Cys Val Arg His Gly Asn Phe Gly Asn Ser Tyr Val Ser
    450                 455                 460

Trp Phe Ala Tyr Trp Gly Gln Gly Thr Leu Val Thr Val Ser Ser Gly
465                 470                 475                 480

Val Glu Pro Lys Ser Cys
                485

<210> SEQ ID NO 128
<211> LENGTH: 1458
<212> TYPE: DNA
<213> ORGANISM: Artificial Sequence
<220> FEATURE:
<223> OTHER INFORMATION: Synthetic nucleotide sequence

<400> SEQUENCE: 128
gacaaaactc acacatgccc accgtgccca gcacctgaag ccgcgggggc accgtcagtc      60
ttcctcttcc ccccaaaacc caaggacacc ctcatgatct cccggacccc tgaggtcaca     120
tgcgtggtgg tggacgtgag ccacgaagac cctgaggtca agttcaactg gtacgtggac     180
ggcgtggagg tgcataatgc caagacaaag ccgcgggagg agcagtacaa cagcacgtac     240
cgtgtggtca gcgtcctcac cgtcctgcac caggactggc tgaatggcaa ggagtacaag     300
tgcaaggtct ccaacaaagc cctcccagcc cccatcgaga aaccatctc caaagccaaa      360 gggcagcccc gagaaccaca ggtgtacacc ctgcccccat cccgggagga gatgaccaag     420
aaccaggtca gcctgtggtg cctggtcaaa ggcttctatc ccagcgacat cgccgtggag     480
tgggagagca tgggcagcc ggagaacaac tacaagacca cgcctcccgt gctggactcc      540
gacggctcct tcttcctcta cagcaagctc accgtggaca agagcaggtg gcagcagggg     600
aacgtcttct catgctccgt gatgcatgag gctctgcaca accactacac gcagaagagc     660 ctctcctgt ctccgggtaa agccccttcc agctcccta ggaacagtc cgtcctgact         720 cagcctccct ccgtgtccgc agctcctggg cagaaggtca caatcagttg ctctgggtca     780
tcctcaaaca ttggcaacaa ttacgtgtct tggtatcagc agctgcccgg acagcccct      840 aagctgctga tctacgacaa caacaagcgg ccaagtggca ttcccgatcg gttcagcggc     900
```

```
agcaagtctg gcaccagcgc cacactgggc atcactgggc tgcagaccgg ggacgaggct    960
gattactatt gcggaacctg ggactcttca ctgtctgccg tcgtcttcgg aggggggaacc   1020 aaactgaccg tgctgggtgg aggcggatcc ggcggcggag gcgaggtgca gctggtggag   1080
tctgggggag gcttggtcca gcctggaggg tccctgagac tctcctgtgc agcctctgga   1140
ttcaccttca gcacatacgc tatgaattgg gtccgccagg ctccagggaa ggggctggag   1200
tgggttggaa ggatcaggtc caagtacaac aattatgcaa cctactatgc cgactctgtg   1260
aagggtagat tcaccatctc aagagatgat tcaaagaact cactgtatct gcaaatgaac   1320
agcctgaaaa ccgaggacac ggccgtgtat tactgtgtga cacacggtaa cttcggcaat   1380
tcttacgtgt cttggtttgc ttattgggga caggggacac tggtgactgt gtcttccgga   1440
gttgagccca aatcttgt                                                 1458
```

<210> SEQ ID NO 129
<211> LENGTH: 243
<212> TYPE: PRT
<213> ORGANISM: Artificial Sequence
<220> FEATURE:
<223> OTHER INFORMATION: Synthetic peptide sequence

<400> SEQUENCE: 129

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Gln Ser Gly Ala Glu
        115                 120                 125

Val Lys Lys Pro Gly Ala Ser Val Lys Val Ser Cys Lys Ala Ser Gly
    130                 135                 140

Tyr Thr Phe Thr Ser Tyr Gly Ile Ser Trp Val Arg Gln Ala Pro Gly
145                 150                 155                 160

Gln Gly Leu Glu Trp Met Gly Trp Ile Ser Ala Tyr Asn Gly Asn Thr
                165                 170                 175

Asn Tyr Ala Gln Lys Leu Gln Gly Arg Val Thr Met Thr Thr Asp Thr
            180                 185                 190

Ser Thr Ser Thr Ala Tyr Met Glu Leu Arg Ser Leu Arg Ser Asp Asp
        195                 200                 205

Thr Ala Val Tyr Tyr Cys Ala Thr Ile Asp Thr Ala Ser Ala Phe Asp
    210                 215                 220

Ile Trp Gly Gln Gly Thr Met Val Thr Val Ser Ser Gly Phe Asn Arg
225                 230                 235                 240

Gly Glu Cys
```

<210> SEQ ID NO 130

<211> LENGTH: 729
<212> TYPE: DNA
<213> ORGANISM: Artificial Sequence
<220> FEATURE:
<223> OTHER INFORMATION: Synthetic nucleotide sequence

<400> SEQUENCE: 130

```
caggctgtgg tgactcagga gccttcactg accgtgtccc caggcggaac tgtgaccctg      60
acatgcagat ccagcacagg cgcagtgacc acatctaact acgccaattg ggtgcagcag     120
aagccaggac aggcaccaag gggcctgatc ggggtacaa acaaaagggc tccctggacc     180
cctgcacggt tttctggaag tctgctgggc ggaaaggccg ctctgactat taccggggca     240
caggccgagg acgaagccga ttactattgt gctctgtggt atagcaatct gtgggtgttc     300
gggggtggca caaaactgac tgtgctggga ggggtggat ccggcggagg tggagaagtc      360
cagctggtgc agagtggggc agaagtcaag aaacccggcg catcagtgaa agtctcatgt     420
aaagcatcag gctataacctt tacatcatac ggaatcagct gggtgaggca ggctccagga     480
cagggactgg agtggatggg atggatttct gcatacaacg gcaatacaaa ctatgcccag     540
aagctgcagg gccgggtgac tatgaccaca gacactagca cctccacagc ctatatggaa     600
ctgcggtctc tgagaagtga cgatactgcc gtctactatt gcgctaccat tgataccgct     660
tcagccttcg acatttgggg gcaggggact atggtgacag tgagctccgg attcaacagg     720
ggagagtgt                                                             729
```

<210> SEQ ID NO 131
<211> LENGTH: 486
<212> TYPE: PRT
<213> ORGANISM: Artificial Sequence
<220> FEATURE:
<223> OTHER INFORMATION: Synthetic peptide sequence

<400> SEQUENCE: 131

```
Asp Lys Thr His Thr Cys Pro Pro Cys Pro Ala Pro Glu Ala Ala Gly
  1               5                  10                  15

Ala Pro Ser Val Phe Leu Phe Pro Pro Lys Pro Lys Asp Thr Leu Met
                 20                  25                  30

Ile Ser Arg Thr Pro Glu Val Thr Cys Val Val Val Asp Val Ser His
             35                  40                  45

Glu Asp Pro Glu Val Lys Phe Asn Trp Tyr Val Asp Gly Val Glu Val
         50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190
```

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys Ala Pro Ser Ser Pro Met Glu Gln Ser Val Leu Thr
225                 230                 235                 240

Gln Pro Pro Ser Val Ser Ala Ala Pro Gly Gln Lys Val Thr Ile Ser
                245                 250                 255

Cys Ser Gly Ser Ser Ser Asn Ile Gly Asn Asn Tyr Val Ser Trp Tyr
            260                 265                 270

Gln Gln Leu Pro Gly Thr Ala Pro Lys Leu Leu Ile Tyr Asp Asn Asn
        275                 280                 285

Lys Arg Pro Ser Gly Ile Pro Asp Arg Phe Ser Gly Ser Lys Ser Gly
290                 295                 300

Thr Ser Ala Thr Leu Gly Ile Thr Gly Leu Gln Thr Gly Asp Glu Ala
305                 310                 315                 320

Asp Tyr Tyr Cys Gly Thr Trp Asp Ser Ser Leu Ser Gly Val Val Phe
                325                 330                 335

Gly Gly Gly Thr Lys Leu Thr Val Leu Gly Gly Gly Ser Gly Gly
            340                 345                 350

Gly Gly Glu Val Gln Leu Val Glu Ser Gly Gly Leu Val Gln Pro
        355                 360                 365

Gly Gly Ser Leu Arg Leu Ser Cys Ala Ala Ser Gly Phe Thr Phe Ser
        370                 375                 380

Thr Tyr Ala Met Asn Trp Val Arg Gln Ala Pro Gly Lys Gly Leu Glu
385                 390                 395                 400

Trp Val Gly Arg Ile Arg Ser Lys Tyr Asn Asn Tyr Ala Thr Tyr Tyr
                405                 410                 415

Ala Asp Ser Val Lys Gly Arg Phe Thr Ile Ser Arg Asp Asp Ser Lys
            420                 425                 430

Asn Ser Leu Tyr Leu Gln Met Asn Ser Leu Lys Thr Glu Asp Thr Ala
        435                 440                 445

Val Tyr Tyr Cys Val Arg His Gly Asn Phe Gly Asn Ser Tyr Val Ser
        450                 455                 460

Trp Phe Ala Tyr Trp Gly Gln Gly Thr Leu Val Thr Val Ser Ser Gly
465                 470                 475                 480

Val Glu Pro Lys Ser Cys
                485

<210> SEQ ID NO 132
<211> LENGTH: 1458
<212> TYPE: DNA
<213> ORGANISM: Artificial Sequence
<220> FEATURE:
<223> OTHER INFORMATION: Synthetic nucleotide sequence

<400> SEQUENCE: 132
gacaaaactc acacatgccc accgtgccca gcacctgaag ccgcgggggc accgtcagtc      60
ttcctcttcc ccccaaaacc caaggacacc ctcatgatct cccggacccc tgaggtcaca     120
tgcgtggtgg tggacgtgag ccacgaagac cctgaggtca agttcaactg gtacgtggac     180
ggcgtggagg tgcataatgc caagacaaag ccgcgggagg agcagtacaa cagcacgtac     240
cgtgtggtca gcgtcctcac cgtcctgcac caggactggc tgaatggcaa ggagtacaag     300
tgcaaggtct ccaacaaagc cctcccagcc cccatcgaga aaaccatctc caaagccaaa     360

```
gggcagcccc gagaaccaca ggtgtacacc ctgcccccat cccgggagga gatgaccaag    420
aaccaggtca gcctgtggtg cctggtcaaa ggcttctatc ccagcgacat cgccgtggag    480
tgggagagca atgggcagcc ggagaacaac tacaagacca cgcctcccgt gctggactcc    540
gacggctcct tcttcctcta cagcaagctc accgtggaca agagcaggtg gcagcagggg    600
aacgtcttct catgctccgt gatgcatgag gctctgcaca accactacac gcagaagagc    660
ctctcccgtg ctccgggtaa agccccttcc agctcccta tggaacagtc cgtcctgact    720
cagcctccct ccgtgtccgc agctcctggg cagaaggtca caatcagttg ctctgggtca    780
tcctcaaaca ttggcaacaa ttacgtgtct tggtatcagc agctgcccgg acagccccct    840
aagctgctga tctacgacaa caacaagcgg ccaagtggca ttcccgatcg gttcagcggc    900
agcaagtctg gcaccagcgc cacactgggc atcactgggc tgcagaccgg ggacgaggct    960
gattactatt gcggaaacctg ggactcttca ctgtctggcg tcgtcttcgg agggggaacc    1020
aaactgaccg tgctgggtgg aggcggatcc ggcggcggag gcgaggtgca gctggtggag    1080
tctgggggag gcttggtcca gcctggaggg tccctgagac tctcctgtgc agcctctgga    1140
ttcaccttca gcacatacgc tatgaattgg gtccgccagg ctccagggaa ggggctggag    1200
tgggttggaa ggatcaggtc caagtacaac aattatgcaa cctactatgc cgactctgtg    1260
aagggtagat tcaccatctc aagagatgat tcaaagaact cactgtatct gcaaatgaac    1320
agcctgaaaa ccgaggacac ggccgtgtat tactgtgtga gacacggtaa cttcggcaat    1380
tcttacgtgt cttggtttgc ttattgggga caggggacac tggtgactgt gtcttccgga    1440
gttgagccca aatcttgt    1458
```

<210> SEQ ID NO 133
<211> LENGTH: 243
<212> TYPE: PRT
<213> ORGANISM: Artificial Sequence
<220> FEATURE:
<223> OTHER INFORMATION: Synthetic peptide sequence

<400> SEQUENCE: 133

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Gln Ser Gly Ala Glu
        115                 120                 125

Val Lys Lys Pro Gly Ala Ser Val Lys Val Ser Cys Lys Ala Ser Gly
    130                 135                 140

Tyr Thr Phe Thr Ser Tyr Gly Ile Ser Trp Val Arg Gln Ala Pro Gly
145                 150                 155                 160
```

Gln Gly Leu Glu Trp Met Gly Trp Ile Ser Ala Tyr Asn Gly Asn Thr
                165                 170                 175

Asn Tyr Ala Gln Lys Leu Gln Gly Arg Val Thr Met Thr Thr Asp Thr
            180                 185                 190

Ser Thr Ser Thr Ala Tyr Met Glu Leu Arg Ser Leu Arg Ser Asp Asp
        195                 200                 205

Thr Ala Val Tyr Tyr Cys Ala Thr Ile Asp Thr Ala Asn Ala Phe Gly
    210                 215                 220

Ile Trp Gly Gln Gly Thr Met Val Thr Val Ser Ser Gly Phe Asn Arg
225                 230                 235                 240

Gly Glu Cys

<210> SEQ ID NO 134
<211> LENGTH: 729
<212> TYPE: DNA
<213> ORGANISM: Artificial Sequence
<220> FEATURE:
<223> OTHER INFORMATION: Synthetic nucleotide sequence

<400> SEQUENCE: 134
caggctgtgg tgactcagga gccttcactg accgtgtccc caggcggaac tgtgaccctg      60
acatgcagat ccagcacagg cgcagtgacc acatctaact acgccaattg ggtgcagcag     120
aagccaggac aggcaccaag gggcctgatc gggggtacaa acaaaagggc tccctggacc     180
cctgcacggt tttctggaag tctgctgggc ggaaaggccg ctctgactat accggggca     240 caggccgagg acgaagccga ttactattgt gctctgtggt atagcaatct gtgggtgttc     300
gggggtggca caaactgac tgtgctggga ggggtggat ccggcggagg tggagaagtc      360
cagctggtgc agagtggggc agaagtcaag aaacccggcg catcagtgaa agtctcatgt     420
aaagcatcag gctatacctt tacatcatac ggaatcagct gggtgaggca ggctccagga     480
cagggactgg agtggatggg atggattct gcatacaacg gcaatacaaa ctatgcccag     540
aagctgcagg gccgggtgac tatgaccaca gacactagca cctccacagc ctatatggaa     600
ctgcggtctc tgagaagtga cgatactgcc gtctactatt gcgctaccat tgataccgct     660
aacgccttcg gcatttgggg gcaggggact atggtgacag tgagctccgg attcaacagg     720
ggagagtgt                                                              729

<210> SEQ ID NO 135
<211> LENGTH: 486
<212> TYPE: PRT
<213> ORGANISM: Artificial Sequence
<220> FEATURE:
<223> OTHER INFORMATION: Synthetic peptide sequence

<400> SEQUENCE: 135

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly 85                  90                  95
Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
        130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Ala Pro Ser Ser Pro Met Glu Gln Ser Val Leu Thr
225                 230                 235                 240

Gln Pro Pro Ser Val Ser Ala Ala Pro Gly Gln Lys Val Thr Ile Ser
                245                 250                 255

Cys Ser Gly Ser Ser Asn Ile Gly Asn Asn Tyr Val Ser Trp Tyr
            260                 265                 270

Gln Gln Leu Pro Gly Thr Ala Pro Lys Leu Leu Ile Tyr Asp Asn Asn
        275                 280                 285

Lys Arg Pro Ser Gly Ile Pro Asp Arg Phe Ser Gly Ser Lys Ser Gly
    290                 295                 300

Thr Ser Ala Thr Leu Gly Ile Thr Gly Leu Gln Thr Gly Asp Glu Ala
305                 310                 315                 320

Asp Tyr Tyr Cys Gly Thr Trp Asp Ser Ser Leu Ser Ser Tyr Val Phe
                325                 330                 335

Gly Thr Gly Thr Lys Val Thr Val Leu Gly Gly Gly Ser Gly Gly
            340                 345                 350

Gly Gly Glu Val Gln Leu Val Glu Ser Gly Gly Gly Leu Val Gln Pro
        355                 360                 365

Gly Gly Ser Leu Arg Leu Ser Cys Ala Ala Ser Gly Phe Thr Phe Ser
    370                 375                 380

Thr Tyr Ala Met Asn Trp Val Arg Gln Ala Pro Gly Lys Gly Leu Glu
385                 390                 395                 400

Trp Val Gly Arg Ile Arg Ser Lys Tyr Asn Asn Tyr Ala Thr Tyr Tyr
                405                 410                 415

Ala Asp Ser Val Lys Gly Arg Phe Thr Ile Ser Arg Asp Asp Ser Lys
            420                 425                 430

Asn Ser Leu Tyr Leu Gln Met Asn Ser Leu Lys Thr Glu Asp Thr Ala
        435                 440                 445

Val Tyr Tyr Cys Val Arg His Gly Asn Phe Gly Asn Ser Tyr Val Ser
    450                 455                 460

Trp Phe Ala Tyr Trp Gly Gln Gly Thr Leu Val Thr Val Ser Ser Gly
465                 470                 475                 480

Val Glu Pro Lys Ser Cys
                485

<210> SEQ ID NO 136

<211> LENGTH: 1458
<212> TYPE: DNA
<213> ORGANISM: Artificial Sequence
<220> FEATURE:
<223> OTHER INFORMATION: Synthetic nucleotide sequence

<400> SEQUENCE: 136

```
gacaaaactc acacatgccc accgtgccca gcacctgaag ccgcgggggc accgtcagtc    60
ttcctcttcc ccccaaaacc caaggacacc ctcatgatct cccggacccc tgaggtcaca   120
tgcgtggtgg tggacgtgag ccacgaagac cctgaggtca agttcaactg gtacgtggac   180
ggcgtggagg tgcataatgc caagacaaag ccgcgggagg agcagtacaa cagcacgtac   240
cgtgtggtca gcgtcctcac cgtcctgcac caggactggc tgaatggcaa ggagtacaag   300
tgcaaggtct ccaacaaagc cctcccagcc cccatcgaga aaaccatctc caaagccaaa   360
gggcagcccc gagaaccaca ggtgtacacc ctgcccccat cccgggagga gatgaccaag   420
aaccaggtca gcctgtggtg cctggtcaaa ggcttctatc ccagcgacat cgccgtggag   480
tgggagagca atgggcagcc ggagaacaac tacaagacca cgcctcccgt gctggactcc   540
gacggctcct tcttcctcta cagcaagctc accgtggaca agagcaggtg gcagcagggg   600
aacgtcttct catgctccgt gatgcatgag gctctgcaca accactacac gcagaagagc   660
ctctccctgt ctccgggtaa agccccttcc agctccccta tggaacagtc cgtcctgact   720
cagcctccct ccgtgtccgc agctcctggg cagaaggtca acatcagttg ctctgggtca   780
tcctcaaaca ttggcaacaa ttacgtgtct tggtatcagc agctgcccgg acagcccct   840
aagctgctga tctacgacaa caacaagcgg ccaagtggca ttcccgatcg gttcagcggc   900
agcaagtctg gcaccagcgc cacactgggc atcactgggc tgcagaccgg ggacgaggct   960
gattactatt gcgcaacctg ggactcttca ctgtcttcct acgtcttcgg aacgggaacc  1020
aaagtgaccg tgctgggtgg aggcggatcc ggcggcggag gcgaggtgca gctggtggag  1080
tctgggggag gcttggtcca gcctggaggg tccctgagac tctcctgtgc agcctctgga  1140
ttcaccttca gcacatacgc tatgaattgg gtccgccagg ctccagggaa ggggctggag  1200
tgggttggaa ggatcaggtc caagtacaac aattatgcaa cctactatgc cgactctgtg  1260
aagggtagat tcaccatctc aagagatgat tcaaagaact cactgtatct gcaaatgaac  1320
agcctgaaaa ccgaggacac ggccgtgtat tactgtgtga cacacggtaa cttcggcaat  1380
tcttacgtgt cttggtttgc ttattgggga caggggacac tggtgactgt gtcttccgga  1440
gttgagccca aatcttgt                                                1458
```

<210> SEQ ID NO 137
<211> LENGTH: 243
<212> TYPE: PRT
<213> ORGANISM: Artificial Sequence
<220> FEATURE:
<223> OTHER INFORMATION: Synthetic peptide sequence

<400> SEQUENCE: 137

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Gln Ser Gly Ala Glu
        115                 120                 125

Val Lys Lys Pro Gly Ala Ser Val Lys Val Ser Cys Lys Ala Ser Gly
130                 135                 140

Tyr Thr Phe Thr Ser Tyr Gly Ile Ser Trp Val Arg Gln Ala Pro Gly
145                 150                 155                 160

Gln Gly Leu Glu Trp Met Gly Trp Ile Ser Ala Tyr Asn Gly Asn Thr
                165                 170                 175

Asn Tyr Ala Gln Lys Leu Gln Gly Arg Val Thr Met Thr Thr Asp Thr
            180                 185                 190

Ser Thr Ser Thr Ala Tyr Met Glu Leu Arg Ser Leu Arg Ser Asp Asp
        195                 200                 205

Thr Ala Val Tyr Tyr Cys Ala Thr Ile Asp Thr Ala Thr Ala Phe Asp
    210                 215                 220

Ile Trp Gly Gln Gly Thr Met Val Thr Val Ser Ser Gly Phe Asn Arg
225                 230                 235                 240

Gly Glu Cys

<210> SEQ ID NO 138
<211> LENGTH: 729
<212> TYPE: DNA
<213> ORGANISM: Artificial Sequence
<220> FEATURE:
<223> OTHER INFORMATION: Synthetic nucleotide sequence

<400> SEQUENCE: 138
caggctgtgg tgactcagga gccttcactg accgtgtccc caggcggaac tgtgaccctg    60
acatgcagat ccagcacagg cgcagtgacc acatctaact acgccaattg ggtgcagcag   120
aagccaggac aggcaccaag gggcctgatc ggggtacaa acaaaagggc tccctggacc    180
cctgcacggt tttctggaag tctgctgggc ggaaaggccg ctctgactat accggggca    240 caggccgagg acgaagccga ttactattgt gctctgtggt atagcaatct gtgggtgttc    300 ggggtggca caaaactgac tgtgctggga ggggtggat ccggcggagg tggagaagtc     360
cagctggtgc agagtggggc agaagtcaag aaacccggcg catcagtgaa agtctcatgt   420
aaagcatcag gctataccct tacatcatac ggaatcagct gggtgaggca ggctccagga   480
cagggactgg agtggatggg atggatttct gcatacaacg gcaatacaaa ctatgcccag   540
aagctgcagg gccgggtgac tatgaccaca gacactagca cctccacagc ctatatggaa   600
ctgcggtctc tgagaagtga cgatactgcc gtctactatt gcgctaccat tgataccgct   660
acagccttcg acatttgggg gcaggggact atggtgacag tgagctccgg attcaacagg   720
ggagagtgt                                                            729

<210> SEQ ID NO 139
<211> LENGTH: 486
<212> TYPE: PRT
<213> ORGANISM: Artificial Sequence
<220> FEATURE:
<223> OTHER INFORMATION: Synthetic peptide sequence

<400> SEQUENCE: 139

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Ala Pro Ser Ser Pro Met Glu Gln Ser Val Leu Thr
225                 230                 235                 240

Gln Pro Pro Ser Val Ser Ala Ala Pro Gly Gln Lys Val Thr Ile Ser
                245                 250                 255

Cys Ser Gly Ser Ser Ser Asn Ile Gly Asn Asn Tyr Val Ser Trp Tyr
            260                 265                 270

Gln Gln Leu Pro Gly Thr Ala Pro Lys Leu Leu Ile Tyr Asp Asn Asn
        275                 280                 285

Lys Arg Pro Ser Gly Ile Pro Asp Arg Phe Ser Gly Ser Lys Ser Gly
    290                 295                 300

Thr Ser Ala Thr Leu Gly Ile Thr Gly Leu Gln Thr Gly Asp Glu Ala
305                 310                 315                 320

Asp Tyr Tyr Cys Gly Thr Trp Asp Ser Ser Leu Ser Ala Tyr Val Phe
                325                 330                 335

Gly Thr Gly Thr Lys Val Thr Val Leu Gly Gly Gly Ser Gly Gly
            340                 345                 350

Gly Gly Glu Val Gln Leu Val Glu Ser Gly Gly Gly Leu Val Gln Pro
        355                 360                 365

Gly Gly Ser Leu Arg Leu Ser Cys Ala Ala Ser Gly Phe Thr Phe Ser
    370                 375                 380

Thr Tyr Ala Met Asn Trp Val Arg Gln Ala Pro Gly Lys Gly Leu Glu
385                 390                 395                 400

Trp Val Gly Arg Ile Arg Ser Lys Tyr Asn Asn Tyr Ala Thr Tyr Tyr
```

```
                   405                 410                 415
Ala Asp Ser Val Lys Gly Arg Phe Thr Ile Ser Arg Asp Asp Ser Lys
            420                 425                 430

Asn Ser Leu Tyr Leu Gln Met Asn Ser Leu Lys Thr Glu Asp Thr Ala
            435                 440                 445

Val Tyr Tyr Cys Val Arg His Gly Asn Phe Gly Asn Ser Tyr Val Ser
    450                 455                 460

Trp Phe Ala Tyr Trp Gly Gln Gly Thr Leu Val Thr Val Ser Ser Gly
465                 470                 475                 480

Val Glu Pro Lys Ser Cys
                485

<210> SEQ ID NO 140
<211> LENGTH: 1458
<212> TYPE: DNA
<213> ORGANISM: Artificial Sequence
<220> FEATURE:
<223> OTHER INFORMATION: Synthetic nucleotide sequence

<400> SEQUENCE: 140
```

| | | | | | |
|---|---|---|---|---|---|
| gacaaaactc | acacatgccc | accgtgccca | gcacctgaag | ccgcgggggc | accgtcagtc | 60 |
| ttcctcttcc | ccccaaaacc | caaggacacc | ctcatgatct | cccggacccc | tgaggtcaca | 120 |
| tgcgtggtgg | tggacgtgag | ccacgaagac | cctgaggtca | agttcaactg | gtacgtggac | 180 |
| ggcgtggagg | tgcataatgc | caagacaaag | ccgcgggagg | agcagtacaa | cagcacgtac | 240 |
| cgtgtggtca | gcgtcctcac | cgtcctgcac | caggactggc | tgaatggcaa | ggagtacaag | 300 |
| tgcaaggtct | ccaacaaagc | cctcccagcc | cccatcgaga | aaaccatctc | caaagccaaa | 360 |
| gggcagcccc | gagaaccaca | ggtgtacacc | ctgcccccat | cccgggagga | gatgaccaag | 420 |
| aaccaggtca | gcctgtggtg | cctggtcaaa | ggcttctatc | ccagcgacat | cgccgtggag | 480 |
| tgggagagca | atgggcagcc | ggagaacaac | tacaagacca | cgcctcccgt | gctggactcc | 540 |
| gacggctcct | tcttcctcta | cagcaagctc | accgtggaca | agagcaggtg | gcagcagggg | 600 |
| aacgtcttct | catgctccgt | gatgcatgag | gctctgcaca | accactacac | gcagaagagc | 660 |
| ctctcccctgt | ctccgggtaa | agcccctttcc | agctccccta | tggaacagtc | cgtcctgact | 720 |
| cagcctccct | ccgtgtccgc | agctcctggg | cagaaggtca | caatcagttg | ctctgggtca | 780 |
| tcctcaaaca | ttggcaacaa | ttacgtgtct | tggtatcagc | agctgcccgg | acagccccct | 840 |
| aagctgctga | tctacgacaa | caacaagcgg | ccaagtggca | ttcccgatcg | gttcagcggc | 900 |
| agcaagtctg | gcaccagcgc | cacactgggc | atcactgggc | tgcagaccgg | ggacgaggct | 960 |
| gattactatt | gcggaacctg | ggactcttca | ctgtctgcct | acgtcttcgg | aacgggaacc | 1020 |
| aaagtgaccg | tgctgggtgg | aggcggatcc | ggcggcggag | gcgaggtgca | gctggtggag | 1080 |
| tctgggggag | gcttggtcca | gcctggaggg | tccctgagac | tctcctgtgc | agcctctgga | 1140 |
| ttcaccttca | gcatatacgc | tatgaattgg | gtccgccagg | ctccagggaa | ggggctggag | 1200 |
| tgggttggaa | ggatcaggtc | caagtacaac | aattatgcaa | cctactatgc | cgactctgtg | 1260 |
| aagggtagat | tcaccatctc | aagagatgat | tcaaagaact | cactgtatct | gcaaatgaac | 1320 |
| agcctgaaaa | ccgaggacac | ggccgtgtat | tactgtgtga | gacacggtaa | cttcggcaat | 1380 |
| tcttacgtgt | cttggtttgc | ttattgggga | caggggacac | tggtgactgt | gtcttccgga | 1440 |
| gttgagccca | aatcttgt | | | | | 1458 |

```
<210> SEQ ID NO 141
```

<211> LENGTH: 243
<212> TYPE: PRT
<213> ORGANISM: Artificial Sequence
<220> FEATURE:
<223> OTHER INFORMATION: Synthetic peptide sequence

<400> SEQUENCE: 141

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Gln Ser Gly Ala Glu
        115                 120                 125

Val Lys Lys Pro Gly Ala Ser Val Lys Val Ser Cys Lys Ala Ser Gly
    130                 135                 140

Tyr Thr Phe Thr Ser Tyr Gly Ile Ser Trp Val Arg Gln Ala Pro Gly
145                 150                 155                 160

Gln Gly Leu Glu Trp Met Gly Trp Ile Ser Ala Tyr Asn Gly Asn Thr
                165                 170                 175

Asn Tyr Ala Gln Lys Leu Gln Gly Arg Val Thr Met Thr Thr Asp Thr
            180                 185                 190

Ser Thr Ser Thr Ala Tyr Met Glu Leu Arg Ser Leu Arg Ser Asp Asp
        195                 200                 205

Thr Ala Val Tyr Tyr Cys Ala Thr Ile Asp Thr Ala Asn Ala Phe Asp
    210                 215                 220

Ile Trp Gly Gln Gly Thr Met Val Thr Val Ser Ser Gly Phe Asn Arg
225                 230                 235                 240

Gly Glu Cys
```

<210> SEQ ID NO 142
<211> LENGTH: 729
<212> TYPE: DNA
<213> ORGANISM: Artificial Sequence
<220> FEATURE:
<223> OTHER INFORMATION: Synthetic nucleotide sequence

<400> SEQUENCE: 142

```
caggctgtgg tgactcagga gccttcactg accgtgtccc caggcggaac tgtgaccctg      60
acatgcagat ccagcacagg cgcagtgacc acatctaact acgccaattg ggtgcagcag     120
aagccaggac aggcaccaag gggcctgatc gggggtacaa acaaaagggc tccctggacc     180
cctgcacggt tttctggaag tctgctgggc ggaaaggccg ctctgactat taccggggca     240
caggccgagg acgaagccga ttactattgt gctctgtggt atagcaatct gtgggtgttc     300
gggggtggca aaaactgac tgtgctggga ggggtggat ccggcggagg tggagaagtc      360
cagctggtgc agagtggggc agaagtcaag aaacccggcg catcagtgaa agtctcatgt     420
```

```
aaagcatcag gctatacctt tacatcatac ggaatcagct gggtgaggca ggctccagga    480
cagggactgg agtggatggg atggatttct gcatacaacg gcaatacaaa ctatgcccag    540
aagctgcagg gccgggtgac tatgaccaca gacactgcac cctccacagc ctatatggaa    600
ctgcggtctc tgagaagtga cgatactgcc gtctactatt gcgctaccat tgataccgct    660
aacgccttcg acatttgggg gcaggggact atggtgacag tgagctccgg attcaacagg    720
ggagagtgt                                                            729
```

```
<210> SEQ ID NO 143
<211> LENGTH: 478
<212> TYPE: PRT
<213> ORGANISM: Artificial Sequence
<220> FEATURE:
<223> OTHER INFORMATION: Synthetic peptide sequence

<400> SEQUENCE: 143

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu Gly Gly
            100                 105                 110

Gly Gly Ser Gly Gly Gly Gly Glu Val Gln Leu Val Glu Ser Gly Gly
        115                 120                 125

Gly Leu Val Gln Pro Gly Gly Ser Leu Arg Leu Ser Cys Ala Ala Ser
    130                 135                 140

Gly Phe Thr Phe Ser Thr Tyr Ala Met Asn Trp Val Arg Gln Ala Pro
145                 150                 155                 160

Gly Lys Gly Leu Glu Trp Val Gly Arg Ile Arg Ser Lys Tyr Asn Asn
                165                 170                 175

Tyr Ala Thr Tyr Tyr Ala Asp Ser Val Lys Gly Arg Phe Thr Ile Ser
            180                 185                 190

Arg Asp Asp Ser Lys Asn Ser Leu Tyr Leu Gln Met Asn Ser Leu Lys
        195                 200                 205

Thr Glu Asp Thr Ala Val Tyr Tyr Cys Val Arg His Gly Asn Phe Gly
    210                 215                 220

Asn Ser Tyr Val Ser Trp Phe Ala Tyr Trp Gly Gln Gly Thr Leu Val
225                 230                 235                 240

Thr Val Ser Ser Gly Val Glu Pro Lys Ser Cys Asp Lys Thr His Thr
                245                 250                 255

Cys Pro Pro Cys Pro Ala Pro Glu Ala Ala Gly Ala Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300
```

```
Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
            325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
        355                 360                 365

Lys Ala Lys Gly Gln Pro Arg Glu Pro Gln Val Tyr Thr Leu Pro Pro
370                 375                 380

Ser Arg Glu Glu Met Thr Lys Asn Gln Val Ser Leu Trp Cys Leu Val
385                 390                 395                 400

Lys Gly Phe Tyr Pro Ser Asp Ile Ala Val Glu Trp Glu Ser Asn Gly
            405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
450                 455                 460

Asn His Tyr Thr Gln Lys Ser Leu Ser Leu Ser Pro Gly Lys
465                 470                 475

<210> SEQ ID NO 144
<211> LENGTH: 1434
<212> TYPE: DNA
<213> ORGANISM: Artificial Sequence
<220> FEATURE:
<223> OTHER INFORMATION: Synthetic nucleotide sequence

<400> SEQUENCE: 144
cagtccgtcc tgactcagcc tccctccgtg tccgcagctc ctgggcagaa ggtcacaatc      60
agttgctctg gtcatcctc aaacattggc aacaattacg tgtcttggta tcagcagctg     120
cccgggacag cccctaagct gctgatctac gacaacaaca gcggccaag tggcattccc      180 gatcggttca gcggcagcaa gtctggcacc agcgccacac tgggcatcac tgggctgcag     240
accggggacg aggctgatta ctattgcgga acctgggact cttcactgtc tgccgtcgtc     300
ttcggagggg gaaccaaact gaccgtgctg ggtggaggcg gatccggcgg cggaggcgag     360
gtgcagctgg tggagtctgg gggaggcttg gtccagcctg gagggtccct gagactctcc     420
tgtgcagcct ctggattcac cttcagcaca tacgctatga attgggtccg ccaggctcca     480
gggaaggggc tggagtgggt tggaaggatc aggtccaagt acaacaatta tgcaacctac     540
tatgccgact ctgtgaaggg tagattcacc atctcaagag atgattcaaa gaactcactg     600
tatctgcaaa tgaacagcct gaaaaccgag gacacggccg tgtattactg tgtgagacac     660
ggtaacttcg gcaattctta cgtgtcttgg tttgcttatt ggggacaggg gacactggtg     720
actgtgtctt ccggagttga gcccaaatct tgtgacaaaa ctcacacatg cccaccgtgc     780
ccagcacctg aagccgcggg ggcaccgtca gtcttcctct tccccccaaa acccaaggac     840
accctcatga tctcccggac ccctgaggtc acatgcgtgg tggtggacgt gagccacgaa     900
gaccctgagg tcaagttcaa ctggtacgtg gacggcgtgg aggtgcataa tgccaagaca     960
aagccgcggg aggagcagta caacagcacg taccgtgtgg tcagcgtcct caccgtcctg    1020
caccaggact ggctgaatgg caaggagtac aagtgcaagg tctccaacaa agccctccca    1080
```

```
gcccccatcg agaaaaccat ctccaaagcc aaagggcagc cccgagaacc acaggtgtac    1140
accctgcccc catcccggga ggagatgacc aagaaccagg tcagcctgtg gtgcctggtc    1200
aaaggcttct atcccagcga catcgccgtg gagtgggaga gcaatgggca gccggagaac    1260
aactacaaga ccacgcctcc cgtgctggac tccgacggct ccttcttcct ctacagcaag    1320
ctcaccgtgg acaagagcag gtggcagcag gggaacgtct tctcatgctc cgtgatgcat    1380
gaggctctgc acaaccacta cacgcagaag agcctctccc tgtctccggg taaa          1434
```

<210> SEQ ID NO 145
<211> LENGTH: 243
<212> TYPE: PRT
<213> ORGANISM: Artificial Sequence
<220> FEATURE:
<223> OTHER INFORMATION: Synthetic peptide sequence

<400> SEQUENCE: 145

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Gln Ser Gly Ala Glu
        115                 120                 125

Val Lys Lys Pro Gly Ala Ser Val Lys Val Ser Cys Lys Ala Ser Gly
    130                 135                 140

Tyr Thr Phe Thr Ser Tyr Gly Ile Ser Trp Val Arg Gln Ala Pro Gly
145                 150                 155                 160

Gln Gly Leu Glu Trp Met Gly Trp Ile Ser Ala Tyr Asn Gly Asn Thr
                165                 170                 175

Asn Tyr Ala Gln Lys Leu Gln Gly Arg Val Thr Met Thr Thr Asp Thr
            180                 185                 190

Ser Thr Ser Thr Ala Tyr Met Glu Leu Arg Ser Leu Arg Ser Asp Asp
        195                 200                 205

Thr Ala Val Tyr Tyr Cys Ala Thr Ile Asp Thr Ala Ser Ala Phe Asp
    210                 215                 220

Ile Trp Gly Gln Gly Thr Met Val Thr Val Ser Ser Gly Phe Asn Arg
225                 230                 235                 240

Gly Glu Cys
```

<210> SEQ ID NO 146
<211> LENGTH: 729
<212> TYPE: DNA
<213> ORGANISM: Artificial Sequence
<220> FEATURE:
<223> OTHER INFORMATION: Synthetic nucleotide sequence

<400> SEQUENCE: 146

```
caggctgtgg tgactcagga gccttcactg accgtgtccc caggcggaac tgtgaccctg      60
acatgcagat ccagcacagg cgcagtgacc acatctaact acgccaattg ggtgcagcag     120
aagccaggac aggcaccaag gggcctgatc ggggtacaa acaaaagggc tccctggacc      180
cctgcacggt tttctggaag tctgctgggc ggaaaggccg ctctgactat taccggggca     240
caggccgagg acgaagccga ttactattgt gctctgtggt atagcaatct gtgggtgttc     300
gggggtggca aaaactgac tgtgctggga ggggtggat ccggcggagg tggagaagtc       360
cagctggtgc agagtggggc agaagtcaag aaacccggcg catcagtgaa agtctcatgt     420
aaagcatcag gctataccttt acatcatac ggaatcagct gggtgaggca ggctccagga     480
cagggactgg agtggatggg atggatttct gcatacaacg gcaatacaaa ctatgcccag     540
aagctgcagg gccgggtgac tatgaccaca gacactagca cctccacagc ctatatggaa     600
ctgcggtctc tgagaagtga cgatactgcc gtctactatt gcgctaccat tgataccgct     660
tcagccttcg acatttgggg gcaggggact atggtgacag tgagctccgg attcaacagg     720
ggagagtgt                                                             729
```

<210> SEQ ID NO 147
<211> LENGTH: 478
<212> TYPE: PRT
<213> ORGANISM: Artificial Sequence
<220> FEATURE:
<223> OTHER INFORMATION: Synthetic peptide sequence

<400> SEQUENCE: 147

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Val Val Phe Gly Gly Gly Thr Lys Leu Thr Val Leu Gly Gly
            100                 105                 110

Gly Gly Ser Gly Gly Gly Gly Glu Val Gln Leu Val Glu Ser Gly Gly
        115                 120                 125

Gly Leu Val Gln Pro Gly Gly Ser Leu Arg Leu Ser Cys Ala Ala Ser
    130                 135                 140

Gly Phe Thr Phe Ser Thr Tyr Ala Met Asn Trp Val Arg Gln Ala Pro
145                 150                 155                 160

Gly Lys Gly Leu Glu Trp Val Gly Arg Ile Arg Ser Lys Tyr Asn Asn
                165                 170                 175

Tyr Ala Thr Tyr Tyr Ala Asp Ser Val Lys Gly Arg Phe Thr Ile Ser
            180                 185                 190

Arg Asp Asp Ser Lys Asn Ser Leu Tyr Leu Gln Met Asn Ser Leu Lys
        195                 200                 205

Thr Glu Asp Thr Ala Val Tyr Tyr Cys Val Arg His Gly Asn Phe Gly
    210                 215                 220

Asn Ser Tyr Val Ser Trp Phe Ala Tyr Trp Gly Gln Gly Thr Leu Val
```

```
                        225                 230                 235                 240
        Thr Val Ser Ser Gly Val Glu Pro Lys Ser Cys Asp Lys Thr His Thr
                            245                 250                 255

Cys Pro Pro Cys Pro Ala Pro Glu Ala Ala Gly Ala Pro Ser Val Phe
                        260                 265                 270

Leu Phe Pro Pro Lys Pro Lys Asp Thr Leu Met Ile Ser Arg Thr Pro
                    275                 280                 285

Glu Val Thr Cys Val Val Val Asp Val Ser His Glu Asp Pro Glu Val
                290                 295                 300

Lys Phe Asn Trp Tyr Val Asp Gly Val Glu Val His Asn Ala Lys Thr
        305                 310                 315                 320

Lys Pro Arg Glu Glu Gln Tyr Asn Ser Thr Tyr Arg Val Val Ser Val
                        325                 330                 335

Leu Thr Val Leu His Gln Asp Trp Leu Asn Gly Lys Glu Tyr Lys Cys
                    340                 345                 350

Lys Val Ser Asn Lys Ala Leu Pro Ala Pro Ile Glu Lys Thr Ile Ser
                355                 360                 365

Lys Ala Lys Gly Gln Pro Arg Glu Pro Gln Val Tyr Thr Leu Pro Pro
        370                 375                 380

Ser Arg Glu Glu Met Thr Lys Asn Gln Val Ser Leu Trp Cys Leu Val
        385                 390                 395                 400

Lys Gly Phe Tyr Pro Ser Asp Ile Ala Val Glu Trp Glu Ser Asn Gly
                        405                 410                 415

Gln Pro Glu Asn Asn Tyr Lys Thr Thr Pro Pro Val Leu Asp Ser Asp
                    420                 425                 430

Gly Ser Phe Phe Leu Tyr Ser Lys Leu Thr Val Asp Lys Ser Arg Trp
                435                 440                 445

Gln Gln Gly Asn Val Phe Ser Cys Ser Val Met His Glu Ala Leu His
            450                 455                 460

Asn His Tyr Thr Gln Lys Ser Leu Ser Leu Ser Pro Gly Lys
        465                 470                 475

<210> SEQ ID NO 148
<211> LENGTH: 1434
<212> TYPE: DNA
<213> ORGANISM: Artificial Sequence
<220> FEATURE:
<223> OTHER INFORMATION: Synthetic nucleotide sequence

<400> SEQUENCE: 148
cagtccgtcc tgactcagcc tccctccgtg tccgcagctc ctgggcagaa ggtcacaatc     60
agttgctctg gtcatcctc aaacattggc aacaattacg tgtcttggta tcagcagctg    120
cccgggacag cccctaagct gctgatctac gacaacaaca gcggccaagt ggcattccc    180 gatcggttca gcggcagcaa gtctggcacc agcgccacac tgggcatcac tgggctgcag    240
accggggacg aggctgatta ctattgcgga acctgggact cttcactgtc tggcgtcgtc    300
ttcggagggg gaaccaaact gaccgtgctg gtggaggcg atccggcgg cggaggcgag    360 gtgcagctgg tggagtctgg gggaggcttg gtccagcctg gagggtccct gagactctcc    420
tgtgcagcct ctggattcac cttcagcaca tacgctatga attgggtccg ccaggctcca    480
gggaaggggc tggagtgggt tggaaggatc aggtccaagt acaacaatta tgcaacctac    540
tatgccgact ctgtgaaggg tagattcacc atctcaagag atgattcaaa gaactcactg    600
tatctgcaaa tgaacagcct gaaaaccgag gacacggccg tgtattactg tgtgagacac    660
```

```
ggtaacttcg gcaattctta cgtgtcttgg tttgcttatt ggggacaggg gacactggtg    720
actgtgtctt ccggagttga gcccaaatct tgtgacaaaa ctcacacatg cccaccgtgc    780
ccagcacctg aagccgcggg ggcaccgtca gtcttcctct tccccccaaa acccaaggac    840
accctcatga tctcccggac ccctgaggtc acatgcgtgg tggtggacgt gagccacgaa    900
gaccctgagg tcaagttcaa ctggtacgtg gacggcgtgg aggtgcataa tgccaagaca    960
aagccgcggg aggagcagta caacagcacg taccgtgtgg tcagcgtcct caccgtcctg   1020
caccaggact ggctgaatgg caaggagtac aagtgcaagg tctccaacaa agccctccca   1080
gcccccatcg agaaaaccat ctccaaagcc aaagggcagc cccgagaacc acaggtgtac   1140
accctgcccc catcccggga ggagatgacc aagaaccagg tcagcctgtg gtgcctggtc   1200
aaaggcttct atcccagcga catcgccgtg gagtgggaga gcaatgggca gccggagaac   1260
aactacaaga ccacgcctcc cgtgctggac tccgacggct ccttcttcct ctacagcaag   1320
ctcaccgtgg acaagagcag gtggcagcag gggaacgtct tctcatgctc cgtgatgcat   1380
gaggctctgc acaaccacta cacgcagaag agcctctccc tgtctccggg taaa          1434
```

<210> SEQ ID NO 149
<211> LENGTH: 243
<212> TYPE: PRT
<213> ORGANISM: Artificial Sequence
<220> FEATURE:
<223> OTHER INFORMATION: Synthetic peptide sequence

<400> SEQUENCE: 149

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Gln Ser Gly Ala Glu
        115                 120                 125

Val Lys Lys Pro Gly Ala Ser Val Lys Val Ser Cys Lys Ala Ser Gly
    130                 135                 140

Tyr Thr Phe Thr Ser Tyr Gly Ile Ser Trp Val Arg Gln Ala Pro Gly
145                 150                 155                 160

Gln Gly Leu Glu Trp Met Gly Trp Ile Ser Ala Tyr Asn Gly Asn Thr
                165                 170                 175

Asn Tyr Ala Gln Lys Leu Gln Gly Arg Val Thr Met Thr Thr Asp Thr
            180                 185                 190

Ser Thr Ser Thr Ala Tyr Met Glu Leu Arg Ser Leu Arg Ser Asp Asp
        195                 200                 205

Thr Ala Val Tyr Tyr Cys Ala Thr Ile Asp Thr Ala Asn Ala Phe Gly
    210                 215                 220

Ile Trp Gly Gln Gly Thr Met Val Thr Val Ser Ser Gly Phe Asn Arg

```
<210> SEQ ID NO 150
<211> LENGTH: 729
<212> TYPE: DNA
<213> ORGANISM: Artificial Sequence
<220> FEATURE:
<223> OTHER INFORMATION: Synthetic nucleotide sequence

<400> SEQUENCE: 150
caggctgtgg tgactcagga gccttcactg accgtgtccc caggcggaac tgtgaccctg      60
acatgcagat ccagcacagg cgcagtgacc acatctaact acgccaattg ggtgcagcag     120
aagccaggac aggcaccaag gggcctgatc gggggtacaa acaaaagggc tccctggacc     180
cctgcacggt tttctggaag tctgctgggc ggaaaggccg ctctgactat taccggggca     240
caggccgagg acgaagccga ttactattgt gctctgtggt atagcaatct gtgggtgttc     300
gggggtggca caaaactgac tgtgctggga ggggtggat ccggcggagg tggagaagtc      360
cagctggtgc agagtgggc agaagtcaag aaacccggcg catcagtgaa agtctcatgt      420
aaagcatcag gctataccct tacatcatac ggaatcagct gggtgaggca ggctccagga     480
cagggactgg agtggatggg atggatttct gcatacaacg gaatacaaa ctatgcccag      540
aagctgcagg gccgggtgac tatgaccaca gacactagca cctccacagc ctatatggaa     600
ctgcggtctc tgagaagtga cgatactgcc gtctactatt gcgctaccat tgataccgct     660
aacgccttcg gcatttgggg gcaggggact atggtgacag tgagctccgg attcaacagg     720
ggagagtgt                                                            729

<210> SEQ ID NO 151
<211> LENGTH: 478
<212> TYPE: PRT
<213> ORGANISM: Artificial Sequence
<220> FEATURE:
<223> OTHER INFORMATION: Synthetic peptide sequence

<400> SEQUENCE: 151

Gln Ser Val Leu Thr Gln Pro Pro Ser Val Ser Ala Ala Pro Gly Gln
  1               5                  10                  15

Lys Val Thr Ile Ser Cys Ser Gly Ser Ser Ser Asn Ile Gly Asn Asn
             20                  25                  30

Tyr Val Ser Trp Tyr Gln Gln Leu Pro Gly Thr Ala Pro Lys Leu Leu
         35                  40                  45

Ile Tyr Asp Asn Asn Lys Arg Pro Ser Gly Ile Pro Asp Arg Phe Ser
     50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ser Tyr Val Phe Gly Thr Gly Thr Lys Val Thr Val Leu Gly Gly
            100                 105                 110

Gly Gly Ser Gly Gly Gly Gly Glu Val Gln Leu Val Glu Ser Gly Gly
        115                 120                 125

Gly Leu Val Gln Pro Gly Gly Ser Leu Arg Leu Ser Cys Ala Ala Ser
    130                 135                 140

Gly Phe Thr Phe Ser Thr Tyr Ala Met Asn Trp Val Arg Gln Ala Pro
145                 150                 155                 160
```

Gly Lys Gly Leu Glu Trp Val Gly Arg Ile Arg Ser Lys Tyr Asn Asn
            165                 170                 175

Tyr Ala Thr Tyr Tyr Ala Asp Ser Val Lys Gly Arg Phe Thr Ile Ser
        180                 185                 190

Arg Asp Asp Ser Lys Asn Ser Leu Tyr Leu Gln Met Asn Ser Leu Lys
            195                 200                 205

Thr Glu Asp Thr Ala Val Tyr Tyr Cys Val Arg His Gly Asn Phe Gly
        210                 215                 220

Asn Ser Tyr Val Ser Trp Phe Ala Tyr Trp Gly Gln Gly Thr Leu Val
225                 230                 235                 240

Thr Val Ser Ser Gly Val Glu Pro Lys Ser Cys Asp Lys Thr His Thr
            245                 250                 255

Cys Pro Pro Cys Pro Ala Pro Glu Ala Ala Gly Ala Pro Ser Val Phe
        260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
        290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
            325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
        355                 360                 365

Lys Ala Lys Gly Gln Pro Arg Glu Pro Gln Val Tyr Thr Leu Pro Pro
370                 375                 380

Ser Arg Glu Glu Met Thr Lys Asn Gln Val Ser Leu Trp Cys Leu Val
385                 390                 395                 400

Lys Gly Phe Tyr Pro Ser Asp Ile Ala Val Glu Trp Glu Ser Asn Gly
            405                 410                 415

Gln Pro Glu Asn Asn Tyr Lys Thr Thr Pro Pro Val Leu Asp Ser Asp
        420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
        450                 455                 460

Asn His Tyr Thr Gln Lys Ser Leu Ser Leu Ser Pro Gly Lys
465                 470                 475

<210> SEQ ID NO 152
<211> LENGTH: 1434
<212> TYPE: DNA
<213> ORGANISM: Artificial Sequence
<220> FEATURE:
<223> OTHER INFORMATION: Synthetic nucleotide sequence

<400> SEQUENCE: 152
cagtccgtcc tgactcagcc tccctccgtg tccgcagctc ctgggcagaa ggtcacaatc    60
agttgctctg gtcatcctc aaacattggc aacaattacg tgtcttggta tcagcagctg   120
cccgggacag cccctaagct gctgatctac gacaacaaca gcggccaagt ggcattccc   180 gatcggttca gcggcagcaa gtctggcacc agcgccacac tgggcatcac tgggctgcag   240

```
accggggacg aggctgatta ctattgcgga acctgggact cttcactgtc ttcctacgtc    300
ttcggaacgg gaaccaaagt gaccgtgctg ggtggaggcg gatccggcgg cggaggcgag    360
gtgcagctgg tggagtctgg gggaggcttg gtccagcctg agggtccct gagactctcc     420 tgtgcagcct ctggattcac cttcagcaca tacgctatga attgggtccg ccaggctcca    480
gggaaggggc tggagtgggt tggaaggatc aggtccaagt acaacaatta tgcaacctac    540
tatgccgact ctgtgaaggg tagattcacc atctcaagag atgattcaaa gaactcactg    600
tatctgcaaa tgaacagcct gaaaaccgag gacacggccg tgtattactg tgtgagacac    660
ggtaacttcg gcaattctta cgtgtcttgg tttgcttatt ggggacaggg gacactggtg    720
actgtgtctt ccggagttga gcccaaatct tgtgacaaaa ctcacacatg cccaccgtgc    780
ccagcacctg aagccgcggg ggcaccgtca gtcttcctct ccccccaaa acccaaggac     840 accctcatga tctcccggac ccctgaggtc acatgcgtgg tggtggacgt gagccacgaa    900
gaccctgagg tcaagttcaa ctggtacgtg gacggcgtgg aggtgcataa tgccaagaca    960
aagccgcggg aggagcagta caacagcacg taccgtgtgg tcagcgtcct caccgtcctg   1020
caccaggact ggctgaatgg caaggagtac aagtgcaagg tctccaacaa agccctccca   1080 gccccatcg agaaaaccat ctccaaagcc aagggcagc cccgagaacc acaggtgtac     1140
accctgcccc catcccggga ggagatgacc aagaaccagg tcagcctgtg gtgcctggtc   1200
aaaggcttct atcccagcga catcgccgtg gagtgggaga gcaatgggca gccggagaac   1260
aactacaaga ccacgcctcc cgtgctggac tccgacggct ccttcttcct ctacagcaag   1320
ctcaccgtgg acaagagcag gtggcagcag gggaacgtct tctcatgctc cgtgatgcat   1380
gaggctctgc acaaccacta cacgcagaag agcctctccc tgtctccggg taaa          1434
```

<210> SEQ ID NO 153
<211> LENGTH: 243
<212> TYPE: PRT
<213> ORGANISM: Artificial Sequence
<220> FEATURE:
<223> OTHER INFORMATION: Synthetic peptide sequence

<400> SEQUENCE: 153

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Gln Ser Gly Ala Glu
        115                 120                 125

Val Lys Lys Pro Gly Ala Ser Val Lys Val Ser Cys Lys Ala Ser Gly
    130                 135                 140

Tyr Thr Phe Thr Ser Tyr Gly Ile Ser Trp Val Arg Gln Ala Pro Gly
145                 150                 155                 160
```

Gln Gly Leu Glu Trp Met Gly Trp Ile Ser Ala Tyr Asn Gly Asn Thr
                165                 170                 175

Asn Tyr Ala Gln Lys Leu Gln Gly Arg Val Thr Met Thr Thr Asp Thr
            180                 185                 190

Ser Thr Ser Thr Ala Tyr Met Glu Leu Arg Ser Leu Arg Ser Asp Asp
        195                 200                 205

Thr Ala Val Tyr Tyr Cys Ala Thr Ile Asp Thr Ala Thr Ala Phe Asp
    210                 215                 220

Ile Trp Gly Gln Gly Thr Met Val Thr Val Ser Ser Gly Phe Asn Arg
225                 230                 235                 240

Gly Glu Cys

<210> SEQ ID NO 154
<211> LENGTH: 729
<212> TYPE: DNA
<213> ORGANISM: Artificial Sequence
<220> FEATURE:
<223> OTHER INFORMATION: Synthetic nucleotide sequence

<400> SEQUENCE: 154
caggctgtgg tgactcagga gccttcactg accgtgtccc caggcggaac tgtgaccctg    60
acatgcagat ccagcacagg cgcagtgacc acatctaact acgccaattg ggtgcagcag   120
aagccaggac aggcaccaag gggcctgatc ggggtacaa acaaaagggc tccctggacc    180
cctgcacggt tttctggaag tctgctgggc ggaaaggccg ctctgactat taccggggca   240
caggccgagg acgaagccga ttactattgt gctctgtggt atagcaatct gtgggtgttc   300
gggggtggca aaaactgac tgtgctggga ggggtggat ccggcggagg tggagaagtc     360
cagctggtgc agagtgggc agaagtcaag aaacccggcg catcagtgaa agtctcatgt    420
aaagcatcag gctataccct tacatcatac ggaatcagct gggtgaggca ggctccagga   480
cagggactgg agtggatggg atggattct gcatacaacg gcaatacaaa ctatgcccag    540
aagctgcagg gccgggtgac tatgaccaca gacactagca cctccacagc ctatatggaa   600
ctgcggtctc tgagaagtga cgatactgcc gtctactatt gcgctaccat tgataccgct   660
acagccttcg acatttgggg gcaggggact atggtgacag tgagctccgg attcaacagg   720
ggagagtgt                                                            729

<210> SEQ ID NO 155
<211> LENGTH: 478
<212> TYPE: PRT
<213> ORGANISM: Artificial Sequence
<220> FEATURE:
<223> OTHER INFORMATION: Synthetic peptide sequence

<400> SEQUENCE: 155

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Tyr Val Phe Gly Thr Thr Lys Val Thr Val Leu Gly Gly
            100                 105                 110

Gly Gly Ser Gly Gly Gly Gly Glu Val Gln Leu Val Glu Ser Gly Gly
            115                 120                 125

Gly Leu Val Gln Pro Gly Gly Ser Leu Arg Leu Ser Cys Ala Ala Ser
130                 135                 140

Gly Phe Thr Phe Ser Thr Tyr Ala Met Asn Trp Val Arg Gln Ala Pro
145                 150                 155                 160

Gly Lys Gly Leu Glu Trp Val Gly Arg Ile Arg Ser Lys Tyr Asn Asn
                165                 170                 175

Tyr Ala Thr Tyr Tyr Ala Asp Ser Val Lys Gly Arg Phe Thr Ile Ser
            180                 185                 190

Arg Asp Asp Ser Lys Asn Ser Leu Tyr Leu Gln Met Asn Ser Leu Lys
            195                 200                 205

Thr Glu Asp Thr Ala Val Tyr Tyr Cys Val Arg His Gly Asn Phe Gly
            210                 215                 220

Asn Ser Tyr Val Ser Trp Phe Ala Tyr Trp Gly Gln Gly Thr Leu Val
225                 230                 235                 240

Thr Val Ser Ser Gly Val Glu Pro Lys Ser Cys Asp Lys Thr His Thr
                245                 250                 255

Cys Pro Pro Cys Pro Ala Pro Glu Ala Gly Ala Pro Ser Val Phe
            260                 265                 270

Leu Phe Pro Pro Lys Pro Lys Asp Thr Leu Met Ile Ser Arg Thr Pro
            275                 280                 285

Glu Val Thr Cys Val Val Val Asp Val Ser His Glu Asp Pro Glu Val
            290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
            355                 360                 365

Lys Ala Lys Gly Gln Pro Arg Glu Pro Gln Val Tyr Thr Leu Pro Pro
370                 375                 380

Ser Arg Glu Glu Met Thr Lys Asn Gln Val Ser Leu Trp Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
            435                 440                 445

Gln Gln Gly Asn Val Phe Ser Cys Ser Val Met His Glu Ala Leu His
450                 455                 460

Asn His Tyr Thr Gln Lys Ser Leu Ser Leu Ser Pro Gly Lys
465                 470                 475

<210> SEQ ID NO 156
<211> LENGTH: 1434
<212> TYPE: DNA

<210> ORGANISM: Artificial Sequence
<220> FEATURE:
<223> OTHER INFORMATION: Synthetic nucleotide sequence

<400> SEQUENCE: 156

```
cagtccgtcc tgactcagcc tccctccgtg tccgcagctc ctgggcagaa ggtcacaatc      60
agttgctctg gtcatcctc aaacattggc aacaattacg tgtcttggta tcagcagctg     120
cccgggacag cccctaagct gctgatctac gacaacaaca gcggccaag tggcattccc      180
gatcggttca gcggcagcaa gtctggcacc agcgccacac tgggcatcac tgggctgcag     240
accggggacg aggctgatta ctattgcgga acctgggact cttcactgtc tgcctacgtc     300
ttcggaacgg gaaccaaagt gaccgtgctg ggtggaggcg gatccggcgg cggaggcgag     360
gtgcagctgg tggagtctgg gggaggcttg gtccagcctg agggtccct gagactctcc      420
tgtgcagcct ctggattcac cttcagcaca tacgctatga attgggtccg ccaggctcca     480
gggaagggc tggagtgggt tggaaggatc aggtccaagt acaacaatta tgcaacctac      540
tatgccgact ctgtgaaggg tagattcacc atctcaagag atgattcaaa gaactcactg     600
tatctgcaaa tgaacagcct gaaaaccgag gacacggccg tgtattactg tgtgagacac     660
ggtaacttcg gcaattctta cgtgtcttgg tttgcttatt ggggacaggg gacactggtg     720
actgtgtctt ccggagttga gcccaaatct tgtgacaaaa ctcacacatg cccaccgtgc     780
ccagcacctg aagccgcggg ggcaccgtca gtcttcctct ccccccaaa acccaaggac      840
accctcatga tctcccggac ccctgaggtc acatgcgtgg tggtggacgt gagccacgaa     900
gaccctgagg tcaagttcaa ctggtacgtg gacggcgtgg aggtgcataa tgccaagaca     960
aagccgcggg aggagcagta caacagcacg taccgtgtgg tcagcgtcct caccgtcctg    1020
caccaggact ggctgaatgg caaggagtac aagtgcaagg tctccaacaa agccctccca    1080
gccccatcg agaaaaccat ctccaaagcc aaagggcagc ccgagaaacc acaggtgtac     1140
accctgcccc catcccggga ggagatgacc aagaaccagg tcagcctgtg gtgcctggtc    1200
aaaggcttct atcccagcga catcgccgtg gagtgggaga gcaatgggca gccggagaac    1260
aactacaaga ccacgcctcc cgtgctggac tccgacggct ccttcttcct ctacagcaag    1320
ctcaccgtgg acaagagcag gtggcagcag gggaacgtct tctcatgctc cgtgatgcat    1380
gaggctctgc acaaccacta cacgcagaag agcctctccc tgtctccggg taaa          1434
```

<210> SEQ ID NO 157
<211> LENGTH: 243
<212> TYPE: PRT
<213> ORGANISM: Artificial Sequence
<220> FEATURE:
<223> OTHER INFORMATION: Synthetic peptide sequence

<400> SEQUENCE: 157

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80
```

Gln Ala Glu Asp Glu Ala Asp Tyr Tyr Cys Ala Leu Trp Tyr Ser Asn
            85                  90                  95

Leu Trp Val Phe Gly Gly Gly Thr Lys Leu Thr Val Leu Gly Gly Gly
        100                 105                 110

Gly Ser Gly Gly Gly Gly Glu Val Gln Leu Val Gln Ser Gly Ala Glu
        115                 120                 125

Val Lys Lys Pro Gly Ala Ser Val Lys Val Ser Cys Lys Ala Ser Gly
        130                 135                 140

Tyr Thr Phe Thr Ser Tyr Gly Ile Ser Trp Val Arg Gln Ala Pro Gly
145                 150                 155                 160

Gln Gly Leu Glu Trp Met Gly Trp Ile Ser Ala Tyr Asn Gly Asn Thr
                165                 170                 175

Asn Tyr Ala Gln Lys Leu Gln Gly Arg Val Thr Met Thr Thr Asp Thr
            180                 185                 190

Ser Thr Ser Thr Ala Tyr Met Glu Leu Arg Ser Leu Arg Ser Asp Asp
        195                 200                 205

Thr Ala Val Tyr Tyr Cys Ala Thr Ile Asp Thr Ala Asn Ala Phe Asp
    210                 215                 220

Ile Trp Gly Gln Gly Thr Met Val Thr Val Ser Ser Gly Phe Asn Arg
225                 230                 235                 240

Gly Glu Cys

<210> SEQ ID NO 158
<211> LENGTH: 729
<212> TYPE: DNA
<213> ORGANISM: Artificial Sequence
<220> FEATURE:
<223> OTHER INFORMATION: Synthetic nucleotide sequence

<400> SEQUENCE: 158
caggctgtgg tgactcagga gccttcactg accgtgtccc caggcggaac tgtgaccctg     60
acatgcagat ccagcacagg cgcagtgacc acatctaact acgccaattg ggtgcagcag    120
aagccaggac aggcaccaag gggcctgatc gggggtacaa acaaaagggc tccctggacc    180
cctgcacggt tttctggaag tctgctgggc ggaaaggccg ctctgactat accggggca    240
caggccgagg acgaagccga ttactattgt gctctgtggt atagcaatct gtgggtgttc    300
gggggtggca caaaactgac tgtgctggga ggggtggat ccggcggagg tggagaagtc    360
cagctggtgc agagtggggc agaagtcaag aaacccggcg catcagtgaa agtctcatgt    420
aaagcatcag gctataccct tacatcatac ggaatcagct gggtgaggca ggctccagga    480
cagggactgg agtggatggg atggatttct gcatacaacg gcaatacaaa ctatgcccag    540
aagctgcagg gccgggtgac tatgaccaca gacactagca cctccacagc ctatatggaa    600
ctgcggtctc tgagaagtga cgatactgcc gtctactatt gcgctaccat tgataccgct    660
aacgccttcg acatttgggg gcaggggact atggtgacag tgagctccgg attcaacagg    720
ggagagtgt                                                            729

<210> SEQ ID NO 159
<211> LENGTH: 829
<212> TYPE: PRT
<213> ORGANISM: Homo sapiens

<400> SEQUENCE: 159

Met Gly Leu Pro Arg Gly Pro Leu Ala Ser Leu Leu Leu Leu Gln Val
1               5                   10                  15

```
Cys Trp Leu Gln Cys Ala Ala Ser Glu Pro Cys Arg Ala Val Phe Arg
            20                  25                  30

Glu Ala Glu Val Thr Leu Glu Ala Gly Gly Ala Glu Gln Pro Gly
            35                  40                  45

Gln Ala Leu Gly Lys Val Phe Met Gly Cys Pro Gly Gln Glu Pro Ala
 50                  55                  60

Leu Phe Ser Thr Asp Asn Asp Phe Thr Val Arg Asn Gly Glu Thr
 65                  70                  75                  80

Val Gln Glu Arg Arg Ser Leu Lys Glu Arg Asn Pro Leu Lys Ile Phe
                85                  90                  95

Pro Ser Lys Arg Ile Leu Arg Arg His Lys Arg Asp Trp Val Val Ala
            100                 105                 110

Pro Ile Ser Val Pro Glu Asn Gly Lys Gly Pro Phe Pro Gln Arg Leu
            115                 120                 125

Asn Gln Leu Lys Ser Asn Lys Asp Arg Asp Thr Lys Ile Phe Tyr Ser
130                 135                 140

Ile Thr Gly Pro Gly Ala Asp Ser Pro Pro Glu Gly Val Phe Ala Val
145                 150                 155                 160

Glu Lys Glu Thr Gly Trp Leu Leu Leu Asn Lys Pro Leu Asp Arg Glu
                165                 170                 175

Glu Ile Ala Lys Tyr Glu Leu Phe Gly His Ala Val Ser Glu Asn Gly
            180                 185                 190

Ala Ser Val Glu Asp Pro Met Asn Ile Ser Ile Ile Val Thr Asp Gln
            195                 200                 205

Asn Asp His Lys Pro Lys Phe Thr Gln Asp Thr Phe Arg Gly Ser Val
210                 215                 220

Leu Glu Gly Val Leu Pro Gly Thr Ser Val Met Gln Val Thr Ala Thr
225                 230                 235                 240

Asp Glu Asp Asp Ala Ile Tyr Thr Tyr Asn Gly Val Val Ala Tyr Ser
                245                 250                 255

Ile His Ser Gln Glu Pro Lys Asp Pro His Asp Leu Met Phe Thr Ile
            260                 265                 270

His Arg Ser Thr Gly Thr Ile Ser Val Ile Ser Ser Gly Leu Asp Arg
            275                 280                 285

Glu Lys Val Pro Glu Tyr Thr Leu Thr Ile Gln Ala Thr Asp Met Asp
290                 295                 300

Gly Asp Gly Ser Thr Thr Thr Ala Val Ala Val Val Glu Ile Leu Asp
305                 310                 315                 320

Ala Asn Asp Asn Ala Pro Met Phe Asp Pro Gln Lys Tyr Glu Ala His
                325                 330                 335

Val Pro Glu Asn Ala Val Gly His Glu Val Gln Arg Leu Thr Val Thr
            340                 345                 350

Asp Leu Asp Ala Pro Asn Ser Pro Ala Trp Arg Ala Thr Tyr Leu Ile
            355                 360                 365

Met Gly Gly Asp Asp Gly Asp His Phe Thr Ile Thr Thr His Pro Glu
370                 375                 380

Ser Asn Gln Gly Ile Leu Thr Thr Arg Lys Gly Leu Asp Phe Glu Ala
385                 390                 395                 400

Lys Asn Gln His Thr Leu Tyr Val Glu Val Thr Asn Glu Ala Pro Phe
                405                 410                 415

Val Leu Lys Leu Pro Thr Ser Thr Ala Thr Ile Val Val His Val Glu
            420                 425                 430

Asp Val Asn Glu Ala Pro Val Phe Val Pro Pro Ser Lys Val Val Glu
```

```
                435                 440                 445
Val Gln Glu Gly Ile Pro Thr Gly Glu Pro Val Cys Val Tyr Thr Ala
450                 455                 460

Glu Asp Pro Asp Lys Glu Asn Gln Lys Ile Ser Tyr Arg Ile Leu Arg
465                 470                 475                 480

Asp Pro Ala Gly Trp Leu Ala Met Asp Pro Asp Ser Gly Gln Val Thr
                485                 490                 495

Ala Val Gly Thr Leu Asp Arg Glu Asp Glu Gln Phe Val Arg Asn Asn
                500                 505                 510

Ile Tyr Glu Val Met Val Leu Ala Met Asp Asn Gly Ser Pro Pro Thr
            515                 520                 525

Thr Gly Thr Gly Thr Leu Leu Leu Thr Leu Ile Asp Val Asn Asp His
        530                 535                 540

Gly Pro Val Pro Glu Pro Arg Gln Ile Thr Ile Cys Asn Gln Ser Pro
545                 550                 555                 560

Val Arg Gln Val Leu Asn Ile Thr Asp Lys Asp Leu Ser Pro His Thr
                565                 570                 575

Ser Pro Phe Gln Ala Gln Leu Thr Asp Ser Asp Ile Tyr Trp Thr
                580                 585                 590

Ala Glu Val Asn Glu Glu Gly Asp Thr Val Val Leu Ser Leu Lys Lys
            595                 600                 605

Phe Leu Lys Gln Asp Thr Tyr Asp Val His Leu Ser Leu Ser Asp His
        610                 615                 620

Gly Asn Lys Glu Gln Leu Thr Val Ile Arg Ala Thr Val Cys Asp Cys
625                 630                 635                 640

His Gly His Val Glu Thr Cys Pro Gly Pro Trp Lys Gly Gly Phe Ile
                645                 650                 655

Leu Pro Val Leu Gly Ala Val Leu Ala Leu Leu Phe Leu Leu Leu Val
                660                 665                 670

Leu Leu Leu Leu Val Arg Lys Lys Arg Lys Ile Lys Glu Pro Leu Leu
            675                 680                 685

Leu Pro Glu Asp Asp Thr Arg Asp Asn Val Phe Tyr Tyr Gly Glu Glu
        690                 695                 700

Gly Gly Gly Glu Glu Asp Gln Asp Tyr Asp Ile Thr Gln Leu His Arg
705                 710                 715                 720

Gly Leu Glu Ala Arg Pro Glu Val Val Leu Arg Asn Asp Val Ala Pro
                725                 730                 735

Thr Ile Ile Pro Thr Pro Met Tyr Arg Pro Arg Pro Ala Asn Pro Asp
                740                 745                 750

Glu Ile Gly Asn Phe Ile Ile Glu Asn Leu Lys Ala Ala Asn Thr Asp
            755                 760                 765

Pro Thr Ala Pro Pro Tyr Asp Thr Leu Leu Val Phe Asp Tyr Glu Gly
        770                 775                 780

Ser Gly Ser Asp Ala Ala Ser Leu Ser Ser Leu Thr Ser Ser Ala Ser
785                 790                 795                 800

Asp Gln Asp Gln Asp Tyr Asp Tyr Leu Asn Glu Trp Gly Ser Arg Phe
                805                 810                 815

Lys Lys Leu Ala Asp Met Tyr Gly Gly Gly Glu Asp Asp
            820                 825

<210> SEQ ID NO 160
<211> LENGTH: 24
<212> TYPE: PRT
<213> ORGANISM: Homo sapiens
```

<400> SEQUENCE: 160

Met Gly Leu Pro Arg Gly Pro Leu Ala Ser Leu Leu Leu Leu Gln Val
1               5                   10                  15

Cys Trp Leu Gln Cys Ala Ala Ser
            20

<210> SEQ ID NO 161
<211> LENGTH: 83
<212> TYPE: PRT
<213> ORGANISM: Homo sapiens

<400> SEQUENCE: 161

Glu Pro Cys Arg Ala Val Phe Arg Glu Ala Glu Val Thr Leu Glu Ala
1               5                   10                  15

Gly Gly Ala Glu Gln Pro Gly Gln Ala Leu Gly Lys Val Phe Met
                20                  25                  30

Gly Cys Pro Gly Gln Glu Pro Ala Leu Phe Ser Thr Asp Asn Asp Asp
            35                  40                  45

Phe Thr Val Arg Asn Gly Glu Thr Val Gln Glu Arg Arg Ser Leu Lys
        50                  55                  60

Glu Arg Asn Pro Leu Lys Ile Phe Pro Ser Lys Arg Ile Leu Arg Arg
65                  70                  75                  80

His Lys Arg

<210> SEQ ID NO 162
<211> LENGTH: 108
<212> TYPE: PRT
<213> ORGANISM: Homo sapiens

<400> SEQUENCE: 162

Asp Trp Val Val Ala Pro Ile Ser Val Pro Glu Asn Gly Lys Gly Pro
1               5                   10                  15

Phe Pro Gln Arg Leu Asn Gln Leu Lys Ser Asn Lys Asp Arg Asp Thr
                20                  25                  30

Lys Ile Phe Tyr Ser Ile Thr Gly Pro Gly Ala Asp Ser Pro Pro Glu
            35                  40                  45

Gly Val Phe Ala Val Glu Lys Glu Thr Gly Trp Leu Leu Leu Asn Lys
        50                  55                  60

Pro Leu Asp Arg Glu Glu Ile Ala Lys Tyr Glu Leu Phe Gly His Ala
65                  70                  75                  80

Val Ser Glu Asn Gly Ala Ser Val Glu Asp Pro Met Asn Ile Ser Ile
                85                  90                  95

Ile Val Thr Asp Gln Asn Asp His Lys Pro Lys Phe
            100                 105

<210> SEQ ID NO 163
<211> LENGTH: 113
<212> TYPE: PRT
<213> ORGANISM: Homo sapiens

<400> SEQUENCE: 163

Thr Gln Asp Thr Phe Arg Gly Ser Val Leu Gly Val Leu Pro Gly
1               5                   10                  15

Thr Ser Val Met Gln Val Thr Ala Thr Asp Glu Asp Asp Ala Ile Tyr
                20                  25                  30

Thr Tyr Asn Gly Val Val Ala Tyr Ser Ile His Ser Gln Glu Pro Lys
            35                  40                  45

```
Asp Pro His Asp Leu Met Phe Thr Ile His Arg Ser Thr Gly Thr Ile
        50                  55                  60

Ser Val Ile Ser Ser Gly Leu Asp Arg Glu Lys Val Pro Glu Tyr Thr
 65                  70                  75                  80

Leu Thr Ile Gln Ala Thr Asp Met Asp Gly Asp Gly Ser Thr Thr Thr
                 85                  90                  95

Ala Val Ala Val Val Glu Ile Leu Asp Ala Asn Asp Asn Ala Pro Met
                100                 105                 110

Phe

<210> SEQ ID NO 164
<211> LENGTH: 112
<212> TYPE: PRT
<213> ORGANISM: Homo sapiens

<400> SEQUENCE: 164

Asp Pro Gln Lys Tyr Glu Ala His Val Pro Glu Asn Ala Val Gly His
 1               5                  10                  15

Glu Val Gln Arg Leu Thr Val Thr Asp Leu Asp Ala Pro Asn Ser Pro
                20                  25                  30

Ala Trp Arg Ala Thr Tyr Leu Ile Met Gly Gly Asp Asp Gly Asp His
                35                  40                  45

Phe Thr Ile Thr Thr His Pro Glu Ser Asn Gln Gly Ile Leu Thr Thr
        50                  55                  60

Arg Lys Gly Leu Asp Phe Glu Ala Lys Asn Gln His Thr Leu Tyr Val
 65                  70                  75                  80

Glu Val Thr Asn Glu Ala Pro Phe Val Leu Lys Leu Pro Thr Ser Thr
                 85                  90                  95

Ala Thr Ile Val Val His Val Glu Asp Val Asn Glu Ala Pro Val Phe
                100                 105                 110

<210> SEQ ID NO 165
<211> LENGTH: 106
<212> TYPE: PRT
<213> ORGANISM: Homo sapiens

<400> SEQUENCE: 165

Val Pro Pro Ser Lys Val Val Glu Val Gln Glu Gly Ile Pro Thr Gly
 1               5                  10                  15

Glu Pro Val Cys Val Tyr Thr Ala Glu Asp Pro Asp Lys Glu Asn Gln
                20                  25                  30

Lys Ile Ser Tyr Arg Ile Leu Arg Asp Pro Ala Gly Trp Leu Ala Met
                35                  40                  45

Asp Pro Asp Ser Gly Gln Val Thr Ala Val Gly Thr Leu Asp Arg Glu
        50                  55                  60

Asp Glu Gln Phe Val Arg Asn Asn Ile Tyr Glu Val Met Val Leu Ala
 65                  70                  75                  80

Met Asp Asn Gly Ser Pro Pro Thr Thr Gly Thr Gly Thr Leu Leu Leu
                 85                  90                  95

Thr Leu Ile Asp Val Asn Asp His Gly Pro
                100                 105

<210> SEQ ID NO 166
<211> LENGTH: 104
<212> TYPE: PRT
<213> ORGANISM: Homo sapiens
```

-continued

<400> SEQUENCE: 166

Val Pro Glu Pro Arg Gln Ile Thr Ile Cys Asn Gln Ser Pro Val Arg
1               5                   10                  15

Gln Val Leu Asn Ile Thr Asp Lys Asp Leu Ser Pro His Thr Ser Pro
            20                  25                  30

Phe Gln Ala Gln Leu Thr Asp Ser Asp Ile Tyr Trp Thr Ala Glu
        35                  40                  45

Val Asn Glu Glu Gly Asp Thr Val Val Leu Ser Leu Lys Lys Phe Leu
50                  55                  60

Lys Gln Asp Thr Tyr Asp Val His Leu Ser Leu Ser Asp His Gly Asn
65                  70                  75                  80

Lys Glu Gln Leu Thr Val Ile Arg Ala Thr Val Cys Asp Cys His Gly
                85                  90                  95

His Val Glu Thr Cys Pro Gly Pro
            100

<210> SEQ ID NO 167
<211> LENGTH: 179
<212> TYPE: PRT
<213> ORGANISM: Homo sapiens

<400> SEQUENCE: 167

Trp Lys Gly Gly Phe Ile Leu Pro Val Leu Gly Ala Val Leu Ala Leu
1               5                   10                  15

Leu Phe Leu Leu Leu Val Leu Leu Leu Val Arg Lys Lys Arg Lys
            20                  25                  30

Ile Lys Glu Pro Leu Leu Leu Pro Glu Asp Asp Thr Arg Asp Asn Val
        35                  40                  45

Phe Tyr Tyr Gly Glu Glu Gly Gly Glu Gly Asp Gln Asp Tyr Asp
50                  55                  60

Ile Thr Gln Leu His Arg Gly Leu Glu Ala Arg Pro Glu Val Val Leu
65                  70                  75                  80

Arg Asn Asp Val Ala Pro Thr Ile Ile Pro Thr Pro Met Tyr Arg Pro
                85                  90                  95

Arg Pro Ala Asn Pro Asp Glu Ile Gly Asn Phe Ile Ile Glu Asn Leu
            100                 105                 110

Lys Ala Ala Asn Thr Asp Pro Thr Ala Pro Pro Tyr Asp Thr Leu Leu
        115                 120                 125

Val Phe Asp Tyr Glu Gly Ser Gly Ser Asp Ala Ala Ser Leu Ser Ser
130                 135                 140

Leu Thr Ser Ser Ala Ser Asp Gln Asp Gln Tyr Asp Tyr Leu Asn
145                 150                 155                 160

Glu Trp Gly Ser Arg Phe Lys Lys Leu Ala Asp Met Tyr Gly Gly Gly
                165                 170                 175

Glu Asp Asp

<210> SEQ ID NO 168
<211> LENGTH: 221
<212> TYPE: PRT
<213> ORGANISM: Homo sapiens

<400> SEQUENCE: 168

Asp Trp Val Val Ala Pro Ile Ser Val Pro Glu Asn Gly Lys Gly Pro
1               5                   10                  15

Phe Pro Gln Arg Leu Asn Gln Leu Lys Ser Asn Lys Asp Arg Asp Thr
            20                  25                  30

-continued

```
Lys Ile Phe Tyr Ser Ile Thr Gly Pro Gly Ala Asp Ser Pro Pro Glu
            35                  40                  45

Gly Val Phe Ala Val Glu Lys Glu Thr Gly Trp Leu Leu Leu Asn Lys
 50                  55                  60

Pro Leu Asp Arg Glu Glu Ile Ala Lys Tyr Glu Leu Phe Gly His Ala
 65                  70                  75                  80

Val Ser Glu Asn Gly Ala Ser Val Glu Asp Pro Met Asn Ile Ser Ile
                 85                  90                  95

Ile Val Thr Asp Gln Asn Asp His Lys Pro Lys Phe Thr Gln Asp Thr
            100                 105                 110

Phe Arg Gly Ser Val Leu Glu Gly Val Leu Pro Gly Thr Ser Val Met
            115                 120                 125

Gln Val Thr Ala Thr Asp Glu Asp Ala Ile Tyr Thr Tyr Asn Gly
130                 135                 140

Val Val Ala Tyr Ser Ile His Ser Gln Glu Pro Lys Asp Pro His Asp
145                 150                 155                 160

Leu Met Phe Thr Ile His Arg Ser Thr Gly Thr Ile Ser Val Ile Ser
                165                 170                 175

Ser Gly Leu Asp Arg Glu Lys Val Pro Glu Tyr Thr Leu Thr Ile Gln
            180                 185                 190

Ala Thr Asp Met Asp Gly Asp Gly Ser Thr Thr Thr Ala Val Ala Val
            195                 200                 205

Val Glu Ile Leu Asp Ala Asn Asp Asn Ala Pro Met Phe
210                 215                 220
```

<210> SEQ ID NO 169
<211> LENGTH: 333
<212> TYPE: PRT
<213> ORGANISM: Homo sapiens

<400> SEQUENCE: 169

```
Asp Trp Val Val Ala Pro Ile Ser Val Pro Glu Asn Gly Lys Gly Pro
 1               5                  10                  15

Phe Pro Gln Arg Leu Asn Gln Leu Lys Ser Asn Lys Asp Arg Asp Thr
                20                  25                  30

Lys Ile Phe Tyr Ser Ile Thr Gly Pro Gly Ala Asp Ser Pro Pro Glu
            35                  40                  45

Gly Val Phe Ala Val Glu Lys Glu Thr Gly Trp Leu Leu Leu Asn Lys
 50                  55                  60

Pro Leu Asp Arg Glu Glu Ile Ala Lys Tyr Glu Leu Phe Gly His Ala
 65                  70                  75                  80

Val Ser Glu Asn Gly Ala Ser Val Glu Asp Pro Met Asn Ile Ser Ile
                 85                  90                  95

Ile Val Thr Asp Gln Asn Asp His Lys Pro Lys Phe Thr Gln Asp Thr
            100                 105                 110

Phe Arg Gly Ser Val Leu Glu Gly Val Leu Pro Gly Thr Ser Val Met
            115                 120                 125

Gln Val Thr Ala Thr Asp Glu Asp Ala Ile Tyr Thr Tyr Asn Gly
130                 135                 140

Val Val Ala Tyr Ser Ile His Ser Gln Glu Pro Lys Asp Pro His Asp
145                 150                 155                 160

Leu Met Phe Thr Ile His Arg Ser Thr Gly Thr Ile Ser Val Ile Ser
                165                 170                 175

Ser Gly Leu Asp Arg Glu Lys Val Pro Glu Tyr Thr Leu Thr Ile Gln
```

```
                180             185             190
Ala Thr Asp Met Asp Gly Asp Gly Ser Thr Thr Thr Ala Val Ala Val
            195                 200             205

Val Glu Ile Leu Asp Ala Asn Asp Asn Ala Pro Met Phe Asp Pro Gln
210                 215                 220

Lys Tyr Glu Ala His Val Pro Glu Asn Ala Val Gly His Glu Val Gln
225                 230                 235                 240

Arg Leu Thr Val Thr Asp Leu Asp Ala Pro Asn Ser Pro Ala Trp Arg
                245                 250                 255

Ala Thr Tyr Leu Ile Met Gly Gly Asp Asp Gly Asp His Phe Thr Ile
            260                 265                 270

Thr Thr His Pro Glu Ser Asn Gln Gly Ile Leu Thr Thr Arg Lys Gly
        275                 280                 285

Leu Asp Phe Glu Ala Lys Asn Gln His Thr Leu Tyr Val Glu Val Thr
    290                 295                 300

Asn Glu Ala Pro Phe Val Leu Lys Leu Pro Thr Ser Thr Ala Thr Ile
305                 310                 315                 320

Val Val His Val Glu Asp Val Asn Glu Ala Pro Val Phe
                325                 330

<210> SEQ ID NO 170
<211> LENGTH: 439
<212> TYPE: PRT
<213> ORGANISM: Homo sapiens

<400> SEQUENCE: 170

Asp Trp Val Val Ala Pro Ile Ser Val Pro Glu Asn Gly Lys Gly Pro
1               5                   10                  15

Phe Pro Gln Arg Leu Asn Gln Leu Lys Ser Asn Lys Asp Arg Asp Thr
            20                  25                  30

Lys Ile Phe Tyr Ser Ile Thr Gly Pro Gly Ala Asp Ser Pro Pro Glu
        35                  40                  45

Gly Val Phe Ala Val Glu Lys Glu Thr Gly Trp Leu Leu Leu Asn Lys
    50                  55                  60

Pro Leu Asp Arg Glu Glu Ile Ala Lys Tyr Glu Leu Phe Gly His Ala
65                  70                  75                  80

Val Ser Glu Asn Gly Ala Ser Val Glu Asp Pro Met Asn Ile Ser Ile
                85                  90                  95

Ile Val Thr Asp Gln Asn Asp His Lys Pro Lys Phe Thr Gln Asp Thr
            100                 105                 110

Phe Arg Gly Ser Val Leu Glu Gly Val Leu Pro Gly Thr Ser Val Met
        115                 120                 125

Gln Val Thr Ala Thr Asp Glu Asp Asp Ala Ile Tyr Thr Tyr Asn Gly
    130                 135                 140

Val Val Ala Tyr Ser Ile His Ser Gln Glu Pro Lys Asp Pro His Asp
145                 150                 155                 160

Leu Met Phe Thr Ile His Arg Ser Thr Gly Thr Ile Ser Val Ile Ser
                165                 170                 175

Ser Gly Leu Asp Arg Glu Lys Val Pro Glu Tyr Thr Leu Thr Ile Gln
            180                 185                 190

Ala Thr Asp Met Asp Gly Asp Gly Ser Thr Thr Thr Ala Val Ala Val
        195                 200                 205

Val Glu Ile Leu Asp Ala Asn Asp Asn Ala Pro Met Phe Asp Pro Gln
    210                 215                 220
```

```
Lys Tyr Glu Ala His Val Pro Glu Asn Ala Val Gly His Glu Val Gln
225                 230                 235                 240

Arg Leu Thr Val Thr Asp Leu Asp Ala Pro Asn Ser Pro Ala Trp Arg
            245                 250                 255

Ala Thr Tyr Leu Ile Met Gly Gly Asp Gly Asp His Phe Thr Ile
        260                 265                 270

Thr Thr His Pro Glu Ser Asn Gln Gly Ile Leu Thr Thr Arg Lys Gly
        275                 280                 285

Leu Asp Phe Glu Ala Lys Asn Gln His Thr Leu Tyr Val Glu Val Thr
    290                 295                 300

Asn Glu Ala Pro Phe Val Leu Lys Leu Pro Thr Ser Thr Ala Thr Ile
305                 310                 315                 320

Val Val His Val Glu Asp Val Asn Glu Ala Pro Val Phe Val Pro Pro
                325                 330                 335

Ser Lys Val Val Glu Val Gln Glu Gly Ile Pro Thr Gly Glu Pro Val
            340                 345                 350

Cys Val Tyr Thr Ala Glu Asp Pro Asp Lys Glu Asn Gln Lys Ile Ser
        355                 360                 365

Tyr Arg Ile Leu Arg Asp Pro Ala Gly Trp Leu Ala Met Asp Pro Asp
370                 375                 380

Ser Gly Gln Val Thr Ala Val Gly Thr Leu Asp Arg Glu Asp Glu Gln
385                 390                 395                 400

Phe Val Arg Asn Asn Ile Tyr Glu Val Met Val Leu Ala Met Asp Asn
                405                 410                 415

Gly Ser Pro Pro Thr Thr Gly Thr Gly Thr Leu Leu Thr Leu Ile
            420                 425                 430

Asp Val Asn Asp His Gly Pro
            435

<210> SEQ ID NO 171
<211> LENGTH: 543
<212> TYPE: PRT
<213> ORGANISM: Homo sapiens

<400> SEQUENCE: 171

Asp Trp Val Val Ala Pro Ile Ser Val Pro Glu Asn Gly Lys Gly Pro
1               5                   10                  15

Phe Pro Gln Arg Leu Asn Gln Leu Lys Ser Asn Lys Asp Arg Asp Thr
                20                  25                  30

Lys Ile Phe Tyr Ser Ile Thr Gly Pro Gly Ala Asp Ser Pro Pro Glu
            35                  40                  45

Gly Val Phe Ala Val Glu Lys Glu Thr Gly Trp Leu Leu Leu Asn Lys
    50                  55                  60

Pro Leu Asp Arg Glu Glu Ile Ala Lys Tyr Glu Leu Phe Gly His Ala
65                  70                  75                  80

Val Ser Glu Asn Gly Ala Ser Val Glu Asp Pro Met Asn Ile Ser Ile
                85                  90                  95

Ile Val Thr Asp Gln Asn Asp His Lys Pro Lys Phe Thr Gln Asp Thr
            100                 105                 110

Phe Arg Gly Ser Val Leu Glu Gly Val Leu Pro Gly Thr Ser Val Met
        115                 120                 125

Gln Val Thr Ala Thr Asp Glu Asp Ala Ile Tyr Thr Tyr Asn Gly
    130                 135                 140

Val Val Ala Tyr Ser Ile His Ser Gln Glu Pro Lys Asp Pro His Asp
145                 150                 155                 160
```

Leu Met Phe Thr Ile His Arg Ser Thr Gly Thr Ile Ser Val Ile Ser
                                    165                 170                 175

Ser Gly Leu Asp Arg Glu Lys Val Pro Glu Tyr Thr Leu Thr Ile Gln
                                180                 185                 190

Ala Thr Asp Met Asp Gly Asp Gly Ser Thr Thr Ala Val Ala Val
                                195                 200                 205

Val Glu Ile Leu Asp Ala Asn Asp Asn Ala Pro Met Phe Asp Pro Gln
                    210                 215                 220

Lys Tyr Glu Ala His Val Pro Glu Asn Ala Val Gly His Glu Val Gln
                    225                 230                 235                 240

Arg Leu Thr Val Thr Asp Leu Asp Ala Pro Asn Ser Pro Ala Trp Arg
                                    245                 250                 255

Ala Thr Tyr Leu Ile Met Gly Asp Asp Gly Asp His Phe Thr Ile
                                    260                 265                 270

Thr Thr His Pro Glu Ser Asn Gln Gly Ile Leu Thr Thr Arg Lys Gly
                                    275                 280                 285

Leu Asp Phe Glu Ala Lys Asn Gln His Thr Leu Tyr Val Glu Val Thr
                                290                 295                 300

Asn Glu Ala Pro Phe Val Leu Lys Leu Pro Thr Ser Thr Ala Thr Ile
                    305                 310                 315                 320

Val Val His Val Glu Asp Val Asn Glu Ala Pro Val Phe Val Pro Pro
                                    325                 330                 335

Ser Lys Val Val Glu Val Gln Glu Gly Ile Pro Thr Gly Glu Pro Val
                                340                 345                 350

Cys Val Tyr Thr Ala Glu Asp Pro Asp Lys Glu Asn Gln Lys Ile Ser
                                355                 360                 365

Tyr Arg Ile Leu Arg Asp Pro Ala Gly Trp Leu Ala Met Asp Pro Asp
                    370                 375                 380

Ser Gly Gln Val Thr Ala Val Gly Thr Leu Asp Arg Glu Asp Glu Gln
                    385                 390                 395                 400

Phe Val Arg Asn Asn Ile Tyr Glu Val Met Val Leu Ala Met Asp Asn
                                    405                 410                 415

Gly Ser Pro Pro Thr Thr Gly Thr Gly Thr Leu Leu Leu Thr Leu Ile
                                420                 425                 430

Asp Val Asn Asp His Gly Pro Val Pro Glu Pro Arg Gln Ile Thr Ile
                                435                 440                 445

Cys Asn Gln Ser Pro Val Arg Gln Val Leu Asn Ile Thr Asp Lys Asp
                        450                 455                 460

Leu Ser Pro His Thr Ser Pro Phe Gln Ala Gln Leu Thr Asp Asp Ser
                    465                 470                 475                 480

Asp Ile Tyr Trp Thr Ala Glu Val Asn Glu Glu Gly Asp Thr Val Val
                                    485                 490                 495

Leu Ser Leu Lys Lys Phe Leu Lys Gln Asp Thr Tyr Asp Val His Leu
                                500                 505                 510

Ser Leu Ser Asp His Gly Asn Lys Glu Gln Leu Thr Val Ile Arg Ala
                                515                 520                 525

Thr Val Cys Asp Cys His Gly His Val Glu Thr Cys Pro Gly Pro
                    530                 535                 540

<210> SEQ ID NO 172
<211> LENGTH: 112
<212> TYPE: PRT
<213> ORGANISM: Mus musculus

<400> SEQUENCE: 172

Glu Pro Gln Lys Tyr Glu Ala Trp Val Pro Glu Asn Glu Val Gly His
1               5                   10                  15

Glu Val Gln Arg Leu Thr Val Thr Asp Leu Asp Val Pro Asn Ser Pro
            20                  25                  30

Ala Trp Arg Ala Thr Tyr His Ile Val Gly Gly Asp Gly Asp His
        35                  40                  45

Phe Thr Ile Thr Thr His Pro Glu Thr Asn Gln Gly Val Leu Thr Thr
    50                  55                  60

Lys Lys Gly Leu Asp Phe Glu Ala Gln Asp Gln His Thr Leu Tyr Val
65                  70                  75                  80

Glu Val Thr Asn Glu Ala Pro Phe Ala Val Lys Leu Pro Thr Ala Thr
                85                  90                  95

Ala Thr Val Val Val His Val Lys Asp Val Asn Glu Ala Pro Val Phe
            100                 105                 110

<210> SEQ ID NO 173
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 173
gctggtaaag gtgtaagcag aagccttgca gga                                    33

<210> SEQ ID NO 174
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 174
accgtagctg gtaaaggtag caccagaagc cttgcagga                              39

<210> SEQ ID NO 175
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 175
gataccgtag ctggtaaaag cgtaaccaga agccttgca                              39

<210> SEQ ID NO 176
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 176
gataccgtag ctggtagcgg tgtaaccaga agc                                    33

<210> SEQ ID NO 177
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 177
ccagctgata ccgtagctag caaaggtgta accagaagc         39

<210> SEQ ID NO 178
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 178
cacccagctg ataccgtaag cggtaaaggt gtaaccaga         39

<210> SEQ ID NO 179
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 179
tcgcacccag ctgataccag cgctggtaaa ggtgtaacc         39

<210> SEQ ID NO 180
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 180
tcgcacccag ctgatagcgt agctggtaaa ggt         33

<210> SEQ ID NO 181
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 181
ctgtcgcacc cagctagcac cgtagctggt aaa         33

<210> SEQ ID NO 182
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 182
ggcctgtcgc acccaagcga taccgtagct ggt         33

<210> SEQ ID NO 183
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 183
accattgtaa gcgctgatag ctcccatcca ctcaagccc         39

<210> SEQ ID NO 184
<211> LENGTH: 39

<212> TYPE: DNA
<213> ORGANISM: Artificial Sequence
<220> FEATURE:
<223> OTHER INFORMATION: Synthetic nucleotide sequence

<400> SEQUENCE: 184
gttaccattg taagcgctag cccatcccat ccactcaag                     39

<210> SEQ ID NO 185
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 185
tgtgttacca ttgtaagcag cgatccatcc catccactc                     39

<210> SEQ ID NO 186
<211> LENGTH: 45
<212> TYPE: DNA
<213> ORGANISM: Artificial Sequence
<220> FEATURE:
<223> OTHER INFORMATION: Synthetic nucleotide sequence

<400> SEQUENCE: 186
tgcatagttt gtgttaccat tagcagcgct gatccatccc atcca              45

<210> SEQ ID NO 187
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 187
tgcatagttt gtgttaccag cgtaagcgct gatccatcc                     39

<210> SEQ ID NO 188
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 188
ctgtgcatag tttgtgttag cattgtaagc gctgatcca                     39

<210> SEQ ID NO 189
<211> LENGTH: 45
<212> TYPE: DNA
<213> ORGANISM: Artificial Sequence
<220> FEATURE:
<223> OTHER INFORMATION: Synthetic nucleotide sequence

<400> SEQUENCE: 189
gagcttctgt gcatagtttg tagcaccatt gtaagcgctg atcca              45

<210> SEQ ID NO 190
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 190
gagcttctgt gcatagttag cgttaccatt gtaagcgct        39

<210> SEQ ID NO 191
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 191
ctggagcttc tgtgcataag ctgtgttacc attgtaagc        39

<210> SEQ ID NO 192
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 192
gccctggagc ttctgtgcag cgtttgtgtt accattgta        39

<210> SEQ ID NO 193
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 193
gactctgccc tggagcttag ctgcatagtt tgtgttacc        39

<210> SEQ ID NO 194
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 194
ggtgactctg ccctggagag cctgtgcata gtttgtgtt        39

<210> SEQ ID NO 195
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 195
catggtgact ctgccctgag ccttctgtgc atagtttgt        39

<210> SEQ ID NO 196
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 196
ggtcatggtg actctgccag cgagcttctg tgcatagtt        39

<210> SEQ ID NO 197
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 197
ggtcatggtg actctagcct ggagcttctg tgc                          33

<210> SEQ ID NO 198
<211> LENGTH: 45
<212> TYPE: DNA
<213> ORGANISM: Artificial Sequence
<220> FEATURE:
<223> OTHER INFORMATION: Synthetic nucleotide sequence

<400> SEQUENCE: 198
accaaaagca ttagctgtat cagcagtcgc acagtaatac acggc              45

<210> SEQ ID NO 199
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 199
aaaagcatta gctgtagcga tagtcgcaca gta                           33

<210> SEQ ID NO 200
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 200
gataccaaaa gcattagcag catcgatagt cgcacagta                     39

<210> SEQ ID NO 201
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 201
gccccagata ccaaaagcag cagctgtatc gatagtcgc                     39

<210> SEQ ID NO 202
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 202
ttggccccag ataccagcag cattagctgt atc                           33

<210> SEQ ID NO 203
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 203
cccttggccc cagatagcaa aagcattagc tgt                           33

<210> SEQ ID NO 204
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 204
cattgtccct tggccccaag caccaaaagc attagctgt                                 39

<210> SEQ ID NO 205
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 205
gttggagctg cttccagcgc aggagatggt gac                                       33

<210> SEQ ID NO 206
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 206
aatgttggag ctgctagcag agcaggagat ggt                                       33

<210> SEQ ID NO 207
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 207
attcccaatg ttggagctag ctccagagca ggagatggt                                 39

<210> SEQ ID NO 208
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 208
attattccca atgttggaag cgcttccaga gcaggagat                                 39

<210> SEQ ID NO 209
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 209
ataattattc ccaatgttag cgctgcttcc agagcagga                                 39

<210> SEQ ID NO 210
<211> LENGTH: 45
<212> TYPE: DNA
<213> ORGANISM: Artificial Sequence
<220> FEATURE:
<223> OTHER INFORMATION: Synthetic nucleotide sequence

<400> SEQUENCE: 210
ggatacataa ttattcccaa tagcggagct gcttccagag cagga                           45

<210> SEQ ID NO 211
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 211
ggatacataa ttattcccag cgttggagct gcttccaga                                  39

<210> SEQ ID NO 212
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 212
ccaggataca taattattag caatgttgga gctgcttcc                                  39

<210> SEQ ID NO 213
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 213
gtaccaggat acataattag ccccaatgtt ggagctgct                                  39

<210> SEQ ID NO 214
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 214
ctggtaccag gatacataag cattcccaat gttggagct                                  39

<210> SEQ ID NO 215
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 215
ctgctggtac caggatacag cattattccc aatgttgga                                  39

<210> SEQ ID NO 216
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 216
gagctgctgg taccaggaag cataattatt cccaatgtt                                  39

<210> SEQ ID NO 217

```
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 217
tgggagctgc tggtaccaag ctacataatt attcccaat                                  39

<210> SEQ ID NO 218
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 218
tgagggtcgc ttattattag cataaatgag gagtttggg                                  39

<210> SEQ ID NO 219
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 219
ccctgagggt cgcttattag cgtcataaat gaggagttt                                  39

<210> SEQ ID NO 220
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 220
aatccctgag ggtcgcttag cattgtcata aatgaggag                                  39

<210> SEQ ID NO 221
<211> LENGTH: 45
<212> TYPE: DNA
<213> ORGANISM: Artificial Sequence
<220> FEATURE:
<223> OTHER INFORMATION: Synthetic nucleotide sequence

<400> SEQUENCE: 221
gtcaggaatc cctgagggtc gagcattatt gtcataaatg aggag                           45

<210> SEQ ID NO 222
<211> LENGTH: 45
<212> TYPE: DNA
<213> ORGANISM: Artificial Sequence
<220> FEATURE:
<223> OTHER INFORMATION: Synthetic nucleotide sequence

<400> SEQUENCE: 222
tcggtcagga atccctgagg gagccttatt attgtcataa atgag                           45

<210> SEQ ID NO 223
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 223
```

```
tcggtcagga atccctgaag ctcgcttatt attgtcata                   39
```

<210> SEQ ID NO 224
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 224

```
tcggtcagga atcccagcgg gtcgcttatt att                         33
```

<210> SEQ ID NO 225
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 225

```
gctgctatcc catgtagcgc agtaataatc ggc                         33
```

<210> SEQ ID NO 226
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 226

```
caggctgcta tcccaagctc cgcagtaata atc                         33
```

<210> SEQ ID NO 227
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 227

```
accactcagg ctgctatcag ctgttccgca gtaataatc                   39
```

<210> SEQ ID NO 228
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 228

```
accactcagg ctgctagccc atgttccgca gta                         33
```

<210> SEQ ID NO 229
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 229

```
cacaccactc aggctagcat cccatgttcc gca                         33
```

<210> SEQ ID NO 230
<211> LENGTH: 39
<212> TYPE: DNA

<213> ORGANISM: Artificial Sequence
<220> FEATURE:
<223> OTHER INFORMATION: Synthetic nucleotide sequence

<400> SEQUENCE: 230
gaataccaca ccactcagag cgctatccca tgttccgca                39

<210> SEQ ID NO 231
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 231
gccgaatacc acaccactag cgctgctatc ccatgttcc                39

<210> SEQ ID NO 232
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 232
gccgaatacc acaccagcca ggctgctatc cca                33

<210> SEQ ID NO 233
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 233
tccgccgaat accacagcac tcaggctgct atc                33

<210> SEQ ID NO 234
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 234
ccctccgccg aatacagcac cactcaggct gct                33

<210> SEQ ID NO 235
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 235
ggtccctccg ccgaaagcca caccactcag gct                33

<210> SEQ ID NO 236
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 236

Ala Ile Gln Met Thr Gln Ser Pro Ser Ser Leu Ser Ala Ser Val Gly

```
            1               5                   10                  15
Asp Arg Val Thr Ile Thr Cys Arg Ala Ser Gln Ser Ile Gly Lys Tyr
            20                  25                  30

Leu Asn Trp Tyr Gln Gln Ile Pro Gly Lys Ala Pro Lys Leu Leu Ile
            35                  40                  45

Tyr Thr Ala Ser Thr Leu Gln Thr Gly Val Pro Ser Arg Phe Ser Gly
            50                  55                  60

Ser Gly Ser Gly Thr Asp Phe Thr Leu Thr Ile Val Ser Leu Gln Pro
 65                 70                  75                  80

Glu Asp Phe Ala Thr Tyr Tyr Cys Gln Gln Ser Phe Asn Thr Pro Arg
                    85                  90                  95

Thr Phe Gly Gln Gly Thr Lys Val Glu Ile Lys
                100                 105

<210> SEQ ID NO 237
<211> LENGTH: 118
<212> TYPE: PRT
<213> ORGANISM: Artificial Sequence
<220> FEATURE:
<223> OTHER INFORMATION: Synthetic peptide sequence

<400> SEQUENCE: 237

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Arg Ile Asn Pro Asn Ser Gly Gly Thr Asn Tyr Ala Gln Lys Phe
 50                 55                  60

Gln Gly Arg Val Thr Met Thr Arg Asp Thr Ser Ile Ser Thr Ala Tyr
 65                 70                  75                  80

Met Glu Leu Ser Arg Leu Arg Ser Asp Asp Thr Ala Val Tyr Tyr Cys
                    85                  90                  95

Ala Lys Gly Ser Gly Ser Gly Ala Phe Asp Ile Trp Gly Gln Gly Thr
                100                 105                 110

Met Val Thr Val Ser Ser
            115

<210> SEQ ID NO 238
<211> LENGTH: 112
<212> TYPE: PRT
<213> ORGANISM: Artificial Sequence
<220> FEATURE:
<223> OTHER INFORMATION: Synthetic peptide sequence

<400> SEQUENCE: 238

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu His Trp Phe Gln Gln Arg Pro Gly Gln Ser
            35                  40                  45

Pro Arg Arg Leu Ile Tyr Lys Val Ser Asn Arg Asp Ser Gly Val Pro
        50                  55                  60

Asp Arg Phe Ser Gly Ser Gly Ser Gly Thr Asp Phe Thr Leu Lys Ile
 65                 70                  75                  80
```

```
Ser Arg Val Glu Ala Glu Asp Val Gly Val Tyr Tyr Cys Met Gln Gly
                    85              90                  95

Thr His Trp Pro Pro Leu Phe Gly Gln Gly Thr Lys Val Glu Ile Lys
                100             105                 110

<210> SEQ ID NO 239
<211> LENGTH: 118
<212> TYPE: PRT
<213> ORGANISM: Artificial Sequence
<220> FEATURE:
<223> OTHER INFORMATION: Synthetic peptide sequence

<400> SEQUENCE: 239

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Ser Asp Arg Thr Phe Asp Tyr Trp Gly Gln Gly Thr
                100                 105                 110

Leu Val Thr Val Ser Ser
            115
```